(12) United States Patent
Beaubier et al.

(10) Patent No.: US 11,367,508 B2
(45) Date of Patent: Jun. 21, 2022

(54) SYSTEMS AND METHODS FOR DETECTING CELLULAR PATHWAY DYSREGULATION IN CANCER SPECIMENS

(71) Applicant: Tempus Labs, Inc., Chicago, IL (US)

(72) Inventors: Nike T. Beaubier, Chicago, IL (US); Joshua S K Bell, Chicago, IL (US); Catherine Igartua, Chicago, IL (US); Hailey B. Lefkofsky, Chicago, IL (US); Lee F. Langer, Chicago, IL (US); Joshua Drews, Chicago, IL (US)

(73) Assignee: Tempus Labs, Inc., Chicago, IL (US)

( * ) Notice: Subject to any disclaimer, the term of this patent is extended or adjusted under 35 U.S.C. 154(b) by 0 days.

(21) Appl. No.: 16/994,315

(22) Filed: Aug. 14, 2020

(65) Prior Publication Data

US 2021/0057042 A1 Feb. 25, 2021

Related U.S. Application Data

(63) Continuation-in-part of application No. PCT/US2019/056713, filed on Oct. 17, 2019.

(60) Provisional application No. 62/888,163, filed on Aug. 16, 2019, provisional application No. 62/904,300, filed on Sep. 23, 2019, provisional application No. 62/986,201, filed on Mar. 6, 2020.

(51) Int. Cl.
*G16B 25/10* (2019.01)
*G16B 40/20* (2019.01)
*G16B 40/30* (2019.01)
*G16B 30/10* (2019.01)
*G16B 5/20* (2019.01)

(52) U.S. Cl.
CPC .............. *G16B 25/10* (2019.02); *G16B 5/20* (2019.02); *G16B 30/10* (2019.02); *G16B 40/20* (2019.02); *G16B 40/30* (2019.02)

(58) Field of Classification Search
None
See application file for complete search history.

(56) References Cited

U.S. PATENT DOCUMENTS

| | | | |
|---|---|---|---|
| 2009/0299646 A1* | 12/2009 | Shams | G16B 5/00 702/19 |
| 2018/0195123 A1* | 7/2018 | Johnson | C12Q 1/6883 |
| 2018/0357374 A1 | 12/2018 | Bagaev | |
| 2020/0075169 A1 | 3/2020 | Lau | |
| 2020/0098448 A1 | 3/2020 | Shah | |
| 2020/0118644 A1 | 4/2020 | Khan | |
| 2020/0210852 A1 | 7/2020 | Igartua | |
| 2021/0104321 A1* | 4/2021 | Lipsky | G16H 70/40 |

FOREIGN PATENT DOCUMENTS

| | | |
|---|---|---|
| EP | 3369826 A1 | 9/2018 |
| WO | 2013011479 A2 | 1/2013 |
| WO | 2015077725 A1 | 5/2015 |
| WO | 2020068880 A1 | 4/2020 |
| WO | 2020142563 A1 | 7/2020 |

OTHER PUBLICATIONS

Ziemann et al. Gene name errors are widespread in the scientific literature. 2016. Genome Biology. vol. 17, No. 177, 3 pages. (Year: 2016).*
PCT/US2020/046513 International Written Opinion and Search, dated Dec. 30, 2020. 10 pages. (Year: 2020).*
Way et al. Machine Learning Detects Pan-cancer Ras Pathway Activation in The Cancer Genome Atlas. Apr. 3, 2018. Cell Rep. vol. 23, No. 1, pp. 172-180. (Year: 2018).*
U.S. Appl. No. 62/855,913, filed May 31, 2019.
U.S. Appl. No. 62/873,693, filed Jul. 12, 2019.
U.S. Appl. No. 62/888,163, filed Aug. 16, 2019.
U.S. Appl. No. 62/889,510, filed Aug. 20, 2019.
U.S. Appl. No. 62/902,950, filed Sep. 19, 2019.
U.S. Appl. No. 62/924,054, filed Oct. 21, 2019.
U.S. Appl. No. 62/924,073, filed Oct. 21, 2019.
U.S. Appl. No. 62/924,515, filed Oct. 22, 2019.
U.S. Appl. No. 62/924,621, filed Oct. 22, 2019.
U.S. Appl. No. 62/931,600, filed Novembers, 2019.
U.S. Appl. No. 62/943,712, filed Dec. 4, 2019.
U.S. Appl. No. 62/944,292, filed Decembers, 2019.
U.S. Appl. No. 62/944,995, filed Dec. 30, 2019.
International Searching Authority. International Search Report and Written Opinion for application PCT/US2020/046513. dated Dec. 30, 2020. 15 pages.
Alvarez, M. J., et al. "Functional characterization of somatic mutations in cancer using network-based inference of protein activity." Nature 201: 6. 2016.
Barbie, D., et al. Systematic RNA interference reveals that oncogenic KRAS-driven cancers require TBK1. Nature 462, 108-112 (2009).
Bray, NL et al. Near-optimal probabilistic RNA-seq quantification, Nature Biotechnology 34, 525-527 (2016).
Cancer Genome Atlas Research Network. "Comprehensive molecular profiling of lung adenocarcinoma." Nature 511.7511 (2014): 543-550.
Cheng, F., et al. A genome-wide positioning systems network algorithm for in silico drug repurposing. Nat Commun. 2019; 10: 3476.
Ciriello, G., et al. "Mutual exclusivity analysis identifies oncogenic network modules." Genome research 22.2 (2012): 398-406.
Cseh B, et al. "RAF" neighborhood: protein-protein interaction in the Raf/Mek/Erk pathway. FEBS Lett. 2014;588:2398-2406.
Ding, H., et al. "Quantitative assessment of protein activity in orphan tissues and single cells using the metaVIPER algorithm." Nature communications 9.1 (2018): 1-10.

(Continued)

*Primary Examiner* — Channing S Mahatan
(74) *Attorney, Agent, or Firm* — Quarles & Brady LLP

(57) ABSTRACT

Disclosed herein are systems, methods, and compositions useful for determining cellular pathway disruption comprising the use of RNA expression level information. This determined level of disruption can assist in the identification of genetic variants that alter pathway activity, to correlate these variants with disease state and disease progression, and to identify those therapeutics most likely to be effective and which should be avoided.

35 Claims, 124 Drawing Sheets

(56) References Cited

OTHER PUBLICATIONS

GSEA. FAQs. Version dated Jan. 2019. https://software.broadinstitute.org/cancer/software/gsea/wiki/index.php/FAQ.
Hanzelmann, S., et al. GSVA: gene set variation analysis for microarray and RNA-Seq data. BMC Bioinformatics 14, 7 (2013).
Hoadley, K. A., et al. "Cell-of-origin patterns dominate the molecular classification of 10,000 tumors from 33 types of cancer." Cell 173.2 (2018): 291-304.
Huang, A., et al. "Synthetic lethality as an engine for cancer drug target discovery." Nature Reviews Drug Discovery 19.1 (2020): 23-38.
Huang, C-T, et al. "Perturbational gene-expression signatures for combinatorial drug discovery." Iscience 15 (2019): 291-306.
Huang, D-S et al, editors. Intelligent Computing Theories and Application Proceedings, part II. 15th International Conferences, ICIC 2019. Nanchang, China. Aug. 3-6, 2019.
Knight T, let al. Ras/Raf/MEK/ERK pathway activation in childhood acute lymphoblastic leukemia and its therapeutic targeting. Front Oncol. 2014;4:160.
Lamb, J. et al. "The Connectivity Map: using gene-expression signatures to connect small molecules, genes, and disease." science 313.5795 (2006): 1929-1935.
Lord, C. J., et al. (2015). Synthetic lethality and cancer therapy: lessons learned from the development of PARP inhibitors. Annual review of medicine, 66, 455-470.
Magen, A., et al. (2019). Beyond synthetic lethality: Charting the landscape of pairwise gene expression states associated with survival in cancer. Cell reports, 28(4), 938-948.
Margolin, A. A., et al. "ARACNE: an algorithm for the reconstruction of gene regulatory networks in a mammalian cellular context." BMC bioinformatics. vol. 7. No. S1. BioMed Central, 2006.
Mina, M., et al. "Conditional selection of genomic alterations dictates cancer evolution and oncogenic dependencies." Cancer cell 32.2 (2017): 155-168.
Paananen, J., et al. (2020). An omics perspective on drug target discovery platforms. Briefings in bioinformatics, 21(6), 1937-1953.
Patro, R. et al. (2014) Sailfish enables alignment-free isoform quantification from RNA-seq reads using lightweight algorithms. Nature Biotechnology.
Patro, R., et al. (2017). Salmon provides fast and bias-aware quantification of transcript expression. Nature Methods.
Pennock, N. D., et al. "RNA-seq from archival FFPE breast cancer samples: molecular pathway fidelity and novel discovery." BMC medical genomics 12.1 (2019): 1-18.
Pineiro-Yanez, E., et al. (2018). PanDrugs: a novel method to prioritize anticancer drug treatments according to individual genomic data. Genome medicine, 10(1), 1-11.
Sanchez-Vega, F. et al. "Oncogenic signaling pathways in the cancer genome atlas." Cell 173.2 (2018): 321-337.
Santos, R., et al. "A comprehensive map of molecular drug targets." Nature reviews Drug discovery 16.1 (2017): 19-34.
Schubert, M, et al. "Perturbation-response genes reveal signaling footprints in cancer gene expression." Nature communications 9.1 (2018): 1-11.
Sinha, S., et al. "Systematic discovery of mutation-specific synthetic lethals by mining pan-cancer human primary tumor data." Nature Communications 8 (2017).
Skoulidis, F, et al. "STK11/LKB1 mutations and PD-1 inhibitor resistance in KRAS-mutant lung adenocarcinoma." Cancer discovery 8.7 (2018): 822-835.
Subramanian, A., et al. "Gene set enrichment analysis: a knowledge-based approach for interpreting genome-wide expression profiles" Proceedings of the National Academy of Sciences 102.43 (2005): 15545-15550.
Tutuncuoglu, B. et al. "Mapping genetic interactions in cancer: a road to rational combination therapies." Genome Medicine 11 (2019).
Way, G. P., et al. "Machine learning detects pan-cancer ras pathway activation in the cancer genome atlas." Cell reports 23.1 (2018): 172-180.
Wikipedia. Coordinate Descent. Version dated Jul. 24, 2019. https://en.wikipedia.org/w/index.php?title=Coordinate_descent&oldid=907633327.
Wikipedia. Kullbeck-Liebler Divergence. Version dated Aug. 7, 2019. https://en.wikipedia.org/w/index.php?title=Kullback%E2%80%93Leibler_divergence&oldid=909755160.
Yao, Z, et al. "Tumours with class 3 BRAF mutants are sensitive to the inhibition of activated RAS." Nature 548.7666 (2017): 234-238.
Ye, H., et al. "Ranking novel cancer driving synthetic lethal gene pairs using TCGA data." Oncotarget 7.34 (2016): 55352.
Zeitouni, D., et al. "KRAS mutant pancreatic cancer: no lone path to an effective treatment." Cancers 8.4 (2016): 45.
U.S. Appl. No. 16/657,804, filed Oct. 18, 2019.
U.S. Appl. No. 16/693,117, filed Nov. 22, 2019.
U.S. Appl. No. 62/746,997, filed Oct. 17, 2018.
U.S. Appl. No. 62/786,739, filed Dec. 31, 2018.
U.S. Appl. No. 62/786,756, filed Dec. 31, 2018.
U.S. Appl. No. 62/804,458, filed Feb. 12, 2019.
U.S. Appl. No. 62/804,509, filed Feb. 12, 2019.
U.S. Appl. No. 62/804,724, filed Feb. 12, 2019.
U.S. Appl. No. 62/804,730, filed Feb. 12, 2019.
U.S. Appl. No. 62/824,039, filed Mar. 26, 2019.
U.S. Appl. No. 62/854,400, filed May 30, 2019.
U.S. Appl. No. 62/855,750, filed May 31, 2019.
International Searching Authority. International Search Report and Written Opinion for application PCT/US20/64969, dated Apr. 21, 2021. 14 pages.

* cited by examiner

| Specimen ID | Transcriptome Value Set | Pathway Label 1 | Pathway Label 2 | Pathway Label N |
|---|---|---|---|---|
| 1 | T.V. 1 | Label 1 | Label 2 | Label 3 |
| 2 | T.V. 2 | Label | Label | Label |
| ... | ... | Label | Label | Label |
| N | T.V. N | Label | Label | Label |

Fig. 4

| | ERBB2_KLD_score | PTEN_KLD_score | PIK3C_KLD_score | AKT_KLD_score | TSC1_KLD_score | TSC2_KLD_score | RHEB_KLD_score | TOR_KLD_score | STK11_KLD_score | EGFR_KLD_score | RAS_KLD_score | RAF_KLD_score | Disruption Score |
|---|---|---|---|---|---|---|---|---|---|---|---|---|---|
| POLG1 c.4894_663+4G>GCigTT connected to RAF | 0.06772 | 0.913678 | 0.497594 | 0.323082 | 0.476869 | 0.680063 | 0.016406 | 0.107603 | 0.419509 | 0.038468 | 0.033640 | 0.016550 | 0.016550 |
| GATA3 c.673C>T connected to RAF | 0.144592 | 0.320408 | 0.052410 | 0.129517 | 0.112105 | 0.724140 | 0.020131 | 0.031861 | 0.209707 | 0.090638 | 0.022946 | 0.019300 | 0.019300 |
| GATA3 c.673C>T connected to RAS | 0.114592 | 0.320408 | 0.052410 | 0.129517 | 0.112105 | 0.724140 | 0.020131 | 0.031861 | 0.209707 | 0.090638 | 0.022946 | 0.019300 | 0.019300 |
| GNAS c.1120C>A connected to RAS | 0.052403 | 0.112705 | 0.182308 | 0.075853 | 0.137966 | 0.203737 | 0.024733 | 0.096774 | 0.129271 | 0.071211 | 0.014813 | 0.032115 | 0.021734 |
| MXD07 c.878_838delGTGCCinsATGCT connected to RAS | 0.074784 | 0.343795 | 0.292568 | 0.077834 | 0.166028 | 0.159932 | 0.030208 | 0.080923 | 0.152816 | 0.039450 | 0.016616 | 0.032207 | 0.022852 |

FIG. 6Y

Select cancer type of interest

Subset patients by mutation status

Identify differentially expressed genes between patient subsets and determine relevant ssGSEA scores Train, cross-validate, and finalize logistic regression model Validate biological relevance
using protein activation data Validate model performance
on external data set

ERBB2 (HER2)

*PIK3CA ⊢ ┌── Alpelisib +/- Fulvestrant
         │   (PI3Ka Inhibitor +/- SERD)
         └── Alpelisib or Pictilisib + Ribociclib
             (PI3K Inhibitor + Cyclin Inhibitor)

PTEN ⊣ AKT

↓ mTOR

↓

Cell Growth & Proliferation

PI3K Pathway

This patient has a PIK3CA gain of function mutation thus activating the PI3K pathway. Therapies that target this pathway are highlighted in the diagram as well as in the therapies section of the report.

🔍 pik3ca

35_3_PIK3CA_GOF_HER2_Breast

▶ Template Actions

[ PIK3CA ]

■ Remove All Therapies

| Drug Class | Drug | Variant Type | Variant | Tissue | Evidence | Association | FDA | Origin |
|---|---|---|---|---|---|---|---|---|
| PI3K Inhibitor | Alpelisib | snv/indel | Gain-of-function | ER+ HER2- Breast Cancer | Clinical Research PMID 29401002 *ACTID 7739* | ●Response | No | Somatic |
| Combination (Estrogen Receptor Antagonist + PI3K Inhibitor) | Fulvestrant + Alpelisib | snv/indel | Gain-of-function | ER + Breast Cancer | Clinical Research PMID 30543347 *ACTID 8374* | ●Response | No | Somatic |
| Combination (PI3K Inhibitor+ CDK4/6 Inhibitor) | Pictilisib, Alpelisib + Ribociclib | snv/indel | Gain-of-function | Breast Cancer | Preclinical PMID 2500202 *ACTID 2385* | ●Response | No | Somatic |

Eligibility Criteria
- Breast Cancer
- PIK3CA GOF -- gain of function mutation
- HER2 not known to be positive

Fig. 11E

| Name | Primary Site | Category | Sub-category |
|---|---|---|---|
| 1,25-Dihydroxyvitamin D3 | Multiple sites | Differentiation inducing agent | N/A |
| 1-Methyl-D-tryptophan | Melanoma;Other types, NOS | Chemotherapy | Enzyme inhibitor |
| 1018-ISS | Lymphoma | Chemotherapy | Targeted therapy--antisense |
| 109881 | Brain cancer | Chemotherapy | Natural product--taxane |
| 131I-MIBG | Neuroblastoma | Radiation | Radioisotope |
| 131I-TM-601 | Glioma | Radiation | Immunotoxin conjugated with radiation (radioisotope) |
| 17-DMAG | Solid tumors | Chemotherapy | Targeted therapy--heat shock protein 90 inhibitor |
| 2B1 bispecific murine MAb | Breast cancer;Ovarian cancer | Biologic therapy (BRM, immunotherapy) | Passive monoclonal antibody |
| 4-Hydroxyphenyl retinamide | Kaposi's sarcoma;breast | Differentiation inducing agent | N/A |
| 4-Nitroestrone | Breast | Hormones and hormonal mechanisms | Estrogen |
| 5-Aza-2'Deoxy-cytidine | CML | Chemotherapy | Cytostatic agent--DNA methyl transferase inhibitor |
| 5-FP | Breast;gastric;head & neck;liver cancer | Chemotherapy | Antimetabolite |
| 5-fluoro-2-deoxycytidine | Advanced solid tumors | Chemotherapy | Antimetabolite |
| 845 4B5 | Head & neck;skin cancer | Biologic therapy (BRM, immunotherapy) | N/A |
| 90Y-hPAM4 | Pancreas | Other therapy | immunotherapy |
| ABT 888 | Ovary | Chemotherapy | PARP Inhibitor |
| ABT-510 | Liver;other cancer | Chemotherapy | Cytostatic agent--antiangiogenic agent |
| ABT-518 | Other cancer | Chemotherapy | Inhibitor--matrix metalloproteinase/antimitotic agent |
| ABT-751 | neuroblastoma;Pediatric ALL | Chemotherapy | Cytostatic agent--tubulin binding agent |
| ABX-IL-8 | Skin cancer | Chemotherapy | Cytostatic agent--monoclonal antibody |
| ABX-MA1 | Skin cancer | Biologic therapy (BRM, immunotherapy) | Passive monoclonal antibody |
| ADXS-HPV | Cervix | Biologic therapy (BRM, immunotherapy) | Therapeutic vaccine |
| AEE 788 | Other cancer | Biologic therapy (BRM, immunotherapy) | Tyrosine kinase inhibitor |
| AFP464 | Solid tumors | Chemotherapy | Cytotoxic-cytostatic agent |
| AG-2037 | Breast;colon;lung;other cancer | Chemotherapy | Inhibitor--glycinamide ribonucleotide formyl transferase |
| AG3340 | Prostate cancer | Biologic therapy (BRM, immunotherapy) | Inhibitor--matrix metalloproteinase |
| ALVAC-B7.1 Vaccine with StemSep | Ovarian;skin cancer | Biologic therapy (BRM, immunotherapy) | Adoptive immunotherapy |
| ALVAC-CEA Vaccine | Colon cancer | Biologic therapy (BRM, immunotherapy) | Adoptive immunotherapy |
| ALVAC-IL-12 | Skin cancer | Biologic therapy (BRM, immunotherapy) | Adoptive immunotherapy |
| AMD-473 | Breast;lung;ovarian;pancreatic;prostate cancer | Chemotherapy | Miscellaneous agent |
| AMG 386 | Breast;GYN | Chemotherapy | Angiopoietin inhibitor |

Fig. 26A

| Name | Primary Site | Category | Sub-category |
|---|---|---|---|
| AMG-479 | Carcinoids;NSCLC;pancreas;solid tumors | Biologic therapy (BRM, immunotherapy) | Monoclonal antibody inhibitor of IGF-IR |
| AN-152/AN-238/AN-215 | Other cancer | Chemotherapy | Cytostatic agent--antiangiogenic agent |
| AP-23573 | Lymphoma;other cancer | Chemotherapy | Cytostatic agent--antiangiogenic agent |
| APC 8024 Therapeutic Vaccine | Breast;colorectal;ovarian cancer | Biologic therapy (BRM, immunotherapy) | Therapeutic vaccine |
| AR54 | Ovarian cancer | Biologic therapy (BRM, immunotherapy) | Immunotherapy passive |
| AT-101 | Small cell lung cancer | Chemotherapy | Cytostatic agent--apoptosis inducer |
| ATG J591RC | Prostate cancer | Biologic therapy (BRM, immunotherapy) | Monoclonal antibody |
| ATN-161 | Glioma | Chemotherapy | Cytostatic agent--antiangiogenic agent |
| ATRA-IV | Lymphoma;Acute promyelocytic leukemia | Differentiation inducing agent | Retinoid: please see Remarks for coding instructions |
| AZD 3409 | Other cancer | Chemotherapy | Cytostatic agent--inhibitor;farnesyl transferase |
| AZD2281 | Melanoma | Chemotherapy | Cytostatic agent--apoptosis inducer |
| AZD6244 | Multiple sites | Chemotherapy | Protein inhibitor |
| Abarelix | breast;Prostate | Hormones and hormonal mechanisms | Estrogen production antagonist |
| Abemaciclib | Breast | Chemotherapy | Cyclin-dependent kinase inhibitor |
| Abiraterone acetate | Prostate | Hormones and hormonal mechanisms | Antiandrogenic |
| Abraxane | Metastatic breast cancer;NSCLC;Non small cell lung cancer;cervix;melanoma;pancreas | Chemotherapy | Taxane |
| Acalabrutinib | mantle cell lymphoma, chronic lymphocytic leukemia (CLL) or small lymphocytic lymphoma (SLL). | Chemotherapy | kinase inhibitor |
| Acapodene | November 21, 2019 FDA approved acalabrutinib (CALQUENCE) for adults with chronic lymphocytic leukemia (CLL) or small lymphocytic lymphoma (SLL). | Biologic therapy (BRM, immunotherapy) | Gene therapy |
| Accutane | Prostate cancer | Differentiation inducing agent | Retinoid |
| Aclarubicin | Leukemia;solid tumors | Chemotherapy | Cytostatic agent--topoisomerase inhibitor |
| Ad5CMV-p53 (adenovirus p53) | Glioma;Head & neck;lung cancer | Biologic therapy (BRM, immunotherapy) | p53 tumor suppressor gene |
| Adenazole | Colorectal cancer | Chemotherapy | Nucleoside analog |

Fig. 26B

| Name | Primary Site | Category | Sub-category |
|---|---|---|---|
| Adeno-Interleukin-2 | other cancer;Skin | Biologic therapy (BRM, immunotherapy) | Viral encoded human protein |
| Ado-trastuzumab emtansine | Metastatic HER-2 breast cancer | Biologic therapy (BRM, immunotherapy) | Antibody-drug conjugate |
| Advexin | Bladder;brain;breast;head & neck;liver;lung;ovarian;prostate cancer | Biologic therapy (BRM, immunotherapy) | p53 tumor suppressor gene |
| Affinitak | Lung;lymphoma;ovarian cancer | Chemotherapy | Targeted therapy |
| Afinitor | breast;Lung;other cancer | Chemotherapy | Cytostatic agent--antiangiogenesis agent and mTOR inhibitor |
| Aflibercept | fallopian tube;Lymphoma;ovary;primary peritoneal carcinoma | Chemotherapy | Cytostatic agent--VEGF inhibitor |
| Alanosine | Lung;pancreatic cancer;sarcoma | Chemotherapy | Antimetabolite |
| Albuleukin | Other cancer | Biologic therapy (BRM, immunotherapy) | Recombinant human protein |
| Alectinib | Lung | Chemotherapy | ALK Inhibitor |
| Alemtuzumab | Leukemia;lymphoma | Biologic therapy (BRM, immunotherapy) | Targeted therapy |
| Alitretinoin | Breast;Kaposi sarcoma;leukemia;sarcoma;skin cancer | Differentiation inducing agent | Retinoid |
| Allogeneic cells | Bone marrow | Biologic therapy (BRM, immunotherapy) | Cellular therapy |
| Allogenic colon cancer vaccine | Colorectal cancer | Biologic therapy (BRM, immunotherapy) | Adoptive immunotherapy |
| Allogenic glioma cancer vaccine | Brain cancer | Biologic therapy (BRM, immunotherapy) | Adoptive immunotherapy |
| Allovectin-7 | Head & neck cancer;melanoma | Biologic therapy (BRM, immunotherapy) | Gene therapy |
| Alpha Interferon | Kaposi's sarcoma | Biologic therapy (BRM, immunotherapy) | Human protein |
| Alpharadin | Bone metastases | Radiation | alpha radiation (radiopharmaceutical) |
| Altretamine | Ovarian cancer | Chemotherapy | Ccytotoxic antineoplastic |
| AlvacCEA/B7.1 | Colorectal cancer | Biologic therapy (BRM, immunotherapy) | Adoptive immunotherapy |
| Amadinone Acetate | Prostate cancer | Hormones and hormonal mechanisms | Progestin |
| Aminocamptothecin | Leukemia;breast;lung cancer;lymphoma | Chemotherapy | Cytostatic agent--topoisomerase inhibitor |
| Aminopterin | Leukemia | Chemotherapy | Antimetabolite |
| Amonafide | Breast and prostate | Chemotherapy | Cytostatic agent--topoisomerase inhibitor |
| Amrubicin | Small cell lung | Chemotherapy | Anthracycline |
| Amsacrine | All cancers | Chemotherapy | Miscellaneous agent |
| Anagrelide HCl | Essential thrombocythemia | Differentiation inducing agent | Code as 'other' therapy for essential thrombocythemia ONLY;otherwise do not code |
| Anastrozole | Breast cancer | Hormones and hormonal mechanisms | Non-steroidal Aromatase inhibitor |

Fig. 26C

| Name | Primary Site | Category | Sub-category |
|---|---|---|---|
| Angiostatin | Lung;other cancer | Chemotherapy | Cytostatic agent--antiangiogenic agent |
| Angiostatin w/ Paclitaxel & Carboplatin | Lung cancer | Chemotherapy | combination chemo |
| Angiozyme | Breast;colorectal;other cancer | Chemotherapy | Cytostatic agent--VGF target antiangiogenic agent |
| Anhydrovinblastine | Lung cancer | Chemotherapy | Vinca plant alkaloid |
| Annamycin | Breast cancer;leukemia | Chemotherapy | Anthracycline antibiotic |
| Anthramycin | Sarcomas, lymphomas, GI cancers | Chemotherapy | Antitumor antibiotic |
| Anti-EpCam | Colorectal cancer | Biologic therapy (BRM, immunotherapy) | Antibody |
| Anti-PSMA Antibody | Prostate cancer | Biologic therapy (BRM, immunotherapy) | Antibody |
| Anti-gastrin Therapeutic Vaccine | Colorectal;gastric;liver;pancreatic cancer | Biologic therapy (BRM, immunotherapy) | Therapeutic vaccine |
| Antineoplaston A10 | Breast;other cancer | Other therapy | Unproven therapy |
| Antineoplaston AS2.1 | Breast;other cancer | Other therapy | Unproven therapy |
| Anvirzel | Lung;prostate;skin cancer | Other therapy | extract of oleander plant;Unproven therapy |
| Apolizumab | Leukemia;lymphoma;other cancer | Biologic therapy (BRM, immunotherapy) | Monoclonal antibody |
| Apra | Prostate cancer;sarcoma | Chemotherapy | Cytostatic agent--antiangiogenic agent |
| Aptosyn | Breast;colorectal;head & neck;lung;prostate cancer | Differentiation inducing agent | Enzymatic inhibitor |
| Aroplatin | Colorectal;kidney;lung;ovarian;pancreatic cancer | Chemotherapy | Miscellaneous agent |
| Arzoxifene | Breast;endometrial cancer;ovarian | Hormones and hormonal mechanisms | Selective estrogen receptor modulator (SERM) |
| Asparaginase | Acute lymphoblastic leukemia (ALL) | Chemotherapy | Antineoplastic agent |
| Asparaginase (Erwinia carotovora) | Acute lymphoblastic leukemia (ALL) | Chemotherapy | Antineoplastic agent |
| Asparaginase-PEG | Acute lymphoblastic leukemia (ALL) | Chemotherapy | Antineoplastic agent |
| Asparaginase-PEG (K-H) | Acute lymphoblastic leukemia (ALL) | Chemotherapy | Antineoplastic agent |
| Asparlas | Acute lymphoblastic leukemia (ALL) | Chemotherapy | Antineoplastic agent |
| Aspirin | Essential Thrombocythemia | Other therapy | Code as 'Other' therapy for essential thrombocythemia ONLY;otherwise it is a differentiating agent (do not code) |
| Atamestane | Breast cancer | Hormones and hormonal mechanisms | Aromatase inhibitor |
| Atezolizumab | Bladder;Lung;Liver;Breast | Biologic therapy (BRM, immunotherapy) | monoclonal antibody |
| Atiprimod | carcinoid;Myeloma | Chemotherapy | Cytostatic agent--anti-angiogenesis agent |
| Atragen | Kidney;Lymphoma;Prostate;Skin cancer | Differentiation inducing agent | Liposomal tretinoin |
| Atrasentan | Bladder;breast;kidney;lung;other cancer;ovarian;prostate | Chemotherapy | Cytostatic agent |

Fig. 26D

| Name | Primary Site | Category | Sub-category |
|---|---|---|---|
| Aut Tum Vac/BCG/IL-2 | Multiple sites | Biologic therapy (BRM, immunotherapy) | Therapeutic vaccine |
| Aut Tum Vac/IL-2/BCG | Multiple sites | Biologic therapy (BRM, immunotherapy) | Therapeutic vaccine |
| Aut Tum Vac/IL-2/BCG, Tice BCG Vaccine, frozen | Multiple sites | Biologic therapy (BRM, immunotherapy) | Therapeutic vaccine |
| Autol Tumor-Trnsdcd/Gene for TNF (Cetus) | Multiple sites | Biologic therapy (BRM, immunotherapy) | Cellular therapy |
| Autol Tumor-Trnsdcd/Gene for TNF (GTI), | Multiple sites | Biologic therapy (BRM, immunotherapy) | Cellular therapy |
| Autol Tumor-Trnsdcd/Gene for TNF-COMPA (Cetus), | Multiple sites | Biologic therapy (BRM, immunotherapy) | Cellular therapy |
| Autologous Tumor Cell (BCG + IL-2 (Cetus), | Multiple sites | Biologic therapy (BRM, immunotherapy) | Cellular therapy |
| Autologous Tumor Cell (BCG) + IL-2 (Bionetics), | Multiple sites | Biologic therapy (BRM, immunotherapy) | Cellular therapy |
| Autologous Tumor Cell Vaccine + BCG (Bionetics) | Multiple sites | Biologic therapy (BRM, immunotherapy) | Cellular therapy |
| Autologous Tumor Cell Vaccine + IL-2 (Cetus) | Multiple sites | Biologic therapy (BRM, immunotherapy) | Cellular therapy |
| Avapritinib | Gastrointestinal stromal tumor (GIST) | Chemotherapy | kinase inhibitor |
| Avelumab | Skin;Bladder | Biologic therapy (BRM, immunotherapy) | Monoclonal antibody |
| Avicine | Colorectal;pancreatic;prostate cancer | Biologic therapy (BRM, immunotherapy) | Active immunotherapy |
| Avodart | Code as treatment for pancreatic cancer;Do Not Code as treatment for prostate cancer. this drug is used to help shrink the prostate. | Chemotherapy | Cytostatic agent--alpha reductase inhibitor |
| Avrend | Kidney cancer | Biologic therapy (BRM, immunotherapy) | Stimulates T-cell dendritic cells |
| Axitinib | Colorectal;kidney;melanoma;pancreas;thyroid | Chemotherapy | Tyrosine kinase inhibitor |
| Azacitidine | Leukemia | Chemotherapy | Antimetabolite |
| Azidothymidine | Kaposi's sarcoma | Chemotherapy | Cytostatic agent--reverse transcriptase inhibitor |
| BABS protein | Breast cancer | Biologic therapy (BRM, immunotherapy) | Bi-specific antibodies |
| BAM-002 | Lung cancer | Chemotherapy | Cytostatic agent |
| BBR 3464 and 5-FU | Other cancer | Chemotherapy | combination chemo |
| BBR3464 | Lung;pancreatic cancer | Chemotherapy | Miscellaneous agent--triplatinum;Tri-nuclear platinum complex |
| BCG | Bladder cancer | Biologic therapy (BRM, immunotherapy) | Immunotherapy active |
| BCG - Connaught | Bladder cancer | Biologic therapy (BRM, immunotherapy) | Bacterial therapy |
| BCG - TheraCys | Bladder cancer | Biologic therapy (BRM, immunotherapy) | Bacterial therapy |
| BCG - Tice | Bladder cancer | Biologic therapy (BRM, immunotherapy) | Bacterial therapy |

Fig. 26E

| Name | Primary Site | Category | Sub-category |
|---|---|---|---|
| BCG Vaccine | Bladder | Biologic therapy (BRM, immunotherapy) | Immuntherapy active |
| BCG Vaccine - Connaught | Bladder cancer | Biologic therapy (BRM, immunotherapy) | Bacterial therapy |
| BCI Immune Activator | Bladder cancer | Biologic therapy (BRM, immunotherapy) | N/A |
| BCX-1777 | Leukemia;lymphoma | Chemotherapy | Antimetabolite |
| BEC2 | Lung;skin cancer | Biologic therapy (BRM, immunotherapy) | Adjuvant vaccination |
| BIBW 2992 | Breast;H&N | Chemotherapy | Tyrosine kinase inhibitor |
| BLP25 | Lung;prostate cancer | Biologic therapy (BRM, immunotherapy) | Immunotherapy active |
| BMS 184476 | Other cancer | Chemotherapy | Antimitotic agent |
| BMS 188797 | Colorectal;gastric;other cancer;pancreatic | Chemotherapy | Antimitotic agent |
| BMS 214662 | Colorectal;other cancer;pancreatic | Chemotherapy | Antimetabolite |
| BMS 247615 | Colorectal;pancreatic cancer | Chemotherapy | Topoisomerase inhibitor |
| BMS 275291 | Breast;lung;other cancer;ovarian | Chemotherapy | Cytostatic agent--matrix metaloprotease inhibitor (MMPI) |
| BMS 354825 | CML | Chemotherapy | Cytostatic agent--tyrosine kinase inhibitor |
| BMS 863233 | CML, MDS | Chemotherapy | CDC7 Kinase Inhibitor- see remarks |
| BMS-663513 | NSCLC | Biologic therapy (BRM, immunotherapy) | Monoclonal antibody |
| BMS-936558 | melanoma;NSCLC;prostate;RCC | Biologic therapy (BRM, immunotherapy) | IgG4 mAb specific |
| BNP1350 | Other cancer | Chemotherapy | Camtothecin derivative--topoisomerase inhibitor |
| BNP7787 | Breast cancer | Chemotherapy | Topoisomerase inhibitor |
| BSI-201 | metastatic breast;Pancreas | Chemotherapy | PARP inhibitor |
| BXQ-350 | Brain | Chemotherapy | Anti-cancer nanovesicle technology;Target therapy |
| Bcl-2/Bcl-x1 Inhibitor | Other cancer | Chemotherapy | Apoptosis inducer |
| Bectumomab | B-cell lymphomas and leukemias | Biologic therapy (BRM, immunotherapy) | Immunotherapy passive |
| Belinostat | CLL;Multiple myeloma;NHL;advanced malignancies;others;peripheral T-cell lymphoma (PTCL) | Chemotherapy | Cytostatic agent--histone deacetylation inhibitor;HDAC inhibitor |
| Belotecan | NSCLC | Chemotherapy | Topoisomerase Inhibitor |
| Bemcentinib | Acute myeloid leukemia (AML) | Chemotherapy | AXL inhibitor |
| Bendamustine | breast;CLL;HL;Multiple myeloma;NHL | Chemotherapy | Alkyalating agent |
| Benzoylphenylurea | Advanced solid tumors | Chemotherapy | Antimitotic agent |
| Besponsa | B-cell precursor acute lymphoblastic leukemia (ALL) | Biologic therapy (BRM, immunotherapy) | A CD22-targeted cytotoxic immunoconjugate |
| Bestatin | Squamous cell lung carcinoma | Biologic therapy (BRM, immunotherapy) | Enzymatic inhibitor |
| Beta LT | Lymphoma;multiple myeloma | Biologic therapy (BRM, immunotherapy) | Human protein |

Fig. 26F

| Name | Primary Site | Category | Sub-category |
|---|---|---|---|
| Bethasone Benzoate | adult leukemia and lymphoma;Childhood leukemia | Hormones and hormonal mechanisms | Corticosteroid |
| Bevacizumab | Breast- see remarks;Fallopian tube;Ovary;Peritoneum;colorectal;kidney;lung;multiple myeloma;Brain | Biologic therapy (BRM, immunotherapy) | Cytostatic agent--antiangiogenesis agent;Recombinant human anti-VEGF.;Vascular endothelial growth factor receptor inhibitor |
| Bexarotene | Breast;colorectal;Cutaneous T-cell lymphoma;head & neck;kidney;lung;prostate cancer | Chemotherapy | cytostatic agent--Retinoid X receptor agonist |
| Bicalutamide | Prostate cancer | Hormones and hormonal mechanisms | Antiandrogenic |
| Binimetinib | Melanoma | Chemotherapy | MEK 1/2 Inhibitor |
| Biomed 101 and Interleukin-2 | Kidney cancer | Biologic therapy (BRM, immunotherapy) | Human proteins |
| Bisantrene Hydrochloride | Leukemia | Chemotherapy | Topoisomerase inhibitor |
| Bleomycin | Squamous cell cancers | Chemotherapy | Antitumor antibiotic |
| Blinatumomab | B-cell precursor acute lymphoblastic leukemia (R/R ALL) | Biologic therapy (BRM, immunotherapy) | Monoclonal antiboies, bi-specific T-cell engagers |
| Bortezomib | Breast;Mantle cell lymphoma;colorectal;leukemia;lung cancer;multiple myeloma | Chemotherapy | Proteasome Inhibitor |
| Bosutinib | CML | Chemotherapy | Tyrosine kinase inhibitor |
| Brentuximab vedotin | Anaplastic large cell lymphoma (ALCL);Hodgkin Lymphoma | Chemotherapy | Antibody-drug conjugate;(ADC) |
| BrevaRex | Breast;multiple myeloma;pancreatic cancer | Biologic therapy (BRM, immunotherapy) | Passive monoclonal antibody |
| Briciclib sodium | Leukemias;Solid tumors (See remarks) | Chemotherapy | analog |
| Brigatinib | Lung | Chemotherapy | anaplastic lymphoma kinase |
| Brivanib | hepatocellular carcinoma;Solid tumors | Chemotherapy | Antiangiogenic agent |
| Bromocriptine mesylate | Breast cancer;pituitary tumors | Hormones and hormonal mechanisms | Inhibits prolactin secretion from pituitary gland |
| Bropirimine | Bladder | Biologic therapy (BRM, immunotherapy) | changed from 1 |
| Brostallicin | Soft tissue sarcoma | Chemotherapy | Alkylating agent |
| Bruceantin | Multiple myeloma | Chemotherapy | Natural product |
| Bryostatin | Breast;cervical;esophageal;gastric;head & neck;kidney;leukemia;metastatic solid tumors;ovarian;prostate cancer | Chemotherapy | Protein kinase activator |
| Bryostatin 1 | Multiple sites | Chemotherapy | Protein Kinase C Inhibitor |
| Buserelin Acetate | Prostate cancer | Hormones and hormonal mechanisms | Gonadotropin-releasing hormone |
| Busulfan | CML | Chemotherapy | Alkylating agent |
| Buthionine Sulfoximine | Neuroblastoma | Chemotherapy | Antimetabolite |

Fig. 26G

| Name | Primary Site | Category | Sub-category |
|---|---|---|---|
| CAL | Breast cancer | Other therapy | Mechanism not known |
| CAP-1 | Gastric cancer | Chemotherapy | Antimetabolite |
| CAR-T | B-cell acute lymphoblastic leukemia (ALL) | Biologic therapy (BRM, immunotherapy) | Cellular therapy |
| CAT-8015 | CLL;hairy cell leukemia;small cell lymphoma | Chemotherapy | Immunotoxin |
| CDC-801 | Leukemia | Chemotherapy | Antimetabolite |
| CDC117 | Breast cancer | Hormones and hormonal mechanisms | Selective estrogen receptor modulator (SERM) |
| CEA (CAP1-6D) peptide vaccine | Pancreas | Biologic therapy (BRM, immunotherapy) | Vaccine |
| CEA B7.1 | Colon cancer | Biologic therapy (BRM, immunotherapy) | Therapeutic vaccine |
| CEA-Cide | Breast;colorectal;gastric;pancreatic cancer | Biologic therapy (BRM, immunotherapy) | Fusion protein |
| CEA-Tricom | Colorectal cancer | Biologic therapy (BRM, immunotherapy) | Therapeutic vaccine |
| CEA-Vac | Breast;colorectal;gastric;lung;pancreatic cancer | Biologic therapy (BRM, immunotherapy) | Therapeutic vaccine |
| CEA-Vac-Triab | Breast cancer | Biologic therapy (BRM, immunotherapy) | Immunotherapy active |
| CEP-2563 | Other cancer | Chemotherapy | Cytostatic agent--inhibitor--receptor tyrosine kinase |
| CEP-7055 | Other cancer | Chemotherapy | Cytostatic agent--antiangiogenic agent |
| CG 7980 | Colorectal cancer | Biologic therapy (BRM, immunotherapy) | Oncolytic virus |
| CG 8840 | Bladder cancer | Chemotherapy | Oncolytic adenovirus |
| CG7060 | Prostate cancer | Chemotherapy | Prostate-specific adenovirus |
| CG7870 | Prostate cancer | Chemotherapy | Prostate-specific adenovirus |
| CG8900 | Liver cancer | Chemotherapy | Oncolytic adenovirus |
| CHIR-258 | Multiple myeloma | Chemotherapy | Cytostatic agent--tyrosine kinase inhibitor |
| CI 1033 ErbB | Breast;Other cancer | Chemotherapy | Cytostatic agent--tyrosine kinase inhibitor |
| CI-1033 | Breast;head & neck;lung cancer | Chemotherapy | Cytostatic agent--dual inhibitor |
| CI-980 | Brain;leukemia;lung cancer | Chemotherapy | Cytostatic agent--mitotic inhibitor |
| CI-994 | Pancreatic cancer | Chemotherapy | Cytostatic agent |
| CM101 | Pancreatic cancer | Chemotherapy | Cytostatic agent--antiangiogenesis agent |
| CN706 | Prostate cancer | Biologic therapy (BRM, immunotherapy) | Gene therapy |
| COL-3 | Brain;other cancer;skin | Chemotherapy | Cytostatic agent--antiangiogenesis agent |
| CP-724-714 | Breast cancer | Biologic therapy (BRM, immunotherapy) | HER2 inhibitor |
| CP-870,893 | Solid tumors | Biologic therapy (BRM, immunotherapy) | Monoclonal antibody |
| CP461 | Kidney;leukemia;other cancer;prostate | Chemotherapy | Apoptosis inducer |
| CP547632 | Breast;lung;other cancer | Chemotherapy | Cytostatic inhibitor--VEGFR inhibitor |
| CP609754 | Other cancer | Chemotherapy | Antimetabolite |

Fig. 26H

| Name | Primary Site | Category | Sub-category |
|---|---|---|---|
| CPX-1 | Colorectal cancer | Chemotherapy | Antimetabolite |
| CS-1008 | Pancreas | Chemotherapy | Cytostatic agent--apoptosis inducer |
| CT-2106 | Colon cancer | Chemotherapy | Cytostatic agent--topoisomerase inhibitor |
| CTCE-9908 | glioblastoma;Osteosarcoma | Chemotherapy | Cytostatic agent--antiangiogenic agent |
| CTL019 | Diffuse large B-cell lymphoma | Biologic therapy (BRM, immunotherapy) | chimeric antigen receptor T cell (CAR-T) |
| CV787 | Prostate cancer | Chemotherapy | Cytotoxic adenovirus |
| CX-3543 | Solid tumors, lymphomas | Chemotherapy | Cytostatic agent--histone deacetylation inhibitor |
| CX-4945 | Breast;Colorectal;H&N;Kidney;Lung;Mult Myeloma;Prostate | Chemotherapy | CK2 inhibitor |
| Cabazitaxel | Prostate | Chemotherapy | Microtubule inhibitor |
| Cabergoline | Pituitary (prolactinoma) | Hormones and hormonal mechanisms | Prolactin supression |
| Cabozantinib | Thyroid;Kidney | Chemotherapy | kinase inhibitor |
| Camptothecin Glycoconjugate | Other cancer | Chemotherapy | Topoisomerase inhibitor |
| Cancer Vaccine | Bladder;breast;kidney;ovarian;skin cancer | Biologic therapy (BRM, immunotherapy) | Immunotherapy active |
| Canvaxin | Colorectal;skin cancer | Biologic therapy (BRM, immunotherapy) | Immunotherapy active |
| Capecitabine | Breast cancer;colorectal cancer | Chemotherapy | Antimetabolite |
| Caracemide | Renal cell cancer | Chemotherapy | Antimetabolite |
| Carboplatin | All cancers | Chemotherapy | Alkylating agent;Platinum analog |
| Carboxyamidotriazole | Kidney;lung;ovarian cancer | Chemotherapy | Cytostatic agent--antiangiogenic agent |
| Carfilzomib | Multiple myeloma | Chemotherapy | Proteasome inhibitor |
| Carmustine | Brain;Hodgkin Lymphoma;Kidney cancer;Multiple myeloma;Non-Hodgkin lymphoma | Chemotherapy | Alkylating agent |
| Carubicin (HCl) | Leukemia;lymphoma;solid tumors | Chemotherapy | Anthracycline antineoplastic antibiotic |
| Casodex | Prostate cancer | Hormones and hormonal mechanisms | Anti-androgen |
| CeaVac Anti-idiotype antibody | Colon cancer | Biologic therapy (BRM, immunotherapy) | Monoclonal antibody |
| Cediranib | glioblastoma;NSCLC;renal cell | Chemotherapy | Cytostatic agent--antiangiogenic agent |
| Celengitide | Brain cancer | Chemotherapy | Cytostatic agent--antiangiogenic agent |
| Cemiplimab | CSCC | Biologic therapy (BRM, immunotherapy) | Monoclonal antibody |
| Ceplene | Kidney cancer;leukemia | Biologic therapy (BRM, immunotherapy) | Histamine salt |
| Cetuximab | Breast;colorectal;head & neck;lung;ovarian;pancreatic cancer | Biologic therapy (BRM, immunotherapy) | Monoclonal antibody, anti-EGFR antibody |

Fig. 26I

| Name | Primary Site | Category | Sub-category |
|---|---|---|---|
| Chimeric MAb14.18 | melanoma;Neuroblastoma | Biologic therapy (BRM, immunotherapy) | Monoclonal antibody |
| Chlorambucil | chronic lymphocytic leukemia, Hodgkins' and non-Hodgkin's lymphoma. | Chemotherapy | Alkylating agent |
| Chloroquinoxaline Sulfonamide | Lung cancer | Chemotherapy | Topoisomerase inhibitor |
| Chlorotrianisene | Prostate cancer | Hormones and hormonal mechanisms | Estrogen |
| Chlorozotocin | Pancreatic cancer | Chemotherapy | Alkylating agent |
| Chromic Phosphate P32 | CLL and chronic myeloid leukemia;Ovarian and prostatic carcinoma;palliative in bone metastases | Radiation | Radioisotope |
| Cilengitide | Other cancer | Chemotherapy | Cytostatic agent-- antiangiogenic agent |
| Cisplatin | Bladder;ovarian;testicular cancer | Chemotherapy | Alkylating agent;Platinum analog |
| Cladribine | Leukemia;Leukemic reticuloendotheliosis | Chemotherapy | Antimetabolite;purine analogs |
| Clarithromycin | Gastric MALT lymphoma | Other therapy | Antibiotic |
| Clofarabine | ALL;AML;CML;Leukemia;lymphoma;myeloproliferative disease;other cancer | Chemotherapy | Antimetabolite |
| Clogestone Acetate | Prostate cancer | Hormones and hormonal mechanisms | Progestin |
| Clomegestone Acetate | Prostate cancer | Hormones and hormonal mechanisms | Progestin |
| Cloretazine | AML;Leukemia;other cancers;SCLC | Chemotherapy | Alkylating agent |
| Combretastatin A4 Prodrug | Colon;head & neck;lung;other cancer;thyroid | Chemotherapy | Cytostatic agent-- antiangiogenic agent |
| Copanlisib Hydrochloride | Follicular lymphoma | Chemotherapy | Phosphatidylinositide 3-Kinase Inhibitor |
| Cordycepin | Leukemia;TdT positive ALL | Chemotherapy | Antitumor antibiotic |
| Cotara (TNT - Tumor Necrosis Therapy) | Brain;colorectal;liver;pancreatic cancer;sarcoma | Radiation | Radioisotope attached to monoclonal antibody |
| Cotellic | Melanoma | Chemotherapy | MEK inhibitor |
| CpG 7909 | Breast;kidney cancer;melanoma;non-Hodgkin's' lymphoma;skin cancer | Biologic therapy (BRM, immunotherapy) | TLR9 agonist |
| Crisnatol Mesylate | Brain cancer | Chemotherapy | Cytostatic agent-- topoisomerase inhibitor |
| Crizotinib | Lung NSCLC | Chemotherapy | Kinase inhibitor;Targeted therapy anaplastic lymphoma kinase |
| Cryptophycin | Other cancer | Chemotherapy | Antimitotic atimicrotubual |
| Cur-61414 | Skin cancer | Biologic therapy (BRM, immunotherapy) | Hedgehog Pathway inhibitor |
| CxcR4 | Breast cancer | Biologic therapy (BRM, immunotherapy) | Human protein |
| Cyclocytidine (HCl) | Leukemias | Chemotherapy | Miscellaneous agent |

Fig. 26J

| Name | Primary Site | Category | Sub-category |
|---|---|---|---|
| Cyclopentenyl-cytosine | AML | Chemotherapy | Cytostatic agent |
| Cyclophosphamide | Breast;leukemia;lymphoma;multiple myeloma;neuroblastoma;ovarian cancer;retinoblastoma;soft tissue sarcoma;Wilm's tumor | Chemotherapy | Alkylating agent |
| Cyramza | Brain, CNS;Breast;Colorectal;Gastric, GE;Liver;Non-small cell lung cancer (NSCLC);Ovarian;Prostate;Renal Cell Carcinoma (RCC);Urinary | Biologic therapy (BRM, immunotherapy) | Antiangiogenesis;Monoclonal antibody |
| Cytarabine | ALL;AML;CML;head and neck;Hodgkin's disease;leukemia;Meningeal leukemia;NHL | Chemotherapy | Antimetabolite |
| Cytarabine Liposome | Gliomas | Chemotherapy | Antimetabolite |
| Cytosine Deaminase Gene - Adenoviral Vector | Colorectal cancer | Biologic therapy (BRM, immunotherapy) | Viral encoded human protein |
| D1/3-MAGE-3 Peptide Vaccine | Skin cancer | Biologic therapy (BRM, immunotherapy) | Therapeutic vaccine |
| D3967 | Breast cancer | Hormones and hormonal mechanisms | Adrenocortical suppressant |
| D63153 | Prostate cancer | Hormones and hormonal mechanisms | LHRH antagonist |
| DC Vax | Brain cancer | Other therapy | Immuotherapy active |
| DC Vax Injection | Brain | Other therapy | Therapeutic vaccine |
| DCC 2036 | Chronic myeloid leukemia;CML | Chemotherapy | BCR ABL inhibitor |
| DCVax-Lung | Lung cancer | Other therapy | Therapeutic vaccine |
| DCVax-Prostate | Prostate cancer | Other therapy | Therapeutic vaccine |
| DE-310 | Other cancer | Chemotherapy | Cytostatic agent--topoisomerase inhibitor |
| DENSPM | Breast;colorectal;kidney;leukemia;lung;ovarian;pancreatic;skin cancer | Chemotherapy | Antimitotic |
| DTI015 | Brain;kidney;liver cancer | Chemotherapy | Alkylating agent |
| Dacarbazine | Hodgkin's disease;melanoma;Neuroblastoma;Soft tissue sarcomas | Chemotherapy | Antimetabolite;Nonclassic alkylating agent |
| Dacomitinib | Lung | Chemotherapy | Small molecule inhibitor |
| Dactinomycin | Ewing's sarcoma;rhabdomyosarcoma;testicular cancer;Wilm's tumor | Chemotherapy | Antitumor antibiotic |
| Dalotuzumab | Colorectal;NSCLC;pancreas | Biologic therapy (BRM, immunotherapy) | Humanized monoclonal antibody |
| Darzalex | Multiple myeloma | Biologic therapy (BRM, immunotherapy) | monoclonal antibody |
| Dasatinib | breast;CLL;CML;Ph+ALL;prostate | Chemotherapy | Cytostatic agent--multi-target kinase inhibitor |

Fig. 26K

| Name | Primary Site | Category | Sub-category |
|---|---|---|---|
| Daunorubicin Citrate Liposome (encapsulated) | Kaposi sarcoma;Lymphoma | Chemotherapy | Antitumor antibiotic |
| Daunorubicin Hydrochloride | Leukemia | Chemotherapy | Antitumor antibiotic |
| Daurismo | Acute myeloid leukemia (AML) | Chemotherapy | small molecule inhibitor |
| Decapeptyl | Ovarian;prostate cancers | Hormones and hormonal mechanisms | LHRH agonist |
| Decitabine | CML;Leukemia;lung;MDS;skin cancer | Chemotherapy | Antimetabolite |
| Degarelix | Prostate | Hormones and hormonal mechanisms | GnRH receptor antagonist |
| Dehydroemetine Hydrochloride | Leukemia | Biologic therapy (BRM, immunotherapy) | Unknown |
| Dendritic Cell/Tumor Cell Electrofusion Cancer Vaccine | Breast;kidney cancer;melanoma | Biologic therapy (BRM, immunotherapy) | Immunotherapy active |
| Dendritic cell-P53 | Small cell lung | Biologic therapy (BRM, immunotherapy) | Vaccine |
| Denileukin Diftitox | Leukemia;lymphoma | Biologic therapy (BRM, immunotherapy) | Diptheria toxin |
| Depsipeptide | H&N;Lung cancer;lymphoma;soft tissue sarcoma;T cell lymphoma;thyroid | Chemotherapy | Natural product--microorganism toxin |
| Diaziquone | Bladder;brain;skin cancer | Chemotherapy | Alkylating agent |
| Dienestrol | Breast;prostate cancers | Hormones and hormonal mechanisms | Estrogen |
| Diethylstilbestrol | Various cancers including prostate cancer | Hormones and hormonal mechanisms | Estrogen |
| Diethylstilbestrol Diphosphate | Prostate cancer | Hormones and hormonal mechanisms | Estrogen |
| Diethylstilbestrol Dipropionate | Breast, prostate | Hormones and hormonal mechanisms | Estrogen |
| Docetaxel | Breast;gastric;head & neck;non-small cell lung;ovarian;prostate cancer | Chemotherapy | Taxane |
| Dolastatin 10 | Breast;kidney;leukemia;pancreatic cancer | Chemotherapy | Antimototic agent |
| Doxercalciferol | Prostate cancer | Hormones and hormonal mechanisms | Parathyroid hormone antagonist |
| Doxorubicin | Bladder;breast;liver;multiple myeloma;ovarian;pancreatic;prostate cancer | Chemotherapy | Antitumor antibiotic |
| Doxorubicin, liposome-encapsulated | Ovarian cancer | Chemotherapy | Antitumor antibiotic |
| Dromostanolone Propionate | Breast cancer | Hormones and hormonal mechanisms | Anabolic steroid |
| Durvalumab | Bladder;Lung | Biologic therapy (BRM, immunotherapy) | Human protein |
| Duvelisib | Chronic lymphocytic leukemia (CLL) or small lymphocytic lymphoma (SLL) | Chemotherapy | Small moleculr inhibitor |
| E7070 | Colorectal cancer;head & neck;lung cancer | Chemotherapy | Antibiotic |
| E7389 | advanced solit tumors;Breast;H&N;prostate | Chemotherapy | Vinca alkaloid |

Fig. 26L

| Name | Primary Site | Category | Sub-category |
|---|---|---|---|
| EC-2101 Therapeutic, Multi-epitope Vaccine | Colon;lung cancer | Biologic therapy (BRM, immunotherapy) | Therapeutic vaccine |
| EG009 | Brain cancer | Biologic therapy (BRM, immunotherapy) | Immunotherapy active |
| EKB-569 | Other cancer | Chemotherapy | Cytostatic agent--EGFR inhibitor |
| EMD121974 | Brain;other cancer;skin | Chemotherapy | Cytostatic agent--antiangiogenesis agent |
| ENMD 0995 | Lymphoma;Multiple myeloma | Chemotherapy | Cytostatic agent--antiangiogenesis agent |
| ERA 923 | Breast cancer | Hormones and hormonal mechanisms | SERM |
| ESO-1:157-165 Peptide Vaccine | Other cancer | Biologic therapy (BRM, immunotherapy) | Immunotherapy active |
| Echinomycin | Leukemia, lymphoma | Chemotherapy | Antitumor antibiotic |
| Edatrexate | Multiple sites | Chemotherapy | Antimetabolite |
| Edotecarin | Leukemia;other cancer | Chemotherapy | Topoisomerase inhibitor |
| Edrecolomab | Colorectal cancer | Chemotherapy | Targeted therapy |
| Eflornithine | Bladder;brain (glioblastoma);childhood leukemia;CML;skin cancer | Chemotherapy | Miscellaneous agent |
| Egf Cancer Vaccine | Lung cancer | Biologic therapy (BRM, immunotherapy) | Immunotherapy active |
| Eligard | Prostate cancer;Breast | Hormones and hormonal mechanisms | LHRH |
| Elinafide | Other cancer | Chemotherapy | Cytostatic agent--topoisomerase inhibitor |
| Elotuzumab | Multiple myeloma | Biologic therapy (BRM, immunotherapy) | monoclonal antibody |
| Elsamitucin | Lymphoma | Chemotherapy | Antitumor antibiotic |
| Encorafenib | Melanoma | Chemotherapy | RAF Kinase Inhibitor |
| Endostatin | Colorectal;other cancer;skin | Biologic therapy (BRM, immunotherapy) | Cytostatic agent--antiangiogenesis agent |
| Enfortumab vedotin | Bladder | Biologic therapy (BRM, immunotherapy) | Antibody-drug conjugate |
| Enhanzyn | Breast cancer | Biologic therapy (BRM, immunotherapy) | Vaccine |
| Eniluracil | Breast cancer | Chemotherapy | Antimetabolite |
| Enzalutamide | Prostate | Hormones and hormonal mechanisms | Androgen receptor |
| Enzastaurin | Brain;lymphoma;prostate | Chemotherapy | Antiangiogenic agent |
| Epirubicin | Breast cancer;Metastatic breast cancer;Gastric cancer | Chemotherapy | Anthracycline;Antitumor antibiotic |
| Epithilone D | Other cancer | Chemotherapy | Antimitotic agent |
| Epothilone | Breast;colorectal;endometrial;other cancer;ovary;pancreatic;prostate | Chemotherapy | Antimitotic agent |
| Epratuzumab | Lymphoma | Radiation | Radioisotope |
| Erdafitinib | Bladder | Chemotherapy | FGFR inhibitor |
| Eribulin | GYN;Metastatic breast;NSCLC;Pancreas;prostate;urinary sites;Soft tisse | Chemotherapy | Inhibitor of microtubular dynamics |
| Erleada | Prostate | Hormones and hormonal mechanisms | Androgen receptor inhibitor |

Fig. 26M

| Name | Primary Site | Category | Sub-category |
|---|---|---|---|
| Erlotinib | Breast;Non-small cell lung cancer (NSCLC);cervical;colorectal;gastric;head & neck;other cancer;ovarian;pancreatic | Chemotherapy | Cytostatic agent--tyrosine kinase inhibitor;EGF inhibitor |
| Erwinaze | Acute lymphoblastic leukemia (ALL) | Chemotherapy | Antineoplastic agent |
| Estramustine Phosphate Sodium | Prostate cancer | Chemotherapy | Antimicrotubule agent |
| Estrone | Prostate cancer | Hormones and hormonal mechanisms | Estrogen |
| Estropipate | Breast | Hormones and hormonal mechanisms | Estrogen |
| Ethoglucid | Bladder | Chemotherapy | Alkylating agent |
| Ethylchlorformate | Bladder | Biologic therapy (BRM, immunotherapy) | N/A |
| Ethynylcytidine | Other cancer | Chemotherapy | RNA polymerase inhibitor |
| Etoposide | Gastric cancer;Hodgkins lymphoma;Lung cancer (NSCLC, SCLC);Non-Hodgkin lymphoma;testicular cancer (Germ cell tumors) | Chemotherapy | Epipodophyllotoxin, topoisomerase II inhibitor;Plant alkaloid |
| Exatecan mesylate | Sarcoma, leukemia, lymphoma, lung, and liver | Chemotherapy | Topoisomerase inhibitor |
| Exemestane | Breast;other cancer | Hormones and hormonal mechanisms | Aromatase inhibitor |
| FLAG-003 | Brain | Other therapy | Multiple modalities |
| FLT3 Ligand | Leukemia;skin cancer | Biologic therapy (BRM, immunotherapy) | Cytokine |
| Fadrazole HCl | Breast | Hormones and hormonal mechanisms | Aromatase inhibitor |
| Farletuzumab | Ovary | Chemotherapy | Cytotoxic monoclonal antibody |
| Favid Vaccine | Lymphoma | Biologic therapy (BRM, immunotherapy) | Immunotherapy active |
| Fazarabine | Breast | Chemotherapy | Antimetabolite |
| Flavopiridol | B-cell CLL;Colorectal;lung;other cancer;prolymphocytic leukemia arising from CLL;small lymphocytic lymphoma | Chemotherapy | Inhibitor |
| Floxuridine | Colorectal;Gastric cancer | Chemotherapy | Antimetabolite |
| Fludarabine | CLL;Cutaneous T-cell lymphoma;Leukemia;Non-Hodgkin lymphoma (low grade) | Chemotherapy | Antimetabolite |
| Fluorotestosterone | Prostate cancer | Hormones and hormonal mechanisms | Androgen inhibitor |
| Fluorouracil | Breast- adjuvant setting and advanced disease;colorectal- adjuvant setting and advanced disease;GI malignancies: anal, esophageal, gastric and | Chemotherapy | Antimetabolite |

Fig. 26N

| Name | Primary Site | Category | Sub-category |
|---|---|---|---|
| | pancreatic;Head and Neck cancer;Hepatoma;Ovarian cancer;Skin-Basal cell carcinoma (topical application) | | |
| Fluoxymesterone | Breast cancer | Hormones and hormonal mechanisms | Androgen |
| Flutamide | Prostate cancer | Hormones and hormonal mechanisms | Antiandrogenic |
| Fosquidone | Colorectal;renal;NSCLC | Chemotherapy | Unclassified antineoplastic |
| Fotemustine | lung cancer;Melanoma | Chemotherapy | Nitrosourea alkylating agent |
| Fowlpox B7.1 and vaccine B7.1 | Skin cancer | Biologic therapy (BRM, immunotherapy) | Immunotherapy active |
| Fowlpox PSA Vaccine | Prostate cancer | Biologic therapy (BRM, immunotherapy) | Immunotherapy active |
| Fowlpox TRICOM | Breast | Biologic therapy (BRM, immunotherapy) | Vaccine |
| Fowlpox-CEA (6D)-Tricom | Breast;colorectal;lung cancer | Biologic therapy (BRM, immunotherapy) | Immunotherapy active |
| Fulvestrant | Breast cancer | Hormones and hormonal mechanisms | SERD |
| G17DT | Colorectal cancer | Biologic therapy (BRM, immunotherapy) | Immunotherapy active |
| G207 | Brain cancer | Chemotherapy | Miscellaneous agent--cytolytic virus |
| GBC-590 (complex carbohydrate) | Colorectal;pancreatic;prostate cancer | Chemotherapy | Antiangiogenesis agent |
| GCS-100 | Colorectal;pancreatic;prostate cancer | Chemotherapy | Apoptosis inducer |
| GDC-0449 | brain/cns;colorectal;GE;lung;ovarian;Pancreas;stomach | Chemotherapy | Hedgehog Pathway inhibitor |
| GEM-231 | Breast;cervical;colorectal;endometrial;lung;other cancer;ovarian;pancreatic | Chemotherapy | Cytostatic agent |
| GM.CD40L | Lymphoma | Biologic therapy (BRM, immunotherapy) | Vaccine |
| GMK Vaccine | Skin cancer | Biologic therapy (BRM, immunotherapy) | Immunotherapy active |
| GPI-0100 Immune Enhancer (Adjuvant) | Breast;prostate cancer | Biologic therapy (BRM, immunotherapy) | Immunotherapy active |
| GPX100 | Breast cancer | Chemotherapy | Anthracycline;Antitumor antibiotics |
| GPX150 | Sarcoma | Chemotherapy | Anthracycline;Antitumor antibiotic |
| GS7904L | Other cancer | Chemotherapy | Liposomal cytotoxic agent |
| GSK-2118436 | Melanoma | Chemotherapy | BRAF kinase inhibitor |
| GTI-2040 | Breast;colorectal;kidney;lung;other cancer;prostate | Chemotherapy | Antisense oligonucleotide |
| GTI-2501 | Breast;colorectal;lung;pancreatic cancer | Chemotherapy | Antisense oligonucleotide |
| GVAX Lung Cancer Vaccine | Breast;leukemia;lung;multiple myeloma;pancreatic;prostate cancer | Biologic therapy (BRM, immunotherapy) | Immunotherapy active |

Fig. 26O

| Name | Primary Site | Category | Sub-category |
|---|---|---|---|
| GVAX Prostate Cancer Vaccine | Pancreatic caner | Biologic therapy (BRM, immunotherapy) | Immunotherapy active |
| GW120918 | Other cancer | Chemotherapy | Cytostatic agent--inhibitor--tyrosine kinase |
| GW572016 | Other cancer | Chemotherapy | Cytostatic agent--inhibitor--tyrosine kinase |
| Gallium Maltolate | Hepatocellular carcinoma (HCC);Lymphoma;multiple myeloma;prostate cancer | Chemotherapy | Miscellaneous agent--soluble metal (like Platinum) |
| Ganglioside | Lrung | Biologic therapy (BRM, immunotherapy) | Signaling regulator |
| Gastrimmune | Colorectal;pancreatic cancer | Biologic therapy (BRM, immunotherapy) | Therapeutic vaccine |
| Gazyva | Bone marrow | Biologic therapy (BRM, immunotherapy) | monoclonal antibody |
| Gefitinib | Breast;colorectal;gastric;kidney;lung cancer | Chemotherapy | Cytostatic agent--tyrosine kinase inhibitor |
| Gemcitabine | Bladder;Breast;non-small cell lung;ovarian;pancreatic cancer;Soft Tissue Sarcoma | Chemotherapy | Antimetabolite |
| Gemtuzumab Ozogamicin | Leukemia | Biologic therapy (BRM, immunotherapy) | Targeted therapy |
| Genasense | Breast;colorectal;kidney;leukemia;lung;lymphoma;melanoma;multiple myeloma;pancreatic cancer;prostate;sarcoma | Chemotherapy | Apoptosis inducer |
| Gene CC49-zeta | Colorectal cancer | Biologic therapy (BRM, immunotherapy) | Gene therapy |
| Gene Therapy with Interleukin-2 and chemo. | Head & neck cancer | Chemotherapy | Chemo with gene therapy |
| GeneVax | Breast;prostate cancer | Biologic therapy (BRM, immunotherapy) | immunotherapy active |
| Genistein | Pancreas | Chemotherapy | Cytostatic agent |
| Genz-644282 | Solid tumors | Chemotherapy | Topoisomerase 1 inhibitor |
| Gestaclone | Prostate cancer | Hormones and hormonal mechanisms | Progestin |
| Gestonorone Caproate | Prostate cancer | Hormones and hormonal mechanisms | Leuteinizing hormone antagonist |
| Gilotrif | Lung (NSCLC) | Chemotherapy | Tyrosine kinase inhibitor |
| Gilteritinib | Acute myeloid leukemia (AML) | Chemotherapy | RTK Inhibitor |
| Glufosfamide | Pancreas | Chemotherapy | Alkylating agent |
| GnRH Pharmaccine | Breast;prostate cancer | Hormones and hormonal mechanisms | Gonadotropin-releasing hormone |
| Goserelin Acetate | Breast;prostate cancer | Hormones and hormonal mechanisms | Gonadotropin-releasing hormone |
| Gossypol acetic acid | Prostate cancer | Differentiation inducing agent | Enzymatic inhibitor |
| H11-scFv | Breast cancer;other cancer | Chemotherapy | Cytostatic agent |
| HER-2/neu Vaccine | Breast;ovarian;prostate cancer | Biologic therapy (BRM, immunotherapy) | Immunotherapy active |
| HMBA | Multiple myeloma, glioblastoma, | Differentiation inducing agent | AKT/MAPK pathway inhibitor |

Fig. 26P

| Name | Primary Site | Category | Sub-category |
|---|---|---|---|
| | neuroblastoma, and small-cell lung cancer | | |
| HPV vaccine | Cervical cancer | Biologic therapy (BRM, immunotherapy) | Immunotherapy active |
| HPV-16 E7: 86-93 | Cervical and vulvar intraepithelial neoplasia | Biologic therapy (BRM, immunotherapy) | Synthetic peptide |
| HPV16 E7 Peptide Vaccine | Cervical cancer | Biologic therapy (BRM, immunotherapy) | Immunotherapy active |
| HPV16, E6 Peptide Vaccine | Cervical cancer | Biologic therapy (BRM, immunotherapy) | Immunotherapy active |
| HS1-TK | Brain cancer | Biologic therapy (BRM, immunotherapy) | Gene therapy |
| HSPE7 | Cervical cancer | Biologic therapy (BRM, immunotherapy) | Therapeutic vaccine |
| Halofuginone | Other cancer | Chemotherapy | antiangiogenesis agent;Cytostatic agent--inhibitor |
| Haloprogesterone | Prostate cancer | Hormones and hormonal mechanisms | Progestin |
| Hepsulfam | Hematological malignancies | Chemotherapy | Alkylating agent |
| Herzuma | Breast | Biologic therapy (BRM, immunotherapy) | HER2 inhibitor |
| Herzyme | Breast cancer | Chemotherapy | Cytostatic agent--anti-HER2 |
| Histrelin | Prostate cancer | Hormones and hormonal mechanisms | Gonadotropin-releasing hormone |
| Homoharringtonine | Leukemia;myeloid leukemia (CML) and myelodysplastic syndrome (MDS) | Chemotherapy | Plant alkaloid |
| HuC242-DM1/SB-408075 (cantuzumab mertasine) | Colorectal;lung;pancreatic cancer | Chemotherapy | Monoclonal antibody combined with maytansinoid toxin |
| HuLuc63 | Myeloma | Biologic therapy (BRM, immunotherapy) | Monoclonal antibody |
| HuN901-DM1/BB-10901 | Lung cancer | Chemotherapy | Immunotoxin |
| Human leukocyte interferon (Meloy) | Polycythemia vera | Biologic therapy (BRM, immunotherapy) | Human protein |
| Human leukocyte interferon (W-L) | Polycythemia vera | Biologic therapy (BRM, immunotherapy) | Human protein |
| Hydroxyprogesterone Caproate | Endometrial cancer | Hormones and hormonal mechanisms | Progestin |
| Hydroxyurea | Brain cancer;CML;Head and neck cancers;Melanoma;Ovarian cancer;Essential thrombocytosis;Polycythemia Vera | Chemotherapy | Miscellaneous agent |
| ICT-107 | Brain | Biologic therapy (BRM, immunotherapy) | Patient derived dendritic cell immunotherapy |
| IFN: Leukocyte (Meloy) | Leukemia;lymphoma | Biologic therapy (BRM, immunotherapy) | Human protein |
| IL-1 alpha (Immunex) | Head & neck cancer, squamous | Biologic therapy (BRM, immunotherapy) | Human protein |
| IL-1 alpha, Interleukin-1 alpha (Dainippon) | Head & neck cancer, squamous | Biologic therapy (BRM, immunotherapy) | Human protein |

Fig. 26Q

| Name | Primary Site | Category | Sub-category |
|---|---|---|---|
| IL-12 DNA Vaccine | Other cancer | Biologic therapy (BRM, immunotherapy) | Immunotherapy active |
| IL-2 | Melanoma; renal cell carcinoma | Biologic therapy (BRM, immunotherapy) | Human protein |
| IL-2 (CT)/MDELAK | Melanoma; renal cell carcinoma | Biologic therapy (BRM, immunotherapy) | Human protein |
| IL-2 (CT)/TIL (BiorExp) | Melanoma; renal cell carcinoma | Biologic therapy (BRM, immunotherapy) | Human protein |
| IL-2 (HR) | Melanoma; renal cell carcinoma | Biologic therapy (BRM, immunotherapy) | Human protein |
| IL-2 + IL-4 (Cetus + Sterling) | Renal cell cancer; melanoma | Biologic therapy (BRM, immunotherapy) | Human proteins |
| IL-2 + IL-4 HLR/STRLNG | Melanoma; renal cell carcinoma | Biologic therapy (BRM, immunotherapy) | Human protein |
| IL-2 Jurkat Derived | Melanoma; renal cell carcinoma | Biologic therapy (BRM, immunotherapy) | Human protein |
| IL-2 Natural (Collaborative) | Melanoma; renal cell carcinoma | Biologic therapy (BRM, immunotherapy) | Human protein |
| IL-2 Polyethylene Glycol (Peg IL-2) | Renal cell carcinoma, melanoma | Biologic therapy (BRM, immunotherapy) | Human protein |
| IL-2 Recombinant | Melanoma; renal cell carcinoma | Biologic therapy (BRM, immunotherapy) | Human protein |
| IL-2/AutoEduLymph (HLR) | Melanoma; renal cell carcinoma | Biologic therapy (BRM, immunotherapy) | Human protein |
| IL-2/TIL (HLR) | Melanoma; renal cell carcinoma; colorectal | Biologic therapy (BRM, immunotherapy) | Human protein |
| IL-2: Rec (Cetus) + TIL | Melanoma; renal cell carcinoma | Biologic therapy (BRM, immunotherapy) | Human protein |
| IL-2: Rec (Cetus), Aldesleukin, Proleukin | Melanoma; renal cell carcinoma | Biologic therapy (BRM, immunotherapy) | Human protein |
| IL-2: Rec (Shionogi), S6820 | Melanoma; renal cell carcinoma | Biologic therapy (BRM, immunotherapy) | Human protein |
| IL-2: Rec.(HLR) | Melanoma; renal cell carcinoma | Biologic therapy (BRM, immunotherapy) | Human protein |
| IL13-PE38QQR | Brain cancer | Chemotherapy | Cytotoxic immunotherapy |
| ILX-651 | Melanoma;non-small cell lung cancer;prostate | Chemotherapy | Cytostatic agent |
| ILX23-7553 | Colorectal;other cancer | Chemotherapy | Antineoplastic |
| IM862 | Breast;colorectal;kidney;ovarian;prostate;sarcoma;skin cancer | Chemotherapy | Cytostatic agent--angiogenesis inhibitors |
| IMC-1c111 | Colorectal;skin cancer | Chemotherapy | Cytostatic agent--antiangiogenesis agent |
| IMC-A12 | Melanoma, GIST, and prostate | Biologic therapy (BRM, immunotherapy) | Anti-insulin-like growth facotr-1 receptor (IGR-IR) monoclonal antibody |
| INDOXIMOD | Pediatric brain malignancies and AML | Chemotherapy | IDO inhibitor |
| ING-1 Human Engineered Monoclonal Antibody | Adenocarcinomas | Chemotherapy | Cytotoxic and cytostatic |
| INGN 201 | Breast;H&N cancer;lung;ovarian | Biologic therapy (BRM, immunotherapy) | Cytostatic agent--adenovirus |
| INGN 225 | SCLC | Biologic therapy (BRM, immunotherapy) | Vaccine |
| INGN241 | other cancer;Skin | Chemotherapy | Apoptosis inducer |

Fig. 26R

| Name | Primary Site | Category | Sub-category |
|---|---|---|---|
| INGN251 (PTEN) | Colorectal cancer | Biologic therapy (BRM, immunotherapy) | Gene therapy |
| INX-3001 | Brain;kidney;leukemia;lung cancer | Chemotherapy | Targeted therapy |
| INX-3280 | Lymphoma | Chemotherapy | Targeted therapy |
| IPI-504 | breast;GIST;lung;melanoma;Myeloma;prostate;soft tissue;solid tumor | Chemotherapy | HPS90 inhibitor;Molecular inhibitor |
| ISF154 | Leukemia | Chemotherapy | Targeted therapy |
| ISIS 2503 | Breast;colorectal;lung;pancreatic cancer | Other therapy | Antisense compound;did not receive FDA approval |
| IV IL-2 Gene Medicine | Lung cancer | Biologic therapy (BRM, immunotherapy) | Human protein |
| Ibrutinib | B-cell malignancies;CLL;Mantle cell lymphoma;Multiple myeloma;NHL;Waldentrom macroglobulinemia (WM);diffuese B-cell lymphoma | Chemotherapy | Bruton tyrpsine kinase (Btk) |
| Idarubicin | Acute lymphoblastic leukemia (ALL);Acute myelogenous leukemia (AML);Chronic myelogenous leukemia in blast crises;Myelodysplastic syndromes (MDS) | Chemotherapy | Antitumor antibiotic |
| Idhifa | Acute myeloid leukemia (AML) | Chemotherapy | IDH2 inhibitor |
| Idiotype KLH Lymphoma Vaccine | Lymphoma | Biologic therapy (BRM, immunotherapy) | Immunotherapy active |
| Idiotype Tumor Vaccine | Lymphoma | Biologic therapy (BRM, immunotherapy) | Immunotherapy active |
| Idiotype Vaccine Idiotypic | Lymphoma | Biologic therapy (BRM, immunotherapy) | Immunotherapy active |
| Idiotype immuno. | Lymphoma | Biologic therapy (BRM, immunotherapy) | N/A |
| Idoxifene | Breast cancer | Hormones and hormonal mechanisms | Antiestrogen |
| Ifosfamide | Bladder;Cervical cancer;Ewing sarcoma;Head and Neck;Hodgkin lymphoma;Non-Hodgkin lymphoma;Non-small cell and small cell lung cancer;Soft tissue sarcoma, osteogenic sarcoma;Testicular cancer | Chemotherapy | Alkylating agent |
| Imatinib mesylate | aggressive mastocytosis;chronic eosinophilic leukemia;Colorectal;dermatofibrosarcoma protuberans;gastric;GIST;hypereosinophilic | Chemotherapy | Targeted therapy--tyrosine kinase inhibitor |

Fig. 26S

| Name | Primary Site | Category | Sub-category |
|---|---|---|---|
| | syndrome;leukemia;lung;other cancer;Ph+ALL | | |
| Imbruvica | Waldenstrom's macroglobulinemia | Chemotherapy | Bruton's tyrosine kinase (BTK) inhibitor |
| Imexon | Multiple myeloma | Chemotherapy | Apoptosis inducer |
| Imiquimod | Cervical cancer;melanoma;superficial basal cell carcinoma | Biologic therapy (BRM, immunotherapy) | TLR7 activator |
| Imlygic | Melanoma | Biologic therapy (BRM, immunotherapy) | Viral therapy |
| ImmTher | Sarcoma | Biologic therapy (BRM, immunotherapy) | Passive immunotherapy |
| Immunotoxin BL22 | Leukemia;lymphoma | Chemotherapy | Immunotoxin |
| Imuvert | Primary brain malignacies | Biologic therapy (BRM, immunotherapy) | Immunotherapy active |
| Indicine-N-oxide | Multiple sites | Chemotherapy | antimitotic agent;Plant product |
| Interferon | Leukemia, melanoma, AIDS-related Kaposi's sarcoma | Biologic therapy (BRM, immunotherapy) | Human protein |
| Interferon Alfa-2a | AIDS;Opportunistic infection | Biologic therapy (BRM, immunotherapy) | Human protein |
| Interferon Alfa-2b | Leukemia;melanoma | Biologic therapy (BRM, immunotherapy) | Human protein |
| Interferon Alfa-n1 | AIDS;Opportunistic infection | Biologic therapy (BRM, immunotherapy) | Human protein |
| Interferon Beta Gene Therapy | Brain cancer | Biologic therapy (BRM, immunotherapy) | Gene therapy |
| Interferon Gamma | Renal cell carcinoma | Biologic therapy (BRM, immunotherapy) | Human protein |
| Interferon alfa-n3 | Other cancer | Biologic therapy (BRM, immunotherapy) | Human protein |
| Interferon alfacon-1 | AIDS;Opportunistic infection | Biologic therapy (BRM, immunotherapy) | Human protein |
| Interferon alpha-NS | Other cancer | Biologic therapy (BRM, immunotherapy) | Human protein |
| Interferon and Interferon inducers | Multiple sites | Biologic therapy (BRM, immunotherapy) | Human protein |
| Interferon gamma-1b | AIDS;Opportunistic infection | Biologic therapy (BRM, immunotherapy) | Human protein |
| Interferon natural | AIDS;Opportunistic infection | Biologic therapy (BRM, immunotherapy) | Human protein |
| Interferon-alpha | Head & neck cancer | Biologic therapy (BRM, immunotherapy) | Human protein |
| Interleukin-1 beta | AIDS;Opportunistic infection | Biologic therapy (BRM, immunotherapy) | Human protein |
| Interleukin-10 | AIDS;Opportunistic infection | Biologic therapy (BRM, immunotherapy) | Human protein |
| Interleukin-12 | Breast;cervical;head & neck;kidney;lung;melanoma;multiple myeloma;ovarian cancer | Biologic therapy (BRM, immunotherapy) | Human protein |
| Interleukin-12, Interferon-alpha | Skin cancer | Biologic therapy (BRM, immunotherapy) | Human proteins |

Fig. 26T

| Name | Primary Site | Category | Sub-category |
|---|---|---|---|
| Interleukin-2 | AIDS;breast;head & neck cancer;leukemia;lymphoma;Opportunistic infection | Biologic therapy (BRM, immunotherapy) | Human protein |
| Interleukin-2 liposome | Pulmonarp metastases | Biologic therapy (BRM, immunotherapy) | Human protein |
| Interleukin-2/Super Antigen B Gene Combination | Skin cancer | Biologic therapy (BRM, immunotherapy) | Human proteins |
| Interleukin-21 | Other cancer | Biologic therapy (BRM, immunotherapy) | Human protein |
| Interleukin-4 | Breast;colorectal;leukemia;lymphoma;melanoma;ovarian cancer | Biologic therapy (BRM, immunotherapy) | Human protein |
| Interleukin-6 | AIDS;Opportunistic infection | Biologic therapy (BRM, immunotherapy) | Human protein |
| IntraDose | Breast;colorectal;head & neck;liver;melanoma;pancreatic cancer | Chemotherapy | Miscellaneous agent |
| Intravenous Immune Globulin | AIDS;CLL;Opportunistic infection | Biologic therapy (BRM, immunotherapy) | Human protein |
| Iobenguane I-131 | Pheochromocytoma or paraganglioma (PPGL) | Radiation | Radioisotope |
| Iodine-131 Tositumomab | Lymphoma | Radiation | Radioisotope attached to monoclonal antibody |
| Iotrex | Brain | Radiation | Liquid radioisotope |
| Ipilimumab | melanoma;Prostate cancer;colorectal | Biologic therapy (BRM, immunotherapy) | Monoclonal antibody |
| Ipomeanol | Lung cancer | Chemotherapy | Plant product |
| Iproplatin | Multiple sites | Chemotherapy | Miscellaneous agent |
| Irinotecan | Colorectal;head & neck;Non-small cell lung cancer (NSCLC);pancreatic cancer;Small cell lung cancer (SCLC) | Chemotherapy | Topoisomerase inhibitor |
| Irofulven | Brain;breast;cervical;gastric;leukemia;liver;lung;melanoma;multiple myeloma;ovarian;ovary;pancreatic;primary peritoneal carcinoma;prostate cancer;sarcoma | Chemotherapy | Alkylating agent |
| Ispinesib | acute leukemias;Breast;CML;MDS;ovarian cancer | Chemotherapy | Antimitotic agent |
| Ivosidenib | Refractory acute myeloid leukemia (AML) | Chemotherapy | IDH1 Inhibitor |
| J107088 | Other cancer | Chemotherapy | Topoisomerase inhibitor |
| JNJ-68284528 | Multiple myeloma | Biologic therapy (BRM, immunotherapy) | C-ART |
| Javelin | Skin cancer | Biologic therapy (BRM, immunotherapy) | Vaccine |
| KB004 | Brain | Chemotherapy | Eph receptor tyrosine kinases |
| KDR/VEGFR-2 | Other cancer | Biologic therapy (BRM, immunotherapy) | Human protein |

Fig. 26U

| Name | Primary Site | Category | Sub-category |
|---|---|---|---|
| KOS-1022 | hematopoietic;Solid tumors | Chemotherapy | Targeted therapy--heat shock protein |
| KRN 5500 | Other cancer | Chemotherapy | Alkylating agent |
| KS-IL2 | Other cancer | Biologic therapy (BRM, immunotherapy) | Human protein |
| KSA Vaccine | Colorectal cancer | Biologic therapy (BRM, immunotherapy) | Immunotherapy active |
| KW-0761 | Adult T-cell leukemia/lymphoma;peripheral T-cell leukemia/lymphoma | Chemotherapy | Monoclonal antibody |
| KW-2871 | Skin cancer | Biologic therapy (BRM, immunotherapy) | Monoclonal antibody |
| Kahalalide F | Prostate cancer | Chemotherapy | Natural product--sea slug |
| Kanjinti | Breast | Biologic therapy (BRM, immunotherapy) | Biosimilar |
| Karenitecin | Brain | Chemotherapy | Topoisomerase inhibitor |
| Ketoconazole | As a testosterone blocker for advanced prostate cancer;as an antifungal for AIDS;opportunistic infections | Hormones and hormonal mechanisms | Antiandrogenic |
| Keytruda | Multiple sites | Biologic therapy (BRM, immunotherapy) | monoclonal antibody |
| L-377,202 | Prostate cancer | Chemotherapy | Antitumor antibiotic |
| L-778123 | Pancreatic cancer | Chemotherapy | Not in current use |
| L-VAX | Leukemia | Biologic therapy (BRM, immunotherapy) | Immunotherapy active |
| LAF389 | Other cancer | Chemotherapy | Cytostatic agent--methionine aminopeptidase inhibitor |
| LAK cells | Renal cell carcinoma, melanoma | Biologic therapy (BRM, immunotherapy) | Cellular therapy |
| LAQ824 | Other cancer | Chemotherapy | Cytostatic agent--histone deacetylase inhibitor |
| LBH-589 | AML;Hodgkin lymphoma;MDS;multiple myeloma | Chemotherapy | Pan-DAC inhibitor |
| LDI-200 | Leukemia | Chemotherapy | Cytostatic agent--apoptosis stimulator |
| LErafAON | Leukemia;other cancer | Chemotherapy | Antisense oligonucleotide |
| LGD1550 | Cervical;head & neck;other cancer | Differentiation inducing agent;Differentiation | Synthetic aromatic retinoic acid agent |
| LHRH Immunotherapeutic | Prostate cancer | Biologic therapy (BRM, immunotherapy) | Vaccine |
| LMB-1 Immunotoxin | Colorectal cancer | Chemotherapy | Immunotoxin conjugated with monoclonal antibody |
| LMB-7 Immunotoxin | Colorectal cancer | Chemotherapy | Immunotoxin conjugated with monoclonal antibody |
| LMB-9 | Breast;colorectal;gastric cancer | Chemotherapy | Immunotoxin conjugated with monoclonal antibody |
| LMB-9 Immunotoxin | Colorectal cancer | Chemotherapy | Immunotoxin conjugated with monoclonal antibody |
| LY-2181308 | AML;Prostate | Chemotherapy | Apoptosis protein inhibitor |
| LY2603618 | NSC Lung;Pancreas | Chemotherapy | Chk2 inhibitor |

Fig. 26V

| Name | Primary Site | Category | Sub-category |
|---|---|---|---|
| LY573636 | advanced solid tumors;ovary;STS | Chemotherapy | Cytostatic agent--apoptosis inducer |
| Lanreotide Acetate | Gastrointestinal and pacreatic neuroendocrine tumors | Hormones and hormonal mechanisms | growth hormone releasing hormone inhibitor;Somatostatin analogue |
| Lapatinib ditosylate | Breast | Chemotherapy | Tyrosine kinase inhibitor |
| Larotrectinib | Solid tumors | Chemotherapy | Trk inhibitor |
| Lasofoxifene | Breast cancer | Hormones and hormonal mechanisms | Selective estrogen receptor modulator (SERM) |
| Lenalidomide | 5q- MDS;CLL;MDS;Multiple myeloma;melanoma;Lymphoma | Biologic therapy (BRM, immunotherapy) | Cytostatic agent--antiangiogenesis agent |
| Lentinan | AIDS;Opportunistic infection | Biologic therapy (BRM, immunotherapy);AIDS drug | N/A |
| Lenvima | Lung;liver;lymphoma;thyroid | Chemotherapy | Multi-targeted kinase inhibitor;VEGFR inhibitor |
| Lestaurinib | AML;leukemia;other cancer;Pancreatic;prostate | Chemotherapy | Tyrosine kinase inhibitor |
| Letrozole | Breast cancer | Hormones and hormonal mechanisms | Nonsteroidal aromatase inhibitor |
| Leuprolide Acetate | Prostate cancer;See remarks for other site information;Breast;Ovary | Hormones and hormonal mechanisms | Gonadotropin-releasing hormone agonist |
| Leuprorelin | Prostate cancer | Hormones and hormonal mechanisms | Gonadotropin-releasing hormone agonist |
| Leuvectin | Kidney;prostate;skin cancer | Biologic therapy (BRM, immunotherapy) | DNA vector encoding human protein |
| Levamisole | Colon cancer | Biologic therapy (BRM, immunotherapy) | Immunomodulator |
| Levothyroxine Sodium | Thyroid | Hormones and hormonal mechanisms | Thyroid hormone--suppresses TSH |
| Lintuzumab | AML;MDS | Chemotherapy | Cytotoxic agent--Anti-CD33 |
| Liothyronine Sodium | Thyroid | Hormones and hormonal mechanisms | Thyroid hormone--suppresses TSH |
| Liposomal SN38 | Colorectal | Chemotherapy | Metabolite of CPT-11;topoisomerase inhibitor |
| Liposome Encapsulated Mitoxantrone | Other cancer | Chemotherapy | Antitumor antibiotic |
| Liposome Encapsulated Paclitaxel | Breast;gastric;head & neck;lung;ovarian cancer | Chemotherapy | Natural product |
| Liposome encapsulated recombinant interleukin-2 | CNS, kidney and renal pelvis tumors | Biologic therapy (BRM, immunotherapy) | Human protein |
| Liquid IL-2 | Breast cancer;non-Hodgkin's lymphoma | Biologic therapy (BRM, immunotherapy) | Human protein |
| Lometrexol Sodium | NSCLC | Chemotherapy | Antimetabolite--Antifolate |
| Lomustine | Brain tumors: primary or metastatic;Hodgkin lymphoma;Non-Hodgkin lymphoma | Chemotherapy | Alkylating agent |
| Lonafarnib | leukemia;Lung cancer | Chemotherapy | Cytostatic agent--farnesyl transferase inhibitor |
| Lonsurf | Colorectal;Gastroesophageal | Chemotherapy | Thymidine phosphorylase inhibitor |
| Lorlatinib | Lung | Chemotherapy | ALK Inhibitor |

Fig. 26W

| Name | Primary Site | Category | Sub-category |
|---|---|---|---|
| Lovastatin | AML;Hepatoma;stomach | Chemotherapy | Cytostatic agent--apoptosis stimulator |
| Lucanthone | Brain cancer | Chemotherapy | Cytostatic agent--topoisomerase inhibitor |
| Lung Cancer Vaccine | Lung cancer | Biologic therapy (BRM, immunotherapy) | Immunotherapy active |
| Lutrin | Breast;prostate cancer;GI sites | Radiation | Radiosensitizer |
| LymphoRad 131 | Multiple myeloma | Radiation | Radioisotope |
| Lynparza | Ovary | Chemotherapy | PARP Inhibitor |
| M-Vax | Skin cancer | Biologic therapy (BRM, immunotherapy) | Vaccine |
| MAGE-12:170-178 | Breast;skin cancer | Biologic therapy (BRM, immunotherapy) | Vaccine |
| MAGE-A3 peptide vaccine | Melanoma | Biologic therapy (BRM, immunotherapy) | Vaccine |
| MART-1 | Skin cancer | Biologic therapy (BRM, immunotherapy) | Cytokine |
| MART-1 with gp100 (in vivo) Vaccine | Skin cancer | Biologic therapy (BRM, immunotherapy) | Vaccine |
| MAb CC-49 | Lung cancer | Radiation | Radioisotope conjugated to monoclonal antibody |
| MAb antibody 3A1 | Breast cancer | Biologic therapy (BRM, immunotherapy) | Monoclonal antibody |
| MAb antibody B3 | Breast cancer | Biologic therapy (BRM, immunotherapy) | Monoclonal antibody |
| MAbHu1D10 | B-cell Non-Hodgkin's lymphomas | Biologic therapy (BRM, immunotherapy) | Monoclonal antibody |
| MAbHum291 anti-CD3 | Lymphoma | Biologic therapy (BRM, immunotherapy) | Monoclonal antibody |
| MDAM | Other cancer | Chemotherapy | Antimetabolite |
| MDX-010 and Melanoma Vaccine | Skin cancer | Biologic therapy (BRM, immunotherapy) | Immunotherapy active |
| MDX-060 | Lymphoma | Biologic therapy (BRM, immunotherapy) | Monoclonal antibody that targets CD 30 (TNF) |
| MDX-210 | Breast;leukemia;ovarian cancer | Chemotherapy | Cytostatic agent--anti HER2 |
| MDX-22 | Leukemia | Biologic therapy (BRM, immunotherapy) | Monoclonal antibody |
| MDX-220 (bispecific antibody) | Colorectal;prostate cancer | Biologic therapy (BRM, immunotherapy) | Monoclonal antibody |
| MDX-447 (biospecific antibody) | Breast;colorectal;head & neck;kidney cancer | Chemotherapy | Cytostatic agent--EGFR inhibitor |
| MDX-H210 (bispecific antibody) | Colorectal;kidney;prostate cancer | Biologic therapy (BRM, immunotherapy) | Monoclonal antibody |
| MEDI-551 | B-cell malignancies | Biologic therapy (BRM, immunotherapy) | Humanized Monoclonal Antibody BRM |
| MG98 | Head & neck;kidney cancer;leukemia | Chemotherapy | Antisense oligonucleotide |
| MGCD0103 | AML;MDS | Chemotherapy | Cytostatic agent--histone deacetylation inhibitor |
| MGS rCEA (recombinant carcinoembryonic antigen) | Colorectal cancer | Biologic therapy (BRM, immunotherapy) | Immunotherapy active |

Fig. 26X

| Name | Primary Site | Category | Sub-category |
|---|---|---|---|
| MGV Vaccine | Colorectal;gastric;lung cancer;lymphoma;neuroblastoma;sarcoma | Biologic therapy (BRM, immunotherapy) | Immunotherapy active |
| MK-0752 | brain;Breast;CNS | Chemotherapy | Gamma secretase inhibitor |
| MK-2206 | Breast;melanoma | Chemotherapy | Protein inhibitor |
| MK-5108 | solid tumors | Chemotherapy | Aurora-A kinase inhibitor |
| MLN518 | Leukemia | Chemotherapy | Cytostatic agent--receptor tyrosine kinase inhibitor |
| MLN576 | Other cancer | Chemotherapy | Cytostatic agent--topoisomerase inhibitor |
| MLN591 | Prostate cancer | Biologic therapy (BRM, immunotherapy) | Monoclonal antibody for prostate specific membrane |
| MPC-7869 | Prostate cancer | Chemotherapy | Signal transduction modulator |
| MS-275 | Leukemia;lymphoma;other cancer | Chemotherapy | Cytostatic agent--histone deacetylase inhibitors |
| MTC-DOX (Doxorubicin) | Liver cancer | Chemotherapy | Antitumor antibiotic conjugated to delivery mechanism |
| MVA-BN-HER2 | Breast | Biologic therapy (BRM, immunotherapy) | Vaccine |
| MVA-Muc1-IL2 | Breast;lung;prostate cancer | Biologic therapy (BRM, immunotherapy) | Vaccine |
| MX6 | Cervical cancer | Chemotherapy | Cytostatic agent--apoptosis stimulator |
| Mab Hefi-1 | Lymphoma | Biologic therapy (BRM, immunotherapy) | Monoclonal antibody |
| Macrobead | Colorectal;Pancreas;Prostate | Other therapy | See remarks |
| Mafosfamide | Lymphoma, leukemia, meningeal neoplasm, and brain and CNS tumors | Chemotherapy | Alkylating agent |
| Marimastat | Pancreatic cancer | Chemotherapy | Cytostatic agent--antiangiogenesis agent |
| Masoprocol | Precancerous skin lesions | Chemotherapy | Topical antineoplastic |
| Matrix Metalloproteinease Inhibitor | Colorectal;lung cancer | Biologic therapy (BRM, immunotherapy) | This is a mechanism of action |
| Mechlorethamine | CLL;Cutaneous T-cell lymphoma (topical use);Hodgkin lymphoma;lung cancer;Non-Hodgkin lymphoma | Chemotherapy | Alkylating agent |
| Medroxyprogesterone | breast cancer;Endometrial cancer | Hormones and hormonal mechanisms | Hormone |
| Medroxyprogesterone Acetate | Endometrial cancer;renal cancer | Hormones and hormonal mechanisms | Progestin |
| Megestrol Acetate | Breast cancer;endometrial cancer | Hormones and hormonal mechanisms;AIDS drug | Progestin |
| Melanoma peptide vaccine | Melanoma | Biologic therapy (BRM, immunotherapy) | Vaccine |
| Melphalan | Multiple myeloma;ovarian cancer;Polycythemia Vera | Chemotherapy | Alkylating agent |
| Menogaril | Solid tumors | Chemotherapy | Topoisomerase inhibitor |
| Merbarone | Multiple sites | Chemotherapy | Topoisomerase inhibitor |
| Mercaptopurine | Leukemia | Chemotherapy | Antimetabolite |
| Mercaptopurine riboside | Breast;ovarian | Chemotherapy | Antimetabolite |

Fig. 26Y

| Name | Primary Site | Category | Sub-category |
|---|---|---|---|
| Metastat | Brain;sarcoma;skin cancer | Chemotherapy | Cytostatic agent--matrix metaloprotease inhibitor (MMPI) |
| Methotrexate | Acute lymphoblastic leukemia (ALL);Bladder cancer;Breast;Gestational trophoblastic cancer;head & neck cancer;lymphoma;Meningeal leukemia;Non-Hodgkin lymphoma;Osteogenic sarcoma;Primary CNS lymphoma | Chemotherapy | Antimetabolite |
| Methylmercaptopurine riboside | Multiple sites | Chemotherapy | Protein kinase inhibitor |
| Methyltestosterone | Breast cancer | Hormones and hormonal mechanisms | Androgen |
| Metvix | Skin cancer | Other therapy | Photodynamic therapy |
| Mibolerone | Prostate cancer | Hormones and hormonal mechanisms | Androgen |
| Midostaurin | Leukemia;other cancer | Chemotherapy | Cytostatic agent--protein kinase inhibitor |
| Mifepristone | Breast | Hormones and hormonal mechanisms | Progesterone receptor agonist |
| Miltefosine | cutaneous lymphomas;Skin metastases in breast ca | Chemotherapy | Topical antineoplastic |
| Mirena IUD | Cervix;Endometrium | Other therapy | Intrauterine device |
| Mitoguazone | AIDS;Opportunistic infection | Chemotherapy | Antineoplastic hydrazone |
| Mitolactol | Malignant gliomas | Chemotherapy | Alkylating agent |
| Mitomycin | Breast;Cervical cancer;Gastric cancer;Head and Neck (in combination with radiation therapy);Non-small cell lung cancer (NSCLC);Pancreatic cancer;Superficial bladder cancer | Chemotherapy | Alkylating agent |
| Mitotane | Adrenal cortical carcinoma | Chemotherapy | Miscellaneous agent |
| Mitoxantrone | Acute myelogenous leukemia (AML);Breast;Non-Hodgkin lymphoma;Prostate-advanced hormone-refractory | Chemotherapy | Antitumor antibiotic |
| Monamulizmab-kpkc | Mycosis fungoides | Biologic therapy (BRM, immunotherapy) | Monoclonal antibody |
| Monoclonal CC-49 Delta CH2 | Colorectal cancer | Biologic therapy (BRM, immunotherapy) | Monoclonal antibody |
| Motesanib | Colorectal;NSCLC | Chemotherapy | Cystostatic agent--tyrosine kinase inhibitor |
| Moxetumomab pasudotox | Hairy cell leukemia (HCL) | Biologic therapy (BRM, immunotherapy) | Anti-CD22 antibody |
| Multikine (Leukocyte Interleukin Injection) | head & neck cancer;Prostate | Biologic therapy (BRM, immunotherapy) | Immunotherapy active |

Fig. 26Z

| Name | Primary Site | Category | Sub-category |
|---|---|---|---|
| Mvasi | See remarks | Biologic therapy (BRM, immunotherapy) | bio-similar |
| Myeloma-derived Idiotypic Antigen Vaccine | Multiple myeloma | Biologic therapy (BRM, immunotherapy) | Vaccine |
| Mylovenge | Multiple myeloma | Biologic therapy (BRM, immunotherapy) | Dendritic cell vaccine |
| NB1011 | Colorectal cancer | Chemotherapy | Cytotoxic agent and thymidylate synthase inhibitor |
| NBI-3001 | Brain;kidney cancer | Chemotherapy | Interleukin conjugated with pseudomonas toxin |
| NKTR-214 | Melanoma | Biologic therapy (BRM, immunotherapy) | CD122 agonist |
| NM-3 | Breast;other cancer | Chemotherapy | Cytostatic agent--antiangiogenesis agent |
| NV1020 | Colorectal cancer | Chemotherapy | Oncolytic virus |
| NY-ESO-1 | Melanoma | Biologic therapy (BRM, immunotherapy) | Vaccine |
| NY-ESO-1/gp100/MART-1 | Melanoma (see Remarks) | Biologic therapy (BRM, immunotherapy) | Dendritic cell vaccine |
| Nafoxidine HCL | Breasn | Hormones and hormonal mechanisms | Antiestrogen--SERM |
| Nandrolone Phenpropionate | Breast cancer | Hormones and hormonal mechanisms | Anabolic steroid |
| Naptumomab estafenatox | Kidney | Biologic therapy (BRM, immunotherapy) | Immunotherapy |
| Necitumumab | Lung | Biologic therapy (BRM, immunotherapy) | Anti-EFRG monoclonal antibody |
| Nedaplatin | Gastrointestinal and cervical cancer | Chemotherapy | Miscellaneous agent |
| Nelarabine | T-cell ALL;T-cell lymphoblastic lymphoma | Chemotherapy | Antimetabolite |
| Neovastat | Breast;kidney;lung;multiple myeloma;prostate cancer | Chemotherapy | Cytostatic agent--anti-angiogenesis agent |
| Neratinib | breast;Non-small cell lung | Chemotherapy | Tyrosine kinase inhibitor |
| Neugene | Colorectal cancer | Chemotherapy | Antisense drug |
| Nilotinib | CML;GIST | Chemotherapy | Cytostatic agent--tyrosine kinase inhibitor |
| Nilutamide | Prostate cancer | Hormones and hormonal mechanisms | Nonsteroidal antiandrogen |
| Ninlaro | Multiple myeloma | Chemotherapy | Proteasome inhibitor |
| Nintedanib | Lung | Chemotherapy | Tyrosine kinase inhibitor |
| Niraparib | Ovary;prostate;Fallopian tubes;Primary peritoneal | Chemotherapy | PARP inhibitor |
| Nitromifene Citrate | Breast cancer | Hormones and hormonal mechanisms | Anti-estrogen |
| Norelin | Prostate cancer | Biologic therapy (BRM, immunotherapy) | Vaccine |
| Norethandrolone | Aplastic anemia | Hormones and hormonal mechanisms | anabolic steroid;Androgen |
| NovoTTF-100A system | Brain (Recurrent Glioblastoma Multiforme) GBM | Other therapy | Alternating electric field |
| Nubeqa | Prostate | Hormones and hormonal mechanisms | Androgen receptor |

Fig. 27A

| Name | Primary Site | Category | Sub-category |
|---|---|---|---|
| Nylestriol | Prostate cancer | Hormones and hormonal mechanisms | Estrogen |
| O-6-Benzylguanine | Brain;colorectal;multiple myeloma;sarcoma;skin cancer | Chemotherapy | Antineoplastic enzyme inhibitor |
| O-Vax | Ovarian;pancreatic cancer | Biologic therapy (BRM, immunotherapy) | Immunotherapy active |
| ODN698 | Other cancer | Chemotherapy | Antisense oligonucleotide |
| OGX-011 | Prostate cancer | Chemotherapy | Antisense oligonucleotide |
| OK-432 | Lymphangiomas | Biologic therapy (BRM, immunotherapy) | Bacterial therapy |
| ON 01910.Na | CLL;Leukemia;Liver;lymphoma;MDS;ovary | Chemotherapy | Polio-like kinase |
| ONYX-015 | Brain;colorectal;head & neck;liver;lung;ovarian;pancreatic cancer;sarcoma | Chemotherapy | Oncolytic virus |
| OSI-211 | Lung;ovarian cancer | Chemotherapy | Topoisomerase inhibitor |
| OSI-7836 | Other cancer | Chemotherapy | Antimetabolite |
| Obatoclax | advanced solid tumors;Small cell lung cancer | Chemotherapy | Cytostatic agent--apoptosis inducer |
| OctreoTher | other cancer;Pancreatic | Radiation | Radioisotope attached to somatostatin peptide analog |
| Odomzo | Skin | Chemotherapy | Hedgehog signaling inhibitor |
| Oestriol | may be preventive in colon and colorectal cancer;Palliative treatment in breast and prostate cancer | Hormones and hormonal mechanisms | Estrogen |
| Ofatumumab | Chronic lymphocytic leukemia (CLL);Lymphoma | Biologic therapy (BRM, immunotherapy) | Monoclonal antibody |
| Ogivri | Breast | Biologic therapy (BRM, immunotherapy) | bio-similar |
| Olaprib | Ovary, Fallopian tube, Peritoneum;Pancreas | Chemotherapy | PARP Inhibitor |
| Olaratumab | Soft tissue | Biologic therapy (BRM, immunotherapy) | Monoclonal antibody |
| Omacetaxine | Acute lymphoblastic leukemia (ALL);Acute myelogenous leukemia (AML);Chronic myelogenous leukemia (CML);Myelodysplastic syndrome (MDS) | Chemotherapy | Alkaloid;Protein inhibitor |
| Onco-TCS | ALL;leukemia;Lung cancer;lymphoma | Chemotherapy | Plant alkaloid--antimetabolite |
| OncoVAX Autologous Vaccine | Colorectal cancer | Biologic therapy (BRM, immunotherapy) | Immunotherapy active |
| OncoVex GM-CSF | Other cancer | Chemotherapy | Oncolytic virus |
| Oncolar | Breast cancer | Hormones and hormonal mechanisms | Growth hormone releasing hormone inhibitor |
| Oncolym | Brain cancer;lymphoma | Radiation | Radioisotope |
| Oncomyc-NG | Other cancer | Chemotherapy | Antisense oligonucleotide |
| Onconase | Breast;kidney;lung cancer;mesothelioma | Chemotherapy | Cytostatic agent--apoptosis stimulator |

Fig. 27B

| Name | Primary Site | Category | Sub-category |
|---|---|---|---|
| Oncophage | Colorectal;gastric;kidney;lymphoma;pancreatic;sarcoma;skin cancer | Biologic therapy (BRM, immunotherapy) | Vaccine |
| Onivyde | Pancreas | Chemotherapy | analog |
| Ontruzant | Breast | Biologic therapy (BRM, immunotherapy) | Biosimilar |
| Opdivo | Kidney;Bladder;Lung;Skin | Biologic therapy (BRM, immunotherapy) | braf inhibitor |
| Optimized gp100 naked DNA Vaccine with IL-2 | Skin cancer | Biologic therapy (BRM, immunotherapy) | Immunotherapy active |
| Oregovemab | Ovarian cancer | Biologic therapy (BRM, immunotherapy) | Monoclonal antibody targeting CA-125 |
| Ovidrel | Breast cancer;Kaposi sarcoma | Chemotherapy | Cytotoxic agent for KS only;otherwise a hormone (hCG) |
| Oxaliplatin | Colorectal;gastro-esophageal cancers, metastatic;liver;ovarian;pancreatic cancer | Chemotherapy | Platinum analog |
| P16 Program | Pancreatic cancer | Biologic therapy (BRM, immunotherapy) | Gene therapy |
| P53 and RAS vaccine | Breast;cervical;colorectal;lung;ovarian;pancreatic cancer | Biologic therapy (BRM, immunotherapy) | Immunotherapy active |
| PACLIMER Microspheres | Pancreatic cancer | Chemotherapy | Taxane |
| PD 0332991 | ER positive/ HER2-negative breast cancer | Chemotherapy | investigational cell-cycle inhibitor |
| PD-0325901 | Breast;colorectal;melanoma;non-small cell lung | Chemotherapy | MEK inhibitor |
| PEG Paclitaxel | Other cancer | Chemotherapy | Natural product |
| PEG-IL-2 | acute myeloid leukemia;HIV;melanoma;Metastatic renal cell carcinoma;non-Hodgkin's lymphoma | Biologic therapy (BRM, immunotherapy) | PEG-conjugated human protein |
| PF-02341066 | anaplastic large-cell lymphoma;Solid tumors | Chemotherapy | Tyrosine kinase inhibitor |
| PI-166 | Liver cancer | Chemotherapy | Cytotoxic agent |
| PI-88 | melanoma;Skin cancer | Chemotherapy | Cytostatic agent--antiangiogenesis agent |
| PKI-166 | Breast;colorectal;gastric;other cancer | Chemotherapy | Cytostatic agent--antiangiogenesis agent |
| PR-104 | Solid tumors | Chemotherapy | Antimetabolite |
| PR-171 | lymphoma;Multiple myeloma | Chemotherapy | Cytostatic agent--proteasome inhibitor |
| PRO64553 | Prostate cancer | Chemotherapy | Cytotoxic Monoclonal antibody targeted to CD40 |
| PROSTVAC-VF | Prostate cancer | Biologic therapy (BRM, immunotherapy) | Immunotherapy active |
| PSK | Multiple sites | Biologic therapy (BRM, immunotherapy) | Polysaccharide |
| PV701 | Other cancer | Chemotherapy | Oncolytic virus |
| PX-12 | Other cancer | Chemotherapy | Cytostatic agent-thioredoxin inhibitor |
| Paclitaxel | breast;Gastric;head & neck cancer;Kaposi's | Chemotherapy | Mitotic inhibitor;plant alkaloid;Taxane |

Fig. 27C

| Name | Primary Site | Category | Sub-category |
|---|---|---|---|
| | sarcoma;non-small cell lung cancers;ovarian | | |
| Paclitaxel poliglumex | breast;esophagus;NSCLC;ovary;Prostate;stomach | Chemotherapy | Taxane |
| Padcev | Bladder | Chemotherapy | antibody and microtubule inhibitor conjugate |
| Palbociclib | Breast | Chemotherapy | CDK Inhibitor |
| PanVac | Pancreatic caner | Biologic therapy (BRM, immunotherapy) | Vaccine |
| Pancratistatin | Leukemia | Chemotherapy | Plant product |
| Pancreatic tumor cell vaccine | Pancreas | Biologic therapy (BRM, immunotherapy) | Vaccine |
| Panitumumab | Colorectal;kidney;lung;prostate cancer | Biologic therapy (BRM, immunotherapy) | Cytostatic agent--monoclonal antibody |
| Panobinostat | Multiple myeloma | Chemotherapy | HDAC inhibitor |
| Panzem | Breast;multiple myeloma;prostate cancer | Chemotherapy | Angiogenesis inhibitor |
| Pasireotide | Carcinoids | Hormones and hormonal mechanisms | Hormone |
| Paxoral | Breast;gastric lung cancer | Chemotherapy | Taxane |
| Pazopanib | Renal cell;Sarcoma | Chemotherapy | Cytostatic agent--antiangiogenic agent |
| Pegaspargase | Acute lymphoblastic leukemia (ALL) | Chemotherapy | Antineoplastic enzyme |
| Peginterferon alfa-2a | Kidney;leukemia;skin cancer | Biologic therapy (BRM, immunotherapy) | Primarily for Hepatitis C infection |
| Peginterferon alfa-2b | Leukemia;other cancer;skin | Biologic therapy (BRM, immunotherapy) | PEG-conjugated human protein |
| Pemetrexed | Breast;colorectal;gastric;mesothelioma;non-small cell lung;ovarian;pancreatic cancer | Chemotherapy | Antimetabolite |
| Pemtumomab | Gastric;ovarian cancer | Radiation | Radioisotope |
| Penclomedine | Multiple sites | Chemotherapy | Alkylating agent |
| Pentacea | Lung cancer | Radiation | Radioisotope |
| Pentamustine | Lymphomas | Chemotherapy | Alkylating agent |
| Pentostatin | Leukemia | Chemotherapy | Antimetabolite |
| Peptide Vaccine | Sarcoma | Biologic therapy (BRM, immunotherapy) | Immunotherapy active |
| Perifosine | Head & neck;melanoma;metastatic cancers;pancreatic;prostate cancer;sarcoma | Chemotherapy | Cytostatic agent--AKT inhibitor |
| Peripheral Blood Lymphocytes Transduced with a Gene Encoded Chimeric T Cell Receptor | Ovarian;pancreatic cancer | Biologic therapy (BRM, immunotherapy) | Cellular therapy |
| Pertuzumab | Breast | Biologic therapy (BRM, immunotherapy) | Cytostatic agent--tyrosine kinase inhibitor;Humanized monoclonal antibody |
| Pexidartinib | Giant cell tumor | Chemotherapy | Tyrosine kinase inhibitor |
| Phenoxodiol | other cancer;Ovarian | Chemotherapy | Cytostatic agent--signal transduction inhibitor |
| Phenylbutyrate | Brain;Colorectal cancer | Differentiation inducing agent | Differentiating agent |

Fig. 27D

| Name | Primary Site | Category | Sub-category |
|---|---|---|---|
| Pibenzimol HCl | Pancreatic caner | Chemotherapy | Antineoplastic--antimitotic |
| Picibanil | Lymphangioma | Biologic therapy (BRM, immunotherapy) | Bacterial therapy |
| Picoplatin | breast;ovarian;Prostate;small cell lung | Chemotherapy | Miscellaneous agent--platinum compound |
| Pipobroman | Chronic granulomatous leukemia | Chemotherapy | Alkylating agent |
| Piqray | Breast | Chemotherapy | PI3K inhibitor |
| Pirarubicin | Multiple sites | Chemotherapy | Antitumor antibiotic--anthracycline |
| Piritrexim | Urinary tract | Chemotherapy | Folate antagonists |
| Pixantrone dimaleate | Lymphoma | Chemotherapy | Anthracycline--topoisomerase inhibitor |
| Plevitrexed | ovary;pancreas;Stomach | Chemotherapy | Cytostatic agent--thymidylate synthesis inhibitor |
| Plicamycin | Testicular carcinoma | Chemotherapy | Antitumor antibiotic |
| Plitidepsin | Lymphoma;myeloma | Chemotherapy | Cytostatic agent--antiangiogenic agent |
| Polifeprosan 20 with Carmustine Implant | Brain cancer | Chemotherapy | Alkylating agent |
| Polivy | Large B-cell lymphoma (DLBCL) | Biologic therapy (BRM, immunotherapy) | Anti-body conjugate |
| Poly I: Poly C12U | Kidney;skin cancer | Biologic therapy (BRM, immunotherapy) | Double-stranded RNA |
| Polyestradiol Phosphate | Prostate cancer | Hormones and hormonal mechanisms | Estrogen |
| Pomalidomide | Multiple myeloma | Biologic therapy (BRM, immunotherapy) | TNF-alpha production inhibitor/thalidomide analogue |
| Ponatinib | CML;Chronic myeloid leukemia;Ph+ALL;Philadelphia-chromosome positive acute lymphoblastic leukemia;Acute lymphoblastic leukemia;ALL | Chemotherapy | kinase inhibitor |
| Porfiromycin | Head & neck cancer, cervical cancer | Chemotherapy | Antitumor antibiotic |
| Pralatrexate | Lung cancer;lymphoma | Chemotherapy | Antimetabolite--antifolate |
| Pravastatin | Hepatoma | Chemotherapy | Antioangiogenic agent;Cytostatic agent--Ras inhibitor |
| Prednisone | Prednisone is used to treat multiple sites and histologies | Hormones and hormonal mechanisms | Glucocorticoid |
| Pretarget Carcinoma | Gastric cancer | Radiation | Radioisotope bound to streptavidin |
| Pretarget Lymphoma | Lymphoma | Radiation | Radioisotope bound to streptavidin |
| ProMune | basal cell;Breast;kidney;lung;lymphoma;melanoma;NHL;skin cancer | Biologic therapy (BRM, immunotherapy) | Synthetic oligonucleotide |
| Proact | Sarcoma | Biologic therapy (BRM, immunotherapy) | N/A |

Fig. 27E

| Name | Primary Site | Category | Sub-category |
|---|---|---|---|
| Procarbazine | Brain tumors adjuvant and/or advanced disease;Cutaneous T-cell lymphoma;Hodgkin lymphoma;Non-Hodgkin lymphoma | Chemotherapy | Nonclassic alkylating agent |
| Procarbazine Hydrochloride | Hodgkin's lymphoma | Chemotherapy | Alkylating agent |
| Propranolol | Benign hemangioma | Other therapy | Beta blocker |
| Proscar | Prostate | Hormones and hormonal mechanisms | 5-alpha-reductase inhibitor |
| Proteinase 3 Peptide Vaccine | Leukemia | Biologic therapy (BRM, immunotherapy) | Immunotherapy active |
| Prothecan | Gastric;lung;pancreatic cancer | Chemotherapy | Topoisomerase inhibitor |
| Provenge Therapeutic Vaccine | Prostate cancer | Biologic therapy (BRM, immunotherapy) | Immunotherapy active |
| Pure anti-estrogen | Breast cancer | Hormones and hormonal mechanisms | Antiestrogen |
| Pyrazine diazohydroxide | Leukemia | Chemotherapy | Miscellaneous agent |
| Pyrazoloacridine | Brain;breast cancer | Chemotherapy | Topoisomerase inhibitor |
| Quadrakine | Gastric cancer | Biologic therapy (BRM, immunotherapy) | Interleukin |
| Quingestanol Acetate | Prostate cancer | Hormones and hormonal mechanisms | Progestin |
| Quizartinib | Acute myeloid leukemia;AML | Chemotherapy | Tyrosine kinase inhibitor |
| R04929097 | advanced breast;NSCLC;pediatric neuroblastoma;solid tumors | Chemotherapy | Gamma-secretase inhibitor |
| R440 | Breast;colorectal;lung cancer | Chemotherapy | Cytostatic agent--apoptosis inducer |
| RAS 5-17 Peptide Vaccine | Colorectal;lung;other;pancreatic;prostate cancer | Biologic therapy (BRM, immunotherapy) | Immunotherapy active |
| RB894 | Head & neck cancer | Biologic therapy (BRM, immunotherapy) | Adenovirus |
| RC-3095 | Colorectal;gastric;lung;pancreatic;prostate cancer | Biologic therapy (BRM, immunotherapy) | Bombesin/gastrin releasing peptide antagonist |
| RO5072759 | CLL;NHL | Biologic therapy (BRM, immunotherapy) | Anti CD20 Antibody |
| RO5185426 | Malignant Melanoma | Chemotherapy | B-raf Kinase Inhibitor |
| RS7 | Other cancer | Radiation | Radioisotope conjugated to monoclonal antibody |
| RTA744 | Malignant CNS tumors | Chemotherapy | Topoisomerase II inhibitor |
| Radiolabeled J591 | Prostate cancer | Radiation | Radioisotope conjugated to monoclonal antibody |
| Raloxifene | Breast cancer | Hormones and hormonal mechanisms | SERM |
| Rebeccamycin | Gall Bladder;Cholangiocarcinoma;Brain;Breast;Colorectal;Kidney;Liver;Small Cell Lung Cancer (SCLC) | Chemotherapy | Antineoplastic antibiotic |
| Recombinant Soluble Human CD4 | AIDS;Opportunistic infection | Biologic therapy (BRM, immunotherapy) | Human protein |

Fig. 27F

| Name | Primary Site | Category | Sub-category |
|---|---|---|---|
| Recombinant Soluble PSMA Vaccine | Pancreatic caner | Biologic therapy (BRM, immunotherapy) | Immunotherapy active |
| Recombinant Tumor Necrosis Factor | Melanomas; sarcomas | Biologic therapy (BRM, immunotherapy) | Human protein |
| Regorafenib | Breast;Colorectal;Liver | Chemotherapy | Multi-kinase inhibitor |
| Relacatib | Bone metastases | Chemotherapy | Cytostatic agent--cathepsin-K inhibitor |
| Rencarex | Kidney cancer | Biologic therapy (BRM, immunotherapy) | Monoclonal antibody |
| Reolysin | Brain cancer;Ovary;Pancreatic | Chemotherapy | Cytotoxic human reovirus |
| Resmycin | Sarcoma | Chemotherapy | Antitumor antibiotic |
| Retrovector | Skin cancer | Biologic therapy (BRM, immunotherapy) | Exogenous cytokine |
| Ribociclib | Breast | Chemotherapy | CDK 4/6 Inhibitor |
| Rindopepimut | Brain | Biologic therapy (BRM, immunotherapy) | Vaccination |
| Rituximab | Leukemia;NHL | Biologic therapy (BRM, immunotherapy) | Cytostatic monoclonal antibody |
| Roscovitine | Acute myelogenous leukemia (AML);B-cell lymphomas;Non small cell lung cancer (NSCLC) | Chemotherapy | CDK inhibitor- see remarks |
| Rozlytrek | Solid tumors | Chemotherapy | Tyrosine kinase inhibitor |
| Rubitecan | Brain;breast;cervical;colorectal;gastric;head & neck;leukemia;liver;lung;lymphoma;melanoma;ovarian;pancreatic;prostate cancer | Chemotherapy | Topoisomerase inhibitor |
| Rubraca | Ovary | Chemotherapy | PARP (poly-ADP-ribose polymerase) |
| Ruxience | Multiple leukemias/lymphomas | Biologic therapy (BRM, immunotherapy) | Biosimilar |
| Ruxolitinib | Bone marrow (myelofibrosis) | Chemotherapy | JAK 1 and JAK 2 (Janus Kinase Inhibitor) |
| SB-1518 | AML;CML;MDS | Chemotherapy | JAK-2 inhibitor |
| SB249553 | Lung;melanoma;skin cancer | Biologic therapy (BRM, immunotherapy) | Immunotherapy active |
| SB408075 | Colorectal;lung cancer | Chemotherapy | Cytotoxic chemotherapy conjugated to monoclonal antibody |
| SC-1 | Gastric cancer | Chemotherapy | Cytostatic agent--apoptosis inducer |
| SCH-900776 | ALL;AML;CML;Hodgkin;NHL | Chemotherapy | Cell cycle inhibitor |
| SCIO-469 | Multiple myeloma | Chemotherapy | Cytostatic agent--protein kinase inhibitor |
| SDX-101 | Leukemia | Chemotherapy | Cytostatic agent--apoptosis inducer |
| SERM III | Breast;endometrial cancer | Hormones and hormonal mechanisms | Selective estrogen receptor modulator (SERM) |
| SGN 17/19 | Skin cancer | Chemotherapy | Alkylating agent |
| SGN-10 | Breast;colorectal;lung;ovarian;pancreatic;prostate cancer | Chemotherapy | Immunotoxin conjugated with monoclonal antibody |

Fig. 27G

| Name | Primary Site | Category | Sub-category |
|---|---|---|---|
| SGN-15 | Breast;colorectal;lung;ovarian;prostate cancer | Chemotherapy | Antitumor antibiotic conjugated to monoclonal Antibody |
| SGN-25 | Prostate cancer | Chemotherapy | Antimitotic agent conjugated to monoclonal Antibody |
| SGN-30 | ALCL;Lymphoma | Chemotherapy | Cytostatic agent--apoptosis inducer |
| SJG-136 | Solid tumors | Chemotherapy | Alkylating agent |
| SKI-606 | AML | Chemotherapy | Protein kinase inhibitor |
| SL-11047 | Lymphoma | Chemotherapy | Antimetabolite |
| SNS-595 | NSC lung | Chemotherapy | Cytotoxic agent--S phase apoptosis initiator |
| SP1049C | Head & neck cancer | Chemotherapy | Anthracycline |
| SPD424 | Prostate cancer | Hormones and hormonal mechanisms | LHRH agonist |
| SR 271425 | Other cancer | Chemotherapy | Cytolytic agent |
| SR27897 | Pancreatic cancer | Chemotherapy | Protein kinase agonist |
| SR48692 | Pancreatic;prostate cancer | Chemotherapy | Cytotoxic neurotensin antagonist |
| SSI(dsFv)-PE38 | Cervical;head & neck;lung;ovarian cancer | Chemotherapy | Immunotoxin conjugated with monoclonal antibody |
| STA-4783 | Melanoma | Chemotherapy | Cytostatic agent--apoptosis inducer |
| STA-9090 | GIST;Leukemia;MDS;solid tumors | Chemotherapy | HSP 90 inhibitor |
| SU5415 | Colorectal cancer | Chemotherapy | Angiogenesis inhibitor |
| SU6668 | Colorectal;other cancer | Chemotherapy | Angiogenesis inhibitor |
| Samarium SM 153 | Bone mets | Radiation | Radioisotope |
| SarCNU | Colon cancer | Chemotherapy | Alkylating agent |
| Saracatinib | Breast;CML;Pancreas;Stomach | Chemotherapy | Cytostatic agent--dual Src/Abl kinase inhibitor |
| Satraplatin | Lung;ovarian;prostate cancer | Chemotherapy | Miscellaneous agent;Platinum compound |
| Semaxanib | Breast;colorectal;lung cancer;other cancer;sarcoma | Chemotherapy | Angiogenesis inhibitor |
| Simvastatin | Hepatoma | Chemotherapy | Antiangiogenic agent;Cytostatic agent--Ras inhibitor |
| Skeletal Targeted Radiotherapy | Multiple myeloma;sarcoma | Radiation | Radioisotope |
| Soblidotin | Lung;soft tissue | Chemotherapy | Tubuline inhibitor |
| Sodium Phenylacetate | Glioma | Differentiation inducing agent | Promotes ammonia excretion |
| Sodium Phosphate P 32 | Polycythaemia vera, chronic myeloid and chronic lymphocytic leukemia | Radiation | Radioisotope |
| Sodium stibogluconate | Melanoma | Chemotherapy | Cytostatic agent |
| Sorafenib | Kidney;Leukemia;colon;liver;lymphoma;other cancer;prostate;thyroid | Chemotherapy | Targeted therapy--raf kinase inhibitor |
| Squalamine | Brain;lung;ovarian;prostate cancer | Chemotherapy | Angiogenesis inhibitor |

Fig. 27H

| Name | Primary Site | Category | Sub-category |
|---|---|---|---|
| Stanolone | Breast cancer | Hormones and hormonal mechanisms | Anabolic steroid |
| Stilboestrol Dipropionate | Breast;prostate cancer | Hormones and hormonal mechanisms | Estrogen |
| Streptozocin | Panceatic islet cell carcinoma | Chemotherapy | Alkylating agent |
| Strontium | Pancreatic metastases | Radiation | Radioisotope |
| Sunitinib maleate | breast;GIST;pancreas;Renal cell;stomach;Urothelial ca | Chemotherapy | Angiogenesis inhibitor |
| Suramin Sodium | Prostate cancer | Chemotherapy | Growth factor inhibitor |
| T-Cell Therapy | Other cancer | Biologic therapy (BRM, immunotherapy) | Cellular therapy |
| T138067 | Breast;colorectal;liver;lung cancer | Chemotherapy | Cytostatic agent--mitotic inhibitor |
| T900607 | Gastric;liver;other cancer | Chemotherapy | Cytostatic agent--mitotic inhibitor |
| T904064 | Breast;head & neck;lung;sarcoma;skin cancer | Chemotherapy | Antifolate |
| TA-HPV | Cervical cancer | Biologic therapy (BRM, immunotherapy) | Vaccine |
| TBC-CEA | Colorectal;lung cancer | Biologic therapy (BRM, immunotherapy) | Immunotherapy active |
| TGF-Beta | Brain cancer | Biologic therapy (BRM, immunotherapy) | Vaccine |
| TH-302 | lung;pancreas;prostate;Soft tissue | Chemotherapy | Hypoxia-activated prodrug |
| TL-139 | Lung;other cancer | Chemotherapy | Taxane |
| TLC ELL-12 | Breast;lung and prostate cancers;melanoma | Chemotherapy | Apoptosis inducer |
| TNF alpha gene therapy | Breast cancer | Biologic therapy (BRM, immunotherapy) | Gene therapy |
| TNFerade | Esophageal;gastric;pancreatic cancer;sarcoma | Biologic therapy (BRM, immunotherapy) | Gene therapy |
| TNP-470 | Other cancer | Chemotherapy | Cytostatic agent--antiangiogenesis agent |
| TOCOSOL | Bladder;breast;colorectal;lung;ovarian cancers | Chemotherapy | Taxane |
| TP-38 | Brain cancer | Chemotherapy | Immunotoxin conjugated with protein |
| TRAIL-R1 MoAb | Other cancer | Chemotherapy | Apoptosis inducer |
| TRAIL-R2 MoAb | Other cancer | Chemotherapy | Apoptosis inducer |
| TRAIL/AP02 Ligand | NSCLC;other cancer | Chemotherapy | Apoptosis inducer |
| TRIAL Receptor 1 Mab | Other cancer | Chemotherapy | Apoptosis inducer |
| TRP-2:180-188 Peptide Vaccine | Skin cancer | Biologic therapy (BRM, immunotherapy) | Vaccine |
| Tagraxofusp-erzs | Blastic plasmacytoid dendritic cell neoplasm (BPDCN) | Biologic therapy (BRM, immunotherapy) | Human protein-fused diptheria toxin |
| Tagrisso | Lung | Chemotherapy | EGFR-TKI inhibitor |
| Talabostat | brain;Lung;melanoma;pancreas | Chemotherapy | Cytotoxic agent--enzyme inhibitor |
| Talactoferrin | kidney, other sites | Biologic therapy (BRM, immunotherapy) | oral recombinant human lactoferrin |

Fig. 27I

| Name | Primary Site | Category | Sub-category |
|---|---|---|---|
| Talampanel | Brain gliomas | Chemotherapy | Cytostatic agent--AMPA receptor antagonist |
| Talazoparib | Breast | Chemotherapy | PARP inhibitor |
| Tamoxifen | Breast | Hormones and hormonal mechanisms | Nonsteroidal antiestrogen |
| Tanespimycin | advanced solid tumors;CLL;NHL;prolymphocytic leukemia | Chemotherapy | Targeted therapy--heat shock protein 90 inhibitor |
| Tapet-CD | Other cancer | Chemotherapy | Cytotoxic agent conjugated to weakened bacteria |
| Tavokinogene telsaplasmid | Melanoma | Biologic therapy (BRM, immunotherapy) | DNA plasmid |
| Taxane IV | Brain;lung cancer | Chemotherapy | Taxane |
| Taxoprexin | Breast;colorectal;gastric;kidney;lung;pancreatic;prostate;skin cancer | Chemotherapy | Taxane |
| Taxotere and Calcitriol | Prostate cancer | Chemotherapy | combination chemo |
| Taxotere, Adriamycin & Cytoxan | Breast cancer | Chemotherapy | combination chemo |
| Tazemetostat | Malignant rhabdoid tumors | Chemotherapy | EZH2 inhibitor |
| Tazverik | Soft tissue | Chemotherapy | SAM inhibitor |
| Tegafur | Gastric and colorectal cancers | Chemotherapy | Antimetabolite |
| Telcyta | Breast;colorectal;lung;ovarian cancer | Chemotherapy | Glutathione analog |
| Telomerase Cancer Vaccine | Pancreatic caner | Biologic therapy (BRM, immunotherapy) | Immuntherapy active |
| Temozolomide | Lung;other cancer | Chemotherapy | Alkylating agent |
| Tempostatin | Bladder cancer | Chemotherapy | Cytostatic agent--extracellular matrix protein inhibitor |
| Temsirolimus | Kidney;Mantle cell lymphoma;breast;colorectal;lung;ovarian;pancreatic;prostate cancer;sarcoma | Chemotherapy | Cytostatic agent--antiangiogenic agent;mTOR inhibitor |
| Teniposide | Pediatric refractory ALL | Chemotherapy | Topoisomerase inhibitor |
| Terameprocol | Gliomas;solid tumors | Chemotherapy | Cytostatic agent--apoptosis inducer |
| Teroxirone | Lung | Chemotherapy | Alkylating agent |
| Testolactone | Breast cancer | Hormones and hormonal mechanisms | Androgen |
| Testosterone Cypionate | Breast cancer | Hormones and hormonal mechanisms | Androgen |
| Testosterone Propionate | Breast cancer | Hormones and hormonal mechanisms | Androgen |
| Tetrahydrouridine | Advanced solid tumors | Chemotherapy | Antimetabolite |
| Tetraplatin | Multiple sites | Chemotherapy | Miscellaneous agent |
| Tetrathiomolydate | Breast;esophageal | Chemotherapy | Antiangiogenic agent |
| Teverlix | Prostate cancer | Hormones and hormonal mechanisms | LHRH antagonist |
| Tezacitabine | Colorectal;leukemia;lung;other cancer;ovarian | Chemotherapy | Antimetabolite |
| Thalidomide | Brain;kidney;leukemia;liver;lung;lymphoma;multiple | Biologic therapy (BRM, immunotherapy) | Antiangiogenic agent for most indications |

Fig. 27J

| Name | Primary Site | Category | Sub-category |
|---|---|---|---|
| | myeloma;prostate;skin cancer | | |
| TheraFab | Lung cancer | Radiation | Radioisotope conjugated to monoclonal antibody |
| Therasphere | Liver | Radiation | Radioisotope |
| Theratope Vaccine | Breast;colorectal cancer | Biologic therapy (BRM, immunotherapy) | Immunotherapy active |
| Theratope and Detox-B | Adenocarcinoma | Biologic therapy (BRM, immunotherapy) | combination immunotherapy |
| Therex | Breast cancer | Biologic therapy (BRM, immunotherapy) | Immunomodulator |
| Thioguanine | Acute non-lymphocytic leukemia | Chemotherapy | Antimetabolite |
| Thiotepa | Multiple sites | Chemotherapy | Alkylating agent |
| Thymitaq | Colorectal;liver;lung;pancreatic cancer | Chemotherapy | Antimetabolite |
| Thymosin alpha 1 | Breast;liver;skin cancer | Biologic therapy (BRM, immunotherapy) | Peptide fragment |
| Thymosin fraction 5 | Hepatocellular carcinoma | Biologic therapy (BRM, immunotherapy);AIDS drug | Adrenocorticotropic hormone activator |
| Tiazofurin | Leukemia;multiple myeloma | Chemotherapy | Antimitotic |
| Ticilimumab | Melanoma | Biologic therapy (BRM, immunotherapy) | Monoclonal antibody |
| Tigestol | Prostate cancer | Hormones and hormonal mechanisms | Progestin |
| Tipifarnib | Breast;cervical;colorectal;leukemia;lung;multiple myeloma;pancreatic cancer | Chemotherapy | Cytostatic agent--farnesyl transferase inhibitor |
| Tisagenlecleucel | Large B-cell lymphoma, ALL | Biologic therapy (BRM, immunotherapy) | Gene therapy |
| Tivantinib | hepatocellular;lung;solid tumors | Chemotherapy | Tyrosine kinase inhibitor |
| Toca 511 | Brain | Biologic therapy (BRM, immunotherapy) | Prodrug activating enzyme-encoding vector |
| Tocladesine bC1.cAMP | Colon cancer | Chemotherapy | Cytostatic agent--protein kinase inhibitor |
| Tomudex | Colorectal;other cancer | Chemotherapy | Antimetabolite |
| Topotecan | cervix;Colorectal;leukemia;lung;ovarian cancer;small cell lung | Chemotherapy | Topoisomerase inhibitor |
| Toremifene Citrate | Breast | Hormones and hormonal mechanisms | Antiestrogen |
| Trabectedin | Breast;Ewing's family of tumors;endometrial;leiomyosarcoma;melanoma;other;ovarian cancer;sarcoma;soft tissue sarcoma | Chemotherapy | Natural product |
| Trametinib | Melanoma;Thyroid | Chemotherapy | MEK inhibitor |
| Trans-Retinoic Acid | Leukemia;skin cancer | Differentiation inducing agent | Retnioid |
| TransMID-107R | Brain cancer | Chemotherapy | Immunotoxin conjugated with transferin |
| Trastuzumab | Breast;colorectal;lung;ovarian;pancreatic;prostate cancer | Biologic therapy (BRM, immunotherapy) | Targeted therapy--epidermal growth factor receptor |

Fig. 27K

| Name | Primary Site | Category | Sub-category |
|---|---|---|---|
| Trastuzumab Deruxtecan | Breast | Biologic therapy (BRM, immunotherapy) | antibody drug-conjugate;monoclonal antibody |
| Trastuzumab-DM1 | Breast cancer | Biologic therapy (BRM, immunotherapy) | Conjugate |
| Trazimera | Breast | Biologic therapy (BRM, immunotherapy) | Biosimilar |
| Treosulfan | ALL;AML;MDS | Chemotherapy | Alkylating agent |
| Tretinoin | Acute Promyelocytic leukemia (APL);AIDS;head & neck cancer;Opportunistic infection | Differentiation inducing agent | Retnioid |
| TriAb (anti-idiotype antibody) | Breast;lung;ovarian cancer | Biologic therapy (BRM, immunotherapy) | Immunotherapy active |
| TriGem | Lung;skin cancer | Biologic therapy (BRM, immunotherapy) | Vaccine |
| Triapine | biliary;Breast;colorectal;gall bladder;head & neck;leukemia;lung;prostate;skin cancer | Chemotherapy | Cytostatic agent--ribonucleotide reductase inhibitor |
| Triciribine | Breast | Chemotherapy | Cytostatic agent--protein kinase inhibitor |
| Trimetrexate Glucuronate | Breast;colorectal;gastric;lung;prostate cancer | Chemotherapy;AIDS drug | Antimetabolite |
| Trioxifene Mesylate | Breast cancer | Hormones and hormonal mechanisms | Anti-estrogen |
| Triptorelin | Ovarian;prostate cancers | Hormones and hormonal mechanisms | LHRH agonist |
| Trisenox | Cervical;kidney;leukemia;multiple myeloma;neuroblastoma;prostate cancer | Chemotherapy | Miscellaneous agent |
| TroVax | Kidney | Biologic therapy (BRM, immunotherapy) | Vaccine |
| Troxacitabine | acute myelogenous leukemia;Breast;colorectal;kidney;lung;ovarian;pancreatic;prostate;skin cancer | Chemotherapy | Antimetabolite |
| Truxima | B-cell non-Hodgkin's lymphoma (NHL) | Biologic therapy (BRM, immunotherapy) | Biosimilar for rituximab |
| Tumor Necrosis Factor-alpha | Skin cancer | Biologic therapy (BRM, immunotherapy) | Human protein |
| Tumor necrosis factor | Melanomas; sarcomas | Biologic therapy (BRM, immunotherapy) | Human protein |
| Tumor primed Anti-CD3 | Renal cell carcinoma | Biologic therapy (BRM, immunotherapy) | Human protein |
| Tumor specific Fusion Vaccine | Breast cancer | Biologic therapy (BRM, immunotherapy) | Immunotherapy active |
| Type 1 5-alpha Reductase Inhibitor | Prostate cancer | Chemotherapy | Cytostatic agent--alpha reductase inhibitor |
| Tyrosinase 368-376 (370D) Peptide Vaccine | Skin cancer | Biologic therapy (BRM, immunotherapy) | Immunotherapy active |
| UCN-01 | advanced solid tumors;Pancreatic cancer | Chemotherapy | Protein kinase inhibitor |

Fig. 27L

| Name | Primary Site | Category | Sub-category |
|---|---|---|---|
| Ubenimex | Bladder cancer | Biologic therapy (BRM, immunotherapy) | Immunomodulator |
| Unituxin | Brain | Biologic therapy (BRM, immunotherapy) | monoclonal antibody |
| Uracil Mustard | chronic lymphocytic leukemia, chronic myelogenous leukemia, mycosis fungoides, and non-Hodgkin's lymphoma | Chemotherapy | Alkylating agent |
| VAL-083 | Brain | Other therapy | DNA-crosslinker |
| VB2-011 | Other cancer | Chemotherapy | Immunotoxin conjugated to protein |
| VHL Peptide Vaccine | Kidney cancer | Biologic therapy (BRM, immunotherapy) | Immuntherapy active |
| Vaccine for helicobacter pylori | Gastric cancer | Biologic therapy (BRM, immunotherapy) | Immunotherapy active |
| Vaccinia TRICOM | Colorectal | Biologic therapy (BRM, immunotherapy) | Vaccine |
| Vaccinia-CEA (vaccine 180KD) | Breast;gastric;lung cancer | Biologic therapy (BRM, immunotherapy) | Immunotherapy active |
| Vaccinia-MUC-1 Vaccine | Breast;pancreatic cancer | Biologic therapy (BRM, immunotherapy) | Immuontherapy active |
| Valproic acid | AML;CLL;lymphocytic lymphoma | Chemotherapy | Cytostatic agent--histone deacetylation inhibitor |
| Valrubicin | Bladder cancer | Chemotherapy | Antitumor antibiotic |
| Vamidex | Colorectal;lung;other cancer;ovarian;pancreatic cancer | Chemotherapy | Antimetabolite;thymidylate synthase inhibitor |
| Vandetanib | Breast;cervical;endometrial;NSC lung cancer;ovarian;prostate;Thyroid | Chemotherapy | Angiogenesis inhibitor |
| Vatalanib | brain;Colorectal;Myeloma;other cancer | Chemotherapy | Cytostatic agent--antiangiogenesis agent |
| Vaxid | Lymphoma | Biologic therapy (BRM, immunotherapy) | DNA vaccine |
| Vemurafenib | Melanoma, Erdheim-Chester Disease (ECD) | Chemotherapy | Kinase Inhibitor |
| Venclexta | Multiple leukemias/lymphomas | Chemotherapy | Cl-2 inhibitor |
| Vendexta | Chronic lymphocytic leukemia or small lymphocytic lymphoma | Chemotherapy | BCL2 Inhibitor |
| Verteporfin | Skin cancer | Other therapy | Ocular drug for macular degeneration |
| Vidaza | Myelodysplastic syndromes | Chemotherapy | Antimetabolite |
| Vinblastine | Multiple sites | Chemotherapy | Plant alkaloid |
| Vincristine | ALL, Hodgkin's lymphoma, non-Hodgkin's lymphoma, neuroblastoma, rhabomyosarcoma, and Wilm's tumor | Chemotherapy | Plant alkyloid--antimetabolite |
| Vindesine | Multiple sites | Chemotherapy | Plant alkyloid |
| Vinflunine | Bladder;breast;lung;other | Chemotherapy | Plant alkyloid |
| Vinorelbine | Breast;lung cancer | Chemotherapy | Plant alkyloid |

Fig. 27M

| Name | Primary Site | Category | Sub-category |
|---|---|---|---|
| Virulizin | Pancreatic cancer | Biologic therapy (BRM, immunotherapy) | Immune system activator |
| Vismodegib | Basal cell carcinoma, skin | Chemotherapy | Hedgehog signaling pathway targeting agent;cyclopamine-competitive antagonist othe the smoothened receptor (SMO) |
| Vitaxin | Colorectal;other cancer | Chemotherapy | Angiogenesis inhibitor |
| Volasertib | AML trials;Ovarian trials;Solid tumors trials | Chemotherapy | PLK Inhibitor |
| Vorinostat | advanced solid tumors;colorectal;CTCL;Leukemia;other cancer | Chemotherapy | Cytostatic agent--histone deacetylase (HDAC) inhibitor |
| Vyxeos | treatment-related AML or AML with myelodysplasia-related changes (AML-MRC) | Chemotherapy | DNA synthesis inhibitors |
| WT-1 peptide vaccine | Pleura | Biologic therapy (BRM, immunotherapy) | Vaccine |
| WX-UK1 | Gastric;ovarian;pancreatic cancer | Chemotherapy | Cytostatic agent--Urokinase-type Plasminogen Activator (uPA) inhibitor |
| XIAP antisense | AML | Chemotherapy | Targeted therapy--antisense |
| XK-469 | Other cancer | Chemotherapy | Topoisomerase inhibitor |
| XK469 | advanced solid tumors;Lymphoma | Chemotherapy | Topoisomerase II inhibitor |
| XL-139 | GE and esophageal adenocarcinoma;inoperable stomach;mets gastric;multiiple myeloma;SCLC | Chemotherapy | SMO inhibitor |
| XL-147 | Advanced Endometrium;lymphoma;Mets breast;NSCLC;ovarian | Chemotherapy | P13K inhibitor |
| XL-184 | GBM;NSCLC;solid tumors;Thyroid | Chemotherapy | RTK inhibitor |
| XL-281 | colorectal;melanoma;NSC;papillary thyroid | Chemotherapy | RAF kinase inhibitor |
| XL-765 | breast;Malignant glioma;NSCLC | Chemotherapy | P13K inhibitor |
| XL-888 | Failed first course;melanoma;mets;NSCLC;or unresectable: breast | Chemotherapy | HSP90 inhibitor |
| Xalkori | Non Small Cell Lung Cancer (NSCLC) | Chemotherapy | Kinase inhibitor;Targeted therapy anaplastic lymphoma kinase |
| Xcellerate | Kidney;prostate cancer | Biologic therapy (BRM, immunotherapy) | T-cell activator |
| Xeloda | Breast, colorectal | Chemotherapy | DNA synthesis inhibitors |
| Xofigo | Metastatic prostate cancer | Radiation | Alpha-particle emitting radio-theraputic drug |
| Xpovio | Relapsed or refractory multiple myeloma (RRMM) | Chemotherapy | CRM1 Inhibitor |
| Xyotax | Breast;colorectal;lung;ovarian cancer | Chemotherapy | Taxane |

Fig. 27N

| Name | Primary Site | Category | Sub-category |
|---|---|---|---|
| Y-CEA-Cide | Pancreatic cancer | Radiation | Radioisotope conjugated to monoclonal antibody |
| YM598 | Pancreatic caner | Chemotherapy | Angiogenesis inhibitor |
| YMB-1003MAb | Colorectal cancer | Biologic therapy (BRM, immunotherapy) | Monoclonal antibody |
| Yescarta | Large B-cell lymphoma | Biologic therapy (BRM, immunotherapy) | CAR T cell therapy |
| ZD0473 | Lung;ovarian Cancer | Chemotherapy | Miscellaneous agent--platinum compound |
| ZD6126 | Breast;cervical;endometrial; other cancer;ovarian | Chemotherapy | Angiogenesis inhibitor |
| ZK Epothilone | breast;Prostate | Chemotherapy | Antimitotic agent |
| ZYC300 | Breast;colon;kidney;ovary;prostate | Biologic therapy (BRM, immunotherapy) | Immunotherapy |
| Zaltrap | Colorectal | Chemotherapy | Angiogenesis inhibitor |
| Zalutumumab | H&N;NSCLC | Chemotherapy | Cytostatic agent--anti-EGFR |
| Zamyl | Leukemia | Biologic therapy (BRM, immunotherapy) | Anti-CD33 antibody |
| Zanolimumab | Cutaneous T-cell lymphoma;mycosis fungoides | Biologic therapy (BRM, immunotherapy) | Monoclonal antibody |
| Zanubrutinib | Mantle cell lymphoma (MCL) | Chemotherapy | Bruton's tyrosine kinase inhibitor |
| Zeniplatin | Melanoma; renal cancer | Chemotherapy | Miscellaneous agent |
| Zevalin | Lymphoma | Radiation | Radiolabled monoclonal antibody |
| Zinostatin | Hepatocellular carcinoma | Chemotherapy | Antitumor antibiotic |
| Zirabev | Colorectal, lung, glioblastoma, kidney, cervical, and ovarian cancer | Biologic therapy (BRM, immunotherapy) | biosimilar |
| Zorubicin | Acute leukemias | Chemotherapy | Topoisomerase inhibitor |
| Zydelig | CLL | Chemotherapy | PI3K delta inhibitor |
| Zykadia | Lung | Chemotherapy | ALK tyrosine kinase inhibitor |
| anti-CD72 | Leukemia | Biologic therapy (BRM, immunotherapy) | Anti-CD72 antibody |
| anti-Tac(Fv)-PE38 (immunotoxin) | Leukemia | Biologic therapy (BRM, immunotherapy) | Interleukin 2 receptor-targeted antibody |
| cAC10-vcMMAE(4) | Hodgkin lymphoma | Chemotherapy | Cytotoxic agent--conjugate |
| dabrafenib | Melanoma;Lung;Thyroid | Chemotherapy | BRAF inhibitor |
| diazooxonorleucine | Skin cancer | Chemotherapy | Antiviral |
| gp100 DNA Vaccine | Skin cancer | Biologic therapy (BRM, immunotherapy) | Immunotherapy active |
| gp100 Peptide Vaccine | Skin cancer | Biologic therapy (BRM, immunotherapy) | Immunotherapy active |
| gp100 Plasmid Vector in Gold Particles | Skin cancer | Biologic therapy (BRM, immunotherapy) | Therapeutic vaccine |
| hIL13-PE38QQR (ligand targeted toxin) | Kidney cancer | Chemotherapy | Immunotoxin |
| hR3 | Head & neck cancer | Biologic therapy (BRM, immunotherapy) | Cytostatic agent--anti-EGFR |
| p53 Tumor Suppressor Gene | Head & neck;liver;ovarian cancer | Biologic therapy (BRM, immunotherapy) | Gene therapy |
| pivaloyloxymethylbutyrate | Liver;lung cancer | Chemotherapy | Cytostatic agentclinical trial halted due to safety issues |

Fig. 27O

| Name | Primary Site | Category | Sub-category |
|---|---|---|---|
| rF-MART-1 | Skin cancer | Biologic therapy (BRM, immunotherapy) | Human protein gene-carrying virus |
| rF-Mgp100 | Skin cancer | Biologic therapy (BRM, immunotherapy) | Human protein gene-carrying virus |
| rF-Tyrosine Vaccine | Skin cancer | Biologic therapy (BRM, immunotherapy) | Immunotherapy active |
| rF-gp100 | Skin cancer | Biologic therapy (BRM, immunotherapy) | Immunotherapy active |
| rV-GP100 | Skin cancer | Biologic therapy (BRM, immunotherapy) | Immunotherapy active |
| rV-MART-1 | Skin cancer | Biologic therapy (BRM, immunotherapy) | Immunotherapy active |
| recMAGE-A3+AS15 | Melanoma;NSCLC | Biologic therapy (BRM, immunotherapy) | Antigen-specific immunotherapy |
| sibrotuzumab | Breast;colorectal;lung;other cancer;pancreatic | Chemotherapy | Cytostatic agent--monoclonal antibody |
| tgDCC-E1A | Head & neck;ovarian cancer | Biologic therapy (BRM, immunotherapy) | Gene therapy |

Fig. 27P

| Drug | Primary Site | Category | Pathway |
|---|---|---|---|
| Abemaciclib | Breast | CDK4/6 inhibitor | Cell cycle |
| Abiraterone Acetate | Prostate | Androgen signaling inhibitor | Androgen signaling |
| Acalabrutinib | Leukemia, lymphoma | Bruton's tyrosine kinase inhibitor | RTK/RAS and PI3K |
| Ado-Trastuzumab Emtansine | Breast | HER2 inhibitor | RTK/RAS |
| Afatinib Dimaleate | Lung | Tyrosine kinase inhibitor | RTK/RAS |
| Alectinib | Lung | ALK | RTK/RAS |
| Alemtuzumab | Leukemia | Monoclonal antibody against CD52 | Immunotherapy |
| Alitretinoin | Skin, soft tissue sarcoma | Retinoid receptor activator | Retinoid signaling |
| Alpelisib | Breast | PI3K inhibitor | PI3K |
| Anastrozole | Breast | Aromatase inhibitor | Estrogen signaling |
| Apalutamide | Prostate | Androgen receptor inhibitor | Androgen signaling |
| Atezolizumab | Bladder, breast, lung | Monoclonal antibody against PD-L1 | Immunotherapy |
| Avapritinib | Gastrointestinal stromal tumor | PDGFRA/Both inhibitor | RTK/RAS |
| Avelumab | Kidney, skin, bladder, endocrine/neuroendocrine | Monoclonal antibody against PD-L1 | Immunotherapy |
| Axitinib | Kidney | VEGFR inhibitor | VEGF signaling |
| Belinostat | Lymphoma | HDAC inhibitor | Histone acetylation |
| Bevacizumab | Brain, cervical, kidney, colorectal, lung, ovarian epithelial/fallopian tube/primary peritoneal | Monoclonal antibody against VEGF | VEGF signaling |
| Bexarotene | Lymphoma | Retinoid receptor activator | Retinoid signaling |
| Binimetinib | Skin, soft tissue sarcoma | MEK inhibitor | RTK/RAS |
| Blinatumomab | Leukemia | Monoclonal antibody targetting CD3 and CD19 | Immunotherapy |

Fig. 27Q

| Drug | Primary Site | Category | Pathway |
|---|---|---|---|
| Bortezomib | Lymphoma, multiple myeloma | 26S proteosome inhibitor | Protein degradation |
| Bosutinib | Leukemia | Bcr-Abl tyrosine-kinase inhibitor | RTK/RAS and PI3K |
| Brigatinib | Lung | EGFR inhibitor | RTK/RAS |
| Cabozantinib | Thyroid, kidney, liver | Tyrosine kinase inhibitor | RTK/RAS |
| Carfilzomib | Multiple myeloma | 20S proteasome inhibitor | Protein degradation |
| Cemiplimab-Rwlc | Skin | Monoclonal antibody against PD-1 | Immunotherapy |
| Ceritinib | Lung | ALK inhibitor | RTK/RAS |
| Cetuximab | Colorectal, head & neck | Monoclonal antibody against EGFR | RTK/RAS |
| Cobimetinib | Skin | MEK inhibitor | RTK/RAS |
| Copanlisib Hydrochloride | Lymphoma | PI3K inhibitor | PI3K |
| Crizotinib | Lung | MET inhibitor | RTK/RAS |
| Dabrafenib | Lung, skin, thyroid | BRAF inhibitor | RTK/RAS |
| Dacomitinib | Lung | EGFR inhibitor | RTK/RAS |
| Daratumumab | Multiple myeloma | Monoclonal antibody against CD38 | Immunotherapy |
| Darolutamide | Prostate | Androgen receptor inhibitor | Androgen signaling |
| Dasatinib | Leukemia | BCr-Abl tyrosine-kinase inhibitor | RTK/RAS and PI3K |
| Denosumab | Giant cell tumor of the bone | Monoclonal antibody against RANKL | PI3K and MEK |
| Durvalumab | Lung, bladder | Monoclonal antibody against PD-L1 | Immunotherapy |
| Duvelisib | Leukemia, lymphoma | PI3K inhibitor | PI3K |
| Elotuzumab | Multiple myeloma | Monoclonal antibody against SLAMF7 | Immunotherapy |
| Enasidenib Mesylate | Leukemia | Enzymatic inhibitor of IDH2 | Krebs cycle |
| Encorafenib | Skin | RAF inhibitor | RTK/RAS |
| Enfortumab Vedotin-Ejfv | Bladder | Antibody-drug conjugate against PD-1 | Immunotherapy |

Fig. 27R

| Drug | Primary Site | Category | Pathway |
|---|---|---|---|
| Entrectinib | Lung, solid tumors | Tyrosine kinase inhibitor | RTK/RAS |
| Enzalutamide | Prostate | Androgen signaling inhibitor | Androgen signaling |
| Erdafitinib | Bladder | Tyrosine kinase inhibitor | RTK/RAS |
| Erlotinib | Lung, pancreatic | Tyrosine kinase inhibitor | RTK/RAS |
| Everolimus | Pancreatic, brain, breast, kidney | mTORC1 inhibtor | PI3K |
| Exemestane | Breast | Aromatase inhibitor | Estrogen signaling |
| Fam-Trastuzumab Deruxtecan-Nxki | Breast | Monoclonal antibody against ERBB2 conjugated to topoisomerase inhibitor | RTK/RAS |
| Fedratinib Hydrochloride | Myelodysplastic/myeloproliferative disorders | JAK2 inhibitor | RTK/RAS |
| Fulvestrant | Breast, myelodysplastic/myeloproliferative disorders | Estrogen inhibitor | Estrogen signaling |
| Gefitinib | Lung | EGFR inhibitor | RTK/RAS |
| Gilteritinib | Leukemia | AXL inhibitor | RTK/RAS |
| Glasdegib Maleate | Leukemia | Hedgehog inhibitor | Hedgehog signaling |
| Ibrutinib | Leukemia, lymphoma | Bruton's tyrosine kinase inhibitor | RTK/RAS and PI3K |
| Idelalisib | Leukemia, lymphoma | PI3K inhibitor | PI3K |
| Imatinib Mesylate | Dermatofibrosarcoma protuberans, gastrointestinal stromal tumor, leukemia, myelodysplastic/myeloproliferative disorders, systemic mastocytosis | PDGFR inhibitor | RTK/RAS |
| Ipilimumab | Kidney, liver, skin, colorectal | Monoclonal antibody against CTLA4 | Immunotherapy |

Fig. 27S

| Drug | Primary Site | Category | Pathway |
|---|---|---|---|
| Ivosidenib | Leukemia | Isocitrate dehydrogenase-1 inhibitor | Krebs cycle |
| Ixazomib Citrate | Multiple myeloma | Proteosome inhibitor | Proteasome |
| Lapatinib | Endocrine/neuroendocrine tumors, breast | HER2 and EGFR inhibitor | RTK/RAS |
| Larotrectinib Sulfate | Solid tumors with an NTRK gene fusion | TrkA, TrkB, and TrkC receptor inhibitor | RTK/RAS |
| Lenvatinib Mesylate | Thyroid, kidney, liver, endometrial | VEGFR inhibitor | VEGF |
| Letrozole | Letrozole | Aromatase inhibitor | Estrogen signaling |
| Lorlatinib | Lung | ALK and ROS1 inhibitor | RTK/RAS |
| Midostaurin | Leukemia, systemic mastocytosis | FLT3 inhibitor | RTK/RAS |
| Mogamulizumab-Kpkc | Lymphoma | Monoclonal antibody against CCR4 | Immunotherapy |
| Necitumumab | Lung | Monoclonal antibody against EGFR | RTK/RAS |
| Neratinib Maleate | Breast | HER2, HER4, and EGFR inhibitor | RTK/RAS |
| Nilotinib | Leukemia | BCR-Abl tyrosine-kinase inhibitor | RTK/RAS and PI3K |
| Niraparib Tosylate Monohydrate | Ovarian epithelial/fallopian tube/primary peritoneal cancers | PARP inhibitor | DNA repair |
| Nivolumab | Skin, colorectal, kidney, liver, lung, lymphoma, bladder, head & neck | Monoclonal antibody against PD-1 | Immunotherapy |
| Obinutuzumab | Leukemia, lymphoma | Monoclonal antibody against CD20 | Immunotherapy |
| Ofatumumab | Leukemia | Monoclonal antibody against CD20 | Immunotherapy |
| Olaparib | Pancreatic, breast, ovarian epithelial/fallopian tube/primary peritoneal cancers | PARP inhibitor | DNA repair |
| Osimertinib | Lung | EGFR inhibitor | RTK/RAS |

Fig. 27T

| Drug | Primary Site | Category | Pathway |
|---|---|---|---|
| Palbociclib | Breast | CDK4/6 inhibitor | Cell cycle |
| Panitumumab | Colorectal | Monoclonal antibody against EGFR | RTK/RAS |
| Panobinostat | Multiple myeloma | HDAC inhibitor | Histone acetylation |
| Pazopanib | Soft tissue sarcoma, kidney | Tyrosine kinase inhibitor | RTK/RAS |
| Pembrolizumab | Kidney, liver, lung, lymphoma, microsatellite instability-high or mismatch repair-deficient solid tumors, skin, stomach, bladder, cervical, endometrial, esophageal, head & nech | Monoclonal antibody against PD-1 | Immunotherapy |
| Pertuzumab | Breast | Monoclonal antibody against HER2 | RTK/RAS |
| Ponatinib Hydrochloride | Leukemia | BCR-Abl tyrosine-kinase inhibitor | RTK/RAS and PI3K |
| Ramucirumab | Stomach, colorectal, esophageal, liver, lung | Monoclonal antibody against VEGFR2 | VEGF |
| Regorafenib | Colorectal, gastrointestinal stromal, liver | Monoclonal antibody against VEGFR2 | VEGF |
| Ribociclib | Breast | CDK4/6, cyclin D1 inhibitor | Cell cycle |
| Rituximab | Leukemia | Monoclonal antibody against CD20 | Immunotherapy |
| Romidepsin | Lymphoma | HDAC inhibitor | Histone acetylation |
| Rucaparib Camsylate | Ovarian epithelial/fallopian tube/primary peritoneal cancers | PARP inhibitor | DNA repair |
| Ruxolitinib Phosphate | Myelodysplastic/myeloproliferative disorders | JAK/STAT inhibitor | RTK/RAS |
| Selinexor | Multiple myeloma | Nuclear export inhibitor | Nuclear export |

Fig. 27U

| Drug | Primary Site | Category | Pathway |
|---|---|---|---|
| Sonidegib | Skin | Hedgehog inhibitor | Hedgehog signaling |
| Sorafenib | Thyroid, kidney, liver | Tyrosine kinase inhibitor | RTK/RAS |
| Sunitinib | Gastrointestinal stromal tumor, pancreatic, kidney | Tyrosine kinase inhibitor | RTK/RAS |
| Talazoparib Tosylate | Breast | PARP inhibitor | DNA repair |
| Tamoxifen | Breast | Estrogen inhibitor | Estrogen signaling |
| Temsirolimus | Kidney | mTOR inhibitor | PI3K |
| Tisagenlecleucel | Leukemia, lymphoma | CAR-T therapy | Immunotherapy |
| Toremifene | Breast | Estrogen inhibitor | Estrogen signaling |
| Trametinib | Lung, skin, thyroid | MEK inhibitor | RTK/RAS |
| Trastuzumab | Esophageal, stomach, breast | Monoclonal antibody againts HER2 | RTK/RAS |
| Tretinoin | Leukemia | Retinoid receptor activator | Retinoid signaling |
| Vandetanib | Thyroid | Tyrosine kinase inhibitor | RTK/RAS |
| Vemurafenib | Skin | BRAF inhibitor | RTK/RAS |
| Venetoclax | Leukemia, lymphoma | Anti-apoptotic protein inhibitor | Apoptosis |
| Vismodegib | Skin | Hedgehog inhibitor | Hedgehog signaling |
| Vorinostat | Lymphoma | HDAC inhibitor | Histone acetylation |
| Zanubrutinib | Lymphoma | Bruton's tyrosine kinase inhibitor | RTK/RAS and PI3K |
| Ziv-Aflibercept | Colorectal | VEGFR inhibitor | VEGF signaling |

Fig. 27V

SYSTEMS AND METHODS FOR DETECTING CELLULAR PATHWAY DYSREGULATION IN CANCER SPECIMENS

CROSS-REFERENCE TO RELATED APPLICATIONS

This application claims the benefit of U.S. Application No. 62/888,163 filed Aug. 16, 2019, U.S. Application No. 62/904,300, filed Sep. 23, 2019, U.S. Application No. 62/986,201, filed Mar. 6, 2020, and Application No. PCT/US2019/056713, filed on Oct. 17, 2019, which claims the benefit of U.S. Application No. 62/746,997 filed on Oct. 17, 2018, the contents of which are incorporated herein by reference in their entireties.

BACKGROUND

Oncogenesis and tumor maintenance are believed to be largely driven by the disruption of oncogenes and/or their signaling pathways. Well-studied examples of such oncogenes and their related pathways include the receptor tyrosine kinase (RTK)/Ras and Phosphoinositide 3-kinase (PI3K) pathways. Many different pathways have been correlated with certain types of cancers, and indeed, mutations in the genes of these pathways have been identified as drivers of certain cancers. Accordingly, these driver genes and their gene products are key targets for drug development efforts, and such efforts have yielded many life-saving and life-extending therapeutic options for certain patients.

However, not all cancers are associated with a known gene mutation, or with a known pathway. For example, DNA analysis may detect variants of unknown significance (VUS) within oncogenic signaling pathways. Variants of unknown significance (VUS) are alterations with unknown functional consequence and may represent benign passenger mutations (having little to no effect on cellular activity), or may be pathogenic (e.g., new, uncharacterized disease-causing mutations). In some instances, there is no information about the variant because the variant is rare or is difficult to study. These variants may or may not have clinical significance, and the distinction cannot be made with DNA analysis alone. Thus, some mutations in genes that are known to interact with or influence the pathway do not alter the activity of the pathway, and DNA analysis may result in a false positive; that is, a patient who would not respond to targeted therapies may be falsely identified as a responder by DNA analysis.

Accordingly, there is a need in the art to detect pathway disruption using information other than DNA variants.

SUMMARY OF DISCLOSURE

Disclosed herein are systems, methods, and compositions useful for determining cellular pathway disruption comprising the use of RNA expression level information. By way of example, but not by way of limitation, this determined level of disruption can used to (1) assist in the identification of genetic variants that alter pathway activity, (2) correlate identified variants with disease state and disease progression, and (3) identify therapeutics most likely to be effective and therapeutics that should be avoided.

In some embodiments, methods of preparing transcriptome data from a subject sample is provided. In some embodiments, the methods include extracting RNA from the subject sample, obtaining the sequence of the extracted RNA to obtain transcriptome data, providing at least a portion of the transcriptome data to at least one trained pathway disruption engine, and analyzing the portion of the transcriptome data using the at least one trained pathway disruption engine.

In some embodiments, a computer-implemented method for detecting dysregulation in a cellular pathway for a patient sample is provided. In some embodiments, the method includes training one or more pathway disruption engines using a set of training data comprising positive control samples and negative control samples. In some embodiments, the set of training data comprises positive control genetic data and negative control genetic data. In some embodiments, the genetic data of each positive control sample includes at least one detectable, pathogenic or likely pathogenic variant in at least one gene included in the cellular pathway, and the genetic data of each negative control sample includes no detectable variants in any gene included in the cellular pathway, with the exception of variants that are known to be benign. In some embodiments, the one or more trained pathway disruption engines include one or more machine learning models or neural networks. In some embodiments, genetic data associated with the patient sample is received. In some embodiments, the genetic data includes transcriptome data. In some embodiments, a portion of the genetic data is provided to at least one of the one or more trained pathway disruption engines. In some embodiments, at least one pathway disruption score indicative of cellular pathway dysregulation in the cellular pathway from the at least one of the one or more trained pathway disruption engines is received. In some embodiments, a pathway disruption report based on the at least one pathway disruption score is generated

BRIEF DESCRIPTION OF DRAWINGS

FIG. 4 shows a representation of example data from data inputs that may be used to train a pathway engine.

FIG. 6Y shows an exemplary dataframe that can be generated based on VUS data.

FIGS. 11A through 11E collectively illustrate examples of a pathway disruption report generated using the process in FIG. 7C.

FIGS. 26A-27P collectively show a table listing anti-neoplastic drugs, and provides the name of the drug, the site of action/tumor type, the drug classification, and general mechanism of action.

FIGS. 27Q-V collectively show a table listing FDA-approved anti-neoplastic drugs, and provides the name of the drug, the site of action/tumor type, the drug classification, and at least one pathway affected by the drug.

DETAILED DESCRIPTION

Figure 1A:
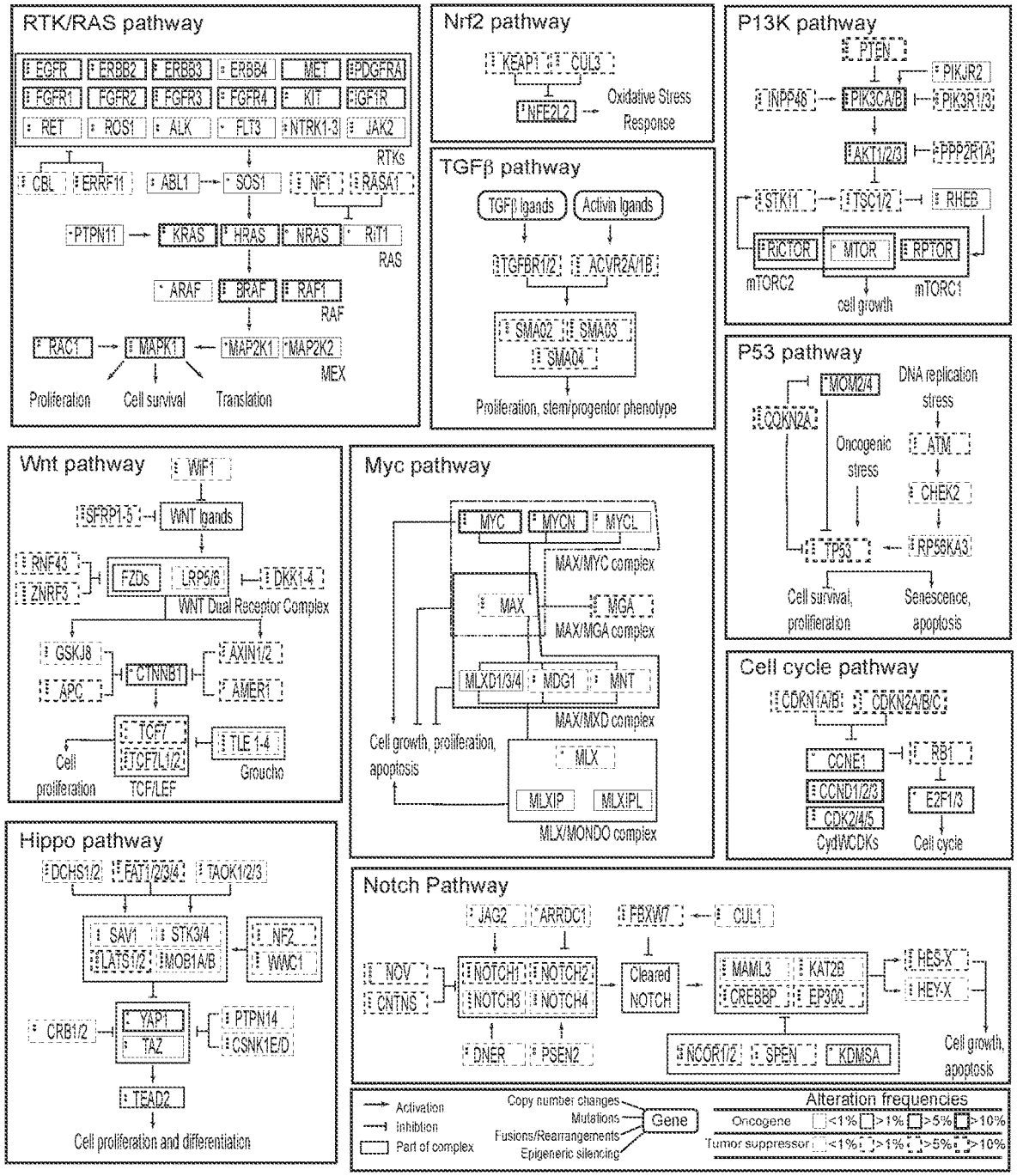
FIG. 1A illustrates examples of signaling pathways.

The various aspects of the subject disclosure are now described with reference to the drawings, wherein like reference numerals correspond to similar elements throughout the several views. It should be understood, however, that the drawings and detailed description hereafter relating thereto are not intended to limit the claimed subject matter to the particular form disclosed. Rather, the intention is to cover all modifications, equivalents, and alternatives falling within the spirit and scope of the claimed subject matter.

In the following detailed description, reference is made to the accompanying drawings which form a part hereof, and in which is shown by way of illustration, specific embodiments in which the disclosure may be practiced. These embodiments are described in sufficient detail to enable those of ordinary skill in the art to practice the disclosure. It should be understood, however, that the detailed description and the specific examples, while indicating examples of embodiments of the disclosure, are given by way of illustration only and not by way of limitation. From this disclosure, various substitutions, modifications, additions rearrangements, or combinations thereof within the scope of the disclosure may be made and will become apparent to those of ordinary skill in the art.

In accordance with common practice, the various features illustrated in the drawings may not be drawn to scale. The illustrations presented herein are not meant to be actual views of any particular method, device, or system, but are merely idealized representations that are employed to describe various embodiments of the disclosure. Accordingly, the dimensions of the various features may be arbitrarily expanded or reduced for clarity. In addition, some of the drawings may be simplified for clarity. Thus, the drawings may not depict all of the components of a given apparatus (e.g., device) or method. In addition, like reference numerals may be used to denote like features throughout the specification and figures.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof. Some drawings may illustrate signals as a single signal for clarity of presentation and description. It will be understood by a person of ordinary skill in the art that the signal may represent a bus of signals, wherein the bus may have a variety of bit widths and the disclosure may be implemented on any number of data signals including a single data signal.

The various illustrative logical blocks, modules, circuits, and algorithm acts described in connection with embodiments disclosed herein may be implemented as electronic hardware, computer software, or combinations of both. To clearly illustrate this interchangeability of hardware and software, various illustrative components, blocks, modules, circuits, and acts are described generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the embodiments of the disclosure described herein.

In addition, it is noted that the embodiments may be described in terms of a process that is depicted as a flowchart, a flow diagram, a structure diagram, or a block diagram. Although a flowchart may describe operational acts as a sequential process, many of these acts can be performed in another sequence, in parallel, or substantially concurrently. In addition, the order of the acts may be re-arranged. A process may correspond to a method, a function, a procedure, a subroutine, a subprogram, etc. Furthermore, the methods disclosed herein may be implemented in hardware, software, or both. If implemented in software, the functions may be stored or transmitted as one or more instructions or code on a computer-readable medium. Computer-readable media includes both computer storage media and communication media including any medium that facilitates transfer of a computer program from one place to another.

It should be understood that any reference to an element herein using a designation such as "first," "second," and so forth does not limit the quantity or order of those elements, unless such limitation is explicitly stated. Rather, these designations may be used herein as a convenient method of distinguishing between two or more elements or instances of an element. Thus, a reference to first and second elements does not mean that only two elements may be employed there or that the first element must precede the second element in some manner. Also, unless stated otherwise a set of elements may comprise one or more elements.

As used herein, the terms "component," "system" and the like are intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a computer and the computer can be a component. One or more components may reside within a process and/or thread of execution and a component may be localized on one computer and/or distributed between two or more computers or processors.

The word "exemplary" is used herein to mean serving as an example, instance, or illustration. Any aspect or design described herein as "exemplary" is not necessarily to be construed as preferred or advantageous over other aspects or designs.

Furthermore, the disclosed subject matter may be implemented as a system, method, apparatus, or article of manufacture using standard programming and/or engineering techniques to produce software, firmware, hardware, or any combination thereof to control a computer or processor based device to implement aspects detailed herein. The term "article of manufacture" (or alternatively, "computer program product") as used herein is intended to encompass a computer program accessible from any computer-readable device, carrier, or media. For example, computer readable media can include but are not limited to magnetic storage devices (e.g., hard disk, floppy disk, magnetic strips, etc.), optical disks (e.g., compact disk (CD), digital versatile disk (DVD), etc.), smart cards, and flash memory devices (e.g., card, stick).

Additionally it should be appreciated that a carrier wave can be employed to carry computer-readable electronic data such as those used in transmitting and receiving electronic mail or in accessing a network such as the Internet or a local area network (LAN). Of course, those skilled in the art will recognize many modifications may be made to this configuration without departing from the scope or spirit of the claimed subject matter.

The terms "polynucleotide", "nucleic acid" and "nucleic acid molecules" are used interchangeably and refer to a covalently linked sequence of nucleotides (i.e., ribonucleotides for RNA and deoxyribonucleotides for DNA) in which the 3' position of the pentose of one nucleotide is joined by a phosphodiester group to the 5' position of the pentose of the next, include sequences of any form of nucleic acid, including, but not limited to RNA, DNA and cfDNA molecules. These terms also refer to complementary DNA (cDNA), which is DNA synthesized from a single-stranded RNA (e.g., messenger RNA (mRNA) or microRNA (miRNA)) template in a reaction catalyzed by the enzyme reverse transcriptase. The term "polynucleotide" includes, without limitation, single- and double-stranded polynucleotide.

As used herein, the terms "proteins" and "polypeptides" are used interchangeably herein to designate a series of amino acid residues connected to the other by peptide bonds between the alpha-amino and carboxy groups of adjacent residues.

The terms "protein" and "polypeptide" refer to a polymer of protein amino acids, including modified amino acids (e.g., phosphorylated, glycated, glycosylated, etc.) and amino acid analogs. "Protein" and "polypeptide" are often used in reference to relatively large polypeptides, whereas the term "peptide" is often used in reference to small polypeptides, but usage of these terms in the art overlaps. Exemplary polypeptides or proteins include gene products, naturally occurring proteins, homologs, orthologs, paralogs, fragments and other equivalents, variants, fragments, and analogs of the foregoing.

As used herein the term "chromosome" refers to a structure of nucleic acids and protein (i.e., chromatin) found in the nucleus of most living cells, which carries genetic information in the form of genes. The conventional internationally recognized human genome chromosome numbering system is employed herein.

As used herein, the term "gene" refers to a nucleic acid sequence that encodes a gene product, either a polypeptide or functional RNA molecule. The term "gene" is to be interpreted broadly herein, encompassing both the genomic DNA form of a gene (i.e., a particular portion of a particular chromosome), and mRNA and cDNA forms of the gene produced therefrom. During gene expression, genomic DNA is transcribed into RNA, which can be immediately functional or can be translated into a polypeptide that performs a function. In addition to a coding region (i.e., the sequence that encodes the gene product), a gene comprises "noncoding regions". Noncoding regions may be immediately adjacent to the coding region (e.g., 5' and 3' noncoding regions that flank the coding region) or may be far removed from the coding region (e.g., many kilobases upstream or downstream). Some noncoding regions are transcribed into RNA but not translated, including "introns" (i.e., regions that are removed via RNA splicing before translation) and translational regulatory elements (e.g., ribosome binding sites, terminators, and start and stop codons). Other noncoding regions are not transcribed, including essential transcriptional regulatory regions. Genes require a "promoter," a sequence that is recognized and bound by proteins (i.e., transcription factors) that recruit and help RNA polymerase bind and initiate transcription. A gene can have more than one promoter, resulting in messenger RNAs (mRNA) that differ in how far they extend on the 5' end. As used herein, genes may also comprise more distally located transcriptional regulatory elements (i.e., "enhancers" and "silencers") that can be looped into proximity of the promoter, allowing proteins (i.e., "transcription factors") bound to these distal regulatory sites to influence transcription. For example, an "enhancer" increases transcription by binding an activator protein that helps to recruit RNA polymerase or initiate transcription. Conversely, "silencers" bind repressor proteins that make the DNA less accessible to RNA polymerase or otherwise inhibit transcription. Genes may also comprise "insulator" elements that protect promoters from inappropriate regulation. Insulators may function by either blocking interaction with an enhancer or silencer or by acting as a barrier that prevents the spreading of condensed chromatin. While enhancers and silencers are generally not considered to be part of a gene per se (given that a single enhance or silencer may regulate the expression of multiple genes), as used herein, the term gene encompasses those distal elements that influence its expression.

As used herein, the term "promoter" refers to a DNA sequence capable of controlling the expression of a coding sequence or functional RNA. In general, a coding sequence is located 3' to a promoter sequence. Promoters may be derived in their entirety from a native gene or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Artificial promoters that cause a gene to be expressed in most cell types at most times are commonly referred to as "constitutive promoters". Artificial promoters that allow the selective expression of a gene in most cell types are referred to as "inducible promoters".

"Genetic analyzer" means a device, system, and/or methods for determining the characteristics (e.g., sequences) of nucleic acid molecules (i.e., DNA, RNA, cDNA.) present in biological specimens. A "genetic analyzer" may also be used to characterize epigenetic features of nucleic acid molecules by employing methods including, for example, bisulfite sequencing, chromatin immunoprecipitation followed by sequencing, Assay for Transposase-Accessible Chromatin using sequencing (ATAC-seq), or 3C-based techniques.

The terms "genetic sequence" and "sequence" are used herein to refer to the series of nucleotides present in a DNA, RNA or cDNA molecule. In the context of the present invention, sequences are determined by sequencing nucleic acids present in a biological specimen.

The term "read" refers to a DNA sequence of sufficient length (e.g., at least about 30 bp) that can be used to identify a larger sequence or region, e.g., by aligning it with a chromosome, genomic region, or gene.

As used herein, the term "reference genome" refers to any particular known genome sequence, whether partial or complete, of any organism or virus which may be used to reference identified sequences from a subject. Many reference genomes are provided by the National Center for Biotechnology Information at world wide web address ncbi.nlm.nih.gov. A "genome" refers to the complete genetic information of an organism or virus, expressed in nucleic acid sequences.

As used herein, the terms "aligned", "alignment", or "aligning" refer to a process used to identify regions of similarity. In the context of the present invention, alignment refers to matching sequences with positions in a reference genome based on the order of their nucleotides in these sequences. Alignment can be performed manually or by a computer algorithm, for example, using the Efficient Local Alignment of Nucleotide Data (ELAND) computer program distributed as part of the Illumina Genomics Analysis pipeline. Alignment can refer to a either a 100% sequence match or a match that is less than 100% (non-perfect match).

The terms "library" and "sequencing library" is used herein refer to a pool of DNA fragments with adapters attached. Adapters are commonly designed to interact with a specific sequencing platform, e.g., the surface of a flow-cell (Illumina) or beads (Ion Torrent), to facilitate a sequencing reaction.

The terms "targeted panel" and "targeted gene sequencing panel" are used interchangeably herein to refer to a select set of genes or gene regions that have known or suspected associations with a particular disease or phenotype. Targeted panels are useful tools for detecting a set of specific mutations in a given sample, as sequencing a targeted panel produces a smaller, more manageable data set compared to broader approaches such as whole-genome sequencing.

The term "sequencing probe" or "sequencing primer" is used herein to refer to a short oligonucleotide that is used to sequence nucleic acids (i.e., cDNA or DNA). The sequencing probe may hybridize with a target sequence within the nucleic acids, or it may hybridize to an adapter sequence that has been attached to the nucleic acids to allow for nonspecific amplification and sequencing.

The term "RNA read count" is used herein to refer to the number of sequencing reads generated from a genetic analyzer. The term "RNA read count" is often used to refer to the number of reads overlapping a given feature (e.g., a gene or chromosome).

The term "bioinformatics pipeline" is used herein to mean a series of processing stages of a pipeline to instantiate bioinformatics reporting regarding next-generation sequencing results obtained from a biological specimen. For example, in the context of the present invention, the goal of the pipeline may be to identify variants present in a patient's genome.

The term "genetic profile" is used herein to refer to information about specific genes in an individual or in a particular type of tissue. This information may include genetic variations (e.g., single nucleotide polymorphisms), gene expression data, other genetic characteristics, or epigenetic characteristics (e.g., DNA methylation patterns) determined by, for example, the analysis of next-generation sequencing data.

The term "variant" is used herein to mean a difference in a genetic sequence or genetic profile, as compared to a reference genome or reference genetic profile.

The term "expression level" is used herein to describe the number of copies of a particular RNA or protein molecule, which may or may not be normalized using standard methods (e.g., counts per million, finding the base 10 logarithm of the raw read count) generated by a gene or other genetic regulatory region (e.g. long non-coding RNAs, enhancers), which may be defined by a chromosomal location or other genetic mapping indicator.

The term "gene product" is used herein to mean a protein or RNA molecule generated by the expression of a gene or other genetic regulatory region (i.e., transcription, translation, post-translational modification, etc.).

As used herein the terms "biological specimen," "patient sample," and "sample" refer to a specimen collected from a patient. Such samples include, without limitation, tumors, biopsies, tumor organoids, other tissues, and bodily fluids. Suitable bodily fluids include, for example, blood, serum, plasma, sputum, lavage fluid, cerebrospinal fluid, urine, semen, sweat, tears, saliva, and the like. Samples may be collected, for example, via a biopsy, swab, or smear.

The terms "extracted", "recovered," "isolated," and "separated," refer to a compound, (e.g., a protein, cell, nucleic acid or amino acid) that has been removed from at least one component with which it is naturally associated and found in nature.

The terms "enriched" or "enrichment" as used herein in conjunction with nucleic acid, refer to the process of enhancing the amount of one or more nucleic acid species in a sample. Exemplary enrichment methods may include chemical and/or mechanical means, and amplifying nucleic acids contained in a sample. Enrichment can be sequence specific or nonspecific (i.e., involving any of the nucleic acids present in a sample).

As used herein, "cancer" shall be taken to mean any one or more of a wide range of benign or malignant tumors, including those that are capable of invasive growth and metastases through a human or animal body or a part thereof, such as, for example, via the lymphatic system and/or the blood stream. As used herein, the term "tumor" includes both benign and malignant tumors and solid growths. Typical cancers include but are not limited to carcinomas, lymphomas, or sarcomas, such as, for example, ovarian cancer, colon cancer, breast cancer, pancreatic cancer, lung cancer, prostate cancer, urinary tract cancer, uterine cancer, acute lymphatic leukemia, Hodgkin's disease, small cell carcinoma of the lung, melanoma, neuroblastoma, glioma, and soft tissue sarcoma of humans.

In the context of the present invention, the term "biomarker" shall be taken to mean any genetic variant or molecule that is indicative of or correlated with a characteristic of interest, for example, the existence of cancer or of a susceptibility to cancer in the subject, the likelihood that the cancer is one subtype vs. another, the probability that a patient will or will not respond to a particular therapy or class of therapy, the degree of the positive response that would be expected for a therapy or class of therapies (e.g., survival and/or progression-free survival), whether a patient is responding to a therapy, or the likelihood that a cancer has progressed or will progress beyond its site of origin (i.e., metastasize).

As used herein the terms "cellular pathway," "signaling pathway," or "pathway" refers to a communication process that governs basic activities of cells and coordinates multiple-cell actions. A pathway involves biochemical reactions between molecules that control cell function (e.g., cell division, cell death). A cellular pathway includes the entire sequence of molecular events that are involved in such processes including, for example, the synthesis and release of a signaling molecule by a cell, transport of a signal to a target cell, binding of a signaling molecular to a specific receptor, receptor activation, and initiation of signal-transduction pathways.

As used herein the terms "cellular pathway dysregulation", "signaling pathway dysregulation", "pathway dysregulation" refer to an abnormality or impairment in the regulation of a cellular pathway. Dysregulation (used interchaneagably herein with the term disruption), can occur at any step in the gene expression process including, without limitation, during transcription, RNA splicing, RNA export, translation, and post-translational modification of a protein. Regulation of gene expression gives control over the timing, location, and amount of a given gene product (i.e., protein or ncRNA) present in a cell. Thus, cellular pathway dysregulation may involve over- or under-expression of genes, as well as changes in protein function or stability. In some cases, genetic variation, such as a mutation, gene fusion, or DNA copy number change, methylation state, contributes to cellular dysregulation. Although cancers are heterogenous in terms of their genetic mutation profiles, many cancers develop and are maintained via abnormal activation or suppression of a molecular signaling pathway. For example, the RAS/Receptor Tyrosine Kinase (RTK) and PI3K pathways can promote unregulated cellular (and tumor) growth when disrupted and are often affected in cancer. In some cases, a dysregulated pathway may be targeted by certain chemotherapeutics in an attempt to suppress the cancer.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. The subject therapy will desirably be administered during the symptomatic stage of the disease, and in some cases after the symptomatic stage of the disease.

The term "effective amount" refers to an amount of an active agent that is sufficient to exhibit a detectable therapeutic effect without excessive adverse side effects (such as toxicity, irritation, and allergic response) commensurate with a reasonable benefit/risk ratio when used in the manner of the present disclosure. The effective amount for a patient will depend upon the type of patient, the patient's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on knowledge in the art and the information provided herein. The optimum dosing regimen can be determined by one skilled in the art without undue experimentation.

As used herein, the term "reference sequence," "reference assembly," "or "reference genome," refer to one or more nucleic acid databases created using DNA sequencing, assembled as a representative example of the set of genes in one idealized individual organism of a species. A "reference transcriptome" is similarly defined as a database created using RNA sequencing and reflecting the set of expressed sequences in one idealized individual organism of a species. As they are assembled from the sequencing of DNA from a number of individual donors, reference genomes do not accurately represent the set of genes of any single individual organism. The most commonly used human reference genomes were derived from thirteen anonymous volunteers and therefore provides a haploid mosaic of different DNA sequences from each donor. The most commonly used human reference genomes are GRCh37 and GRCh38 from the Genome Reference Consortium, with updates being released every 1-4 years. A common use for reference genomes is to map transcripts obtained from DNAseq and RNAseq. For reference transcriptomes, as transcription is highly dynamic and varies with tissue type, developmental stage, environmental conditions, and disease state, reference transcriptomes do not reflect gene expression at all points in time but rather the total set of possible transcripts in an organism or species. Commonly used reference transcriptomes include RefSeq and Ensembl, which are themselves consolidations of multiple independent sequencing projects. Once RNA is sequenced and aligned to the reference genome, the reads are allocated to particular genes using such a database. In some embodiments, one or more reference genomes is used to define wild-type and mutant sequences. In embodiments disclosed herein, a single reference genome and/or a single reference transcriptome is used to define wild-type and mutant sequences in the context of constructing a model. However, embodiments are envisioned in which multiple reference genomes or multiple reference transcriptomes, or an updated reference database is used.

FIG. 1A illustrates examples of cellular pathways. (See, Sanchez-Vega et. al., 2018, Cell. 173: 321-337) This example illustrates The Cancer Genome Atlas (TCGA)-curated pathways, including the following: RTK/RAS, Nrf2, TGFbeta, PI3K, p53, Wnt, Myc, Cell cycle, Hippo, and Notch pathways. Each pathway is outlined by a box, and elements of each pathway are shown as labeled rectangles within the box. Various interactions (including activation, inhibition, etc.) between pathway elements are shown by arrows or lines.

Figure 1B:
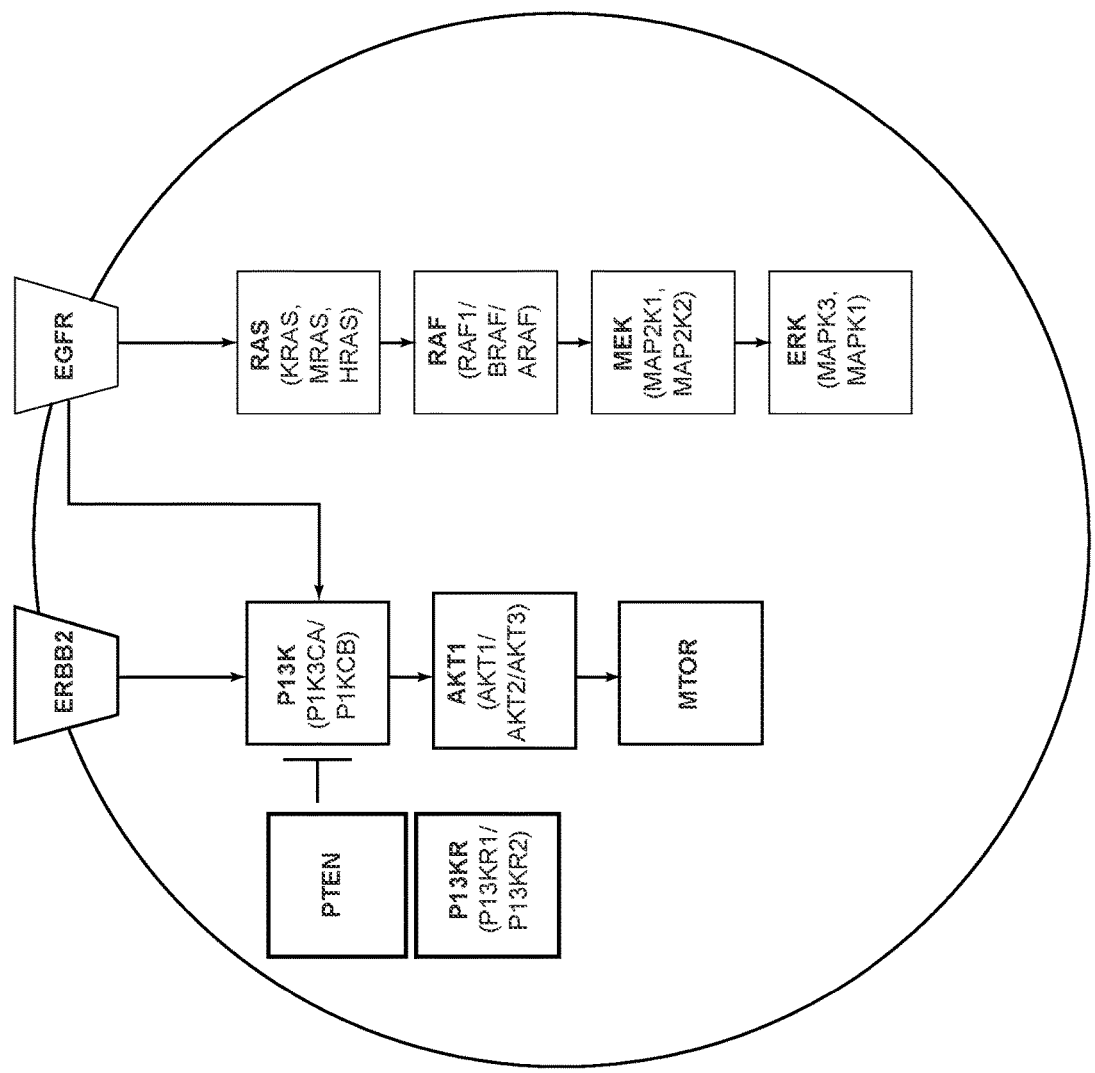
FIG. 1B illustrates custom pathways.

FIG. 1B illustrates custom pathways. In the example shown, the custom pathways are color-coded subsets of the PI3K pathway gene list and the RAS pathway gene list. The color codes illustrate the different functional components of the pathways, meaning that a mutation in any gene in a color group could be predicted to have the same effect on pathway function as a mutation in another gene in the same color group. In this example, the first group is the left column comprising PI3KR (PI3KR1/PI3KR2), the second group is the middle column comprising ERBB2, PI3K (PIK3CA/PIK3CB), AKT (AKT1/AKT2/AKT3), and MTOR, and the third group is the right column comprising EGFR, RAS (KRAS/NRAS/HRAS), RAF (RAF1/BRAF/ARAF), MEK (MAP2K1/MAP2K2), and ERK (MAPK3/MAPK1). In the example shown, the "T"-shaped line from PTEN to PI3K indicates that PTEN inhibits PI3K, and the arrows indicate activation (for example, EGFR activates both RAS and PI3K).

Some of the pathways that drive cancer are well characterized, and many instances of disruption can be traced to mutations in a handful of "driver" genes, e.g., KRAS in the RAS/RTK pathway and STK11 in the PI3K pathway. However, there are numerous cases in which no driver gene mutations are present, but where one or more pathways nonetheless show signs of disruption at the transcriptional and/or protein levels. In such cases, DNA analysis alone (including single nucleotide variants, insertions/deletions [in-dels], and copy number variants), would fail to identify pathway disruption, leading to a missed opportunity to use a therapeutic that targets the pathway. A measure of pathway disruption that is not limited to analyzing DNA may enable the identification of additional patients that may respond to these therapies.

Uses of Systems/Methods

Figure 2A:
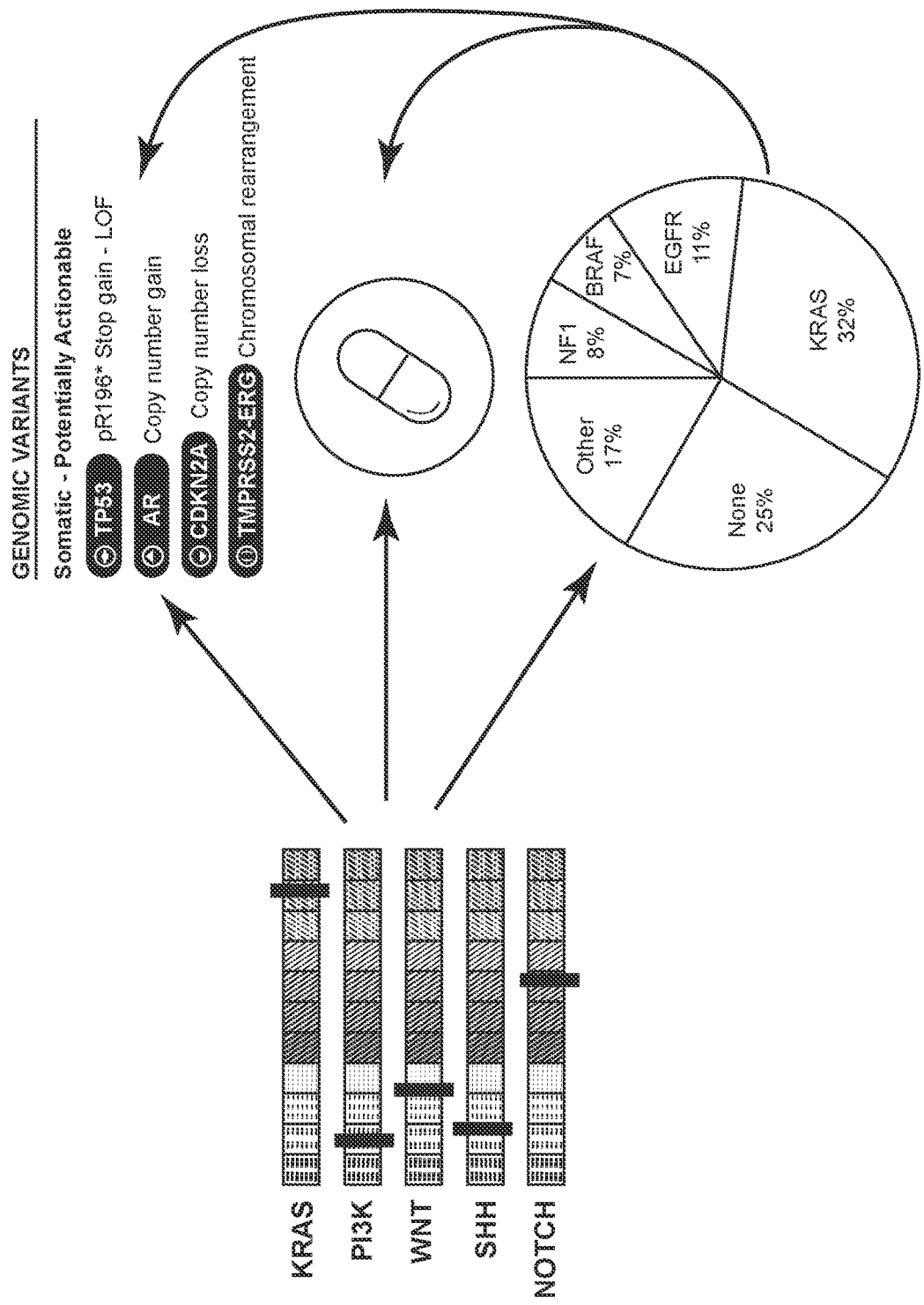
FIG. 2A is a schematic illustrating an example concept of the systems and methods disclosed herein.

FIG. 2A is a schematic illustrating an example concept of the systems and methods disclosed herein.

In one example, the systems and methods analyze RNA data to determine pathway disruption status of a cancer specimen for at least one cellular pathway. In FIG. 2A, the cellular pathways analyzed for the specimen are the RAS, PI3K, WNT, SHH, and NOTCH pathways. Each pathway has an activation range bar with various colors and a black bar to indicate the level of activity of the pathway. Black bars located farther to the left, in the blue or purple areas, indicate a pathway without disruption. Black bars located farther near the middle, in the green areas, indicate a pathway with moderate disruption. Black bars located farther to the right, in the red areas, indicate a pathway that is highly disrupted. In this example, the RAS pathway is highly disrupted, the PI3K, WNT, and SHH pathways are not disrupted, and the NOTCH pathway is moderately disrupted.

The three blue arrows pointing from the pathway disruption bars to the right portion of FIG. 2A indicate downstream uses for the results of the pathway disruption analysis. At the top, the results of the pathway disruption analysis may be used to help determine whether a genetic variant or mutation (especially a variant of unknown significance) qualifies as a pathogenic variant, which is a variant that is causing cancer, or is more likely to be a benign variant, which is a variant that has little to no impact on the disease. In the middle, the results may determine the therapies that are matched with a patient or organoid from which the cancer specimen was obtained. For example, if a pathway is disrupted, a therapy that targets the pathway (for example, by targeting proteins and/or genes in the pathway) may be matched. At the bottom, the pie chart is an example of the portion of cancer cases associated with a variant in a given gene, organized by gene name. In this example, approximately 24% of cancer specimens that may have dysregulated pathways do not have any detected canonical driver mutations in genes related to the pathway.

In some embodiments, the systems and methods analyze RNA rather than or in addition to DNA mutational data to assess potential pathway disruption. In some cases, the mutational cause of pathway disruption is unknown (e.g., the mechanism of RAS pathway disruption is unknown in as many as 24% of lung adenocarcinoma cases). However, the pathway disruption may have a RNA signature, which is captured by the systems and methods disclosed herein, regardless of the presence of DNA evidence.

As a corollary, DNA evidence may suggest pathway disruption when it is, in fact, not present. The systems and methods disclosed herein would have a more robust ability to correctly classify these potential false positives.

In various embodiments, the systems and methods characterize genomic alterations and molecular features into summarized known pathway profiles and connect their relationship to treatment response data from patients, cell lines, and/or tumor organoids. In various embodiments, the systems and methods integrate multiple molecular and genomic profiles into cancer signaling pathways to reveal insights about their relationship with treatment response and disease outcomes instead of characterizing a patient's tumor by the detected genomic alterations and RNA expression levels at the single gene level.

In various embodiments, the systems and methods also analyze data from the entire gene set (≈18,000 genes or more) as compared to a smaller subset of genes. This makes the systems and methods much more flexible than out-of-the-box methods, such as single sample gene set enrichment analysis (ssGSEA, See Barbie, et al., 2010, Nature. 462 (7269): 108-112) in that it allows for the ability to search for potential causes of pathway disruption outside of the canonical pathway genes and curated gene lists.

In some embodiments, the systems and methods leverage the transcriptome along with clinical and DNA variant data or methylation status to detect targetable pathway disruption events that may not be detected by individual gene expression levels (for example, a list of genes that are over or under-expressed in cancer specimens compared to non-cancer specimens) or the DNA variants that are currently detected and/or reported to physicians and patients as pathogenic variants. The transcriptome may be captured by whole exome RNA-seq and is not limited to expression levels of genes associated with a pathway. This is especially relevant in cases where the dysregulation is caused by genes downstream of a pathway or genes that are not known to be related to a pathway. The clinical data may be related to therapies received by a patient or organoid and the patient or organoid response to those therapies (for example, if the growth rate of the cancer cells in the patient or organoid slowed after exposure to the therapy). The methylation status may be related to the methylation of genes and/or promoters associated with the pathway.

In some embodiments, the systems and methods disclosed herein circumvent the limitations of DNA analysis in detecting pathway dysregulation. The systems and methods may include an orthogonal, transcriptomic approach to identify pathway disruption in cancer patients. The systems and methods may include highly sensitive transcriptomic models of oncogenic signaling pathway disruption that pass several validation tests and that identify patients who may respond to targeted therapeutics despite an absence of canonical pathway mutations. In certain embodiments, the systems and methods may include a machine-learning approach for the identification of hidden responders who may respond to a therapy but whose responder status may not be detected by standard, DNA-based diagnostics.

In certain embodiments, the systems and methods include identification of pathway disruption through transcriptomics in human cancer.

In some embodiments, the systems and methods generate a pathway disruption score based only on transcriptomic data, providing an orthogonal indication of pathway disruption that does not rely on a DNA-based understanding of the underlying mechanism of disruption. With sufficient sample sizes, the same systems and methods may be used to generate models of pathway disruption for any pathway and any cancer type.

Figure 2B:
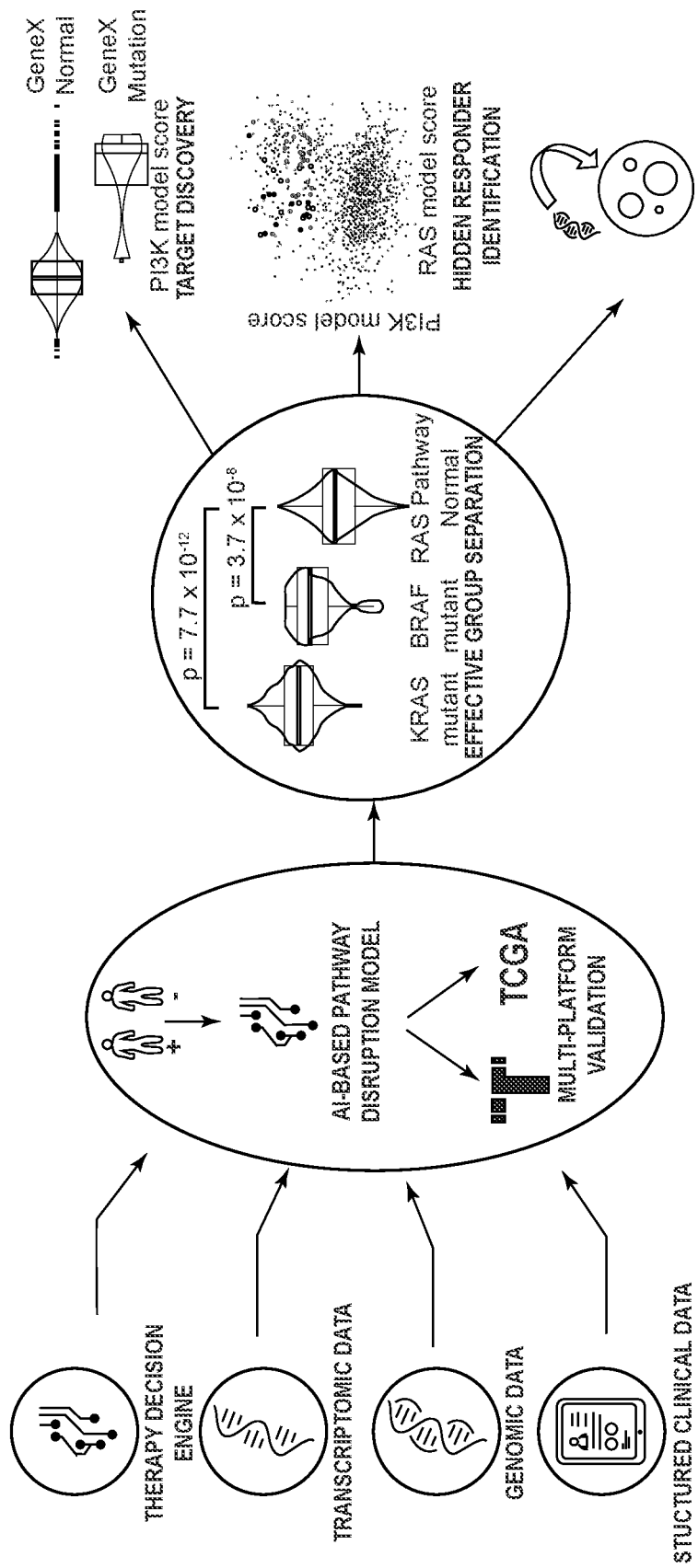
FIG. 2B is a schematic illustrating another example concept of the systems and methods disclosed herein.

FIG. 2B is a schematic illustrating another example concept of the systems and methods disclosed herein.

In some embodiments, the systems and methods include one or more pathway disruption models and the results generated by those pathway disruption models. Training data for the pathway disruption models includes transcriptomic data and may further include genomic data. Training data and/or biological validation data to determine how the model results reflect a biological status may further include structured clinical or organoid data, including any evidence of a therapy slowing the growth of cancer in a patient or tumor organoid, and information from a therapy decision engine, including lists of therapies that target any gene or gene product in a gene set or pathway of interest.

In one example, the pathway disruption models include a RAS pathway disruption model and a PI3K pathway disruption model, each of which was developed using transcriptomic and genomic data from lung adenocarcinoma patients and extensively validated on both public and private data sets (second column from the left). In this example, the RAS model assigns similarly strong disruption scores for patients with mutations in KRAS and BRAF, two adjacent molecules in the RAS pathway. Similarly strong results were achieved for a PI3K disruption model (second column from the right). These results demonstrate that disruption scores generated by these models can quantitatively estimate the effects of genetic variations on biological pathways.

In this example, both models identify candidate target genes or mutations that have an unexpected effect on pathway disruption. For example, the systems and methods disclosed herein may analyze transcriptomes from several specimens having no mutations that are known to cause disruption to a given pathway and predict that the pathway is disrupted in each of these specimens. Then, the specimens may be analyzed to determine if they have a common mutation or mutated gene, even if it is not a mutation or gene known to cause disruption to that pathway, to identify that common mutation or gene as a target mutation or target gene. This analysis may prioritize genes that produce proteins known to interact with members of the pathway. These protein-protein interactions may be listed in a pathways database 300 (See FIG. 3A).

The models indicate that many patients without pathway mutations (pathway normal or wild type) nonetheless have high disruption scores (red, blue, and purple points). These "hidden responders" would potentially benefit from the therapies that are normally used to target these pathways and these model results provide additional opportunities for biomarker and target discovery. Patients having specimens with variants in these target genes may be matched with one of these therapies.

In one example, to verify clinical validity of the model results, data from patient clinical records or tumor organoid growth experiments may be analyzed for an association between therapy responses and the target gene(s) or variants identified by a pathway model. If there is evidence that a therapy can slow the growth of cancer cells in a patient or tumor organoids, where the patient and organoid cancer cells have variants in the target gene(s), then the therapy decision engine may be updated with an entry for the therapy and the pathway that the target gene(s) modify. In the absence of organoid therapy response data for the identified target genes, organoids may be genetically engineered to have the identified target genes or mutations, and their growth rates may be observed after exposure to pathway-targeting therapies.

In some embodiments, the cancer patients have lung adenocarcinoma (LUAD). In some embodiments, the cancer patients have breast, colon, or prostate cancer. In some embodiments, the cancer patients have any cancer type. In some embodiments, the systems and methods refine the clinically relevant pathways of interest by characterizing gene expression data, DNA mutational profiles and immune profiles for PI3K and RTK/RAS pathways across cancer types and test predictions against clinical response and outcomes data. The systems and methods may expand this approach to other networks/pathways prioritized based on relevance to therapeutic targeting. In some embodiments, the systems and methods may include algorithm validation and a retrospective analysis.

In some embodiments, the systems and methods disclosed herein include a binomial logistic regression model that uses normalized transcriptomic data from a database as well as pathway scores generated with the same transcriptomic data in combination with an algorithm and molecular pathway gene sets. In one example, the molecular pathway gene sets are curated. The output of the model may be a single number that indicates the degree to which the sample's transcriptome is consistent with pathway disruption.

In some embodiments, the systems and methods discover integrative, multi-omic pathway signatures that predict treatment response and disease outcomes. These multi-omic pathway signatures may include characteristics of data (for example, data types including clinical, response outcomes, DNA mutational, RNA gene expression, etc.) associated with a patient and/or specimen. Machine learning models may be used to analyze these data types and more, in the context of disease-associated gene and protein networks/pathways. The response outcomes data may contain information about patient or organoid survival and progression-free survival after exposure to various therapies, including over 100 different cancer drugs.

In various embodiments, the systems and methods may be used to discover molecular patterns associated with treatment response by finding novel correlative pathways/networks in DNA alterations, fusions, and RNA-seq gene expression data and imaging (including histopathology and radiology images).

To identify correlative de novo patterns from molecular profiling results, the systems and methods may include integrative comic predictive modeling approaches (mutual information, Bayesian networks, neural networks, and other statistical and machine learning methods) to define disease-associated correlated gene and protein networks. The novel disease-associated networks may be tested for associations with therapies and outcomes data, including data derived from clinical records. Statistically significant associations may be validated with focused data sets that test the sensitivity and recall of the association with tumor therapeutic response or patient survival metrics.

In various embodiments, the systems and methods disclosed herein include artificial intelligence models of pathway disruption. The systems and methods may be used for biomarker discovery, which may include in silico evaluation of genes and/or variants identified by the model(s) to predict the effects of the genes and/or variants on pathway disruption and cancer.

The systems and methods may include the annotation of novel and/or known biomarkers (for example, genes and/or variants), especially the likely status of each biomarker as a viable drug target, which may include the use of private and/or public databases. For example, the databases may include descriptions of observed drug interactions with a biomarker, associations between patient response to a drug and biomarkers observed in the patient, and/or protein structures and the effect of a biomarker on the protein structure of a gene product. These databases may include information for identifying drug targets and prioritizing associations between diseases and drug targets; associations between human diseases and genes, variants, drugs and/or drug targets; information related to drugs and their targets (including interactions between drugs and drug targets); interactions between genes and drugs (including the status of a gene as a target for a drug); information related to therapeutic protein and nucleic acid targets and associated targeted diseases (for example, cancer types); information related to drugs, drug targets, and molecules; information about portions of the genome that are druggable (for example, that may be targeted by drugs); and associations between chemicals, gene products, phenotypes, diseases, and environmental exposures. A drug target may be genes or proteins affected by the drug (for example, a drug may alter, inhibit, or activate the activity or function of a drug target). These databases may contain information that is based on published research studies. Examples of public databases include DrugBank (see drugbank.ca), ChEMBL (see ebi-.ac.uk/chembl), DGIdb (dgidb.org), TTD (see db.idrblab.org/ttd/), Di sGeNET (see disgenet.org), DTC (see drugtargetcommons.fimm.fi), Open Targets (see opentargets.org), PHAROS (see pharos.nih.gov), CTD (see ctdabase.or), ADReCS-Target (see bioinf.xmu.edu.cn), etc. (for additional descriptions of these databases, see Paananen and Fortino, Briefings in Bioinformatics (2019); doi: 10.1093/bib/bbz122), see also FIGS. 26A-Z and FIGS. 27A-V.

The systems and methods may include in vitro validation of candidate target biomarkers in organoids via genetic engineering and/or drug screens. For example, genetic engineering (for example, the use of CRISPR and/or other gene editing tools) may be used to design an organoid having the candidate biomarker and a drug screen may be used to determine which therapies are able to slow the growth of organoids having the candidate biomarker.

The systems and methods disclosed herein may be used to guide treatment of subjects. By way of example, a subject sample may be analyzed according to the systems and methods disclosed herein, and a recommended therapeutic/treatment regimen may be provided by the system. In some embodiments, the methods include treating the subject pursuant to the recommended therapeutic/treatment regimen. In some embodiments, a recommended treatment includes administering to the subject an effective amount of one or more of the compounds listed in FIGS. 26A-27P or FIGS. 27Q-V.

Oncogenic signaling pathways are composed of multiple proteins, and it is often useful to subdivide the pathway into modules based on the similarity of the proteins in terms of their protein sequence or function, their clinical targetability, and the effects of their disruption. For example, the RAS module of the RTK/RAS parent pathway is composed of KRAS, NRAS, and HRAS. Mutations in these genes are present at different proportions in different cancers, with KRAS mutations being most common in lung adenocarcinoma, NRAS in melanoma, and HRAS in melanoma. However, they have highly similar sequences, are characterized by mutations in the same domains that cause unregulated growth, and result in the activation of the same downstream, clinically targetable, effectors when disrupted. For purposes of modeling RTK/RAS pathway disruption, it follows that grouping of these proteins into a module is logical from a biological and clinical perspective and adds strength to the model generator by permitting the combination of patients with mutations in these genes to form the positive control group.

Another rationale for grouping into a module may be based solely on the functional effects of the proteins, such as for the PTEN module in the PI3K pathway, which consists of PTEN, PIK3R1, and PIK3R2. Each of these proteins, although not structurally similar, is involved in the repression of PI3K signaling, potentially providing guidance for treatment. For example, if disruption is detected in this module, a clinician may consider treating with PI3K inhibitors to block the effect of the disabled, inhibitory PTEN module.

FIGS. 12A-12E show several such modules for the RTK/RAS and PI3K pathways, each of which were constructed with the above factors in mind. Other oncogenic signaling pathways will have different associated modules. It is also important to note that additional findings regarding the considered pathways, new treatment recommendations, and/or the specific goals of the disruption model, may necessitate that the modules be re-designed. The depicted modules for the RTK/RAS and PI3K pathways are therefore not intended to and do not exemplify the entirety of potential modules that could be used in this method.

Systems and Methods

Figure 3A:
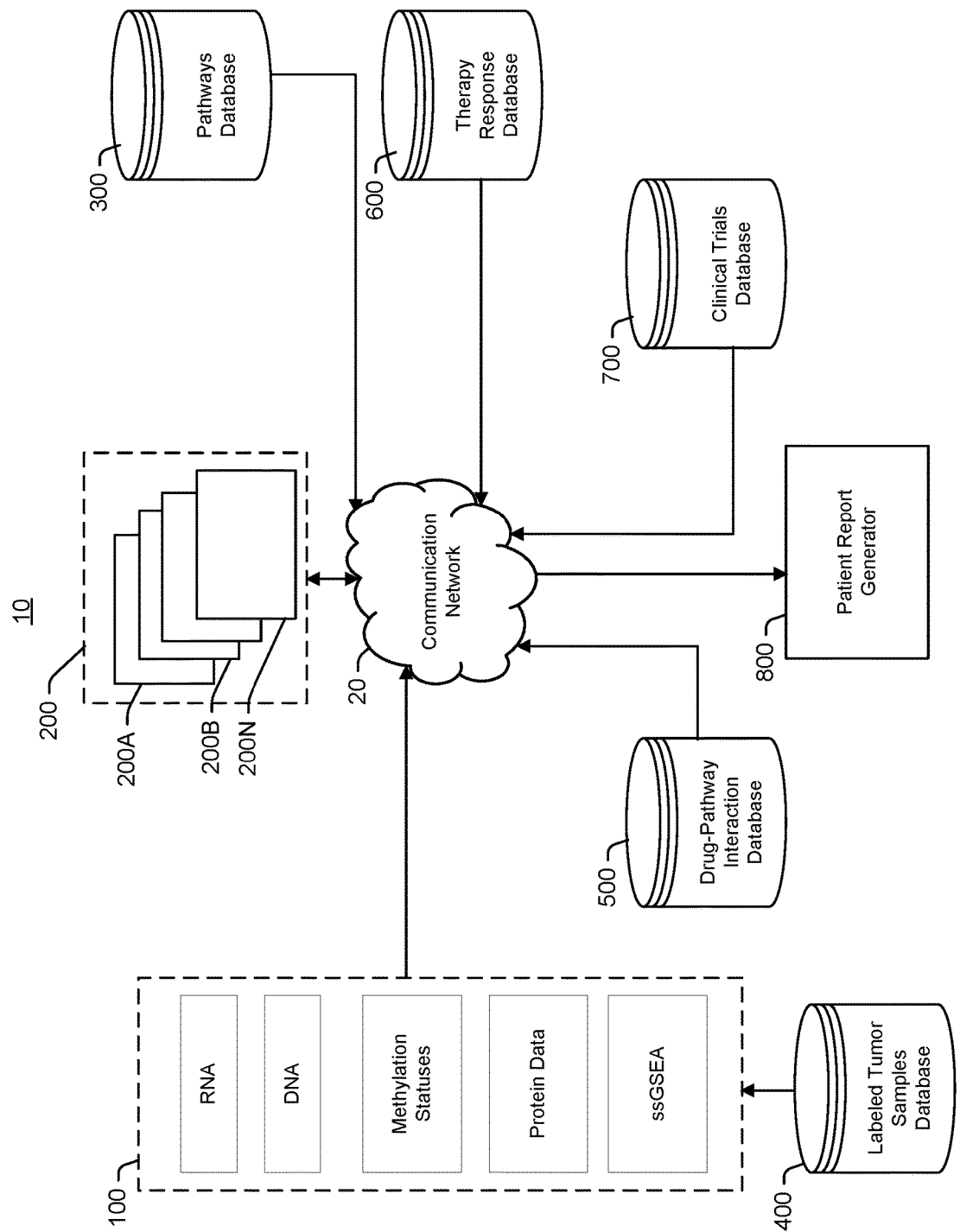
FIG. 3A shows a schematic of a system that can determine pathway disruption status for at least one tissue specimen.

FIG. 3A displays a schematic of a system 10 that can determine pathway disruption status for at least one tissue specimen. The system 10 may comprise one or more data inputs 100, one or more pathway engines 200, a pathways database 300, a labeled tumor samples database 400, a drug-pathway interaction database 500, a therapy response database 600, a clinical trials database 700, and patient report generator 800.

The pathway engines 200 can be in communication with the pathways database 300, the labeled tumor samples database 400, the drug-pathway interaction database 500, the therapy response database 600, the clinical trials database 700, and the patient report generator 800 over a communication network 20. The one or more pathway engines 200 can receive the data inputs 100 and output one or more pathway disruption scores. The pathway engines 200 can be stored on one or more devices that will be described in detail below.

Data inputs 100 may comprise transcriptome value sets and one or more dysregulation indicators (as described in FIG. 4). Data inputs 100 may further comprise DNA variant data, methylation data, cancer type, and/or proteomics data.

Each of the one or more pathway engines 200 may be trained on a set of data from data inputs 100 in order to determine the likelihood that a pathway associated with a tissue specimen has a disruption status. The system 10 may comprise 1, 10, 100, or more pathway engines 200. In this document, the label "200$n$" is intended to refer to a generic pathway engine in one of the one or more pathway engines 200.

In various embodiments, pathway engine 200$n$ predicts pathway disruption status based on RNA data. In various embodiments, pathway engine 200$n$ comprises a predictive model. In various embodiments, pathway engine 200$n$ comprises a support vector machine, random forest, and/or k-nearest neighbor model. In some embodiments, pathway engine 200$n$ comprises a logistic regression model.

In some embodiments, each pathway engine 200$n$ may predict pathway disruption for specimens having a particular cancer type. In various embodiments, each pathway engine 200$n$ may predict pathway disruption for a single pathway of interest, a combination of pathways of interest, or several individual pathways of interest.

In various embodiments, each pathway engine 200$n$ may predict pathway disruption for a single pathway of interest. The pathway of interest may be a cellular pathway contained in pathways database 300. The pathway of interest may be a TCGA-defined pathway or a custom gene set or gene list. For example, the pathways of interest may include the RAS/RTK, PI3K and/or WNT pathways. In some embodiments, the pathways include oncogenic networks/pathways with known regulatory responses to targeted therapy.

In one example, the pathway engine 200n may predict pathway disruption for an RTK-RAS/PI3K pathway (for example, see FIG. 1B) in patients and/or specimens having lung adenocarcinoma. In one example, the pathway engine 200n may predict pathway disruption for the WNT pathway in patients and/or specimens having colorectal cancer. In one example, the pathway engine 200n may predict pathway disruption for the PI3K pathway in patients and/or specimens having breast cancer. In one example, the pathway engine 200n may predict pathway disruption for the vascular endothelial growth factor (VEGF) pathway.

In some embodiments, one or more pathways of interest may be examined for each specimen. For instance, in order to determine whether a therapy may be effective for a patient whose specimen has dysregulation in one or more pathways, especially if at least one pathway is activated and at least one pathway is suppressed, it may be useful to score the dysregulation of multiple pathways and/or the overall dysregulation of multiple pathways that interact. This may include using more than one trained pathway engine 200a, 200b, . . . , 200n, to analyze the input data associated with each specimen.

The pathways database 300 may include descriptions and/or lists of gene or protein networks, for example, sets of genes and/or proteins that interact during the activities of biological cells. Gene-gene, protein-protein, and gene-protein interactions may include one gene or protein inhibiting, activating, or changing the activity, expression level, or status of another gene or protein.

In some embodiments, a pathway is a gene list defined by MSigDB (GSEA), or a TCGA pathway curated list. In some embodiments, the pathway of interest is a custom gene list. The pathway gene list of interest may be selected in collaboration with a team of pathologists or other experts.

The labeled tumor samples database 400 may include data associated with biological specimens having a known pathway disruption status (for example, disrupted or not disrupted) for each of one or more pathways. The pathway disruption status may be based on DNA variants detected in the specimen and located in genes related to the pathway. Data inputs 100 may be stored in labeled tumor samples database 400.

The drug-pathway interaction database 500 may include data entries showing associations among therapies and the genes, gene products, and/or pathways that the therapies target.

Entries in the therapy response database 600 may include observed instances of a therapy slowing the growth of cancer in a specimen from a patient or tumor organoid and various characteristics of the specimen, including the associated list of genetic variants and/or disrupted pathways detected in the specimen.

The clinical trials database 700 may include a list of clinical trials and information about each clinical trial. The clinical trial information may include trial name, exclusion and/or inclusion criteria, enrollment information, contact information, institution name, location, interventions (for example, therapies, drugs, treatments), clinical trial dates (for example, start dates and completion dates), and other information (for example, any information that could be listed on the clinicaltrials.gov website).

The patient report generator 800 may receive data from the pathway engines 200, the drug-pathway interaction database 500, the therapy response database 600, and the clinical trials database 700. The patient report generator 800 can generate a report to present the pathway disruption status determined by pathway engine(s) 200n regarding a specimen and/or multiple specimens to a patient, patient's physician, medical professional, researcher, etc.

The patient report generator 800 can include and/or cause one or more processes for generating pathway disruption scores and/or pathway disruption reports to be executed. In particular, the patient report generator 800 can include and/or cause processes 502, 602, 630, 650, 660, 670, 750, 702 to be executed. The processes 502, 602, 630, 650, 660, 670, 750, 702 will be described below.

A patient data store (for example, labeled tumor samples database 400) may include one or more feature modules which may comprise a collection of features available for every patient (or tumor organoid) in the system. These features (for example, data inputs 100) may be used to generate the artificial intelligence classifiers (for example, pathway engines 200n) in the system. While feature scope across all patients is informationally dense, a patient's feature set may be sparsely populated across the entirety of the collective feature scope of all features across all patients. For example, the feature scope across all patients may expand into the tens of thousands of features while a patient's unique feature set may only include a subset of hundreds or thousands of the collective feature scope based upon the records available for that patient.

Feature collections (for example, data inputs 100) may include a diverse set of fields available within patient health records. Clinical information may be based upon fields which have been entered into an electronic medical record (EMR) or an electronic health record (EHR) by a physician, nurse, or other medical professional or representative. Other clinical information may be curated from other sources, such as molecular fields from genetic sequencing reports. Sequencing may include next-generation sequencing (NGS) and may be long-read, short-read, or other forms of sequencing a patient's somatic and/or normal genome. A comprehensive collection of features in additional feature modules may combine a variety of features together across varying fields of medicine which may include diagnoses, responses to treatment regimens, genetic profiles, clinical and phenotypic characteristics, and/or other medical, geographic, demographic, clinical, molecular, or genetic features. For example, a subset of features may comprise molecular data features, such as features derived from an RNA feature module or a DNA feature module sequencing.

Another subset of features, imaging features from an imaging feature module, may comprise features identified through review of a specimen, for example, through pathologist review, such as a review of stained H&E or IHC slides. As another example, a subset of features may comprise derivative features obtained from the analysis of the individual and combined results of such feature sets. Features derived from DNA and RNA sequencing may include genetic variants from a variant science module which are present in the sequenced tissue. Further analysis of the genetic variants may include additional steps such as identifying single or multiple nucleotide polymorphisms, identifying whether a variation is an insertion or deletion event, identifying loss or gain of function, identifying fusions, calculating copy number variation, calculating microsatellite instability, calculating tumor mutational burden (TMB), or other structural variations within the DNA and RNA. Analysis of slides for H&E staining or IHC staining may reveal features such as tumor infiltration, programmed death-ligand 1 (PD-L1) status, human leukocyte antigen (HLA) status, or other immunological features.

Features derived from structured, curated, or electronic medical or health records may include clinical features such as diagnosis, symptoms, therapies, outcomes, patient demographics such as patient name, date of birth, gender, ethnicity, date of death, address, smoking status, diagnosis dates for cancer, illness, disease, diabetes, depression, other physical or mental maladies, personal medical history, family medical history, clinical diagnoses such as date of initial diagnosis, date of metastatic diagnosis, cancer staging, tumor characterization, tissue of origin, treatments and outcomes such as line of therapy, therapy groups, clinical trials, medications prescribed or taken, surgeries, radiotherapy, imaging, adverse effects, associated outcomes, genetic testing and laboratory information such as performance scores, lab tests, pathology results, prognostic indicators, date of genetic testing, testing provider used, testing method used, such as genetic sequencing method or gene panel, gene results, such as included genes, variants, expression levels/statuses, or corresponding dates to any of the above.

Features may be derived from information from additional medical or research based Omics fields including proteomics, transcriptomics, epigenomics, metabolomics, microbiomics, and other multi-omic fields. Features derived from an organoid modeling lab may include the DNA and RNA sequencing information germane to each organoid and results from treatments applied to those organoids. Features derived from imaging data may further include reports associated with a stained slide, size of tumor, tumor size differentials over time including treatments during the period of change, as well as machine learning approaches for classifying PDL1 status, HLA status, or other characteristics from imaging data. Other features may include the additional derivative features sets from other machine learning approaches based at least in part on combinations of any new features and/or those listed above. For example, imaging results may need to be combined with MSI calculations derived from RNA expressions to determine additional further imaging features. In another example a machine learning model may generate a likelihood that a patient's cancer will metastasize to a particular organ or any other organ. Other features that may be extracted from medical information may also be used. There are many thousands of features, and the above listing of types of features are merely representative and should not be construed as a complete listing of features.

An alterations module may be one or more microservices, servers, scripts, or other executable algorithms which generate alteration features associated with de-identified patient features from the feature collection. Alterations modules may retrieve inputs from the feature collection and may provide alterations for storage. Exemplary alterations modules may include one or more of the following alterations as a collection of alteration modules.

An IHC (Immunohistochemistry) module may identify antigens (proteins) in cells of a tissue section by exploiting the principle of antibodies binding specifically to antigens in biological tissues. IHC staining is widely used in the diagnosis of abnormal cells such as those found in cancerous tumors. Specific molecular markers are characteristic of particular cellular events such as proliferation or cell death (apoptosis). IHC is also widely used in basic research to understand the distribution and localization of biomarkers and differentially expressed proteins in different parts of a biological tissue. Visualizing an antibody-antigen interaction can be accomplished in a number of ways. In the most common instance, an antibody is conjugated to an enzyme, such as peroxidase, that can catalyze a color-producing reaction in immunoperoxidase staining. Alternatively, the antibody can also be tagged to a fluorophore, such as fluorescein or rhodamine in immunofluorescence. Approximations from RNA expression data, H&E slide imaging data, or other data may be generated.

A Therapies module may identify differences in cancer cells (or other cells near them) that help them grow and thrive and drugs that "target" these differences (see e.g., FIGS. 26A-27P or FIGS. 27Q-V for exemplary drugs and their targets). Treatment with these drugs is called targeted therapy. For example, many targeted drugs are lethal to the cancer cells' with inner 'programming' that makes them different from normal, healthy cells, while not affecting most healthy cells. Targeted drugs may block or turn off chemical signals that tell the cancer cell to grow and divide rapidly; change proteins within the cancer cells so the cancer cells die; stop making new blood vessels to feed the cancer cells; trigger a patient's immune system to kill the cancer cells; or carry toxins to the cancer cells to kill them, without affecting normal cells. Some targeted drugs are more "targeted" than others. Some might target only a single change in cancer cells, while others can affect several different changes. Others boost the way a patient's body fights the cancer cells. This can affect where these drugs work and what side effects they cause. Matching targeted therapies may include identifying the therapy targets in the patients and satisfying any other inclusion or exclusion criteria that might identify a patient for whom a therapy may be effective.

A Trial module may identify and test hypotheses for treating cancers having specific characteristics by matching features of a patient to clinical trials. These trials have inclusion and exclusion criteria that must be matched to enroll a patient and which may be ingested and structured from publications, trial reports, or other documentation.

An Amplifications module may identify genes which increase in count (for example, the number of gene products present in a specimen) disproportionately to other genes. Amplifications may cause a gene having the increased count to go dormant, become overactive, or operate in another unexpected fashion. Amplifications may be detected at a gene level, variant level, RNA transcript or expression level, or even a protein level. Detections may be performed across all the different detection mechanisms or levels and validated against one another.

An Isoforms module may identify alternative splicing (AS), the biological process in which more than one mRNA type (isoform) is generated from the transcript of a same gene through different combinations of exons and introns. It is estimated by large-scale genomics studies that 30-60% of mammalian genes are alternatively spliced. The possible patterns of alternative splicing for a gene can be very complicated and the complexity increases rapidly as the number of introns in a gene increases. In silico alternative splicing prediction may find large insertions or deletions within a set of mRNA sharing a large portion of aligned sequences by identifying genomic loci through searches of mRNA sequences against genomic sequences, extracting sequences for genomic loci and extending the sequences at both ends up to 20 kb, searching the genomic sequences (repeat sequences have been masked), extracting splicing pairs (two boundaries of alignment gap with GT-AG consensus or with more than two expressed sequence tags aligned at both ends of the gap), assembling splicing pairs according to their coordinates, determining gene boundaries (splicing pair predictions are generated to this point), generating predicted gene structures by aligning mRNA sequences to genomic templates, and comparing splicing pair predictions and gene structure predictions to find alternatively spliced isoforms.

A SNP (single-nucleotide polymorphism) module may identify a substitution of a single nucleotide that occurs at a specific position in the genome, where each variation is present to some appreciable degree within a population (e.g. >1%). For example, at a specific base position, or loci, in the human genome, the C nucleotide may appear in most individuals, but in a minority of individuals, the position is occupied by an A. This means that there is a SNP at this specific position and the two possible nucleotide variations, C or A, are said to be alleles for this position. SNPs underlie differences in human susceptibility to a wide range of diseases (e.g.—sickle-cell anemia, β-thalassemia and cystic fibrosis result from SNPs). The severity of illness and the way the body responds to treatments are also manifestations of genetic variations. For example, a single-base mutation in the APOE (apolipoprotein E) gene is associated with a lower risk for Alzheimer's disease. A single-nucleotide variant (SNV) is a variation in a single nucleotide without any limitations of frequency and may arise in somatic cells. A somatic single-nucleotide variation (e.g., caused by cancer) may also be called a single-nucleotide alteration. An MNP (Multiple-nucleotide polymorphisms) module may identify the substitution of consecutive nucleotides at a specific position in the genome.

An Indels module may identify an insertion or deletion of bases in the genome of an organism classified among small genetic variations. While indels usually measure from 1 to 10 000 base pairs in length, a microindel is defined as an indel that results in a net change of 1 to 50 nucleotides. Indels can be contrasted with a SNP or point mutation. An indel inserts and/or deletes nucleotides from a sequence, while a point mutation is a form of substitution that replaces one of the nucleotides without changing the overall number in the DNA. Indels, being insertions and/or deletions, can be used as genetic markers in natural populations, especially in phylogenetic studies. Indel frequency tends to be markedly lower than that of single nucleotide polymorphisms (SNP), except near highly repetitive regions, including homopolymers and microsatellites.

An MSI (microsatellite instability) module may identify genetic hypermutability (predisposition to mutation) that results from impaired DNA mismatch repair (MMR). The presence of MSI represents phenotypic evidence that MMR is not functioning normally. MMR corrects errors that spontaneously occur during DNA replication, such as single base mismatches or short insertions and deletions. The proteins involved in MMR correct polymerase errors by forming a complex that binds to the mismatched section of DNA, excises the error, and inserts the correct sequence in its place. Cells with abnormally functioning MMR are unable to correct errors that occur during DNA replication, which causes the cells to accumulate errors in their DNA. This causes the creation of novel microsatellite fragments. Polymerase chain reaction-based assays can reveal these novel microsatellites and provide evidence for the presence of MSI. Microsatellites are repeated sequences of DNA. These sequences can be made of repeating units of one to six base pairs in length. Although the length of these microsatellites is highly variable from person to person and contributes to the individual DNA "fingerprint", each individual has microsatellites of a set length. The most common microsatellite in humans is a dinucleotide repeat of the nucleotides C and A, which occurs tens of thousands of times across the genome. Microsatellites are also known as simple sequence repeats (SSRs).

A TMB (tumor mutational burden) module may identify a measurement of mutations carried by tumor cells and is a predictive biomarker being studied to evaluate its association with response to Immuno-Oncology (I-O) therapy. Tumor cells with high TMB may have more neoantigens, with an associated increase in cancer-fighting T cells in the tumor microenvironment and periphery. These neoantigens can be recognized by T cells, inciting an anti-tumor response. TMB has emerged more recently as a quantitative marker that can help predict potential responses to immunotherapies across different cancers, including melanoma, lung cancer and bladder cancer. TMB is defined as the total number of mutations per coding area of a tumor genome. Importantly, TMB is consistently reproducible. It provides a quantitative measure that can be used to better inform treatment decisions, such as selection of targeted or immunotherapies or enrollment in clinical trials.

A CNV (copy number variation) module may identify deviations from the normal genome, especially in the number of copies of a gene, portions of a gene, or other portions of a genome not defined by a gene, and any subsequent implications from analyzing genes, variants, alleles, or sequences of nucleotides. CNV are the phenomenon in which structural variations may occur in sections of nucleotides, or base pairs, which include repetitions, deletions, or inversions.

A Fusions module may identify hybrid genes formed from two previously separate genes. It can occur as a result of: translocation, interstitial deletion, or chromosomal inversion. Gene fusion can play an important role in tumorigenesis. Fusion genes can contribute to tumor formation because fusion genes can produce much more active abnormal protein than non-fusion genes. Often, fusion genes are oncogenes that cause cancer; these include BCR-ABL, TEL-AML1 (ALL with t(12; 21)), AML1-ETO (M2 AML with t(8; 21)), and TMPRSS2-ERG with an interstitial deletion on chromosome 21, often occurring in prostate cancer. In the case of TMPRSS2-ERG, by disrupting androgen receptor (AR) signaling and inhibiting AR expression by oncogenic ETS transcription factor, the fusion product regulates prostate cancer. Most fusion genes are found from hematological cancers, sarcomas, and prostate cancer. BCAM-AKT2 is a fusion gene that is specific and unique to high-grade serous ovarian cancer. Oncogenic fusion genes may lead to a gene product with a new or different function from the two fusion partners. Alternatively, a proto-oncogene is fused to a strong promoter, and thereby the oncogenic function is set to function by an upregulation caused by the strong promoter of the upstream fusion partner. The latter is common in lymphomas, where oncogenes are juxtaposed to the promoters of the immunoglobulin genes. Oncogenic fusion transcripts may also be caused by trans-splicing or read-through events. Since chromosomal translocations play such a significant role in neoplasia, a specialized database of chromosomal aberrations and gene fusions in cancer has been created. This database is called Mitelman Database of Chromosome Aberrations and Gene Fusions in Cancer.

A VUS (variant of unknown significance) module may identify variants which are detected in the genome of a patient (especially in a patient's cancer specimen) but cannot be classified as pathogenic or benign at the time of detection. VUS may be catalogued from publications to identify if they may be classified as benign or pathogenic.

A DNA Repair Pathways module (for example, a pathway engine 200n) may identify defects in DNA repair pathways which enable cancer cells to accumulate genomic alterations that contribute to their aggressive phenotype. Cancerous tumors rely on residual DNA repair capacities to survive the damage induced by genotoxic stress which leads to isolated DNA repair pathways being inactivated in cancer cells. DNA repair pathways are generally thought of as mutually exclusive mechanistic units handling different types of lesions in distinct cell cycle phases. Recent preclinical studies, however, provide strong evidence that multifunctional DNA repair hubs, which are involved in multiple conventional DNA repair pathways, are frequently altered in cancer. Identifying pathways which may be affected may lead to important patient treatment considerations.

A Raw Counts module may identify a count of the variants that are detected from the sequencing data. For DNA, this may be the number of reads from sequencing which correspond to a particular variant in a gene. For RNA, this may be the gene expression counts or the transcriptome counts from sequencing.

Structural variant classification may include evaluating features from the feature collection, alterations from the alteration module, and other classifications from within itself from one or more classification modules. Structural variant classification may provide classifications to a stored classifications storage. An exemplary classification module may include a classification of a CNV as "Reportable" may mean that the CNV has been identified in one or more reference databases as influencing the tumor cancer characterization, disease state, or pharmacogenomics, "Not Reportable" may mean that the CNV has not been identified as such, and "Conflicting Evidence" may mean that the CNV has both evidence suggesting "Reportable" and "Not Reportable." Furthermore, a classification of therapeutic relevance is similarly ascertained from any reference datasets mention of a therapy which may be impacted by the detection (or non-detection) of the CNV. Other classifications may include applications of machine learning algorithms, neural networks, regression techniques, graphing techniques, inductive reasoning approaches, or other artificial intelligence evaluations within modules. A classifier for clinical trials may include evaluation of variants identified from the alteration module which have been identified as significant or reportable, evaluation of all clinical trials available to identify inclusion and exclusion criteria, mapping the patient's variants and other information to the inclusion and exclusion criteria, and classifying clinical trials as applicable to the patient or as not applicable to the patient. Similar classifications may be performed for therapies, loss-of-function, gain-of-function, diagnosis, microsatellite instability, tumor mutational burden, indels, SNP, MNP, fusions, and other alterations which may be classified based upon the results of the alteration modules.

Each of the feature collection, alteration module(s), structural variant and feature store may be communicatively coupled to a data bus to transfer data between each module for processing and/or storage. In some embodiments, each of the feature collection, alteration module(s), structural variant and feature store may be communicatively coupled to each other for independent communication without sharing the data bus.

In addition to the above features and enumerated modules, feature modules may further include one or more of the following modules within their respective modules as a sub-module or as a standalone module.

Germline/somatic DNA feature module may comprise a feature collection associated with the DNA-derived information of a patient or a patient's tumor. These features may include raw sequencing results, such as those stored in FASTQ, BAM, VCF, or other sequencing file types known in the art; genes; mutations; variant calls; and variant characterizations. Genomic information from a patient's normal sample may be stored as germline and genomic information from a patient's tumor sample may be stored as somatic.

An RNA feature module may comprise a feature collection associated with the RNA-derived information of a patient, such as transcriptome information. These features may include raw sequencing results, transcriptome expressions, genes, mutations, variant calls, and variant characterizations.

A metadata module may comprise a feature collection associated with the human genome, protein structures and their effects, such as changes in energy stability based on a protein structure.

A clinical module may comprise a feature collection associated with information derived from clinical records of a patient and records from family members of the patient. These may be abstracted from unstructured clinical documents, EMR, EHR, or other sources of patient history. Information may include patient symptoms, diagnosis, treatments, medications, therapies, hospice, responses to treatments, laboratory testing results, medical history, geographic locations of each, demographics, or other features of the patient which may be found in the patient's medical record. Information about treatments, medications, therapies, and the like may be ingested as a recommendation or prescription and/or as a confirmation that such treatments, medications, therapies, and the like were administered or taken.

An imaging module may comprise a feature collection associated with information derived from imaging records of a patient. Imaging records may include H&E slides, IHC slides, radiology images, and other medical imaging which may be ordered by a physician during the course of diagnosis and treatment of various illnesses and diseases. These features may include TMB, ploidy, purity, nuclear-cytoplasmic ratio, large nuclei, cell state alterations, biological pathway disruptions, hormone receptor alterations, immune cell infiltration, immune biomarkers of MMR, MSI, PDL1, CD3, FOXP3, HRD, PTEN, PIK3CA; collagen or stroma composition, appearance, density, or characteristics; tumor budding, size, aggressiveness, metastasis, immune state, chromatin morphology; and other characteristics of cells, tissues, or tumors for prognostic predictions.

An epigenome module, such as epigenome module from Omics, may comprise a feature collection associated with information derived from DNA modifications which are not changes to the DNA sequence and regulate the gene expression. These modifications are frequently the result of environmental factors based on what the patient may breathe, eat, or drink. These features may include DNA methylation, histone modification, or other factors which deactivate a gene or cause alterations to gene function without altering the sequence of nucleotides in the gene.

A microbiome module, such as microbiome module from Omics, may comprise a feature collection associated with information derived from the viruses and bacteria of a patient. These features may include viral infections which may affect treatment and diagnosis of certain illnesses as well as the bacteria present in the patient's gastrointestinal tract which may affect the efficacy of medicines ingested by the patient.

A proteome module, such as proteome module from Omics, may comprise a feature collection associated with information derived from the proteins produced in the patient. These features may include protein composition, structure, and activity; when and where proteins are expressed; rates of protein production, degradation, and steady-state abundance; how proteins are modified, for example, post-translational modifications such as phosphorylation; the movement of proteins between subcellular compartments; the involvement of proteins in metabolic pathways; how proteins interact with one another; or modifications to the protein after translation from the RNA such as phosphorylation, ubiquitination, methylation, acetylation, glycosylation, oxidation, or nitrosylation.

Additional Omics module(s) may also be included in Omics, such as a feature collection associated with all the different field of omics, including: cognitive genomics, a collection of features comprising the study of the changes in cognitive processes associated with genetic profiles; comparative genomics, a collection of features comprising the study of the relationship of genome structure and function across different biological species or strains; functional genomics, a collection of features comprising the study of gene and protein functions and interactions including transcriptomics; interactomics, a collection of features comprising the study relating to large-scale analyses of gene-gene, protein-protein, or protein-ligand interactions; metagenomics, a collection of features comprising the study of metagenomes such as genetic material recovered directly from environmental samples; neurogenomics, a collection of features comprising the study of genetic influences on the development and function of the nervous system; pangenomics, a collection of features comprising the study of the entire collection of gene families found within a given species; personal genomics, a collection of features comprising the study of genomics concerned with the sequencing and analysis of the genome of an individual such that once the genotypes are known, the individual's genotype can be compared with the published literature to determine likelihood of trait expression and disease risk to enhance personalized medicine suggestions; epigenomics, a collection of features comprising the study of supporting the structure of genome, including protein and RNA binders, alternative DNA structures, and chemical modifications on DNA; nucleomics, a collection of features comprising the study of the complete set of genomic components which form the cell nucleus as a complex, dynamic biological system; lipidomics, a collection of features comprising the study of cellular lipids, including the modifications made to any particular set of lipids produced by a patient; proteomics, a collection of features comprising the study of proteins, including the modifications made to any particular set of proteins produced by a patient; immunoproteomics, a collection of features comprising the study of large sets of proteins involved in the immune response; nutriproteomics, a collection of features comprising the study of identifying molecular targets of nutritive and non-nutritive components of the diet including the use of proteomics mass spectrometry data for protein expression studies; proteogenomics, a collection of features comprising the study of biological research at the intersection of proteomics and genomics including data which identifies gene annotations; structural genomics, a collection of features comprising the study of 3-dimensional structure of every protein encoded by a given genome using a combination of modeling approaches; glycomics, a collection of features comprising the study of sugars and carbohydrates and their effects in the patient; foodomics, a collection of features comprising the study of the intersection between the food and nutrition domains through the application and integration of technologies to improve consumer's well-being, health, and knowledge; transcriptomics, a collection of features comprising the study of RNA molecules, including mRNA, rRNA, tRNA, and other non-coding RNA, produced in cells; metabolomics, a collection of features comprising the study of chemical processes involving metabolites, or unique chemical fingerprints that specific cellular processes leave behind, and their small-molecule metabolite profiles; metabonomics, a collection of features comprising the study of the quantitative measurement of the dynamic multiparametric metabolic response of cells to pathophysiological stimuli or genetic modification; nutrigenetics, a collection of features comprising the study of genetic variations on the interaction between diet and health with implications to susceptible subgroups; cognitive genomics, a collection of features comprising the study of the changes in cognitive processes associated with genetic profiles; pharmacogenomics, a collection of features comprising the study of the effect of the sum of variations within the human genome on drugs; pharmacomicrobiomics, a collection of features comprising the study of the effect of variations within the human microbiome on drugs; toxicogenomics, a collection of features comprising the study of gene and protein activity within particular cell or tissue of an organism in response to toxic substances; mitointeractome, a collection of features comprising the study of the process by which the mitochondria proteins interact; psychogenomics, a collection of features comprising the study of the process of applying the powerful tools of genomics and proteomics to achieve a better understanding of the biological substrates of normal behavior and of diseases of the brain that manifest themselves as behavioral abnormalities, including applying psychogenomics to the study of drug addiction to develop more effective treatments for these disorders as well as objective diagnostic tools, preventive measures, and cures; stem cell genomics, a collection of features comprising the study of stem cell biology to establish stem cells as a model system for understanding human biology and disease states; connectomics, a collection of features comprising the study of the neural connections in the brain; microbiomics, a collection of features comprising the study of the genomes of the communities of microorganisms that live in the digestive tract; cellomics, a collection of features comprising the study of the quantitative cell analysis and study using bioimaging methods and bioinformatics; tomomics, a collection of features comprising the study of tomography and omics methods to understand tissue or cell biochemistry at high spatial resolution from imaging mass spectrometry data; ethomics, a collection of features comprising the study of high-throughput machine measurement of patient behavior; and videomics, a collection of features comprising the study of a video analysis paradigm inspired by genomics principles, where a continuous image sequence, or video, can be interpreted as the capture of a single image evolving through time of mutations revealing patient insights.

A sufficiently robust collection of features may include all of the features disclosed above; however, models and predictions based from the available features may include models which are trained from a selection of features that are much more limiting than the exhaustive feature set. Such a constrained feature set may include as few as tens to hundreds of features. For example, a model's constrained feature set may include the genomic results of a sequencing of the patient's tumor, derivative features based upon the genomic results, the patient's tumor origin, the patient's age at diagnosis, the patient's gender and race, and symptoms that the patient brought to their physicians attention during a routine checkup.

A feature store may enhance a patient's feature set through the application of machine learning and analytics by selecting from any features, alterations, or calculated output derived from the patient's features or alterations to those features. Such a feature store may generate new features from the original features found in feature module or may identify and store important insights or analysis based upon the features. The selections of features may be based upon an alteration or calculation to be generated, and may include the calculation of single or multiple nucleotide polymorphisms insertion or deletions of the genome, a tumor mutational burden, a microsatellite instability, a copy number variation, a fusion, or other such calculations. An exemplary output of an alteration or calculation generated which may inform future alterations or calculations includes a finding of lung cancer and variants in EGFR, an epidermal growth factor receptor gene that is mutated in ~10% of non-small cell lung cancer and ~50% of lung cancers from non-smokers. Wherein previously classified variants may be identified in the patient's genome which may inform the classification of novel variants or indicate a further risk of disease. An exemplary approach may include the enrichment of variants and their respective classifications to identify a region nearby or with evidence to interact with EGFR and associated with cancer. Any novel variants detected from a patient's sequencing localized to this region or interactions with this region would increase the patient's risk. Features which may be utilized in such an alteration detection include the structure of EGFR and classification of variants therein. A model which focuses on enrichment may isolate such variants.

The above referenced models may be implemented as artificial intelligence engines and may include gradient boosting models, random forest models, neural networks (NN), regression models, Naive Bayes models, or machine learning algorithms (MLA). A MLA or a NN may be trained from a training data set. In an exemplary prediction profile, a training data set may include imaging, pathology, clinical, and/or molecular reports and details of a patient, such as those curated from an EHR or genetic sequencing reports. MLAs include supervised algorithms (such as algorithms where the features/classifications in the data set are annotated) using linear regression, logistic regression, decision trees, classification and regression trees, Naïve Bayes, nearest neighbor clustering; unsupervised algorithms (such as algorithms where no features/classification in the data set are annotated) using Apriori, means clustering, principal component analysis, random forest, adaptive boosting; and semi-supervised algorithms (such as algorithms where an incomplete number of features/classifications in the data set are annotated) using generative approach (such as a mixture of Gaussian distributions, mixture of multinomial distributions, hidden Markov models), low density separation, graph-based approaches (such as mincut, harmonic function, manifold regularization), heuristic approaches, or support vector machines. NNs include conditional random fields, convolutional neural networks, attention based neural networks, deep learning, long short term memory networks, or other neural models where the training data set includes a plurality of tumor samples, RNA expression data for each sample, and pathology reports covering imaging data for each sample. While MLA and neural networks identify distinct approaches to machine learning, the terms may be used interchangeably herein. Thus, a mention of MLA may include a corresponding NN or a mention of NN may include a corresponding MLA unless explicitly stated otherwise. Training may include providing datasets, labeling these traits as they occur in patient records, and training the MLA to predict or classify based on new inputs. Artificial NNs are efficient computing models which have shown their strengths in solving hard problems in artificial intelligence. They have also been shown to be universal approximators (can represent a wide variety of functions when given appropriate parameters). Some MLA may identify features of importance and identify a coefficient, or weight, to them. The coefficient may be multiplied with the occurrence frequency of the feature to generate a score, and once the scores of one or more features exceed a threshold, certain classifications may be predicted by the MLA. A coefficient schema may be combined with a rule-based schema to generate more complicated predictions, such as predictions based upon multiple features. For example, ten key features may be identified across different classifications. A list of coefficients may exist for the key features, and a rule set may exist for the classification. A rule set may be based upon the number of occurrences of the feature, the scaled weights of the features, or other qualitative and quantitative assessments of features encoded in logic known to those of ordinary skill in the art. In other MLA, features may be organized in a binary tree structure. For example, key features which distinguish between the most classifications may exist as the root of the binary tree and each subsequent branch in the tree until a classification may be awarded based upon reaching a terminal node of the tree. For example, a binary tree may have a root node which tests for a first feature. The occurrence or non-occurrence of this feature must exist (the binary decision), and the logic may traverse the branch which is true for the item being classified. Additional rules may be based upon thresholds, ranges, or other qualitative and quantitative tests. While supervised methods are useful when the training dataset has many known values or annotations, the nature of EMR/EHR documents is that there may not be many annotations provided. When exploring large amounts of unlabeled data, unsupervised methods are useful for binning/bucketing instances in the data set. A single instance of the above models, or two or more such instances in combination, may constitute a model for the purposes of models, artificial intelligence, neural networks, or machine learning algorithms, herein.

Figure 3B:
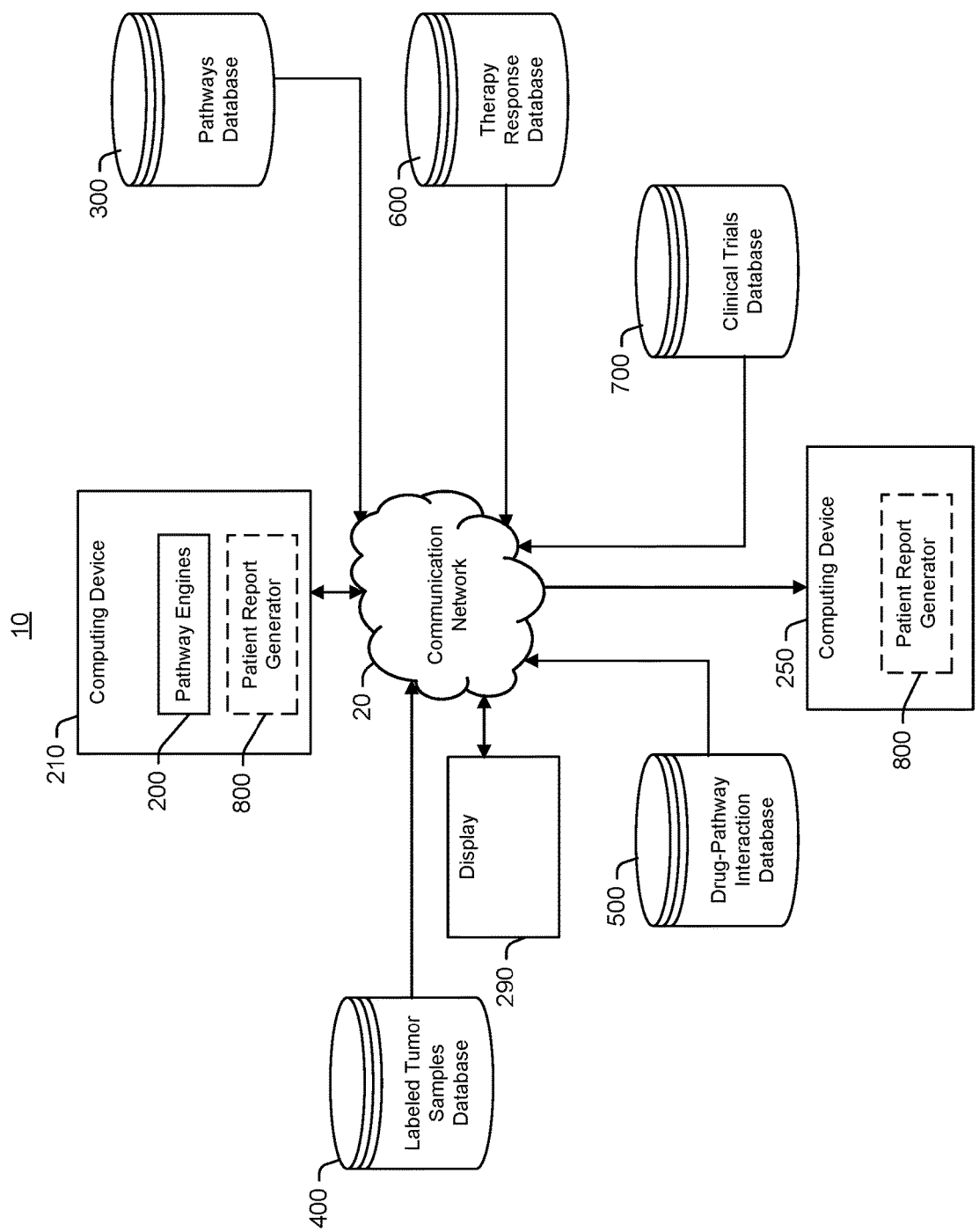
FIG. 3B is a schematic example of devices that can be used in the system.

Referring now to FIG. 3A as well as FIG. 3B, a schematic example of devices that can be used in the system 10 is shown. The pathway engines can be included in a computing device 210 that can be included in the system 10. The computing device 210 can be in communication with (e.g., wired communication, wireless communication) the pathways database 300, the labeled tumor samples database 400, the drug-pathway interaction database 500, the therapy response database 600, the clinical trials database 700, and the patient report generator 800 over the communication network 20. The patient report generator 800 can be included in a secondary computing device 250 that can be included in the system and/or on the computing device 210. The computing device 210 can be in communication with the secondary communication device 250. The computing device 210 and/or the secondary computing device 250 may also be in communication with a display 290 that can be included in the system 10 over the communication network 20.

The communication network 20 can facilitate communication between the computing device 210 and the secondary computing device 250. In some embodiments, communication network 20 can be any suitable communication network or combination of communication networks. For example, communication network 20 can include a Wi-Fi network (which can include one or more wireless routers, one or more switches, etc.), a peer-to-peer network (e.g., a Bluetooth network), a cellular network (e.g., a 3G network, a 4G network, a 5G network, etc., complying with any suitable standard, such as CDMA, GSM, LTE, LTE Advanced, WiMAX, etc.), a wired network, etc. In some embodiments, communication network 20 can be a local area network, a wide area network, a public network (e.g., the Internet), a private or semi-private network (e.g., a corporate or university intranet), any other suitable type of network, or any suitable combination of networks. Communications links shown in FIGS. 3A and 3B can each be any suitable communications link or combination of communications links, such as wired links, fiber optic links, Wi-Fi links, Bluetooth links, cellular links, etc.

Figure 3C:
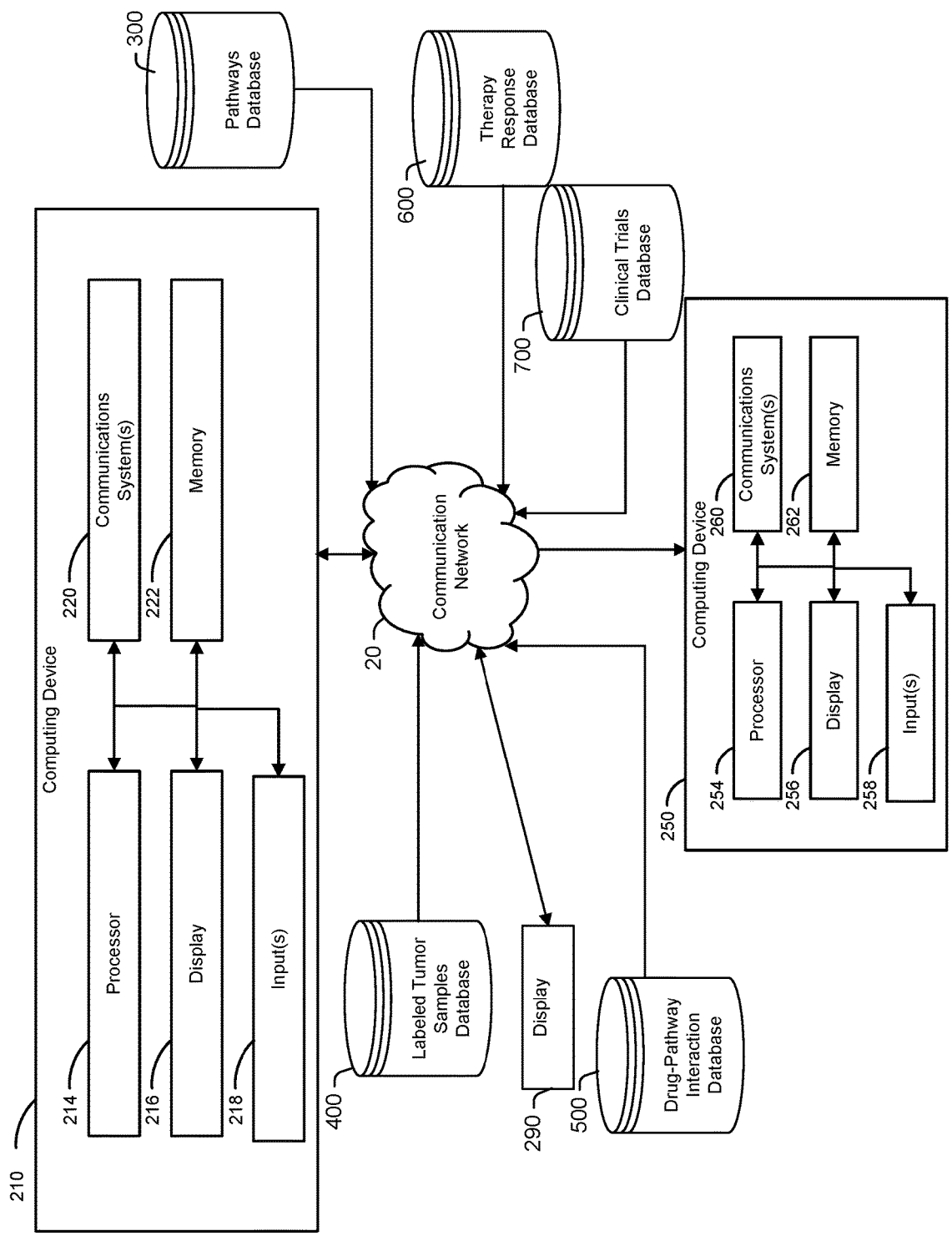
FIG. 3C shows an example of hardware that can be used in some embodiments of the system of FIG. 3A and FIG. 3B.

FIG. 3C shows an example of hardware that can be used in some embodiments of the system 10. The computing device 210 can include a processor 214, a display 216, an input 218, a communication system 220, and memory 222. The processor 214 can be any suitable hardware processor or combination of processors, such as a central processing unit ("CPU"), a graphics processing unit ("GPU"), etc., which can execute a program, which can include the processes described below.

In some embodiments, the display 216 can present a graphical user interface. In some embodiments, the display 216 can be implemented using any suitable display devices, such as a computer monitor, a touchscreen, a television, etc. In some embodiments, the inputs 218 of the computing device 210 can include indicators, sensors, actuatable buttons, a keyboard, a mouse, a graphical user interface, a touch-screen display, etc.

In some embodiments, the communication system 220 can include any suitable hardware, firmware, and/or software for communicating with the other systems, over any suitable communication networks. For example, the communication system 220 can include one or more transceivers, one or more communication chips and/or chip sets, etc. In a more particular example, communication system 220 can include hardware, firmware, and/or software that can be used to establish a coaxial connection, a fiber optic connection, an Ethernet connection, a USB connection, a Wi-Fi connection, a Bluetooth connection, a cellular connection, etc. In some embodiments, the communication system 220 allows the computing device 210 to communicate with the secondary computing device 250.

In some embodiments, the memory 222 can include any suitable storage device or devices that can be used to store instructions, values, etc., that can be used, for example, by processor 214 to present content using display 216, to communicate with the secondary computing device 250 via communications system(s) 220, etc. Memory 222 can include any suitable volatile memory, non-volatile memory, storage, or any suitable combination thereof. For example, memory 222 can include RAM, ROM, EEPROM, one or more flash drives, one or more hard disks, one or more solid state drives, one or more optical drives, etc. In some embodiments, memory 222 can have encoded thereon a computer program for controlling operation of computing device 210 (or secondary computing device 250). In such embodiments, processor 214 can execute at least a portion of the computer program to present content (e.g., user interfaces, images, graphics, tables, reports, etc.), receive content from the secondary computing device 250, transmit information to the secondary computing device 250, etc.

The secondary computing device 250 can include a processor 254, a display 256, an input 258, a communication system 260, and memory 262. The processor 254 can be any suitable hardware processor or combination of processors, such as a central processing unit ("CPU"), a graphics processing unit ("GPU"), etc., which can execute a program, which can include the processes described below.

In some embodiments, the display 256 can present a graphical user interface. In some embodiments, the display 256 can be implemented using any suitable display devices, such as a computer monitor, a touchscreen, a television, etc. In some embodiments, the inputs 258 of the secondary computing device 250 can include indicators, sensors, actuatable buttons, a keyboard, a mouse, a graphical user interface, a touch-screen display, etc.

In some embodiments, the communication system 260 can include any suitable hardware, firmware, and/or software for communicating with the other systems, over any suitable communication networks. For example, the communication system 260 can include one or more transceivers, one or more communication chips and/or chip sets, etc. In a more particular example, communication system 260 can include hardware, firmware, and/or software that can be used to establish a coaxial connection, a fiber optic connection, an Ethernet connection, a USB connection, a Wi-Fi connection, a Bluetooth connection, a cellular connection, etc. In some embodiments, the communication system 260 allows the secondary computing device 250 to communicate with the computing device 210.

In some embodiments, the memory 262 can include any suitable storage device or devices that can be used to store instructions, values, etc., that can be used, for example, by processor 254 to present content using display 256, to communicate with the computing device 210 via communications system(s) 260, etc. Memory 262 can include any suitable volatile memory, non-volatile memory, storage, or any suitable combination thereof. For example, memory 262 can include RAM, ROM, EEPROM, one or more flash drives, one or more hard disks, one or more solid state drives, one or more optical drives, etc. In some embodiments, memory 262 can have encoded thereon a computer program for controlling operation of secondary computing device 250 (or computing device 210). In such embodiments, processor 254 can execute at least a portion of the computer program to present content (e.g., user interfaces, images, graphics, tables, reports, etc.), receive content from the computing device 210, transmit information to the computing device 210, etc. The display 290 can be a computer display, a television monitor, a projector, or other suitable displays.

Exemplary Training Data for the Disclosed Systems and Methods

FIG. 4 shows a representation of example data from data inputs 100 that may be used to train a pathway engine 200*n*. Specifically, FIG. 4 displays a data set 410 which can include a number of transcriptome values. Each transcriptome value set (e.g. Transcriptome Values 1 at 411, Transcriptome Values 2 at 412, . . . . Transcriptome Values N at 413) may be associated with a single tissue specimen. Each transcriptome value 411-413 can represent a raw count or normalized count corresponding to the expression level of all possible RNA products of a gene. Each transcriptome value 411-413 can be associated with a single specimen. The data set 410 can also include one or more pathway labels associated with each specimen and the transcriptome value set. For example, a first specimen may be associated with a first pathway label 414, a second pathway label 415, and a third pathway label 416. Each pathway label can be associated with a pathway (e.g., a pathway included in the pathways database 300). Each pathway label may be "positive control" or "negative control" associated with the detected pathway alterations in the DNA data set associated with the specimen. The transcriptome value and pathway label(s) associated with each specimen can be used as training data to train one more machine learning models, as will be described below.

For example, each transcriptome value set could be generated by sequencing each corresponding tissue specimen using RNA-seq or other sequencing methods. The sequencing may be whole exome sequencing or targeted panel sequencing and may be next generation sequencing. The transcriptome value sets in the data set 410 may be stored in a table where each column is a gene and each row is a specimen, and the cell values reflect expression level values for the specimen-gene pair. The raw expression level values could range from 0 to over 10 million. The column that represents a gene may represent the expression level of all possible RNA products of that gene (for example, all possible transcripts, splice variants, or isoforms) combined, or a subset of a gene's RNA products. In various embodiments, a tissue sample is a biopsy or blood sample from a human patient or a tumor organoid.

In various embodiments, prior to use by the systems and methods, transcriptome value sets from bulk specimens (for example, specimens having two or more tissue types) have been deconvoluted to remove confounding factors, including biopsy tissue site. In one example, deconvolution has been performed according to systems and methods disclosed in U.S. Prov. Patent App. No. 62/786,756, filed on Dec. 31, 2018 and U.S. Prov. Patent App. No. 62/944,995, filed on Dec. 6, 2019, which are both incorporated by reference herein.

In various embodiments, the systems and methods include additional strategies to detect known technical and biological covariates and incorporate them into the calculation of pathway disruption scores. The systems and methods may account for the effects of tissue site and tumor purity when calculating pathway disruption scores.

In various embodiments, the values in the transcriptome value sets may be normalized. Normalized transcriptome values may range from 0 to 8. In one example, the normalization method is done according to the systems and methods disclosed in U.S. patent application Ser. No. 16/581,706, and USPCT19/52801 (filed Sep. 24, 2019, and Sep. 24, 2019, respectively) which are incorporated by reference herein.

A DNA variant data set may also be associated with each transcriptome value set in the data set 410. (not shown in FIG. 4) In one example, each DNA data set could be generated by sequencing the corresponding tissue specimen using DNA-seq or other sequencing methods. The sequencing may be whole exome sequencing or targeted panel sequencing and may be next generation sequencing. In another example, the DNA data set is obtained by microarray or SNP array.

In one example, the DNA data set includes pathway mutation data. Pathway mutation data may include data describing genetic variants in the DNA data set, especially genetic variants in genes and/or promoters related to a cellular pathway of interest. In one example, a cellular pathway of interest is one of the oncogenic signaling pathways defined by the TCGA consortium. In another example, a cellular pathway of interest is a custom gene set or list of genes. In one example, the DNA data set is stored as a variant call format (VCF) file. In another example, the DNA data set is a list of genetic variants. In various embodiments, the subsets of the DNA data set (for example, data related to the cellular pathway of interest) or the entire DNA data set may be used as features to train a pathway engine 200*n*. Genetic variants may include any class of variant, including single nucleotide polymorphisms, fusions, insertion deletions, copy number variations, etc.

Each transcriptome value set in the data set 410 may be associated with one or more data elements reflecting information about the specimen from which the transcriptome value set was derived. As shown in FIG. 4, each transcriptome value is associated with a specimen ID, a cancer type, and one or more dysregulation indicators. Any or all of the dysregulation indicators may be used as features to train a pathway engine 200*n*. Each dysregulation indicator may be associated with one or more pathways of interest. If the transcriptome value set has no associated cancer type or the associated cancer type is likely to be incorrect, then a cancer type may be determined for the transcriptome, for example, by analyzing histopathological slides associated with the transcriptome or by analyzing the transcriptome and any associated data. One example, as described in U.S. Prov. Patent App. No. 62/855,750, titled Systems and Methods for Multi-label Cancer Classification. filed on May 31, 2019, is incorporated herein by reference. One example of a transcriptome without an associated cancer type or with an associated cancer type that may be inaccurate is a transcriptome associated with a tumor of unknown origin, a metastatic tumor, or a cancer sample that was inaccurately labeled.

In one example, the data set 410 may be filtered to generate a subset of the data set 410 for training a pathway engine 200*n*, and may be filtered based on cancer type and/or pathway of interest. For example, if a pathway engine 200*n* is designed to be specific to a cancer type (lung cancer, for example), then rows associated with a different cancer type may be removed from the data set 410 before DEG selection and training (as described in conjunction with FIG. 5). As another example, if a pathway engine 200*n* is specific to a pathway of interest, then dysregulation indicators associated with a different pathway may be removed from the data set 410 before selecting DEGs and training the pathway engine 200*n*. Each transcriptome value set and associated dysregulation indicators selected to train the model will be transformed into a feature vector.

In some embodiments, the data in the data set 410 used to train a pathway engine 200*n* contains more than 30 transcriptome value sets. In some embodiments, the data in the data set 410 used to train a pathway engine 200*n* contains more than 900 transcriptome value sets. In some embodiments, the data in the data set 410 used to train a pathway engine 200*n* contains more than 10,000 transcriptome value sets.

In one example, data in the data set 410 used to train the pathway engine 200*n* may be associated with primary tumor specimens or a single tissue type to minimize transcriptional heterogeneity, but this is not necessary to generate an accurate pathway engine.

One type of dysregulation indicator may be a pathway label, as shown in FIG. 4. For example, the pathway label may be "positive control" or "negative control." The pathway label can be selected based on any detected pathway alterations in the DNA data set associated with the specimen. In one example, if the DNA data set contains genetic variants in one or more genes and/or promoters related to a cellular pathway of interest, the corresponding transcriptome value set is assigned the pathway label positive control for that cellular pathway, while a transcriptome value set associated with a DNA data set that does not contain genetic variants in genes and/or promoters related to a cellular pathway of interest, or in some embodiments contains no variants or benign variants, is assigned the label negative control.

In another example, only if the DNA data set contains pathogenic variants in genes and/or promoters related to a cellular pathway of interest, where pathogenic means that the variants are known to contribute to the progression of cancer (or other disease state of interest), the corresponding transcriptome value set is assigned the pathway label positive control for that cellular pathway, while a transcriptome value set associated with a DNA data set that does not contain genetic variants or contains benign variants in genes and/or promoters related to a cellular pathway of interest is assigned the label negative control.

In yet another example, the negative control transcriptome value sets are wild type for all genes in the pathway and all positive control transcriptome value sets are associated with genetic variants in one or more of the genes in the pathway or one or more genes in one class of genes within the cellular pathway (for example, a gene class or module may be all RAS genes—KRAS, NRAS, HRAS, etc.; all RAF genes—RAF1, ARAF, BRAF, etc.; all PI3K genes—PIKCA, PIKCB, etc.) and in one example, the genetic variants are all pathogenic. For example, transcriptome value sets of patients with known pathway dysregulation (for example, KRAS G12V mutations for the RAS/RTK pathway) are considered "positive controls" and transcriptome value sets of patients who are wild type (WT) for all genes and promoters associated with the pathway are considered "negative controls".

In one example, negative controls have no variants (including copy number variants and variants of unknown significance) in any pathway genes. In one example, any transcriptomes with variants of unknown significance in pathway genes or promoters are excluded from the training data. In another example, only if the DNA data set contains pathogenic variants in genes and/or promoters related to a cellular pathway of interest, where pathogenic means that the variants are known to contribute to the progression of cancer, the corresponding transcriptome value set is assigned the pathway label positive control for that cellular pathway, while a transcriptome value set associated with a DNA data set that does not contain genetic variants or contains benign variants in genes and/or promoters related to a cellular pathway of interest is assigned the label negative control.

In yet another example, the negative control transcriptome value sets are wild type for all genes in the pathway and all positive control transcriptome value sets are associated with genetic variants in a subset of the genes in the pathway or only one class of genes within the cellular pathway (for example, a gene class may be all RAS genes—KRAS, NRAS, HRAS, etc.; all RAF genes—RAF1, ARAF, BRAF, etc.; all PI3K genes—PIKCA, PIKCB, etc.) and in one example, the genetic variants are all pathogenic. For example, transcriptome value sets of patients with known pathway dysregulation (for example, KRAS G12V mutations for the RAS/RTK pathway) are considered "positive controls" and transcriptome value sets of patients who are wild type (WT) for all genes and promoters associated with the pathway are considered "negative controls".

In one example, negative controls have no variants (including copy number variants and variants of unknown significance) in any pathway genes. In one example, any transcriptomes with variants of unknown significance in pathway genes or promoters are excluded from the training data. Non-limiting examples of positive and negative control selection are provided below.

Exemplary Positive and Negative Control Selection for Pathways, Multi-Gene Modules, and Single-Gene Modules
Pathways Referring now to FIG. 4 as well as FIG. 12, in some embodiments, specimens can be labeled as a "positive control" or a "negative control" in order to train a model to detect dysregulation in a pathway. Pathways may be well-characterized pathways, or may be custom pathways. The dysregulation may result in a disease, condition, (.e.g., cancer), etc., and in some embodiments, the degree of dysregulation caused by a nucleic acid variant can be indicated by a classifying a variant or set of variants in the pathway as "benign," "likely benign," "conflicting evidence," "likely pathogenic," "pathogenic," "unknown significance," and "unknown." In some embodiments, a specimen may only be labeled as a positive control if the specimen has a nucleic acid variant or set of variants (e.g., DNA mutations) that are "pathogenic," i.e., that are associated with a disease or condition, such as a cancer. Such a variant may be germline or somatic. By way of example, to train a model to detect dysregulation in the RTK-RAS pathway as exemplified in FIG. 12, a specimen will be labeled as a positive control only if the specimen includes a pathogenic nucleic variant of at least one of the genes included in a pathway module in the RTK-RAS pathway. For example, as shown in FIG. 12, the RTK-RAS pathway 1200 includes a RAS module, 12110, a RAF module 1215, an EGFR module 1205, a PTEN module 1220, an ERBB2 module 1225, a PI3K module 1230, an AKT module 1235, a TOR module 1240, a MEK module 1245, and an ERK module 1250. Accordingly, in some embodiments, only a specimen including a pathogenic nucleic acid mutation in one or more genes of one or more of these modules would be labeled as positive control for the model. To exemplify, with respect to the RAS and RAF modules, only specimens that include one or more pathogenic mutations in one or more of the KRAS, NRAS, HRAS, RAF1, BRAF, and/or ARAF genes will be labeled as a positive control.

In some embodiments, a specimen may only be classified as a positive control if the specimen has at least one pathogenic nucleic acid variant in one or more genes included in the pathway. In some embodiments, a specimen may only be classified as a positive control if the specimen has at least one pathogenic variant and/or a likely pathogenic nucleic acid variant in the pathway. Additionally or alternatively, in some embodiments, a specimen may be classified as a positive control if the RNA expression level of one or more genes in the pathway is aberrant and such aberrant expression level is pathogenic (i.e., is associated with a disease or condition, e.g., cancer).

In some embodiments, a specimen may only be labeled as a negative control if the specimen has no nucleic acid variant of any type in any gene included in the pathway. In some embodiments, a specimen may only be labeled as a negative control if the specimen has no variants, or has only benign or likely benign nucleic acid variants in one or more genes in the pathway in germline samples only. That is, to qualify as a negative control, a benign or likely benign mutation present in one or more genes of a pathway is only allowed if it is germline; if benign or likely benign mutations are present in non-germline samples, the specimen is disqualified as a negative control. In other embodiments, a specimen may only be labeled as a negative control if the specimen includes no variants, or only benign or likely benign variants in one or more genes in the pathway. For example, to train a model to detect dysregulation in the RTK-RAS pathway 1200, a specimen can be labeled as a negative control only if the specimen has no mutations in the genes of the listed modules of the pathway. In other embodiments, a specimen can be labeled as a negative control only if the specimen has no mutations or has benign or likely benign germline mutations in one or more genes of the listed modules. For example, as shown in FIG. 12, the RTK-RAS pathway 1200 includes a RAS module, 12110, a RAF module 1215, an EGFR module 1205, a PTEN module 1220, an ERBB2 module 1225, a PI3K module 1230, an AKT module 1235, a TOR module 1240, a MEK module 1245, and an ERK module 1250. The RAS module includes the KRAS, NRAS, and HRAS genes, and the RAF module includes the RAF1, BRAF, and ARAF genes. Thus, in one embodiment, a negative control for the RAS module would include a specimen having no mutations in any of the KRAS, NRAS and HRSA genes, and a negative control for the RAF module would include a specimen having no mutations in any of the RAF1, BRAF and ARAF genes. Likewise, for the other modules in the pathway. Additionally or alternatively, in some embodiments, a negative control for the RAS module would include a specimen having no mutations in any of the KRAS, NRAS and HRSA genes or only benign or likely benign germline mutations in the KRAS, NRAS and HRAS gene, and a negative control for the RAF module would include a specimen having no mutations in any of the RAF1, BRAF and ARAF genes, or only benign or likely benign germline mutations in the RAF1, BRAF and ARAF genes. Likewise, for the other modules in the pathway. Additionally or alternatively, in some embodiments, a specimen may be classified as a negative control if the RNA expression level of all genes in the pathway is wild-type.

In some embodiments, specimens that cannot be classified as a positive control or a negative control are excluded from training data.

Multi-Gene Modules

In some embodiments, specimens can be labeled as a "positive control" or a "negative control" in order to train a model to detect dysregulation in a module (e.g., a grouping of one or more selected genes). Thus, a model can be associated with a module. In some embodiments, a module may include multiple genes that are selected from a branch of a single pathway, a subset of genes in a pathway, a collection of genes from different pathways, or other suitable groupings of genes. Thus, the pathway may be a well-characterized pathway or may be a custom pathway. The dysregulation may result in a disease, condition, etc., and in some embodiments, the degree of dysregulation caused by a nucleic acid variant can be indicated by classifying a variant or set of variants in the module as "benign," "likely benign," "conflicting evidence," "likely pathogenic," "pathogenic," "unknown significance," and "unknown."

In some embodiments, a specimen may only be labeled as a positive control if the specimen has a nucleic acid variant or set of variants (e.g., DNA mutations) that are "pathogenic," i.e., that are associated with a disease or condition, such as cancer. By way of example, but not by way of limitation, a model can be trained to detect dysregulation in the RAS module 1210. The nucleic acid variant may be germline or somatic. In some embodiments, for a pathway engine or a model trained to detect dysregulation in a module, a specimen can be labeled as a positive control only if the specimen includes a nucleic acid variant in at least one gene included in the module. For example, for a model trained to detect dysregulation in the RAS module 1210, only specimens that include pathogenic nucleic acid variant in one or more of the KRAS, NRAS, and/or HRAS genes of the RAS module 1210 can be labeled as a positive control.

In some embodiments, a specimen may only be classified as a positive control if the specimen has at least one pathogenic nucleic acid variant included in the module associated with the model. Additionally or alternatively, in some embodiments, a specimen may only be classified as a positive control if the specimen has at least one pathogenic nucleic acid variant and/or a likely pathogenic nucleic acid variant in the module associated with the module. Additionally or alternatively, in some embodiments, a specimen may be classified as a positive control if the RNA expression level of one or more genes in module is aberrant and such aberrant expression level is pathogenic (i.e., is associated with a disease or condition).

In some embodiments, a specimen may only be labeled as a negative control if the specimen has no nucleic acid mutations of any type in any gene included in the module associated with the model. For example, to train a model to detect dysregulation in the RAS module 1210, a specimen can be labeled as a negative control sample only if the specimen has no mutations in the KRAS, NRAS, and HRAS genes of the RAS module 1210.

In some embodiments, a specimen may only be labeled as a negative control if the specimen has no nucleic acid variants of any type in any gene included in the module associated with the model or any other module included in the entire pathway that includes the module. For example, for a model trained to detect dysregulation in the RAS module 1210, in some embodiments, a specimen can be labeled as a negative control sample only if the specimen has no mutations in the KRAS, NRAS, and HRAS genes included in the RAS module 1210, as well no mutations in any gene included in the other modules included in the RTK-RAS pathway 1200.

Additionally or alternatively, the negative control includes no mutations, or only benign or likely benign germline mutations in one or more genes in the module. Additionally or alternatively, in some embodiments, the negative control includes no variants or only benign or likely benign germline variants in one or more genes in the module, and/or one or more genes of the other modules included in the pathway of interest.

For example, for a model trained to detect dysregulation in the RAS module 1210, in some embodiments, a specimen can be labeled as a negative control sample only if the specimen has no mutations, or only benign or likely benign germline mutations in the KRAS, NRAS, and HRAS genes included in the RAS module 1210, and in some embodiments, additional has no mutations or only benign or likely benign mutations in other genes included in the other modules included in the RTK-RAS pathway 1200.

Additionally or alternatively, in some embodiments, a specimen may be classified as a negative control only if the RNA expression level all genes in the module is wild-type, and/or if the expression level of all of the genes in all modules of the pathway of interest (e.g., the pathway including the module) is wild-type.

In some embodiments, specimens that cannot be classified as a positive control or a negative control can be excluded from training data.

Single-Gene Modules

In some embodiments, specimens can be labeled as a "positive control" or a "negative control" in order to train a model to detect dysregulation in module comprising a single gene. Thus, the model can be associated with the module. In some embodiments, the gene may be referred to as a module. The module can include a gene included in a pathway module (e.g., RAS module 1210). For example, the module can include the KRAS gene. In some embodiments, each gene included in a pathway module can be associated with a model trained to detect dysregulation in the module (e.g., the KRAS gene).

In some embodiments, the dysregulation may result in a disease, condition, etc., and in some embodiments, the degree of dysregulation can be indicated by classifying a nucleic acid variant or set of variants in the module as "benign," "likely benign," "conflicting evidence," "likely pathogenic," "pathogenic," "unknown significance," and "unknown." In some embodiments, a specimen may only be labeled as a positive control if the specimen has a pathogenic nucleic acid variant or set of variants (e.g., DNA mutations) associated with dysregulation in the module (e.g., the KRAS gene). The nucleic acid variant may be germline or somatic. In some embodiments, for a model trained to detect dysregulation in a module having a single gene, a specimen can be labeled as a positive control sample only if the specimen includes a pathogenic nucleic acid variant in the gene. For example, for a model trained to detect dysregulation in the KRAS gene, only specimens that include at least one pathogenic nucleic acid variant in the KRAS gene can be labeled as a positive control.

In some embodiments, a specimen may only be determined to have a mutation and classified as a positive control if the specimen has at least one pathogenic variant in DNA included in the gene included in the module. In some embodiments, a specimen may only be determined to have a mutation and classified as a positive control if the specimen has at least one pathogenic variant and/or a likely pathogenic variant in DNA included in the gene included in the module. Additionally or alternatively, in some embodiments, a specimen may be classified as a positive control if the RNA expression level of the gene in the module is aberrant and such aberrant expression level is pathogenic (i.e., is associated with a disease or condition).

In some embodiments, a specimen may only be labeled as a negative control if the specimen has no nucleic acid variant of any type in the gene associated with the model. Additionally or alternatively, in some embodiments, a specimen may only be labeled as a negative control if the specimen has either no mutations or has only benign or likely benign germline mutations in the gene associated with the module. In some embodiments, a specimen may only be labeled as a negative control if the specimen has no nucleic acid variants of any type in the gene associated with the model, or only benign variants or likely benign germline variants associated with the model, and only benign or germline variants in genes in the entire pathway that includes the gene. For example, for a model trained to detect dysregulation in the KRAS gene, a specimen can be labeled as a negative control sample only if the specimen has no mutations in the KRAS gene. In some embodiments, a negative control would include specimens having no mutations in the KRAS, NRAS, and HRAS genes included in the RAS module 1210, and only benign or likely benign germline variants in the genes of the other modules included in the RTK-RAS pathway 1200, or no variants of any kind in the genes of the other modules included in the RTK-RAS pathway 1200.

In some embodiments, a specimen may only be labeled as a negative control if the specimen has no nucleic acid variants of any type in the gene associated with the model or any other gene included in the entire pathway that includes the gene. For example, for a model trained to detect dysregulation in the KRAS gene, a specimen can be labeled as a negative control sample only if the specimen has no mutations in the KRAS, NRAS, and/or HRAS genes included in the RAS module 1210, as well no mutations in any gene included in the other modules included in the RTK-RAS pathway 1200. Additionally or alternatively, in some embodiments, a specimen may be classified as a negative control only if the RNA expression level of the gene in the module is wild-type, and/or only if the expression level of all of the genes in a module including the single-gene module is wild-type, and/or if the RNA expression level of all of the genes of all of the modules of the pathway of interest (e.g., the pathway including the single-gene module) is wild-type.

In some embodiments, specimens that cannot be classified as a positive control or a negative control can be excluded from training data.

Using only specimens without nucleic acid variants in a pathway, multi-gene module, or single gene module, as negative control samples to train a model to identify dysregulation in a pathway or module can improve the performance of the model as compared to other techniques. The discrimination ability (e.g., the ability to correctly identify dysregulated modules and non-dysregulated modules) of models trained with transcriptome data from negatively labeled samples that include nucleic acid variants in other modules in the pathway may be reduced because the mutations in the modules may dilute the effect of any dysregulation in the module associated with the model. For example, the negative samples can provide a baseline of RNA expression levels to compare against the positive samples that can indicate the effects of dysregulation on RNA expression levels. If the negative samples have DNA variants in modules other than the module associated with the model, the RNA expression levels of the baseline data may dilute and/or obscure the effect of the dysregulation on the RNA expression levels of the positive samples. In other words, models trained with transcriptome data from negatively labeled samples that do not include DNA variants in both the module associated with the model (e.g., the RAS module 1210) and the other modules in the pathway may better classify the module as dysregulated or non-dysregulated more accurately because the model can more clearly recognize the precise effects of mutations in the module without the diluting effects of other pathway modules.

Notably, some mutations classified as pathogenic or likely pathogenic by the criteria described above may ultimately not be considered pathogenic or likely pathogenic based on additional information found during training. For example, due to its classification as pathogenic or likely pathogenic, samples with the mutation FGFR2 c.1990-106A>G would normally not be allowed in the negative sample set when determining disruption scores for modules in the RTK/RAS pathway. However, in the generation of the model, it became apparent that a significant percentage of the normal population carries this variant and that it is very likely to be benign. Mutations such as this would be identified during model training, and an additional step would be included to disregard these mutations when generating the sets of positive and negative samples.

Another type of dysregulation indicator may be a gene set enrichment analysis result. In some examples, the "positive control" transcriptome value sets and "negative control" transcriptome value sets in the data set 410 may be similar. In these examples, in order to help the pathway engine 200n better differentiate "positive control" transcriptome value sets from "negative control" transcriptome value sets, one or more gene set enrichment analysis scores may be associated with each transcriptome value and used as a feature during pathway engine 200n training. For example, each transcriptome value in the data set 410 may be associated with one or more such gene set enrichment analysis scores, such as a Gene Set Enrichment Analysis (GSEA) or single-sample GSEA (ssGSEA) score (not shown in FIG. 4). In one example, ssGSEA is a standard tool in the field of pathway analysis (See Barbie, et al., 2010, Nature. 462(7269): 108-112).

Multiple ssGSEA scores may be associated with each transcriptome value set in the data set 410. In one example, each ssGSEA score would be an individual dysregulation indicator in the data set 410. Each ssGSEA pathway score may be associated with one or more pathways of interest. The selection of the gene set from which the ssGSEA score will be derived may be dependent on the pathway for which the pathway engine 200n is being trained. For example, if the pathway engine 200n will be trained to generate pathway disruption scores for the RAS pathway, ssGSEA scores for any relevant pathway, including 43 KRAS-associated pathways, may be the most related ssGSEA scores.

In one example, a relevant pathway may be any pathway known to be dysregulated in specimens having mutations in genes that are used to define the positive control specimens. For example, for the RAS/RTK pathway, as KRAS mutations are used to define the positive control specimens, scores are generated for all pathways with names containing the string "KRAS".

Another type of dysregulation indicator may be the methylation status of the specimen associated with the transcriptome value set. The methylation status may be determined by analyzing the methylation of genes and/or promoters associated with the pathway.

In various embodiments, a subset of the rows in the data set 410 is used to train a pathway engine 200n and the remaining rows of the data set 410 that are not used to train the pathway engine 200n are used to test the pathway engine 200n.

A protein expression level data set may also be associated with each transcriptome value set in the data set 410. (not shown in FIG. 4) In one example, each protein expression level data set could be generated by any method known for measuring protein amounts in a specimen, including proteomic methods.

In various embodiments, a transcriptome value set in the data set 410 may be further associated with imaging data. Imaging data may include histopathology and radiology images generated from the specimen associated with the transcriptome value set, features extracted from these images, and any annotations or information developed by manual or automated analysis of these images.

In various embodiments, the data set 410 includes data from the cancer genome atlas (TCGA) consortium.

In various embodiments, each transcriptome value set may be generated by processing a patient or tumor organoid sample through RNA whole exome next generation sequencing (NGS) to generate RNA sequencing data, and the RNA sequencing data may be processed by a bioinformatics pipeline to generate a RNA-seq expression profile for each sample. The patient sample may be a tissue sample or blood sample containing cancer cells In more detail, RNA may be isolated from blood samples or tissue sections using commercially available reagents, for example, proteinase K, TURBO DNase-I, and/or RNA clean XP beads. The isolated RNA may be subjected to a quality control protocol to determine the concentration and/or quantity of the RNA molecules, including the use of a fluorescent dye and a fluorescence microplate reader, standard spectrofluorometer, or filter fluorometer.

cDNA libraries may be prepared from the isolated RNA, purified, and selected for cDNA molecule size selection using commercially available reagents, for example Roche KAPA Hyper Beads. In another example, a New England Biolabs (NEB) kit may be used. cDNA library preparation may include the ligation of adapters onto the cDNA molecules. For example, UDI adapters, including Roche SeqCap dual end adapters, or UMI adapters (for example, full length or stubby Y adapters) may be ligated to the cDNA molecules. The sequence of nucleotides in the adapters may be specific to a sample in order to distinguish between sequencing data obtained for different samples. In this example, adapters are nucleic acid molecules that may serve as barcodes to identify cDNA molecules according to the sample from which they were derived and/or to facilitate the next generation sequencing reaction and/or the downstream bioinformatics processing.

cDNA libraries may be amplified and purified using reagents, for example, Axygen MAG PCR clean up beads. Then the concentration and/or quantity of the cDNA molecules may be quantified using a fluorescent dye and a fluorescence microplate reader, standard spectrofluorometer, or filter fluorometer.

cDNA libraries may be pooled and treated with reagents to reduce off-target capture, for example Human COT-1 and/or IDT xGen Universal Blockers, before being dried in a vacufuge. Pools may then be resuspended in a hybridization mix, for example, IDT xGen Lockdown, and probes may be added to each pool, for example, IDT xGen Exome Research Panel v1.0 probes, IDT xGen Exome Research Panel v2.0 probes, other IDT probe panels, Roche probe panels, or other probes. Pools may be incubated in an incubator, PCR machine, water bath, or other temperature modulating device to allow probes to hybridize. Pools may then be processed with Streptavidin-coated beads, or another means for capturing hybridized cDNA-probe molecules, especially cDNA molecules representing exons of the human genome. In some embodiments, polyA capture may be used. Pools may be amplified and purified once more using commercially available reagents, for example, the KAPA HiFi Library Amplification kit and Axygen MAG PCR clean up beads, respectively.

The cDNA library may be analyzed to determine the concentration or quantity of cDNA molecules, for example by using a fluorescent dye (for example, PicoGreen pool quantification) and a fluorescence microplate reader, standard spectrofluorometer, or filter fluorometer. The cDNA library may also be analyzed to determine the fragment size of cDNA molecules, which may be done through gel electrophoresis techniques and may include the use of a device such as a LabChip GX Touch. Pools may be cluster amplified using a kit (for example, Illumina Paired-end Cluster Kits with PhiX-spike in). In one example, the cDNA library preparation and/or whole exome capture steps may be performed with an automated system, using a liquid handling robot (for example, a SciClone NGSx).

The amplification may be performed on a device, for example, an Illumina C-Bot2, and the resulting flow cell containing amplified target-captured cDNA libraries may be sequenced on a next generation sequencer, for example, an Illumina HiSeq 4000 or an Illumina NovaSeq 6000 to a unique on-target depth selected by the user, for example, 300×, 400×, 500×, 10,000×, etc. The next generation sequencer may generate a FASTQ file for each patient sample.

Each FASTQ file contains reads that may be paired-end or single reads, and may be short-reads or long-reads, where each read shows one detected sequence of nucleotides in an mRNA molecule that was isolated from the patient sample, inferred by using the sequencer to detect the sequence of nucleotides contained in a cDNA molecule generated from the isolated mRNA molecules during library preparation. Each read in the FASTQ file is also associated with a quality rating. The quality rating may reflect the likelihood that an error occurred during the sequencing procedure that affected the associated read. The adapters may facilitate the binding of the cDNA molecules to anchor oligonucleotide molecules on the sequencer flow cell and may serve as a seed for the sequencing process by providing a starting point for the sequencing reaction. If two or more patient samples are processed simultaneously on the same sequencer flow cell, reads from multiple patient samples may be contained in the same FASTQ file initially and then divided into a separate FASTQ file for each patient. A difference in the sequence of the adapters used for each patient sample could serve the purpose of a barcode to facilitate associating each read with the correct patient sample and placing it in the correct FASTQ file.

Each FASTQ file may be processed by a bioinformatics pipeline. In various embodiments, the bioinformatics pipeline may filter FASTQ data. Filtering FASTQ data may include correcting sequencer errors and removing (trimming) low quality sequences or bases, adapter sequences, contaminations, chimeric reads, overrepresented sequences, biases caused by library preparation, amplification, or capture, and other errors. Entire reads, individual nucleotides, or multiple nucleotides that are likely to have errors may be discarded based on the quality rating associated with the read in the FASTQ file, the known error rate of the sequencer, and/or a comparison between each nucleotide in the read and one or more nucleotides in other reads that has been aligned to the same location in the reference genome. Filtering may be done in part or in its entirety by various software tools. FASTQ files may be analyzed for rapid assessment of quality control and reads, for example, by a sequencing data QC software such as AfterQC, Kraken, RNA-SeQC, FastQC, (see Illumina, BaseSpace Labs or https:// world wide web address illumina.com/products/by-type/informatics-products/basespace-sequence-hub/apps/fastqc.html), or another similar software program. For paired-end reads, reads may be merged.

For each FASTQ file, each read in the file may be aligned to the location in the reference genome having a sequence that best matches the sequence of nucleotides in the read. There are many software programs designed to align reads, for example, Bowtie, Burrows Wheeler Aligner (BWA), programs that use a Smith-Waterman algorithm, etc. Alignment may be directed using a reference genome (for example, GRCh38, hg38, GRCh37, other reference genomes developed by the Genome Reference Consortium, etc.) by comparing the nucleotide sequences in each read with portions of the nucleotide sequence in the reference genome to determine the portion of the reference genome sequence that is most likely to correspond to the sequence in the read. The alignment may take RNA splice sites into account. The alignment may generate a SAM file, which stores the locations of the start and end of each read in the reference genome and the coverage (number of reads) for each nucleotide in the reference genome. The SAM files may be converted to BAM files, BAM files may be sorted, and duplicate reads may be marked for deletion.

In one example, kallisto software may be used for alignment and RNA read quantification (see Nicolas L Bray, Harold Pimentel, Pall Melsted and Lior Pachter, Near-optimal probabilistic RNA-seq quantification, Nature Biotechnology 34, 525-527 (2016), doi:10.1038/nbt.3519). In an alternative embodiment, RNA read quantification may be conducted using another software, for example, Sailfish or Salmon (see Rob Patro, Stephen M. Mount, and Carl Kingsford (2014) Sailfish enables alignment-free isoform quantification from RNA-seq reads using lightweight algorithms. Nature Biotechnology (doi:10.1038/nbt.2862) or Patro, R., Duggal, G., Love, M. I., Irizarry, R. A., & Kingsford, C. (2017). Salmon provides fast and bias-aware quantification of transcript expression. Nature Methods.). These RNA-seq quantification methods may not require alignment. There are many software packages that may be used for normalization, quantitative analysis, and differential expression analysis of RNA-seq data.

For each gene, the raw RNA read count for a given gene may be calculated. The raw read counts may be saved in a tabular file for each sample, where columns represent genes and each entry represents the raw RNA read count for that gene. In one example, kallisto alignment software calculates raw RNA read counts as a sum of the probability, for each read that the read aligns to the gene. Raw counts are therefore not integers in this example.

Raw RNA read counts may then be normalized to correct for GC content and gene length, for example, using full quantile normalization and adjusted for sequencing depth, for example, using the size factor method. In one example, RNA read count normalization is conducted according to the methods disclosed in U.S. patent application Ser. No. 16/581,706 or PCT19/52801, titled Methods of Normalizing and Correcting RNA Expression Data and filed Sep. 24, 2019. The rationale for normalization is the number of copies of each cDNA molecule in the sequencer may not reflect the distribution of mRNA molecules in the patient sample. For example, during library preparation, amplification, and capture steps, certain portions of mRNA molecules may be over or under-represented due to artifacts that arise during various aspects of priming of reverse transcription caused by random hexamers, amplification (PCR enrichment), rRNA depletion, and probe binding and errors produced during sequencing that may be due to the GC content, read length, gene length, and other characteristics of sequences in each nucleic acid molecule. Each raw RNA read count for each gene may be adjusted to eliminate or reduce over- or under-representation caused by any biases or artifacts of NGS sequencing protocols. Normalized RNA read counts may be saved in a tabular file for each sample, where columns represent genes and each entry represents the normalized RNA read count for that gene (see also Example 9 for additional discussion on RNA preparation methods).

A transcriptome value set may refer to either normalized RNA read counts or raw RNA read counts, as described above.

Figure 5:
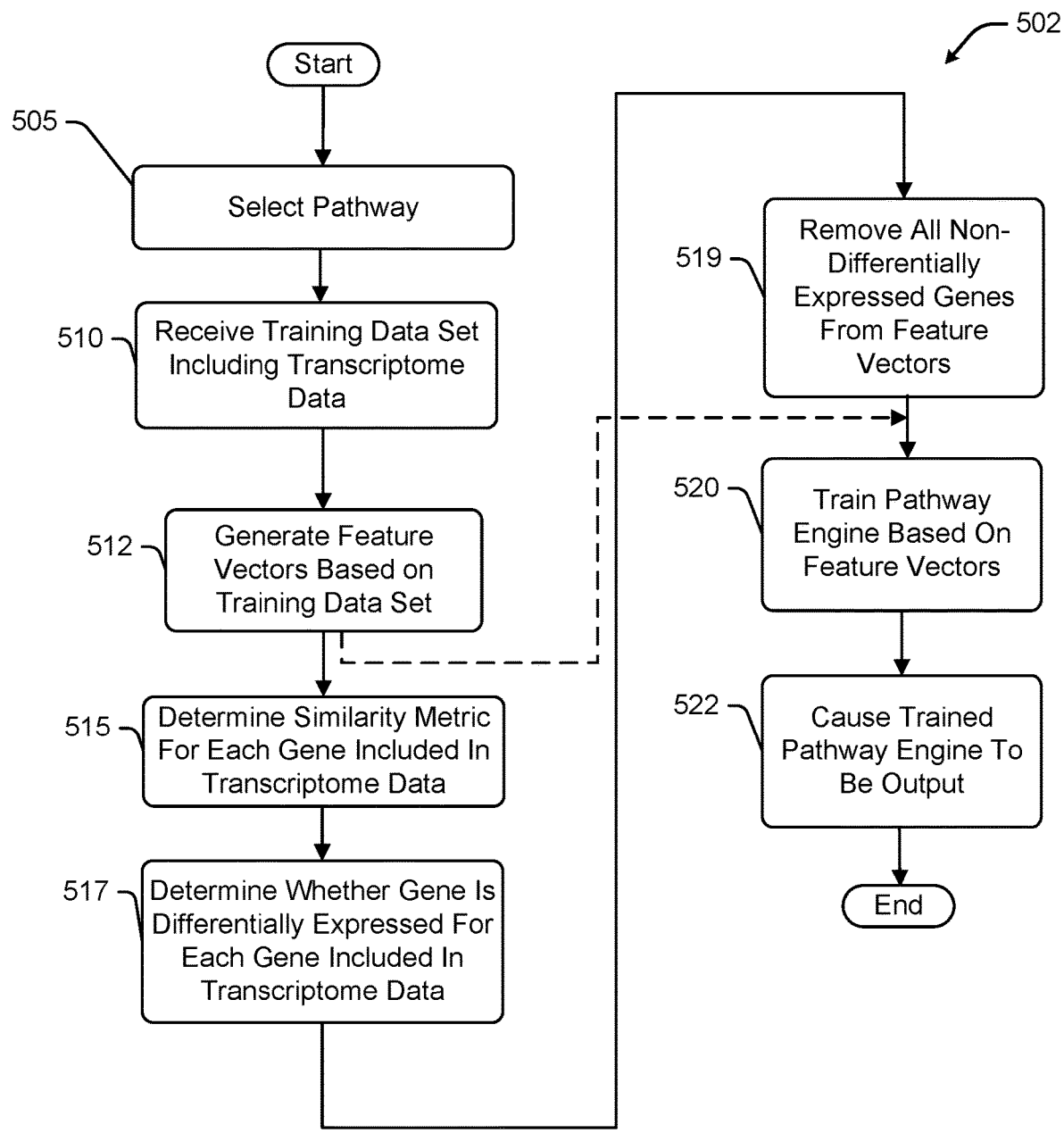
FIG. 5 displays an example of a process that can train a pathway engine.

FIG. 5 displays an example of a process 502 that can train a pathway engine 200n. The process 502 can be implemented as computer readable instructions on one or more memories or other non-transitory computer readable medium, and executed by one or more processors in communication with the one or more memories or media. In some embodiments, the process 502 can be implemented as computer readable instructions on the memory 222 and/or the memory 262 and executed by the processor 214 and/or the processor 254.

At 505, the process 502 can select a pathway from a plurality of pathways, such as the pathways database 300. For example, the pathway selected may be the RTK/RAS pathway. In some embodiments, the process 502 can select the pathway based on input from a user.

Selection of Training Data.

At 510, the process 502 can receive a training data set including transcriptome data. For example, the process 502 can receive the data set 410. The process can generate a matrix of feature vectors for training the pathway engine 200n based on the training data. The training data set may include any of the data inputs 100 including DNA variant data, methylation data, cancer type, and/or proteomics data. The methylation data may be formatted as a positive/negative control.

At 512, the process 502 can generate feature vectors based on the training data set. The process 502 may filter the training data set by cancer type or subtype, by staging, or by other genotypic or phenotypic filters (e.g., by what cancer type a given specimen is associated with). In some embodiments, the process 502 can generate feature vectors based on specimens associated with multiple cancer types. For example, a first specimen may be associated with a lung cancer, and a second specimen may be associated with a breast cancer. The process 502 can generate a matrix of feature vectors for training based on the filtered or unfiltered data set. Each feature vector can include at least a portion of any transcriptome data, DNA data, and pathway label(s) associated with each specimen (e.g., at least a portion of the row of the data set 410). For example, a feature vector can include the transcriptome data and a single pathway label. The transcriptome can include one or more expression levels associated with one or more genes. The process 502 may reserve a portion of the training data set for testing a trained pathways engine 200n. In one example, 10% of the matrix of feature vectors can be reserved. In another example, 20% of the matrix of feature vectors can be reserved.

The pathway labels can be predetermined based on DNA mutation data associated with the transcriptome, as described in FIG. 4. For instance, if DNA data associated with any genes in the pathway (for example EGFR in the RTK/RAS pathway, or any other genes in the RTK/RAS pathway) reflects that the specimen associated with that transcriptome contains a genetic variant in one of those genes, then the corresponding feature vector generated from that transcriptome may include a positive control pathway label.

In some embodiments, at 512, the process 502 can generate one or more pathway labels for each feature vector. In this way, the process 502 can receive transcriptome data and raw DNA data associated with each specimen, and generate the pathway labels for the feature vectors. However, it is appreciated that the training data set can include one or more pathway labels for each specimen. Each specimen with a pathway label such as a dysregulation indicator as described in FIG. 4. Examples of dysregulation indicators include positive control or negative control.

The process 502 can label a transcriptome as a positive control if the transcriptome has a DNA mutation in a gene or subset of genes listed in the pathway selected at 505. For instance, the RTK/RAS pathway, as shown in FIG. 1A, includes the genes EGFR, ERBB2, ERBB3, ERBB4, MET, and PDGFRA, among others. If the EGFR gene, for instance, in a DNA data set reflects a mutational status, then the transcriptome may be labeled as a positive control. The same is true for other genes in the RTK/RAS pathway having a mutated status. In another example, a transcriptome may be labeled as a positive control if it has a DNA alteration in a specific class of genes or section within the pathway, for example, only in RAS genes. In the examples, only transcriptomes with pathogenic mutations in the selected gene(s) may be positive controls.

A transcriptome may be labeled as a negative control if all genes in the pathway selected at 505 are considered wild type (for example, there are no DNA variants, which may include copy number alterations and all other classes of DNA variants, associated with the genes, or there are no pathogenic DNA variants associated with the genes).

Grouping of Positive Training Data to Determine Mean Expression Level and Grouping of Negative Training Data to Determine Mean Expression Level and Calculate a Similarity Metric At 515, the process 502 can determine, for each gene included in the transcriptomes included in the training data set, a similarity metric. For each gene in the transcriptome, the process 502 can compare expression levels associated with the group of positive controls in the training data set (e.g., positive pathway label values) to the expression levels associated with the group of negative controls (e.g., negative pathway label values) to calculate a similarity metric. The comparison may be performed for each gene in the transcriptome. Genes with expression levels that are statistically different between the two groups, are designated as differentially expressed genes (DEGs).

Table 1 shows exemplary information for a sample group of positive controls and a sample group of negative controls. In this example, the similarity metric is a fold-change calculated for the gene expression levels between the two groups. The fold-change is calculated by dividing the mean of the gene expression level in the positive control group by the mean of the gene expression level in the negative control group and taking the log base 2 logarithm of the quotient.

TABLE 1

| Gene | Group of Positive Controls - Mean Expression Level | Group of Negative Controls - Mean Expression Level | log2(Fold Change) | Differentially Expressed? |
| --- | --- | --- | --- | --- |
| EGFR | 281 | 291 | −0.05 | No |
| ERBB2 | 236 | 236 | 0.0001 | No |
| ERBB3 | 174 | 159 | 0.128 | No |
| KRAS | 42 | 27 | 0.63 | Yes |
| MET | 429 | 428 | 0.003 | No |
| MUC2 | 1443 | 413 | 1.8 | Yes |
| ... | ... | ... | ... | ... |

In some embodiments, the expression level comparison can be calculated by using edgeR, a publicly available package in the R software environment. (See bioconductor.org/packages/release/bioc/html/edgeR.html).

Comparing the Similarity Metric to a Threshold to Determine Differential Expression of the Gene At 517, the process 502 can, for each gene in the transcriptome, determine if the gene is differentially expressed or not. The process 502 can, for each gene, compare the absolute value of the log base 2 of the quotient calculated at 515 to a threshold value. The process 502 may designate a gene as a differentially expressed gene (DEG) based on whether the similarity metric is less than, greater than, or equal to the threshold value. In some embodiments, the process can determine if the absolute value of the similarity metric is higher than the threshold value, for example 0.322 (corresponding to a fold difference of 1.25), 0.585 (corresponding to a fold difference of 1.5) or 1.0 (corresponding to a fold difference of 2). If the absolute value of the similarity metric is higher than the threshold value for a gene, the process 502 can designate the gene differentially expressed (i.e., a DEG). The number of DEGs in the training data set may vary depending on the pathway type, the threshold value, and/or the training data set. In one example, approximately 1,000 DEGs are selected.

In some embodiments, the process 502 can include executing edgeR to calculate a fold change and false discovery rate for each gene to identify DEGs. All DEGs identified by edgeR may be selected as training DEGs. In another example, only high-confidence DEGs are selected as training DEGs. In one example, a DEG is determined to be high-confidence if the absolute value of the fold change >1.25 and the false discovery rate (FDR)<0.05. In another example, the stringency is increased, and a DEG is determined to be high-confidence if the absolute value of the fold change is greater than or equal to 2 and the FDR<0.01.

Creating a Feature Vector for Each Transcriptome in the Training Data

At 519, the process 502 can remove all genes that are not DEGs from each transcriptome included in the feature vectors. Each transcriptome can include only DEGs. For example, as shown in Table 1, KRAS and MUC2 may be determined to be DEGs, while EGFR, ERBB2, ERBB3, and MET may be determined to not be DEGs. In this example, the process 502 can remove the expression levels of the EGFR, ERBB2, ERBB3, and MET genes from each transcriptome, while retaining the expression levels of the KRAS and MUC2 genes.

Table 2 shows an exemplary feature vector matrix. As shown, the feature vector can include a number of expression levels associated with a number of genes included in a transcriptome, as well as a pathway control value that may be a one or a zero. The expressions levels can be raw levels or normalized levels. In some embodiments, the feature vectors may also include DNA variant data, methylation data, cancer type data, and/or proteomics data. The methylation data may be formatted in a binary fashion, such as 1 (positive, i.e., methylation), or 0 (negative, i.e., unmethylated).

TABLE 2

| DEGs | Training Feature Vector 1 | Training Feature Vector 2 | Training Feature Vector 3 | Training Feature Vector 4 | Training Feature Vector 5 | Training Feature Vector N |
|---|---|---|---|---|---|---|
| MUC2 | 863 | 1636 | 3990 | 785 | 1030 | ... |
| KRAS | 39 | 119 | 76 | 47 | 87 | ... |
| Additional DEGs | ... | ... | ... | ... | ... | ... |
| Pathway Positive/ Negative Control | 0 | 1 | 1 | 0 | 1 | ... |

Notably, the DEGs can include one or more of the genes associated with a model trained to detect dysregulation. For example, for a model trained to detect dysregulation in the RAS module 1210, the associated DEGs can include the KRAS gene, the NRAS gene, and/or the HRAS gene. While other techniques may remove the genes associated with a model from consideration as DEGs, in some embodiments, the process 502 can only remove the genes associated with the model used in training if the genes are not DEGs. Allowing the genes associated with a model to be selected as DEGs can allow those genes to act as a positive control and may better train the model as compared to other techniques that exclude the genes associated with the model from consideration as DEGs.

In an alternative embodiment shown in Table 2B, RNA expression values for each gene are assigned to their corresponding allele. One way to accomplish this is to use the variant allele fraction (VAF) for each mutation as a proxy. For example, if the variant allele fraction is 50%, then it is likely that the variant is present in one allele only. If a VAF is 75%, then the associated variant is likely to be present in both alleles but the sample included 25% normal, non-cancerous tissue, which didn't have the variant. This is one method for incorporating VAF into the model. An alternative method (not shown), would be to include VAFs in the training data, where each VAF is associated with a variant and further associated with the RNA expression level calculated for the RNA associated with that variant.

TABLE 2B

| DEGs | Training Feature Vector 1 | Training Feature Vector 2 | Training Feature Vector 3 | Training Feature Vector 4 | Training Feature Vector 5 | Training Feature Vector N |
|---|---|---|---|---|---|---|
| MUC2 (allele A) | 431 | 818 | 1995 | 393 | 515 | ... |
| MUC2 (allele B) | 432 | 818 | 1995 | 392 | 515 | |
| KRAS (allele A) | 19 | 59 | 38 | 23 | 43 | ... |
| KRAS (allele B) | 20 | 60 | 38 | 24 | 44 | |

TABLE 2B-continued

| DEGs | Training Feature Vector 1 | Training Feature Vector 2 | Training Feature Vector 3 | Training Feature Vector 4 | Training Feature Vector 5 | Training Feature Vector N |
|---|---|---|---|---|---|---|
| Additional DEGs | ... | ... | ... | ... | ... | ... |
| Pathway Positive/ Negative Control | 0 | 1 | 1 | 0 | 1 | ... |

At 520, the process 502 can train a pathway engine 200n based on the training feature vectors. In one example, each feature vector entry may represent a gene expression value for a DEG in the training data element, or a positive or negative control label. The feature vector may also include dysregulation indicators associated with the transcriptome value set.

In some embodiments, the pathway engine 200n can include a regression model. In some embodiments, the regression model can be trained based on a predetermined alpha parameter value. In some embodiments, the regression model may be a logistic regression model. In some embodiments, the regression model may be a linear regression model, such as a regularized linear regression model. In some embodiments, the regression model can be trained using an Elastic net regularization technique, and may be referred to as an Elastic net model. In some embodiments, the probability that a pathway has been disrupted, which may be used a pathway disruption score, can be calculated according to the below equation:

$$p = \frac{1}{1 + e^{\beta_0 + \beta_1 x_1 + \beta_2 x_2 \cdots \beta_n x_n}} \quad (1)$$

where p is the probability of the positive class (i.e., disruption in the pathway), $\beta_0 \ldots \beta_n$ are learned weights, and $x_1 \ldots x_n$ are independent variables. The independent variables can include a feature vector as is described below.

The regression model can be trained using an alpha parameter value. The alpha parameter can be used to penalize (and thus train) the regression model for misclassifying samples (e.g., included training data). The alpha parameter value may range from zero, exclusive, up to and including one. The alpha parameter value can be determined using a process detailed below. In some embodiments, the process 502 can receive a user input indicative of a preferred alpha parameter value and train a logistic regression model based on the preferred alpha parameter value.

In some embodiments, the regression model can be trained using the alpha parameter and at least one other parameter. For example, in some embodiments, the regression model can be trained using an L1 ratio in addition to the alpha ratio. For certain model, such as Elastic net models, the L1 ratio can determine the type of regularization used to train the model. The L1 ratio can be determined using a similar process to the alpha value, for example, by comparing the performance of multiple models with different L1 values in addition to the alpha values.

In some embodiments, the model used can be an elastic net linear model from SciKit-Learn. In these embodiments, the model can be trained using the objective function:

$$\frac{1}{2*n_{samples}} * \|y - Xw\|_2^2 + \alpha * (l1_{ratio} \|w\|_1 + 0.5 * (1 - l1_{ratio}) * \|w\|_2^2) \quad (2)$$

where w is the weights of the model, a is the alpha parameter, and $l1_{ratio}$ is the L1 ratio. The alpha parameter can be used as a penalty on the model for misclassifying a point, and the L1 ratio can determine the similarity of the elastic net to ridge regression (L1 ratio=0) and to LASSO (L1 ratio=1). A peak of equation (2) can be found using a coordinate descent method.

The values of the alpha parameter a and the L1 ratio l1 two parameters can be determined using gridsearch with 10 or 15-fold cross validation, as will be described below.

The number of DEGs included in each feature vector and/or the number of feature vectors will vary inversely with the alpha parameter. For example, with larger numbers of DEGs and/or feature vectors (e.g., two thousand DEGs and ten thousand feature vectors), the alpha parameter value may 0.1. As another example, with smaller numbers of DEGs and/or feature vectors (e.g., twenty DEGs and two thousand feature vectors), the alpha parameter value may be 0.5. The alpha parameter value can be used in a method of regularization such as elastic net regularization. In some embodiments, the process 502 may set the alpha parameter value to 0.2. In some embodiments, the process 502 can receive an alpha parameter value from another process such as process 602 that will be described below.

At 522, the process 502 can cause the trained pathway engine 200n to be output. In some embodiments, at 522, the process 502 can cause the trained pathway engine 200n to be saved to a memory (e.g., the memory 222 and/or the memory 262). The memory may be included in the computing device 210.

In some embodiments, the process 502 can receive training data that only includes transcriptome data associated with DEGs. In other words, portions steps 515, 517, and 519 may have already been executed to remove non-DEGs from the transcriptomic data. In these embodiments, the process may proceed to step 520 following step 512.

FIGS. 6A, 6B, 6C, 6D, 6E, and 6F are related to example methods for testing and improving performance of a pathway engine 200n.

Figure 6A:
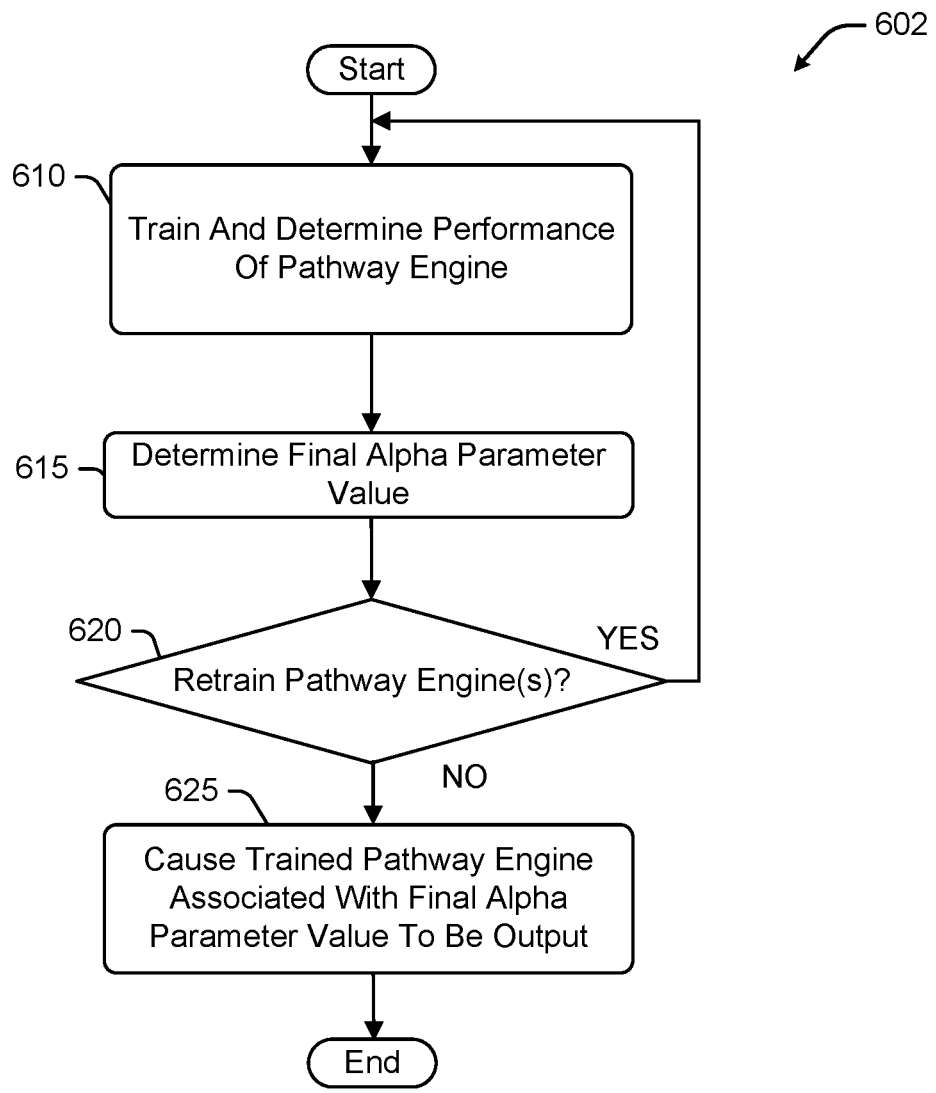
FIG. 6A shows a process that can select an alpha parameter value for training a pathway engine.

FIG. 6A shows an exemplary process 602 that can select an alpha parameter value for training a pathway engine, such as the pathway engine 200n. The process 602 can be implemented as computer readable instructions on one or more memories or other non-transitory computer readable media, and executed by one or more processors in communication with the one or more memories or other media. In some embodiments, the process 602 can be implemented as computer readable instructions on the memory 222 and/or the memory 262 and executed by the processor 214 and/or the processor 254. Referring to both FIG. 5 as well as FIG.

6A, at 610, the process 602 can train a pathway engine and determine the performance of the trained pathway engine. The pathway engine may be the pathway engine 200n that has been trained using the process 502 above. The pathway engine may be tested on transcriptomes that were not included in the training data (for example, reserved for testing as described in step 510) to assess the performance of the pathway engine.

In some embodiments, the process 602 can determine the performance of the trained pathway engine by generating a pathway disruption score for each reserved test transcriptome (see FIG. 7C) using the trained pathway engine. The process 602 may provide a reserved feature vector to the trained pathway engine, and receive the generated pathway disruption score from the trained pathway engine. The process 602 can compare the generated pathway disruption score to the dysregulation indicators (described in FIG. 4) associated with the transcriptome to determine whether the pathway engine 200n accurately predicted the disruption status of the pathway for the test transcriptome, and calculating a performance metric. In one example, calculating a performance metric includes generating a receiver operating characteristic (ROC) curve, and calculating an area under the curve (AUC). In another example, calculating a performance metric includes performing a Wilcoxon Rank Sum test (see FIG. 6B).

For example, the process 602 may use the pathway engine to generate a pathway disruption score and compare the pathway disruption score to a threshold value to determine a qualitative pathway disruption score. In one example, the threshold value may be chosen by selecting the threshold value that maximizes the Area Under Curve (AUC), e.g., using reserved transcriptome training data. In another example the threshold value may be chosen by selecting the threshold value that maximizes F1 score, a statistical measure defined as the harmonic mean of the precision (True positives)/(True positives+False positives) and the recall (True positives)/(True positives+False negatives). In one example, if the distribution of scores returned for the negative control group is irregular for a pathway engine, the outliers may be removed before the maximum F1 score is determined. In other embodiments, due to unbalanced group sizes or the importance of one metric of success over another (e.g., precision over recall), the threshold that maximizes another metric may be desirable, including a) Youden's J statistic (specificity+sensitivity−1), b) accuracy (True positives+True negatives)/(Total number of samples), c) precision, or d) recall.

At 610, the process 602 can train multiple pathway engines using a number of different alpha parameter values. The process 602 can then provide the testing data to each of trained pathway engines and compare the performance of each trained pathway engine. In one example, the logistic regression parameter alpha used to train the pathway engine in process 502 may be varied (for example, from 0.1 to 1 in increments of 0.05). The process 602 can determine the performance of each trained pathway engine by calculating any of the AUC, a Wilcoxon Rank Sum test, Youden's J statistic (specificity+sensitivity−1), accuracy (True positives+True negatives)/(Total number of samples), precision, or recall of each trained pathway engine.

In one example, at 610, the process 602 may perform optional cross-validation of the pathway engine. A possible goal of cross-validation may be to ensure that the pathway engine is not "over-fitting" the data (for example, learning specific aspects of the training dataset that are not generalizable).

In one example of cross-validation, for each pathway engine trained at 610, the pathway engine being tested can be trained on a different portion of the data selected in step 510 and the remainder of the data is reserved for testing in step 610. For example, the data set selected in step 510 may be split into portions with an equal number of transcriptomes, and one portion can become the set of reserved test transcriptomes for each pathway engine trained at 610, with the remaining transcriptomes being used to train the pathway engine as described above in conjunction FIG. 5.

In one example, each portion is 10% of the data set and step 610 is repeated ten times such that each portion serves as the reserved test transcriptomes for one pathway engine trained at step 610, referred to as 10-fold cross-validation. In this example, pathway engine is run on the withheld 10% of samples (out-of-fold) and the AUC is calculated for these withheld samples. The pathway engine 200n output for each withheld (reserved) transcriptome is saved, as is the AUC specific to this test set. This process is repeated 10 times in such a way that the 10× out-of-fold sets do not overlap or intersect. That is, each transcriptome in the entire data set selected in step 510 is in the withheld 10% test set only once and has only one pathway engine output associated with it. The outputs and AUCs for each of the 10 withheld test sets are collected, and in conjunction with their known status in either the positive or negative control set, a final ROC is generated and termed the out-of-fold ROC as it reflects the output of the out-of-fold datasets.

In an alternative embodiment, 5-fold cross-validation with 80/20 splits may be performed. In this example, the transcriptomes in the data set selected in 510 are divided into five equal portions and for each of five pathway engines trained at step 610, one of the portions (20% of the data set) is used for testing a pathway engine that has been trained on the remaining 80% of the transcriptomes in the data set.

In another example, the pathway engine is trained on each subset of the data and tested on the remaining portion as described above, using the same alpha parameter value for each instance of training, such that each AUC generated by each testing data set is associated with the same alpha parameter value.

In some embodiments, at 610, the process 602 can divide a cohort of similar patients into a training set t1 and a holdout set h1. The process 602 can divide the training set t1 into a training set t2 and a holdout set h2. The process 602 can determine differentially expressed genes in the training set t2, and perform cross validation to determine a final alpha parameter value and a final L1 parameter value. The final alpha parameter value and the final L1 parameter value can be an alpha parameter value and an L1 parameter value associated with the best cross validation results. The process 602 can train a final model on the training set t2 using the final alpha parameter value and the final L1 parameter value. The process 602 can apply the final model to the holdout set h2 to choose a final threshold that classifies patients as dysregulated/non-dysregulated. The process 602 can determine the final threshold by selecting a threshold such that a maximum number of patients with disruption (e.g., true positive) score above the threshold and/or as the patients a maximum number of patients without disruption (e.g., true negative) score below the threshold. In some embodiments, the process 602 can determine the final threshold by determining a threshold that maximizes the number of correct classifications and/or minimizes the number of incorrect classifications. To validate the final model and the final threshold, the process 602 may then apply the final model and the final threshold to the holdout set h1 and calculate an AUC for the final model and the final threshold.

At 615, the process 602 can determine a final alpha parameter value based on the performance determined at 610. As described above, the process 602 may have determined performance metrics for a number of pathway engines that were trained using different alpha parameter values. There may be more than one performance metric for a given alpha parameter. In some embodiments, the performance metric can be an AUC. In these embodiments, the process 602 can select the alpha parameter value associated with the largest AUC as the final alpha parameter value. In other embodiments, other performance metrics can include a Wilcoxon Rank Sum test, Youden's J statistic (specificity+sensitivity−1), accuracy (True positives+True negatives)/(Total number of samples), precision, or recall of each trained pathway engine. In these embodiments, the process 602 can select the alpha parameter value associated with the peak value of the selected performance metric, the process 602 can select the alpha parameter value associated with the highest accuracy value.

The AUC's resulting from multiple pathway engines trained at 610 may be compared to analyze the variance of alpha values caused by different training data subsets and/or the effect of each alpha parameter value on the performance of the pathway engine. These analyses may facilitate selecting a final alpha parameter value.

In one example, the process 602 can calculate a standard deviation of the AUCs. In one example, the standard deviation can be calculated for multiple AUCs associated with the same alpha parameter value. In another example, the standard deviation can be calculated for AUCs associated with multiple alpha parameter values.

In some embodiments, the process 602 can determine a final alpha value and a final L1 value. The process 602 may determine the final alpha value and the final L1 value are the alpha value and the L1 value associated with a model trained at 610 that has the highest AUC or other suitable performance metric (e.g., Wilcoxon Rank Sum test, accuracy, etc.).

At 620, the process 602 can determine whether to retrain the pathway engine(s). The process 602 can determine whether to retrain the pathway engines based on the results of 615. The process 602 can compare the performance metric(s) of the chosen final alpha parameter value and the associated pathway engine to predetermined threshold value(s) and determine if the trained pathway engine meets the threshold values. In one example, a low standard deviation (<0.03) and a high AUC (>0.80) is generally characteristic of an accurate model. The process 602 can determine if the standard deviation of the trained pathway engine is lower than a predetermined standard deviation threshold (e.g., 0.03) and if the AUC of the trained pathway engine is higher than a predetermined AUC threshold (e.g., 0.80). If the process 602 determines the standard deviation of the trained pathway engine is lower than the predetermined standard deviation threshold and that the AUC of the trained pathway engine is higher than the AUC predetermined threshold, the process 602 can determine that the pathway engine does not need to be retrained. If the process 602 determines the standard deviation of the trained pathway engine is not lower than the predetermined standard deviation threshold or that the AUC of the trained pathway engine not higher than the AUC predetermined threshold, the process 602 can determine that the pathway engine needs to be retrained. In one example, if the pathway engine needs to be retrained, the process 602 may retrain the pathway engine with the original training data plus additional features that were not present in the original training data. For example, the additional features may include ssGSEA scores or other dysregulation labels, as described in FIG. 4.

If the process 602 determines that the pathway engine needs to be retrained (i.e., "YES" at 620), the process 602 can return to 610. If the process 602 determines that the pathway engine does not need to be retrained (i.e., "NO" at 620), the process 602 can proceed to 625.

At 625, the process 602 can cause a trained pathway engine associated with the final alpha parameter value to be output. The process 602 causes the trained pathway engine that has already been generated to be output, or may train a new pathway engine using all of the training data and the final alpha parameter value and cause the new pathway engine to be output. The process 625 can cause the trained pathway engine to be saved to a memory (e.g., the memory 222 and/or the memory 262). The memory may be included in the computing device 210.

Figure 6B:
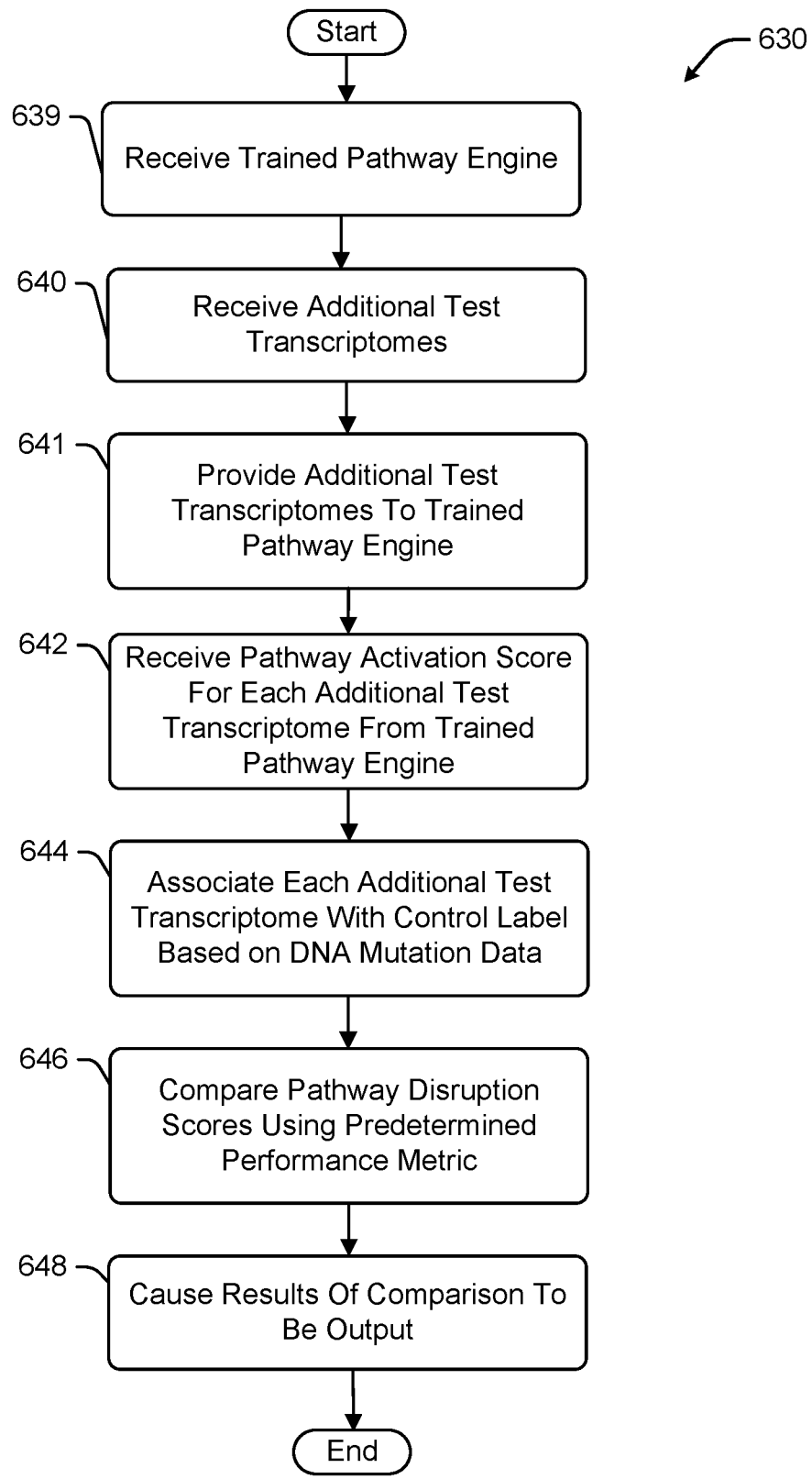
FIG. 6B shows a process that can test a pathway engine using additional test transcriptomes for optional testing.

Referring now to FIG. 5 as well as FIG. 6B, an exemplary process 630 that can test a pathway engine using additional test transcriptomes for optional testing is shown. The process 630 can be implemented as computer readable instructions on one or more memories or other non-transitory computer readable media, and executed by one or more processors in communication with the one or more memories or media. In some embodiments, the process 630 can be implemented as computer readable instructions on the memory 222 and/or the memory 262 and executed by the processor 214 and/or the processor 254.

At 639, the process 630 can receive a trained pathway engine such as the pathway engine 200n. The pathway engine can be trained using the method 502 in FIG. 5.

At 640, the process 630 can receive additional test transcriptomes for optional testing.

At 641, the process 630 can provide each additional test transcriptome to a pathway engine such as the pathway engine 200n. At 642, the process 630 can receive a pathway disruption score for each additional test transcriptome from the pathway engine. The pathway engine can generate and output a pathway disruption score for each additional test transcriptome.

At 644, the process 630 can associate each additional test transcriptome with either a positive or negative control label based on DNA mutation data for the additional test transcriptomes. Step 644 may include at least a portion of step 512.

At 646, the process 630 can compare the pathway disruption scores generated for the positive control transcriptomes to the pathway disruption scores generated for the negative control transcriptomes using a predetermined performance metric. In some embodiments, the process 630 can compare the pathway disruption scores generated for the positive control transcriptomes to the pathway disruption scores generated for the negative control transcriptomes using AUC. The process 630 may calculate AUC for the pathway disruption scores using a threshold associated with a model included in the pathway engine. In some embodiments, the process 630 can compare the pathway disruption scores generated for the positive control transcriptomes to the pathway disruption scores generated for the negative control transcriptomes using a Wilcoxon Rank Sum test. A significant difference (for example, p<0.01) when comparing the scores in these groups, with the same direction as for the training data (for example, showing that the larger scores in the additional testing dataset are associated with the same group as the larger scores in the testing dataset), may be evidence that the systems and methods are robust and generalizable to accurately analyze specimens outside of the original testing dataset.

At 648, the process 630 can cause the results of the Wilcoxon Rank Sum test to be output. The process 630 can cause the results of the Wilcoxon Rank Sum test to be output to a display (e.g., the display 290, the display 256, and/or the display 216) in order to be presented to a user. The process 630 may determine whether the pathway engine is robust and generalizable to accurately analyze specimens outside of the original testing dataset.

Figure 6C:
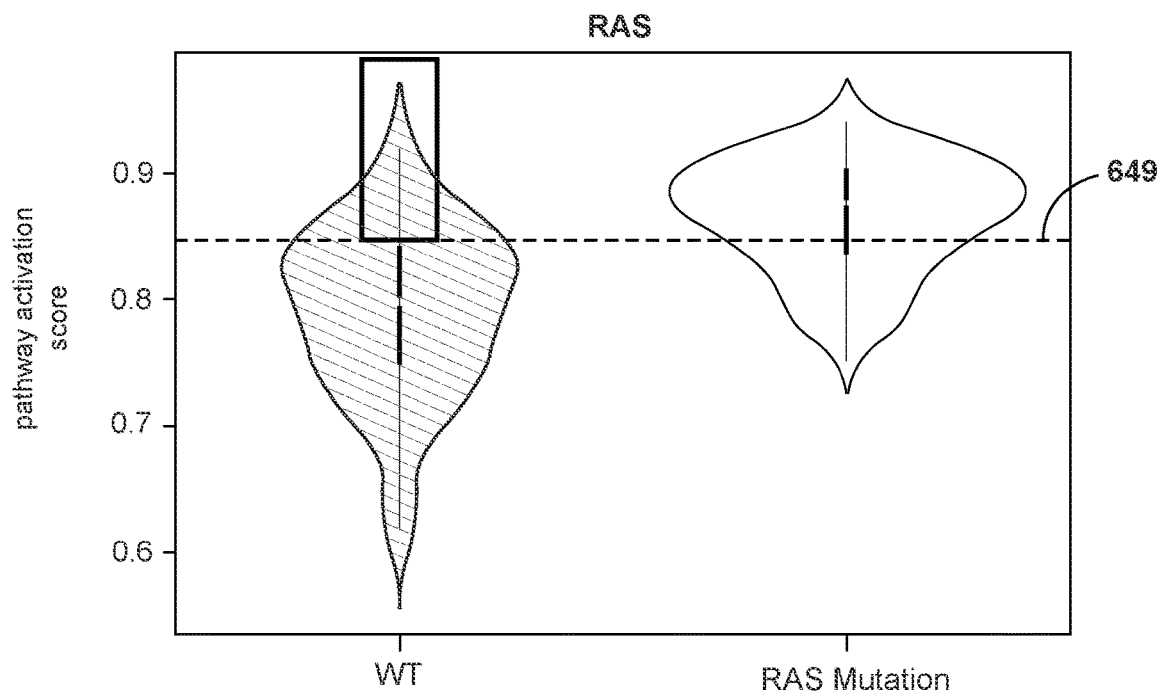
FIG. 6C illustrates an example result of a Wilcoxon Rank Sum test used to analyze pathway disruption scores (used interchangeably with the term "pathway dysregulation scores") generated by a pathway engine.
Figure 6D:
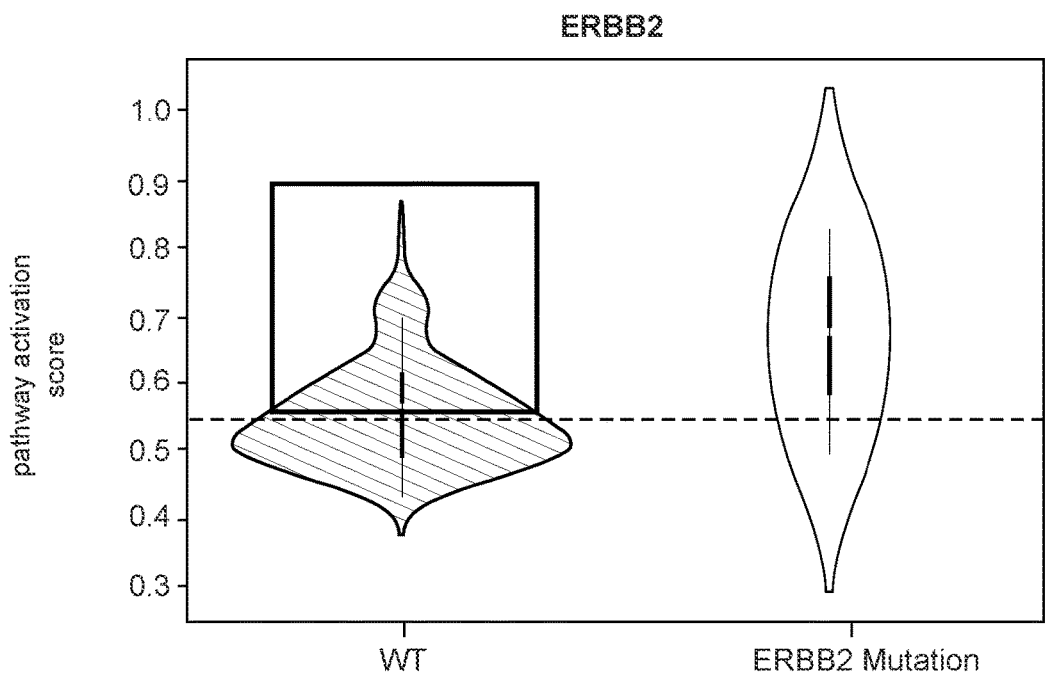
FIG. 6D illustrates another example result of a Wilcoxon Rank Sum test used to analyze pathway disruption scores generated by a pathway engine.

FIGS. 6C and 6D illustrate example results of a Wilcoxon Rank Sum test used to analyze pathway disruption scores generated by a pathway engine. In FIGS. 6C and 6D, the pathway engine was designed to score either the RAS gene group (FIG. 6C) or the ERBB2 gene group (FIG. 6D). In this example, the RAS gene group includes the KRAS, NRAS, and HRAS genes and the ERBB2 gene group includes only the ERBB2 gene.

Figure 7A:
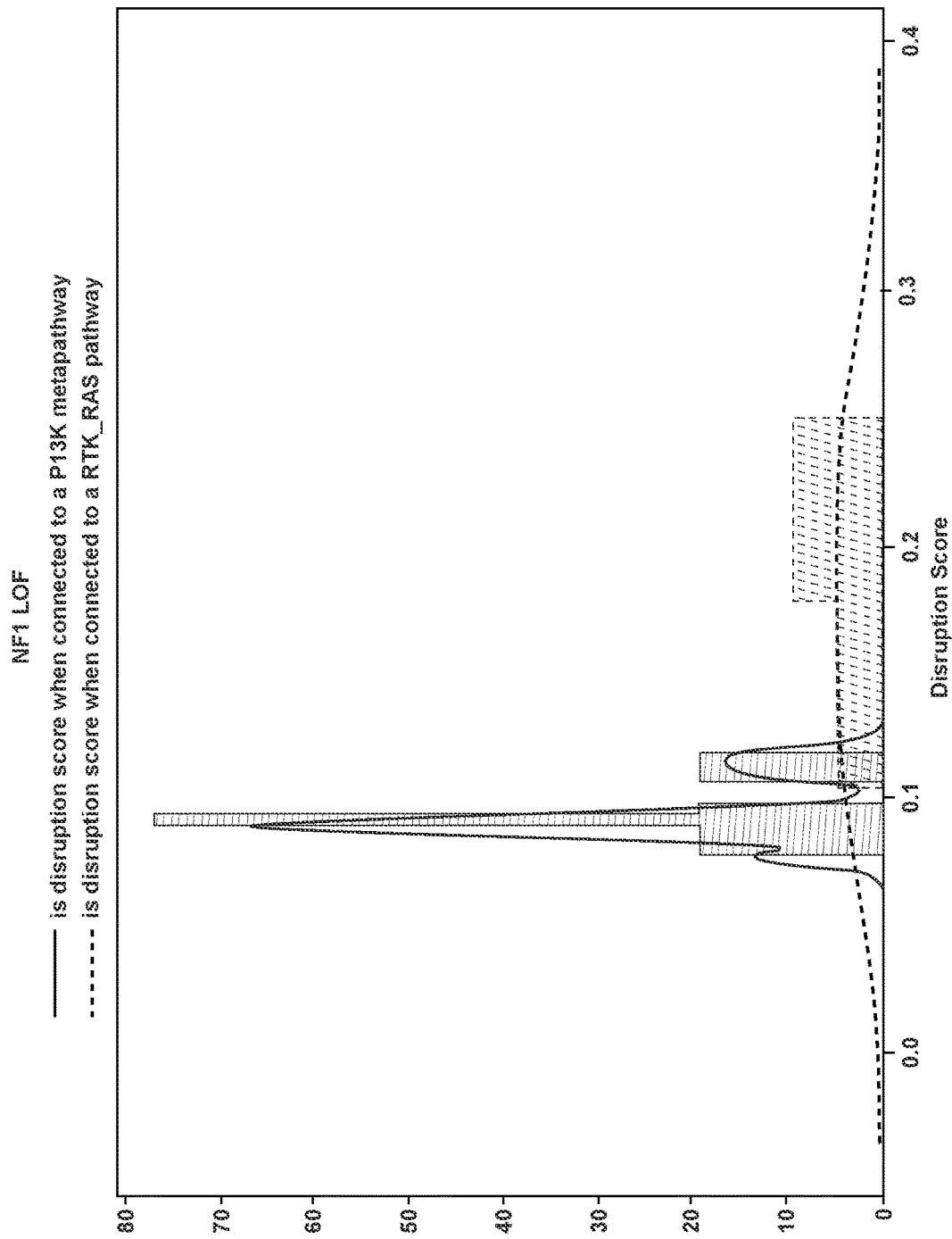
FIG. 7A shows results of a mutation in NF1 that had a cohort larger than one for all possible metapathways.
Figure 7B:
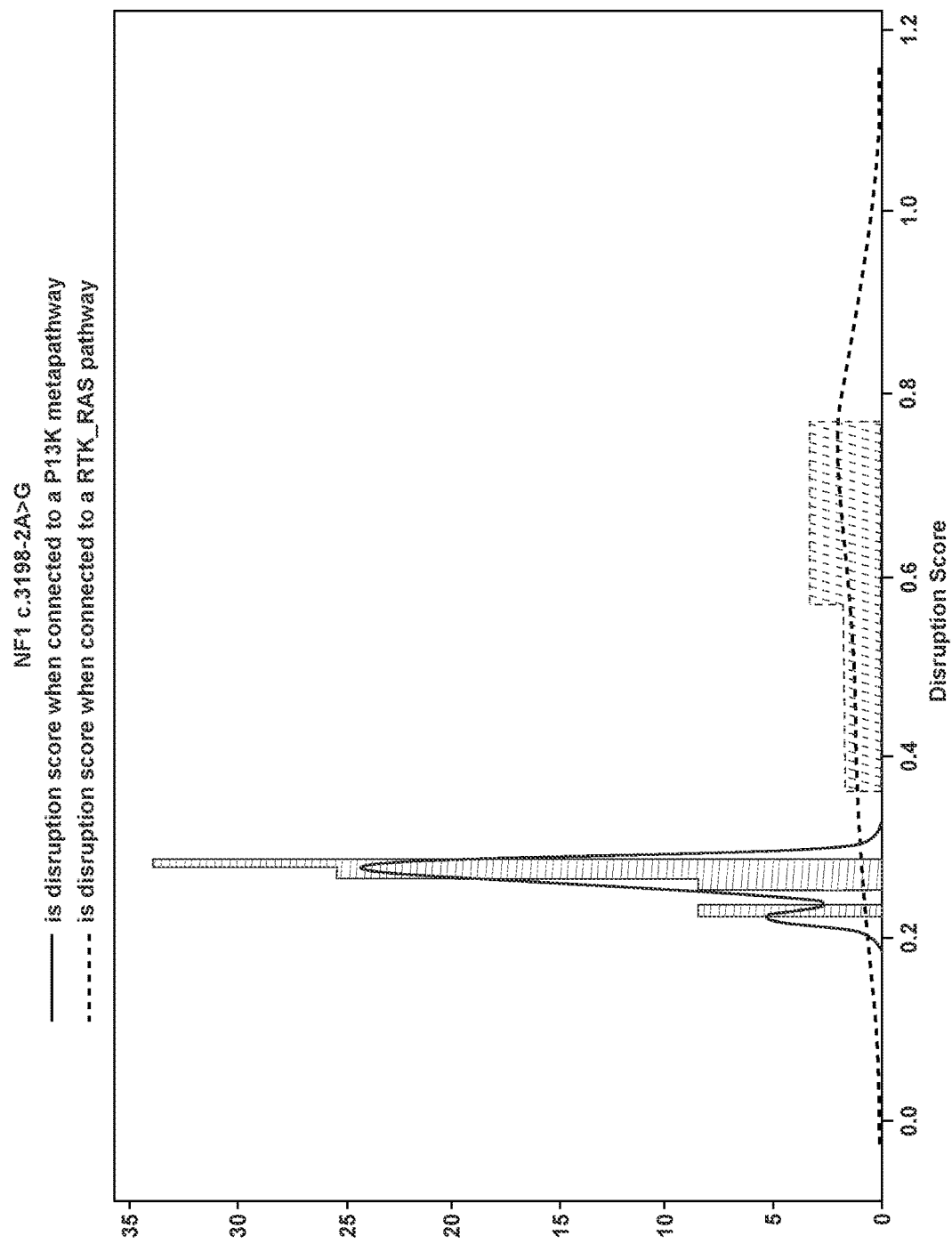
FIG. 7B shows results of another mutation in NF1 that had a cohorts larger than one for all possible metapathways.
Figure 7C:
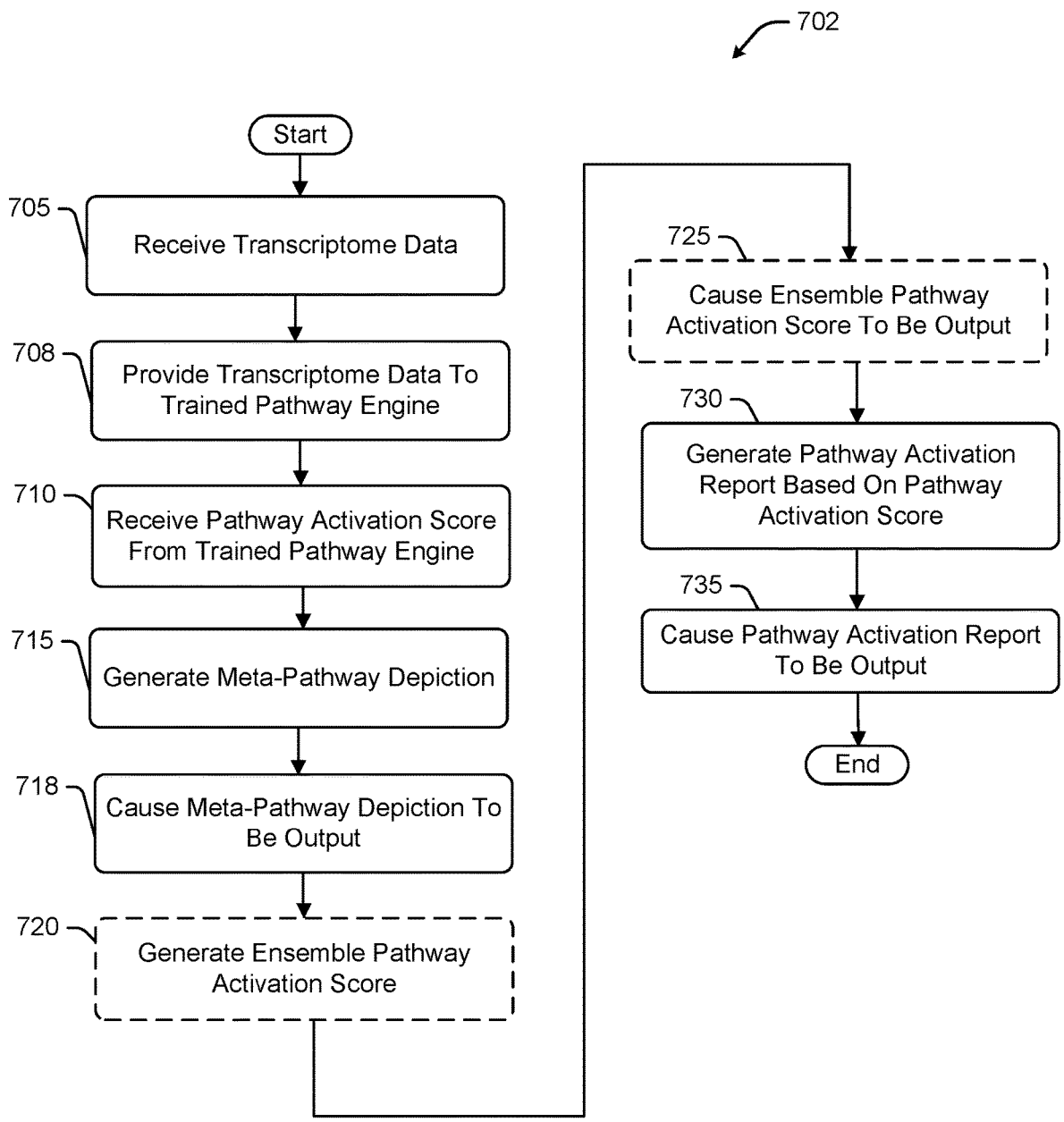
FIG. 7C shows an exemplary process that can generate a pathway disruption score using a trained pathway engine.

In FIGS. 6C and 6D, each transcriptome has been assigned to a wild type (WT) (left) or positive control (right) group, and the pathway engine 200n has been used to generate a pathway disruption score (as described in FIG. 7C). The y-axis shows the numeric value of each pathway disruption score associated with each transcriptome. The x-axis shows the WT or mutation status associated with each transcriptome, for all genes in either the RAS pathway in FIG. 6C or the ERBB2 pathway in FIG. 6D. The horizontal, dashed line indicates a threshold value (0.85 in FIG. 6C and 0.55 in FIG. 6D). Transcriptomes having a pathway disruption score value above the threshold are considered to be associated with pathway disruption.

Referring to FIG. 6B as well as FIGS. 6C and 6D, the results shown in FIGS. 6C and 6D can be determined at step 646 and output at step 648 in the method 630.

In this example, the boxes in FIGS. 6C and 6D outline potential "hidden responders," which are WT patients with pathway engine 200n outputs above the threshold value for disruption (dashed line).

Figure 6E:
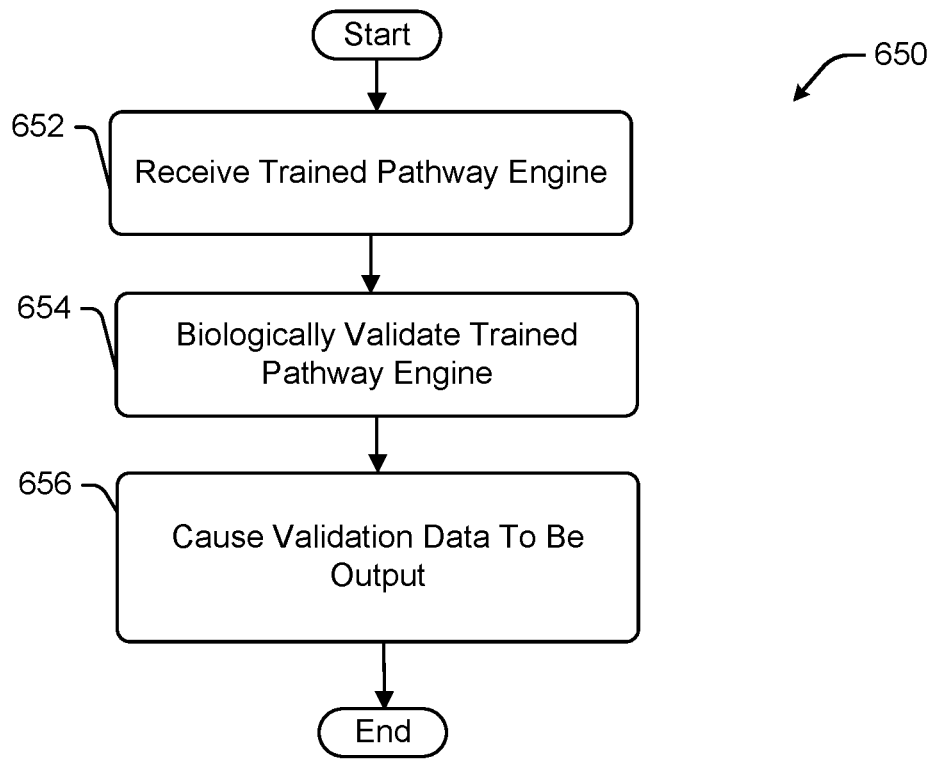
FIG. 6E shows an exemplary process that can biologically validate a trained pathway engine.

Referring now to FIG. 5 as well as FIG. 6E, an exemplary process 650 that can biologically validate a trained pathway engine is shown. The biological validation can be optional. The process 650 can be implemented as computer readable instructions on one or more memories or other non-transitory computer readable media, and executed by one or more processors in communication with the one or more memories or media. In some embodiments, the process 650 can be implemented as computer readable instructions on the memory 222 and/or the memory 262 and executed by the processor 214 and/or the processor 254.

At 652, the process 650 can receive a trained pathway engine. The pathway engine can be the pathway engine 200n. The pathway engine can be trained using the method 502 in FIG. 5.

At 654, the process 650 can biologically validate the pathway engine. For example, the process 650 can determine the degree of correlation between a pathway disruption score generated by the pathway engine and protein data for each specimen represented by a transcriptome value set in the testing datasets and/or additional testing datasets having associated protein data. The process 650 can plot each specimen's protein data on an x-axis and the pathway disruption score generated by the pathway engine output on a y-axis. The process 650 can calculate an $R^2$ value and an associated p-value using the plotted data. Protein data may include measures of protein expression levels (amount of a protein detected in a sample) and/or protein activation levels. For example, protein activation levels may include a total amount of activated protein in a sample or the portion of one or more proteins determined to be present in an activated form, where one example of an activated form of a protein is a phosphorylated protein.

In one example, a strong correlation (for example, an $R^2$ value above 0.2 and/or a p-value<1e-5) may indicate that the results of pathway engine are biologically meaningful, reflecting a pathway dysregulation that affects protein expression or activation levels. The protein expression or activation level of a specimen may be predicted by using a pathway engine to generate a pathway disruption score for the specimen and converting the pathway disruption score to protein levels based on the correlation determined in 654.

At 656, the process 650 can cause validation data to be output. The process 650 may cause the plot, the $R^2$ value, and/or the associated p-value generated at 654 to be output to a display (e.g., the display 290, the display 256, and/or the display 216). A user may then view the plot, the $R^2$ value, and/or the associated p-value to verify whether the pathway engine is biologically validated.

Figure 6F:
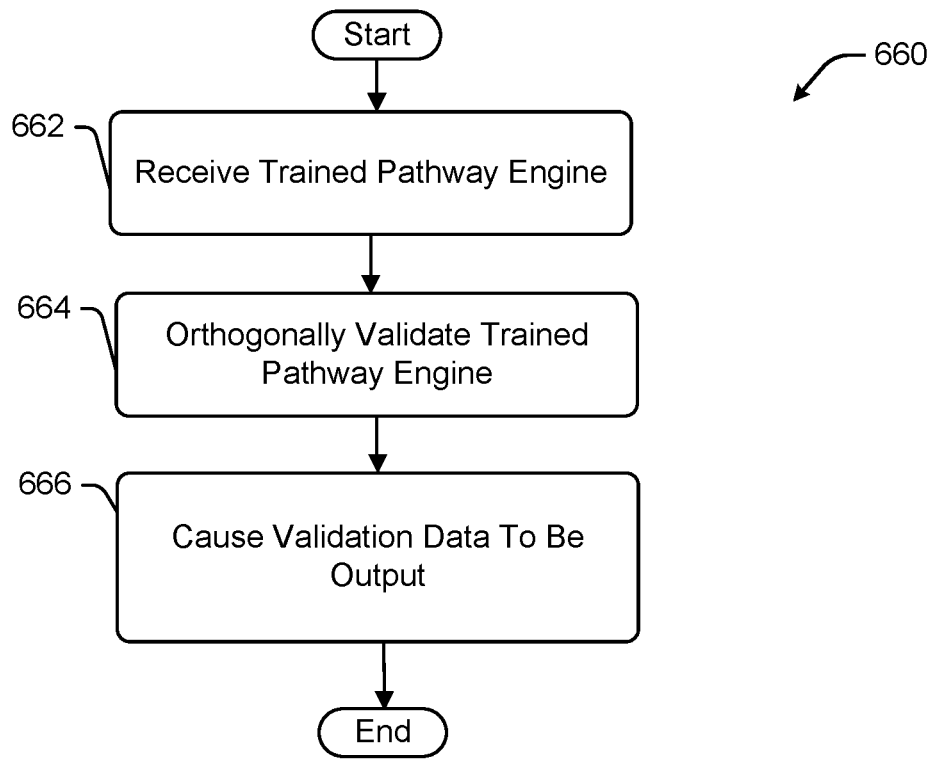
FIG. 6F shows a process that can orthogonally validate a trained pathway engine.

Referring now to FIG. 5 as well as FIG. 6F, an exemplary process 660 that can orthogonally validate a trained pathway engine is shown. The orthogonal validation can be optional. The process 660 can be implemented as computer readable instructions on one or more memories or other non-transitory computer readable media, and executed by one or more processors in communication with the one or more memories or media. In some embodiments, the process 660 can be implemented as computer readable instructions on the memory 222 and/or the memory 262 and executed by the processor 214 and/or the processor 254.

At 662, the process 660 can receive a trained pathway engine, such as the pathway engine 200n. The pathway engine can be trained using the method 502 in FIG. 5.

At 664, the process 660 can orthogonally validate the trained pathway engine. The process 660 may orthogonally validate the trained pathway engine by determining the correlation between pathway disruption scores generated by the pathway engine and the output of a known pathway analysis method for each transcriptome in a set of transcriptomes. The known pathway analysis method may include gene set enrichment analysis (GSEA), gene set variation analysis (GSVA), single sample GSEA (ssGSEA), and/or other pathway analysis methods.

At 666, the process 660 can cause any data generated at 664 to be output. For example, the process 660 can cause the correlation between pathway disruption scores generated by the pathway engine and the output of a known pathway analysis method for each transcriptome in a set of transcriptomes to be output. The process 660 may cause the data to be output to a display (e.g., the display 290, the display 256, and/or the display 216). A user may then view output data to verify whether the pathway engine is orthogonally validated.

Figure 6G:
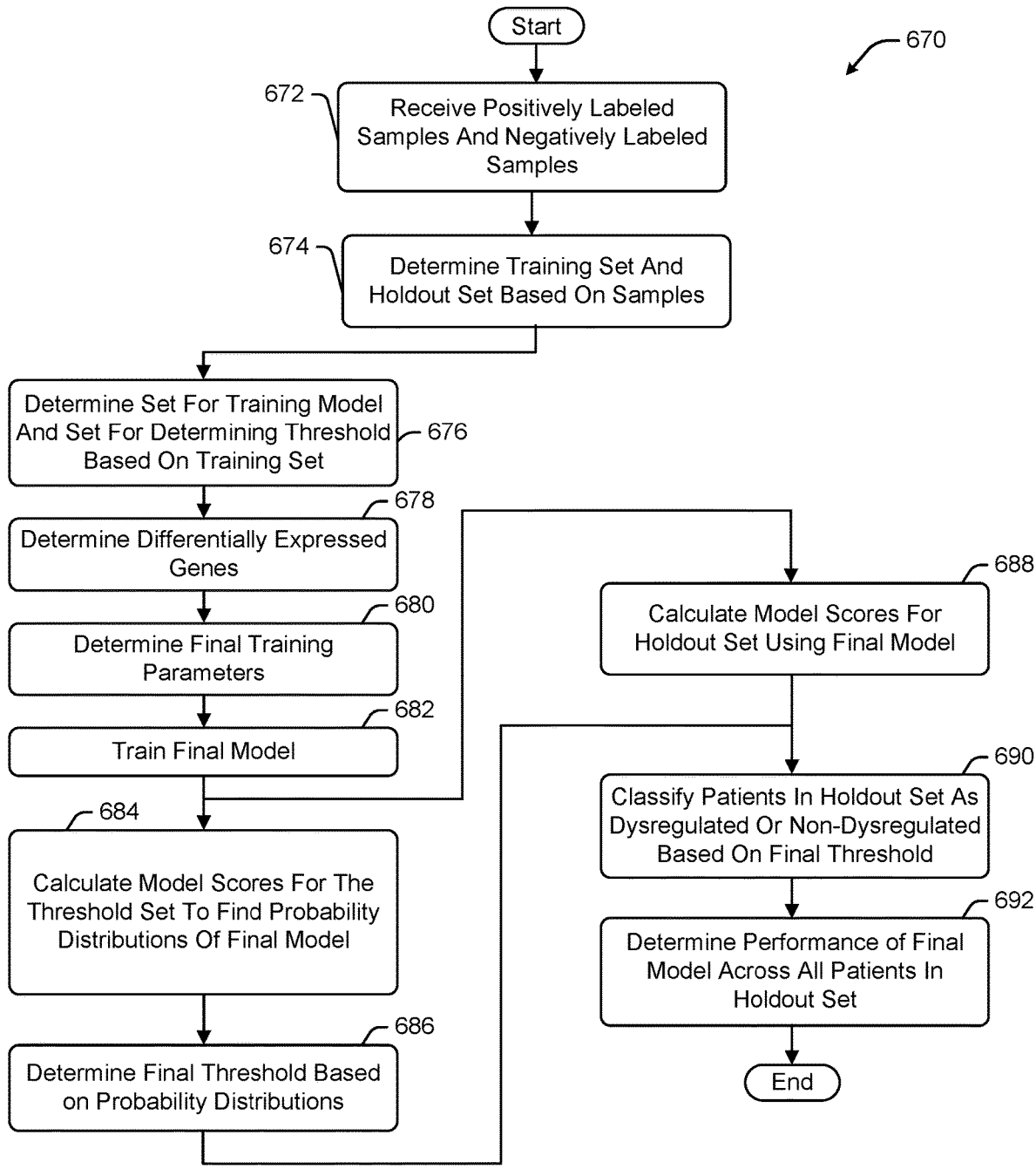
FIG. 6G shows an exemplary process for training a model.
Figure 12A:
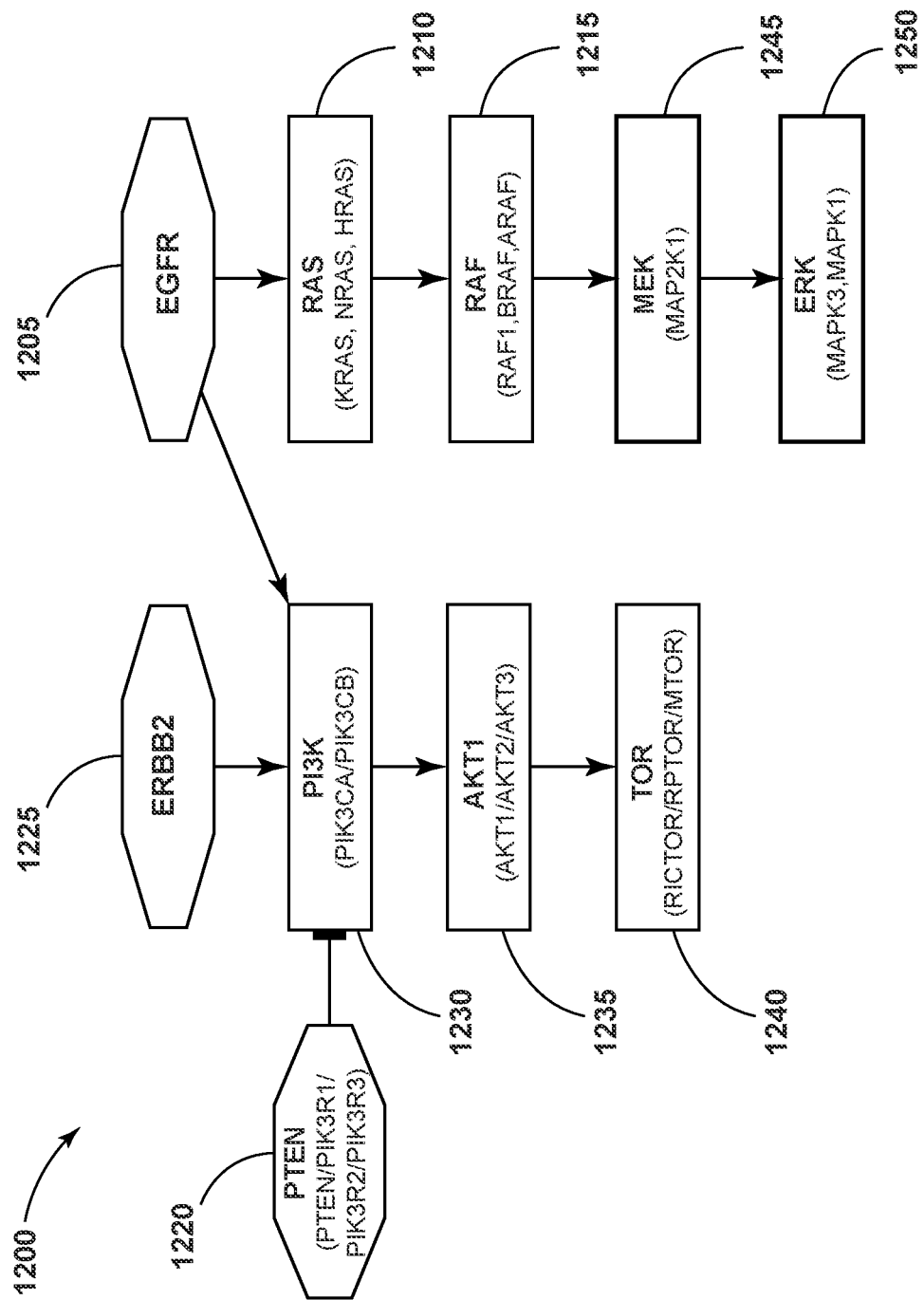
FIG. 12A shows results of a patient transcriptome being analyzed by multiple pathway engines.

Referring now to FIG. 6G, an exemplary process 670 for training a model is shown. The process 670 can train the model to recognize disruption at a module in a pathway. A module can include one or more genes. For example, as shown in FIG. 12A, the RTK/RAS-PI3K-EGFR pathway, which may also be referred to as the RTK-RAS pathway 1200 can include one or more of the EGFR module 1205, the RAS module 1210, the RAF module 1215, the MEK module 1245, the ERK module 1250, the PTEN module 1220, the ERBB2 module 1225, the PI3K module 1230, the AKT module 1235, and the TOR module 1240. The EGFR module 1205 can include the EGFR gene. The RAS module 1210 can include the KRAS gene, the NRAS gene, and the HRAS gene. The RAF module 1215 can include the RAF1 gene, the BRAF gene, and the ARAF gene. For the RTK-RAS pathway, the process 670 can be used to train a model associated with the EGFR module 1205, a model associated with the RAS module 1210, and a model associated with the RAF module 1215.

The process 670 can train a regression model such as a linear regression model. The linear regression model can be an elastic net linear regression model. The model can be included in a pathway engine such as the pathway engine 200n. In some embodiments, the model can be associated with a type of cancer, such as lung cancer, breast cancer, etc. In some embodiments, the model can be associated with multiple types of cancers. In this way, the model can detect dysregulation in a pathway while being agnostic to cancer type. The process 670 can be implemented as computer readable instructions on one or more memories or other non-transitory computer readable media, and executed by one or more processors in communication with the one or more memories or media. In some embodiments, the process 670 can be implemented as computer readable instructions on the memory 222 and/or the memory 262 and executed by the processor 214 and/or the processor 254.

At 672, the process 670 can receive a number of positively labeled samples and a number of negatively labeled samples. Each sample can include transcriptome data generated based on a tissue sample associated with a patient. The positively labeled samples and the negatively labeled samples can be associated with a specific pathway module (e.g., the RAS module 1210). For the pathway module, the positively labeled samples, which may also be referred to as pathogenically altered samples, can be samples with at least one pathogenic variant, and/or in some embodiments, at least one likely pathogenic variant, in at least one of the genes in the module. The negatively labeled samples can be samples with no somatic, pathogenic (or likely pathogenic) variant, or variant of unknown significance mutations in any gene in the pathway as a whole (i.e. any gene in any module in the entire pathway as defined by TCGA). For example, for a model trained on the RAS module 1210, the positive cohort would be samples with mutations in at least one of the KRAS, HRAS, or NRAS genes, and the negative cohort would be samples with no somatic, pathogenic (or likely pathogenic), or variant of unknown significance mutations in any gene in the entire RTK-RAS pathway.

At 674, the process 670 can determine a training set and a holdout set based on the samples received at 672. The process 670 may randomly select a predetermined percentage of both the positively labeled samples and the negatively labeled samples to use as the training set. The remaining positively labeled samples and negatively labeled samples can be used as a holdout set. In some embodiments, the process 670 can select about 80% of the positively labeled samples and the negatively labeled samples to use as the training set. In other embodiments, the process 670 can select about 90% of the positively labeled samples and the negatively labeled samples to use as the training set. The training set can be used to train the model, and the holdout set can be used to evaluate the model.

At 676, the process 670 can determine a set for training the model and a set for determining a threshold value associated with the model based on the training set. The set for training will be referred to as a hyperparameter set, and the set for determining the threshold value will be referred to as a threshold set. The process 670 may randomly select a predetermined percentage of both positively labeled samples and negatively labeled samples included in the training set to use as the hyperparameter set. The remaining positively labeled samples and negatively labeled samples can be used as the threshold set. In some embodiments, the process 670 can select about 80% of the positively labeled samples and the negatively labeled samples in the training set to use as the hyperparameter set. In other embodiments, the process 670 can select about 90% of the positively labeled samples and the negatively labeled samples in the training set to use as the hyperparameter set. In some embodiments, the process 670 can split the training set, select about 80% of the positively labeled samples and the negatively labeled samples as a training set, and two subsets of 10% of the positively labeled samples and the negatively labeled samples, one used to determine the threshold that maximizes the AUC, and one used to validate the model and the selected threshold. In some embodiments, all three sets are selected to contain equivalent percentages of positive and negative samples. The hyperparameter set can determine final value of certain parameters such as an alpha parameter (e.g., a in equation (2) above) and an L1 parameter (e.g., $l1_{ratio}$ in equation (2) above). In some embodiments, the threshold set can be used to evaluate the model.

At 678, the process 670 can determine differentially expressed genes (DEGs). The process can determine the DEGs based on each sample included in the hyperparameter set. The process 670 can calculate a differential metric between the positively labeled samples and negatively labeled samples for each gene included in the transcriptome data. The process 670 can compare the differential metric calculated for each gene to a predetermined threshold, and retain the gene if the differential metric is below the threshold (or in some embodiments, above the threshold). In some embodiments, the process 670 can determine the differentially expressed genes using a t-test between the positively labeled samples and negatively labeled samples for each gene included in the transcriptome data. The process 670 can correct P-values generated using the t-test to Benjamini-Hochberg False Discovery Rates (FDRs). The process 670 can retain genes with a Benjamini-Hochberg FDR below a predetermined threshold, such as 0.05, for modeling and used as the DEGs. Either the P-values or the FDRs may be used as the similarity metric.

At 680, the process 670 can determine final training parameters for the model. In embodiments, where the model is an elastic net linear model, the process 670 can determine the final training parameters using equation (2) described above.). The process 670 can determine a peak of equation (2) using a coordinate descent method. The process 670 can determine the alpha and L1 ratio parameters using grid-search with 10 or 15-fold cross validation on the hyperparameter set. In some embodiments, the parameter values tested can include alpha values in the range [0.1, 0.5, 1, 2, 5, 10] and L1 ratio values in the range [0, 0.05, 0.1, 0.2, 0.4, 0.6, 0.8, 1]. The process 670 can choose the set of alpha and L1 ratio parameters with the highest average AUC from the cross-validation to be the final alpha and L1 ratio parameters.

At 682, the process 670 can train a final model using the final training parameters. In some embodiments, the process 670 can train a final elastic net linear model using the final alpha and L1 ratio parameters. The process 670 can then proceed to 684 and 688 in parallel.

At 684, the process 670 can calculate model scores for the threshold set to find probability distributions of the final model. The output of the model may not directly classify a patient as dysregulated or non-dysregulated. For example, the output distributions for the dysregulated and non-dysregulated patients in the threshold set (not used to train the model) may be graphed as shown in FIG. 6C. The distributions can represent the scores output by the model for the positively labeled samples and the negatively labeled samples in the threshold set.

At 686, the process 670 can determine the final threshold value based on the distributions. The process 670 can determine the threshold by maximizing the AUC over the distributions. In FIG. 6C, a threshold 649 is about 0.85. The process 670 can determine the threshold based on a set that was not used to train the model and is not the true holdout set, which allows the process 670 approximate what the distributions will be on the holdout set and choose an appropriate threshold in order to improve performance as compared to if the threshold was determined using the true holdout set.

At 688, the process 670 can calculate model scores for the holdout set using the calculate model scores for the holdout set using the final model. The process 670 may also generate probability distributions (e.g., the same types of probability distributions generated at 684).

At 690, the process 670 can classify patients included in the holdout set as dysregulated or non-dysregulated based on the final threshold. The process 670 can calculate AUC over the distributions. The AUC can be the average of the sensitivity and specificity of the model if patients above the final threshold are predicted as dysregulated, and patients below the final threshold are predicted as non-dysregulated. The AUC may also be indicative of the overall performance of the final model in the general population because the holdout set was not used to train the model.

At 692, the process 670 can determine the performance of the final model using the AUC calculated at 690. The process 670 may compare the AUC to a predetermined target AUC, and determine to retrain the model if the AUC is below the target AUC. The process 670 may cause the AUC to be displayed (e.g., at the display 290) in order for a human practitioner to analyze and/or evaluate the performance of the final model.

Figure 6H:
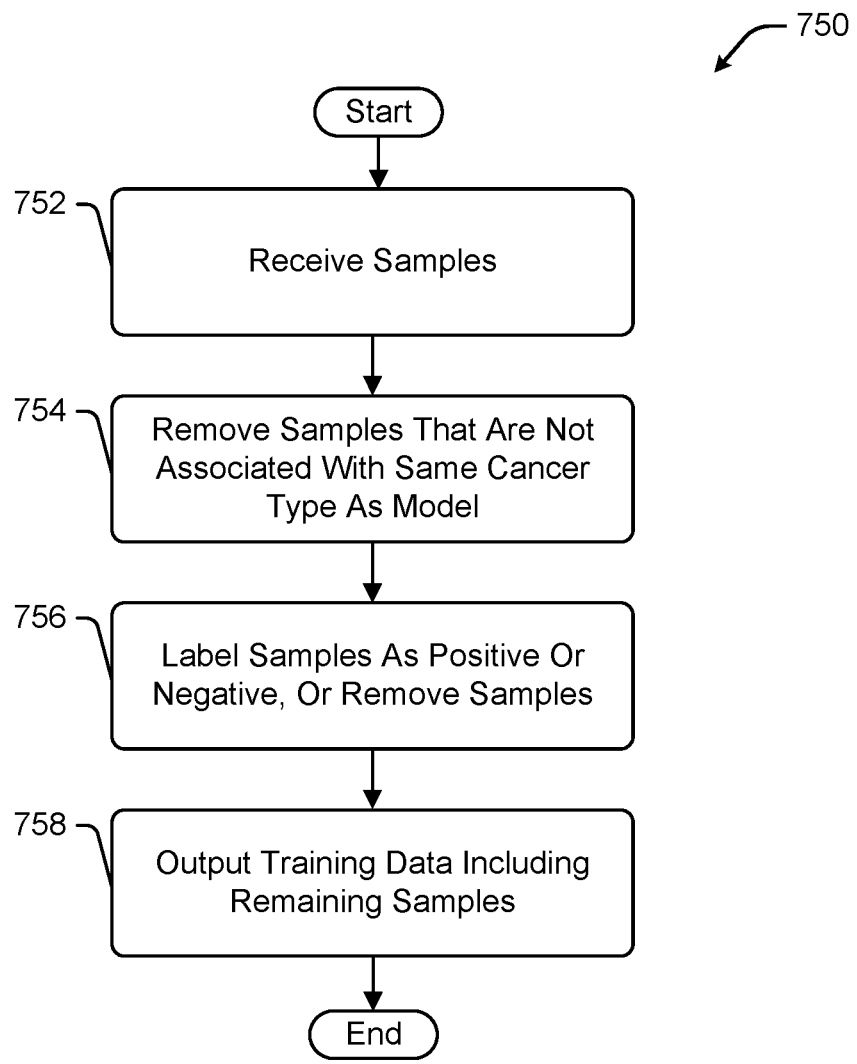
FIG. 6H shows a process that can select training data for training a model.

Referring now to FIG. 6H, a process 750 that can select training data for training a model (e.g., a linear regression model) using a model training process, such as the process 670 in FIG. 6G, is shown. More specifically, the process 750 can determine if a sample should be assigned to a group (e.g., a cohort) of positively labeled samples, a group of negatively labeled samples, or excluded from samples used to train a model associated with either a module (e.g., the EGFR module 1205 in FIG. 12A) or an entire pathway (e.g., the entire RTK-RAS pathway 1200 depicted in FIG. 12A). The sample can include RNA data, DNA data, a cancer type, a quality rating, and other clinically relevant data associated with a tissue sample from a tumor. The model can be associated with a predetermined cancer type.

In some embodiments, the model can be associated with a pathway (e.g., the RTK-RAS pathway 1200). In some embodiments, the model can be associated with a module included in a pathway (e.g., the RAS module 1210 included in the RTK-RAS pathway 1200). In some embodiments, the model can be associated with a module that includes a single gene included in a pathway (e.g., the KRAS gene included in the RTK-RAS pathway 1200). In some embodiments, the module that includes the gene may have multiple genes.

At 752, the process 750 can receive samples associated with patients. The samples may be included in a database. Each sample can include RNA data, DNA data, a cancer type, a methylation status, protein data, ssGSEA data, and/or other clinically relevant data associated with a tissue sample from a tumor. To begin, the process 750 can place all the samples in a sample group. The process 750 can subsequently remove ineligible samples from the sample group, as well as label samples included in the group as positive controls (e.g., showing dysregulation) or negative controls (e.g., showing non-dysregulation). In some embodiments, the RNA data can include expression values for over 19,000 genes.

Each sample can be generated by subjecting a tissue sample to a targeted panel or whole genome DNA sequencing. Each sample can include a complete list of detected variants, a variant allele fraction (VAF), and a log odds ratio (LOR) of the copy number of each gene in the sample. The list of detected variants for the sample can include single nucleotide variations (SNVs) and insertions/deletions (indels). The sample can include a pathogenicity classification of "benign," "likely benign," "conflicting evidence," "likely pathogenic," "pathogenic," "unknown significance," or "unknown" for each variant in the list of detected variants. The determination of which category into which a given variant falls can be made based on criteria set forth by the American College of Medical Genetics and Genomics (ACMG). Multiple levels of evidence can be considered, including the frequency of the variant in the population, direct clinical evidence, and the expected effects of the variant on gene expression and/or the function of the translated protein. These levels of evidence are integrated to generate a final determination of the category. Additional, limited, criteria for variant pathogenicity can be generated using a DNA variant database. The sample can include a classification for each variant indicating whether the variant likely originated in the tumor ("somatic"), or was present in the patient at birth ("germline"). The VAF can be a measure of what proportion of the allele is present in a tissue sample compared to the version of the gene that is present in normal tissue adjacent to a tumor. The log odds ratio of the copy number of each gene can be used by the process 750 to determine if a gene is amplified or deleted can be made. For example, a LOR of 0 may indicate that the gene's copy number is normal (i.e., 2), a LOR>2 may indicate a strong possibility of amplification, and a LOR<−2 may indicate a strong possibility of deletion.

The copy number variation can be used to determine the pathogenicity of the sample. A reference database can include data about whether amplification or deletion is indicative that the gene is pathogenic. For example, an amplification (i.e, copy number increase) of ERBB2 is considered to be pathogenic, whereas a deletion (i.e., copy number loss) is not. The opposite is true for the gene PTEN. Only these pathogenic copy number changes are considered when determining whether and how a sample is used for generating a pathway disruption model.

Whether a given sample has an amplification or deletion in a gene is based on where its copy number log odds ratio (CNLOR) falls within the distribution of CNLORs for that gene for all samples in the considered cohort. Specifically, a gene is considered amplified if its CNLOR is greater than 2.0 standard deviations above the mean CNLOR of all samples in the considered cancer cohort, and a gene is considered deleted if its CNLOR is less than 2.0 standard deviations below the mean CNLOR. For example, the mean CNLOR for ERBB2 may be 0 for a particular cancer type, with a standard deviation of 1.2. A sample will be considered to have ERBB2 amplification if its ERBB2 CNLOR is greater than 0+(2.0*1.2)=2.4. Alternatively, a cancer may have a mean CNLOR for TP53 of −0.1, with a standard deviation of 0.8. A sample will be considered to have TP53 deletion if its TP53 CNLOR is less than −0.1−(2.0*0.8)=−1.7.

At 754, the process 750 can remove any samples in the sample group that are not associated with the same cancer type as the model. For example, the process 750 can remove a lung cancer sample with a squamous diagnosis from the sample group if the model is associated with lung adenocarcinoma.

At 756, the process 750 can label samples as positive samples or negative samples and/or remove samples from the sample group based on the variants, the VAF, and the LOR of the copy number of each gene in the sample. In some embodiments, the process 750 can determine positive controls and negative controls using criteria described in the "Exemplary Positive and Negative Control Selection" section above.

In some embodiments, for a model trained to detect dysregulation in a pathway (e.g., the RTK-RAS pathway 1200), a sample can be labeled as a positive control sample only if the sample includes mutations, either germline or somatic, in the DNA of at least one of the genes included in a pathway module included in the pathway. In some embodiments, a sample may only be labeled as a negative control if the sample has no DNA mutations of any type in any gene included in the pathway, and/or includes only benign or likely benign germline variants in any genes in the pathway.

In some embodiments, for a model trained to detect dysregulation in a pathway module, a sample can be labeled as a positive control sample only if the sample includes a mutation, either germline or somatic, in the DNA of at least one gene included in the pathway module. In some embodiments, a sample may only be labeled as a negative control if the sample has no DNA mutations of any type in any gene included in the module associated with the model. In addition, in some embodiments, a negative control may include only benign or likely benign germline variants in one or more genes in the entire pathway that includes the module.

In some embodiments, for a model trained to detect dysregulation in a single gene included in a pathway module (e.g., the RAS module 1210), a sample can be labeled as a positive control sample only if the sample includes a mutation in the DNA of the gene. In some embodiments, a sample may only be labeled as a negative control if the sample has no DNA mutations of any type in the gene associated with the model, and/or includes only benign or likely benign germline variants in genes in the entire pathway that includes the gene.

The process 750 may only use genetic data about the pathway the model is being trained for or the pathway including the module that the model is being trained for when determining what samples are to be included in the analysis. For example, if training data for a model for the RAF module within the RTK/RAS pathway is being generated, a gene variant in a secondary but unconnected oncogenic pathway (e.g., the WNT pathway) will not be considered in the decision of whether to include the sample in the positive or negative control groups or excluded from the analysis. Moreover, a mutation in other modules within the parent RTK/RAS pathway, for example, the RAS module comprising HRAS, NRAS, and KRAS, will not affect whether the sample is included in the positive control group RAF; only pathogenic mutations within the module are considered by the process 750 for this determination. For example, a sample with pathogenic mutations (either copy number amplification or deletion depending on the gene, as described above) in both BRAF and KRAS would be included as a positive control when generating disruption models for either the RAS or RAF sub modules. Additionally, the process 750 may only consider variants in a sample with a VAF of at least five percent (i.e., >5%), which may help ensure that any variant with a disruptive effect on the pathway is present to an extent sufficient for the effect to be detectable.

In some embodiments, for the process 750 to label a sample as a positive sample, the sample must have a detected pathogenic or likely pathogenic variant in any gene within the module if the model is being trained for a module, or any gene within the pathway the model is being trained for, regardless of whether the variant is somatic or germline. In other words, the process 750 only labels samples as positive if the sample has somatic and/or germline variants in the pathway the model is being trained for or the module the model is being trained for.

In some embodiments, for the process 750 to label a sample as a negative sample, the sample must have no detected somatic mutations, of any type, in any gene within the pathway (whether the model is trained for a pathway or a module), and only benign or likely benign germline variants within the pathway. In some embodiments, the module may interact with multiple pathways, such as for the EGFR and ERBB2 module. In such cases, a sample must have no somatic mutations in any gene within that module to be labeled as a negative sample. These criteria can help ensure that only samples for which the disruption status can confidently be assessed are included in the model generation. Modeling based on patients within the extreme tails of the pathway disruption distribution provides an interpretable continuous score able to quantify the effect of a VUS on the pathway disruption of a patient.

In some embodiments, the process 750 can remove any samples that include a quality rating below a predetermined threshold. The quality rating may reflect the likelihood that an error occurred during a sequencing procedure that affected the associated read. By way of example, a threshold value can be derived by evaluating one or more criteria that can result in poor or unreliable sample quality, such as but not limited to too few reads, poor read quality, read duplication rate being too high, the existence of DNA contamination, contamination with other samples, pathogen contamination, and poor read alignment to the genome assembly.

The process 750 can remove any samples that are not positively labeled or negatively labeled from the sample group. For example, the process 750 can remove samples having pathogenic mutations outside of a module for which that model is being trained.

In some embodiments, the process 750 may end if there is not a sufficient number of positive controls and negative controls. In some embodiments, the process can end if there are not at least sixteen positive control samples and a proportion of negative controls to negative controls of at least five percent. In this way, the process 750 can ensure that a model is only trained if suitable data is available.

At 758, the process 750 can output training data for use with training the model. The training data can include the positively labeled samples and the negatively labeled samples included in the sample group. The process 750 may output the training data to a database (e.g., the labeled tumor samples database 400 in FIG. 3) or to a process such as the process 690 in FIG. 6G.

Examples are presented in Tables 3-7 below for classifying individual samples. The examples are meant to illustrate how a determination is made regarding whether and how the sample is included in model generation, using the applicable criteria described above in conjunction with the process 750.

The example in Table 3 is for a sample considered for inclusion into the ERBB2 sub-module. The sample contains an amplification in the ERBB2 gene, which is sufficient for it to be included as a positive control. The sample has other variants; however, these do not exclude the sample from the positive control group given that only module-level mutations are considered for this determination.

TABLE 3

| Gene | Variant type | Variant | Germline or Somatic | Pathogenicity | VAF | In ERB B2 module | Sufficient for inclusion in positive group | Sufficient for exclusion from negative group |
|---|---|---|---|---|---|---|---|---|
| BARD1 | indel | c.1518_1519_delTGinsCA | Germline | Likely benign | 66% | No | No | No |
| HLA-C | indel | c.648_652delCCCCinsTCCCG | Germline | Unknown significance | 60% | No | No | No |
| EPHA2 | indel | c.570-573delGCTGinsACTA | Germline | Likely benign | 82% | No | No | No |
| FGFR2 | SNP | c.1990-106A > G | Germline | Unknown significance | 3% | No | No | No |
| MKI67 | indel | c.8378-8382delGTGCCinsATGCT | Somatic | Unknown significance | 12% | No | No | No |
| ARID1A | CNV | deletion | NA | Pathogenic | NA | No | No | No |
| ERBB2 | CNV | amplification | NA | Pathogenic | NA | Yes | Yes | Yes |

The example in Table 4 is for a sample considered for inclusion into the RAF sub-module of the RTK/RAS parent pathway. The patient does not have a pathogenic or likely pathogenic mutation in the RAF module and so cannot be included in the positive control group. The patient does have a pathogenic mutation in KRAS, which is in the parent pathway for the RAF module, the RTK/RAS pathway. Therefore, this patient cannot be included in the negative control group and is excluded altogether from model generation. This patient would, however, be able to be included as a positive control for a model of RAS sub-module disruption.

TABLE 4

| Gene | Variant type | Variant | Germline or Somatic | Pathogenicity | VAF | In RAF module | In RTK/RAS pathway | Sufficient for inclusion in positive group | Sufficient for exclusion from negative group |
|---|---|---|---|---|---|---|---|---|---|
| APOB | SNP | c.1343C > The | Germline | Unknown significance | 90% | No | No | No | No |
| HLA-DQB2 | indel | c.687_688delCAinsTG | Germline | Pathogenic | 80% | No | No | No | No |
| KRAS | SNP | c.34G > T | Somatic | Pathogenic | 9% | No | Yes | Yes | Yes |
| MSH6 | indel | c.4002-2delT | Somatic | Unknown significance | 12% | No | No | No | No |
| KEAP1 | SNP | c.1249G > The | Somatic | Likely benign | 18% | No | No | No | No |

The example in Table 5 is for another sample considered for inclusion into the RAF sub-module of the RTK/RAS pathway. This patient has a pathogenic mutation in BRAF, which is a member of the RAF module, and so can be included in the positive control group.

TABLE 5

| Gene | Variant type | Variant | Germline or Somatic | Pathogenicity | VAF | In RAF module | In RTK/RAS pathway | Sufficient for inclusion in positive group | Sufficient for exclusion from negative group |
|---|---|---|---|---|---|---|---|---|---|
| MYH9 | indel | c.4872-4876delGCACAinsTCACG | Germline | Likely pathogenic | 96% | No | No | No | No |
| EPHA2 | indel | c.570-573delGCTGinsACTA | Germline | Likely benign | 82% | No | No | No | No |
| FGFR2 | SNF | c.1990-106A > G | Germline | Unknown significance | 3% | No | Yes | No | No |
| ARID2 | CNV | deletion | NA | Pathogenic | NA | No | No | No | No |
| KRAS | SNP | c.34G > T | Somatic | Pathogenic | 9% | No | Yes | Yes | No |
| BRAF | CNV | amplification | NA | Pathogenic | NA | Yes | Yes | Yes | Yes |
| CALR | SNP | c.566G > C | Germline | Likely pathogenic | 79% | No | No | No | No |
| MSH3 | SNP | c.204T > Genes | Somatic | Benign | 18% | No | No | No | No |

The example in Table 6 is for a sample considered for inclusion into the TOR sub-module of the PI3K pathway. This sample has an amplification in RICTOR, which is a member of the TOR module, and so can be included in the positive control group. The sample also has an amplification of AKT3; however, this does not exclude the sample from the positive control group given that only module-level mutations are considered for this determination.

stream of that module. For example, as shown in FIG. 6J, a VUS in AKT that should be classified as pathogenic would cause disruption in these modules (the numbers are example dysregulation scores for patients with that VUS in each of the modules):

A global dysregulation score that takes into account both the originating module and all the modules downstream of it can be calculated in order to analyze the effect of the

TABLE 6

| Gene | Variant type | Variant | Germline or Somatic | Pathogenicity | VAF | In TOR module | In PI3K Pathway | Sufficient for inclusion in positive group | Sufficient for exclusion from negative group |
| --- | --- | --- | --- | --- | --- | --- | --- | --- | --- |
| HLA-DQB2 | indel | c.687_688delCAinsTG | Germline | Pathogenic | 80% | No | No | No | No |
| HOTS | indel | c.6233_236delTACTinsCACC | Somatic | Likely pathogenic | 8% | No | No | No | No |
| AKT3 | CNV | amplification | Somatic | Pathogenic | NA | No | Yes | Yes | No |
| EPHA2 | indel | c.570-573delGCTGinsACTA | Germline | Likely benign | 82% | No | No | No | No |
| FGFR2 | SNP | c.1990-106A > G | Germline | Unknown significance | 3% | No | Yes | No | No |
| RICTOR | CNV | amplification | NA | Pathogenic | NA | Yes | Yes | Yes | Yes |

The example in Table 7 is for a sample considered for inclusion into the PTEN sub-module of the PI3K pathway. This sample has a benign germline mutation in PTEN, which is insufficient to include it as a positive control or exclude it as a negative control sample. This sample would therefore be a negative control for PTEN module disruption model generation.

VUS(s). Moreover, a pathogenic mutation should cause more dysregulation in the modules closer to the originating module than further, and this can be taken into account when calculating the global dysregulation score.

Possible Confounders

VUS classification scores can be confounded by other Somatic, Pathogenic, or VUS mutations in the same gene as

TABLE 7

| Gene | Variant type | Variant | Germline or Somatic | Pathogenicity | VAF | In TOR module | In PI3K pathway | Sufficient for inclusion in positive group | Sufficient for exclusion from negative group |
| --- | --- | --- | --- | --- | --- | --- | --- | --- | --- |
| PTEN | SNP | c.1619_1620_delTGinsCA | Germline | Benign | 86% | No | Yes | No | No |
| BARD1 | indel | c.1518_1519_delTGinsCA | Germline | Likely benign | 66% | No | No | No | No |
| EPHA2 | indel | c.570-573delGCTGinsACTA | Germline | Likely benign | 82% | No | No | No | No |
| NRG1 | SNP | c.1648C > The | Somatic | Benign | 19% | No | No | No | No |
| MYH9 | indel | c.4872-4876delGCACAinsTCACG | Germline | Likely pathogenic | 96% | No | No | No | No |

Classifying Variants of Unknown Significance

Variants of Unknown Significance (VUSs) are mutations for which it is unknown if they are cancer-driving (pathogenic) or not (benign). Certain databases may have thousands of VUSs. It is desirable to characterize the VUSs effects on the transcriptome to provide evidence to a variant's classification of pathogenicity.

Figure 6I:
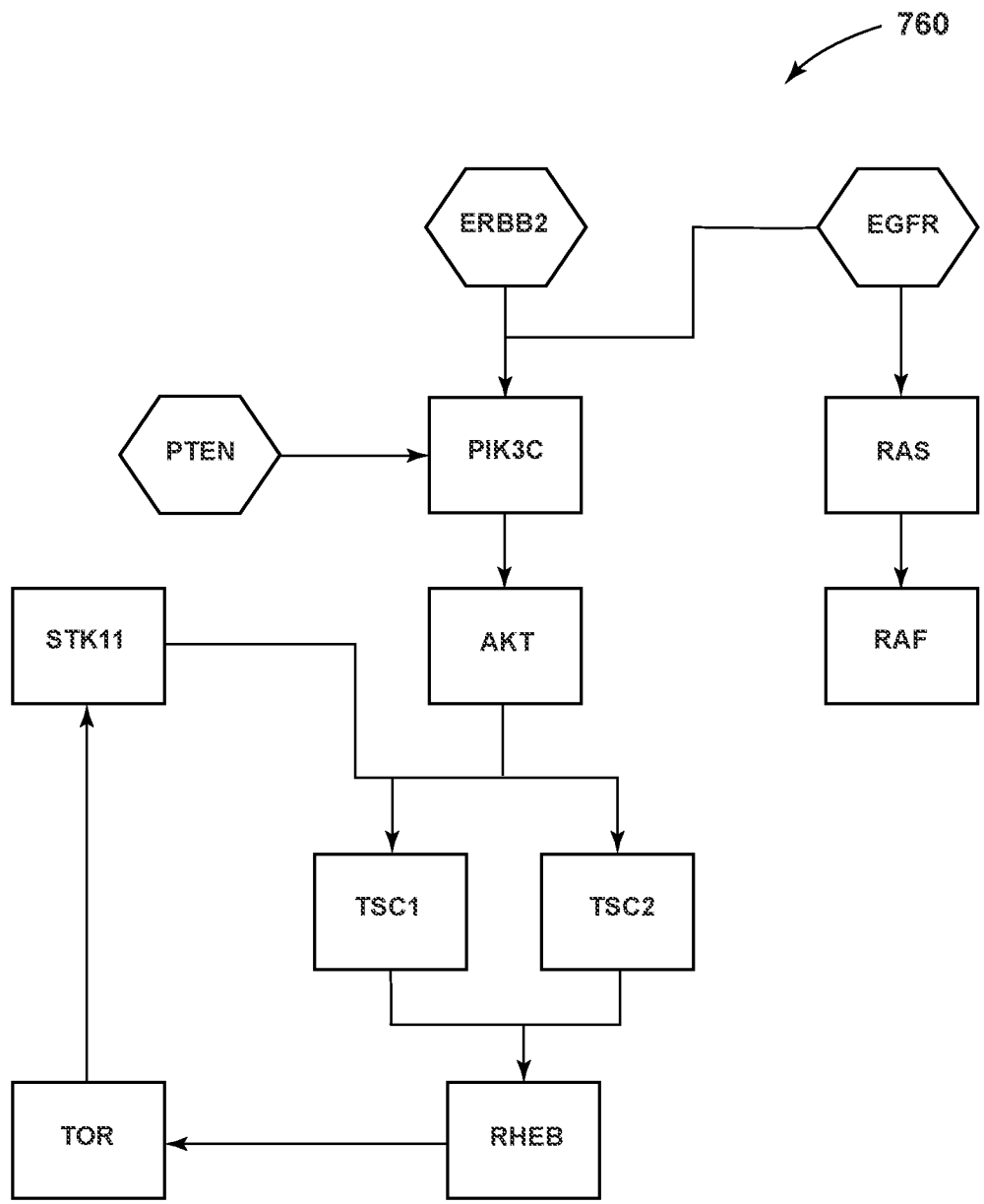
FIG. 6I shows an exemplary model of an RTK-RAS and PI3K pathway having a number of modules.
Figure 6J:
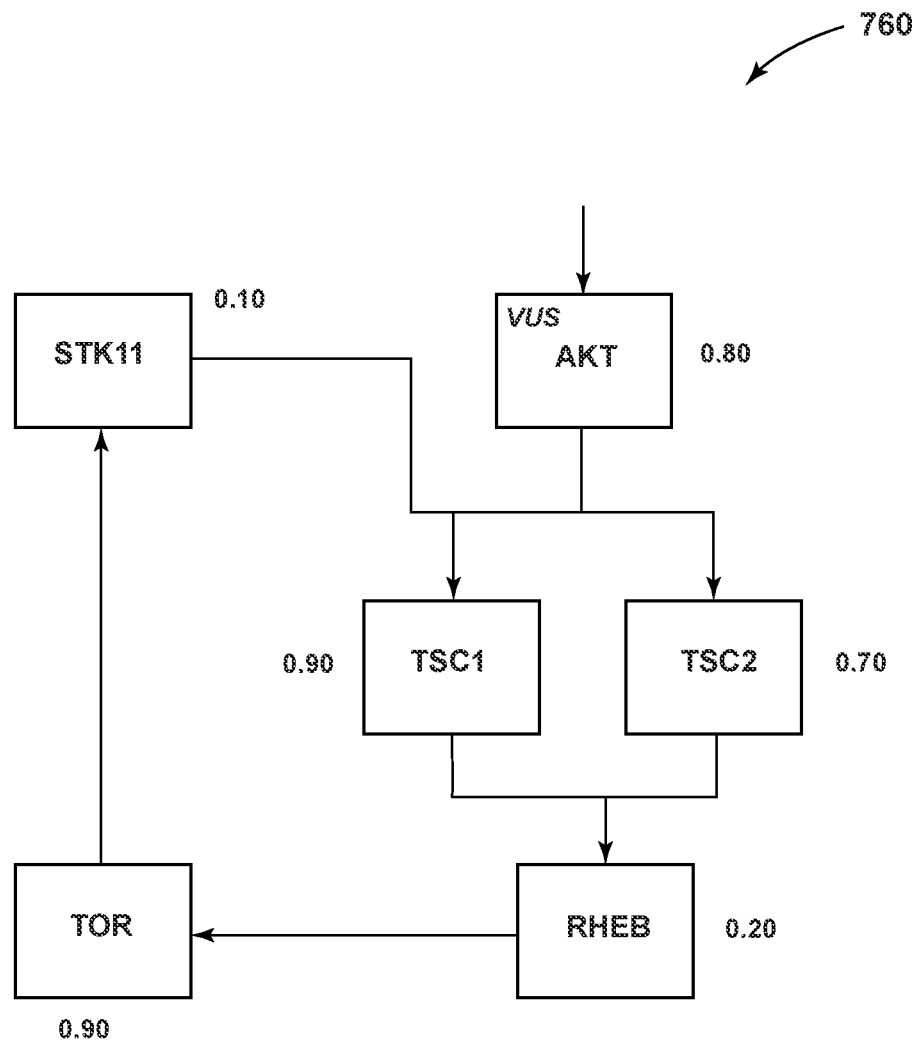
FIG. 6J shows a variant of unknown significance (VUS) in an AKT module.

FIG. 6I shows an exemplary model of an RTK-RAS and PI3K pathway 760 having a number of modules. As described above, each module can be associated with a model trained to identify the pathogenic dysregulation of the module in view of the pathway. If a VUS causes dysregulation in one of the pathway modules (in which case it should be classified as pathogenic), then the combined signal of the models associated with the modules may identify patients with that VUS as having scores corresponding to dysregulation. The combined signal can be referred to as a meta-pathway score.

Figure 6K:
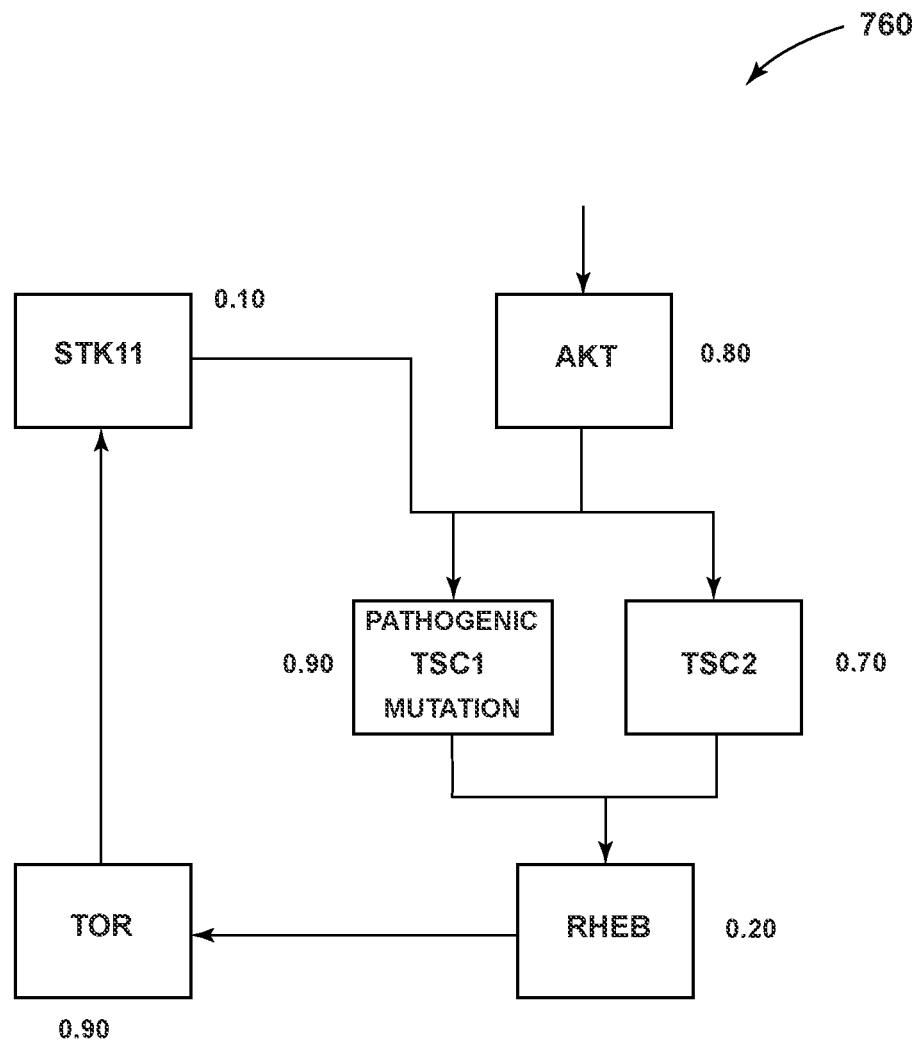
FIG. 6K shows a pathway with a pathogenic mutation in a TSC1 module.

The above approach relies on the assumption that a pathogenic mutation has direct transcriptional or post transcriptional mechanism that causes dysregulation of the pathway module that contains it, and/or the pathways downthe VUS. If there are other potentially pathogenic mutations in the same gene as the VUS (including other VUSs), these could explain the calculated pathway dysregulation. VUS classification scores can also be confounded by pathogenic mutations in any genes that link to the pathway with the VUS. Any pathway module that has a pathogenic mutation and is downstream of the originating module should have a high dysregulation score regardless of the pathogenicity of the VUS because patients with such pathogenic mutations were used to train that model. Because the global dysregulation meta-pathway score takes into account modules downstream of the originating module, including these patients as is would falsely inflate the global dysregulation score. As seen in FIG. 6K, one would expect the TSC1 module to have a high dysregulation score regardless of the pathogenicity of a VUS in AKT.

Figure 6L:
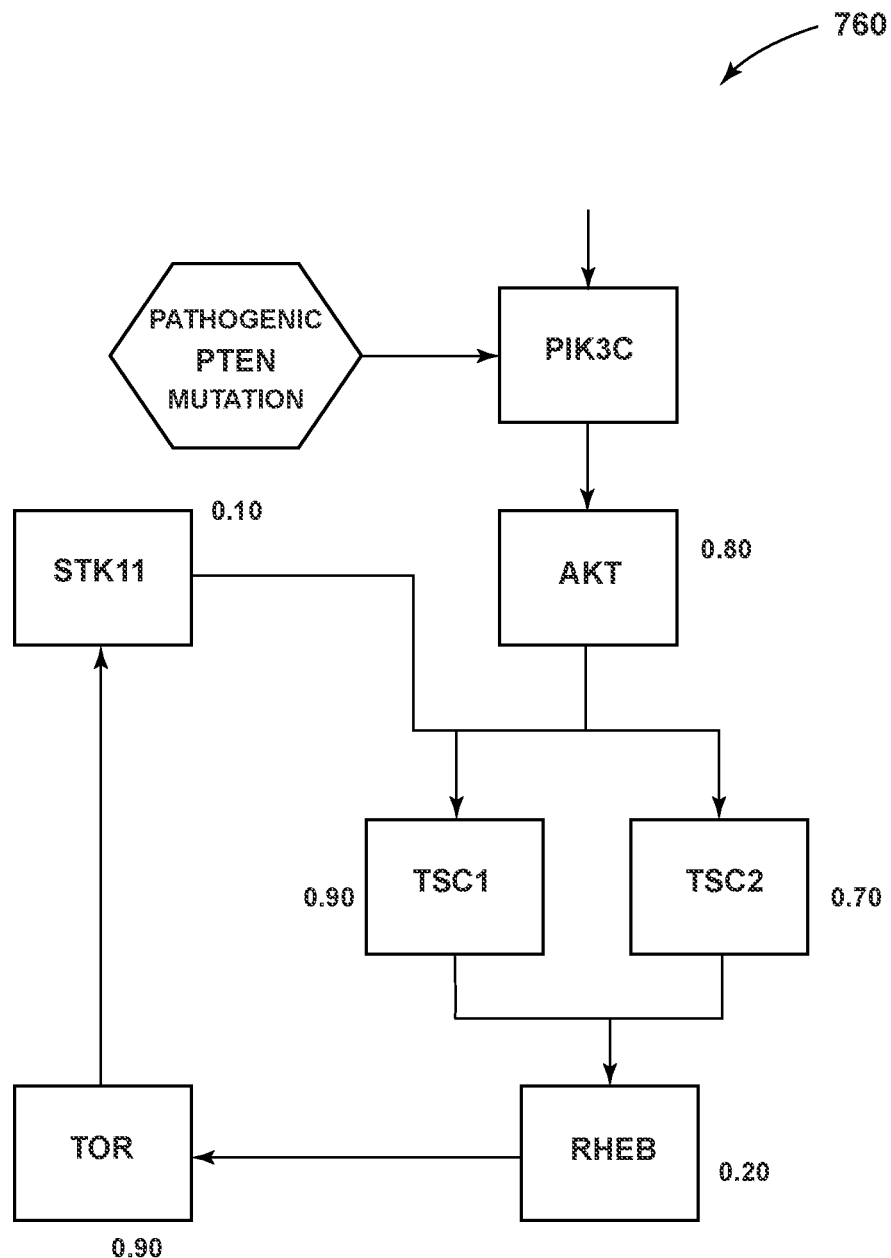
FIG. 6L shows a pathway with a pathogenic mutation in a PTEN module.

A module with a pathogenic mutation in another module upstream of it would also be expected to have a high dysregulation score regardless of the pathogenicity of the VUS, and again including these patients as is would falsely inflate the global dysregulation score. As shown in FIG. 6L, one would expect that the PTEN pathogenic mutation would cause higher dysregulation scores in AKT, TSC1, etc. because they are downstream of PTEN.

Patients with a pathogenic mutation in another module upstream can be excluded from analysis. However, some classifiers, such as classifiers that include linear models, can allow inclusion of mutation status in other genes in the pathway as covariates to account for the contribution of other gene mutation effects on the meta-pathway score while increasing the sample size and power of the analysis.

Figure 6M:
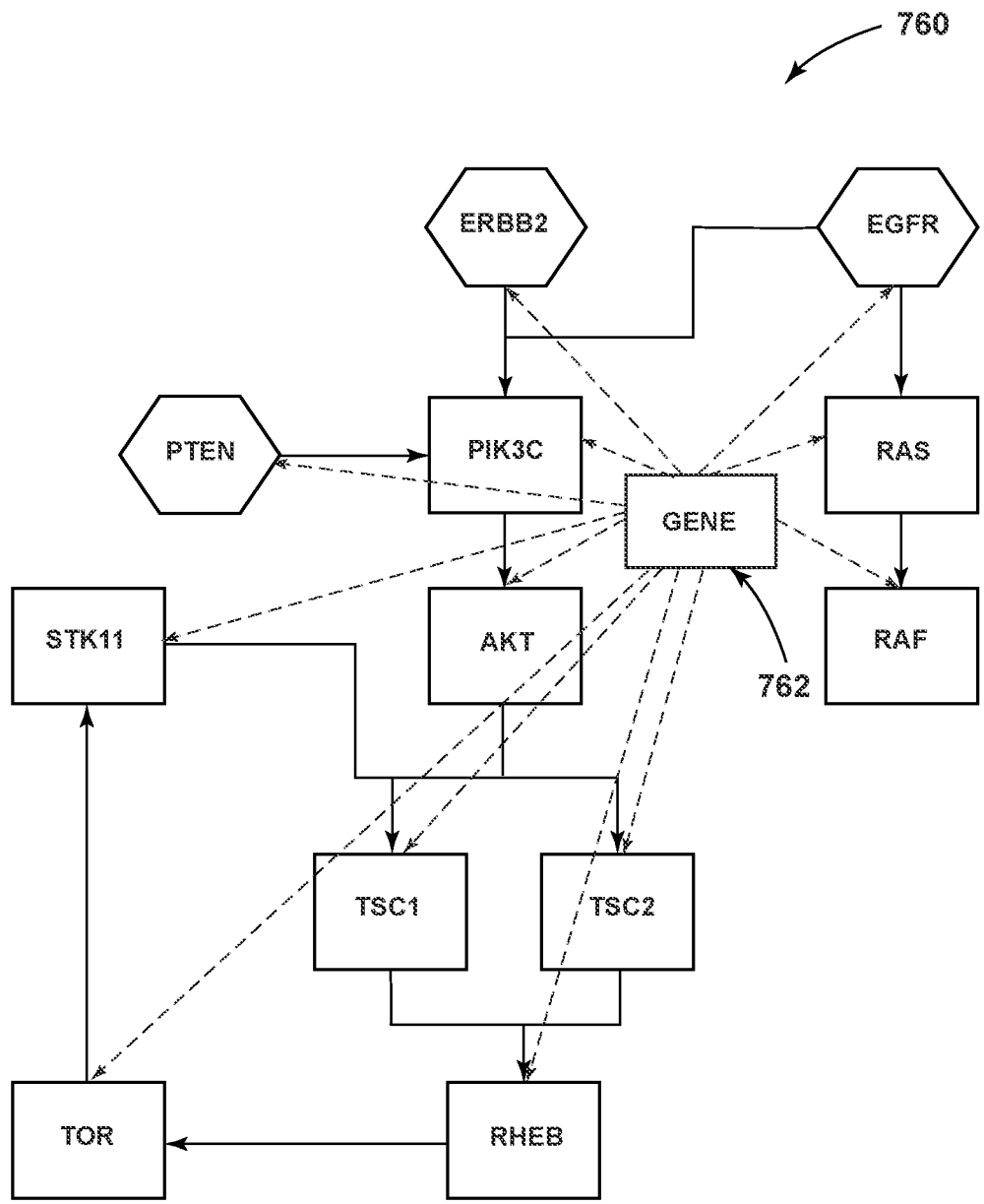
FIG. 6M shows a gene can be connected to each module included in a RTK-RAS and PI3K pathway.

Mutations in genes outside the pre-defined pathway could have an effect on the pathway of interest. To classify VUSs in genes outside of the pathway, it is assumed that a GENE is in turn connected to each module in the pathway. For example, a GENE 762 can be connected to each module included in the RTK-RAS and PI3K pathway 760 shown in FIG. 6M.

For each connection between the additional GENE and each module in the pathway, a global dysregulation score can be calculated as if a GENE was truly connected to the pathway. It ca be assumed that the GENE is connected to pathway at the module connection that yields the highest global dysregulation score in the pathway and then evaluate whether the VUS has similar signal as known pathogenic variants.

Figure 6N:
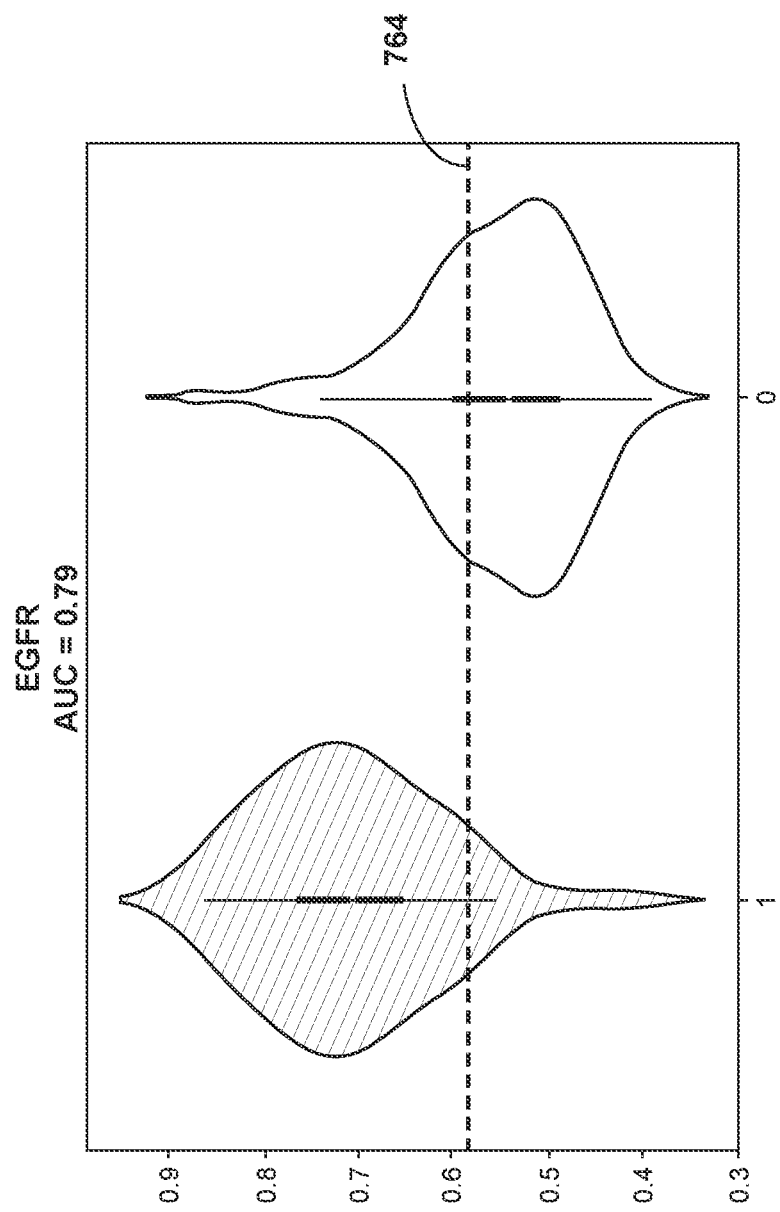
FIG. 6N shows distributions of EGFR pathway dysregulation scores for a Somatic Pathogenic Mutation in EGFR and a Wildtype cohort on a holdout set.

FIG. 6N shows distributions of EGFR pathway dysregulation scores for a Somatic Pathogenic Mutation in EGFR and a Wildtype cohort on a holdout set. Even though an AUC threshold 764 separates the Pathogenic vs WT patients well, there are still WT patients with high EGFR scores and Pathogenic patients with low scores. Even if a VUS is pathogenic, it may not reliably fall above the threshold (or vice versa). Instead of classifying a VUS by looking at all instances of it individually, the pathway module dysregulation scores for patients with that VUS can be used to build a probability distribution then compare that distribution to the corresponding Pathogenic and WT distributions. If a mutation is pathogenic, then its probability distribution will be more like the Pathogenic cohort distribution, and if it does not dysregulate the pathway, it will be more like the WT distribution.

Figure 6O:
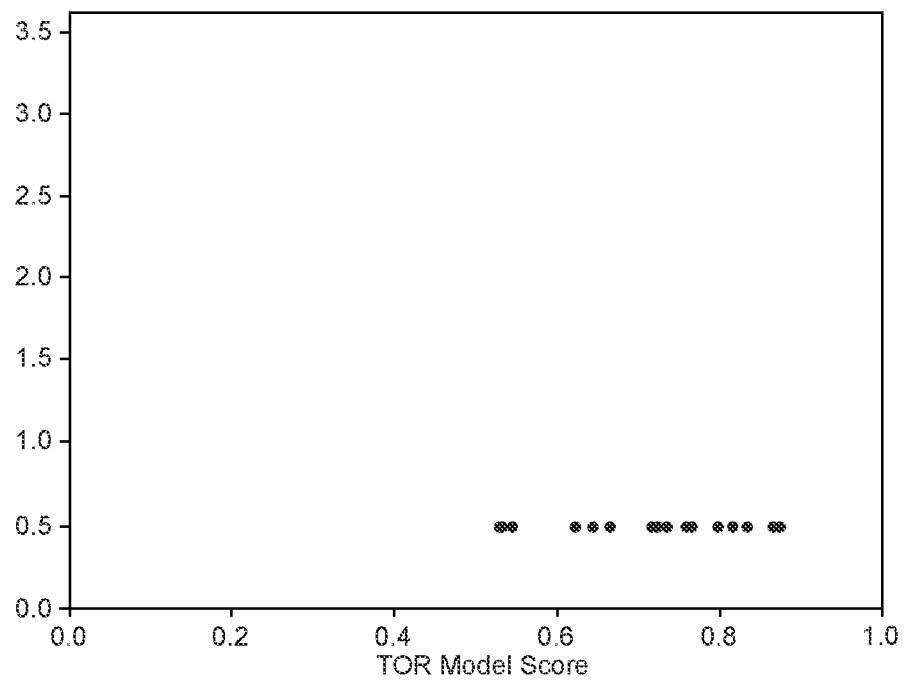
FIG. 6O shows scores produced using the TOR model.
Figure 6P:
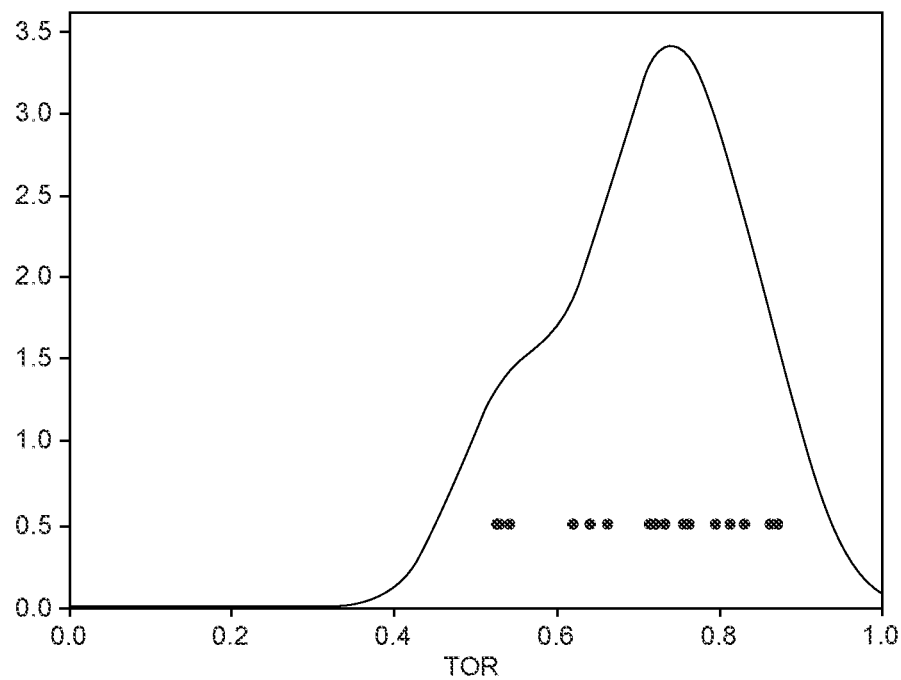
FIG. 6P shows a probability distribution generated using Gaussian Kernel Density Estimation.

For example, a VUS may produce scores shown in FIG. 6O using the TOR model. The scores can be transformed into a probability distribution using Gaussian Kernel Density Estimation as shown in FIG. 6P. Gaussian Kernel Density Estimation builds a Gaussian curve at each datapoint, then adds the Gaussian curves together to get the final result. Note that the final distribution is tallest at the points where the data points are the most dense.

Gaussian KDE also gives some desirable smoothing properties. For example, it makes the probability distribution non-zero between 0.55 and 0.6 for the example shown in FIG. 6P, even though in that interval there are no data points. In addition, Gaussian KDE can model a Gaussian noise model for each data point, which can improve robustness. Gaussian can also normalize for differences in VUS sample size, because all probability distributions have an area of 1.

To quantify the pathogenicity of this VUS in the TOR module pathway score, the distribution can be compared to the TOR Pathogenic Distribution and the TOR WT Distribution using the Kullback-Leibler Divergence. Generally, KLD measures the difference between two probability distributions. Therefore, if the VUS distribution is more similar to the Pathogenic Distribution than the WT, the divergence between the VUS distribution and the Pathogenic will be smaller than between the divergence between the VUS and the WT. The ratio $$KLD_{ratio} = \frac{KLD(VUS, WT)}{KLD(VUS, Path)}$$

can be calculated and then normalized to between 0 and 1 using $$DS = \frac{1}{1 + \frac{1}{KLD_{ratio}}}.$$

The normalization DS has several desirable properties that make it act like a probability. If the VUS distribution is equally similar to the Pathogenic and the WT, the normalized value will be p=0.5; and normalization values are 'symmetric', i.e. values of p and 1−p imply equal similarity to the WT and Pathogenic Distributions respectively.

Figure 6Q:
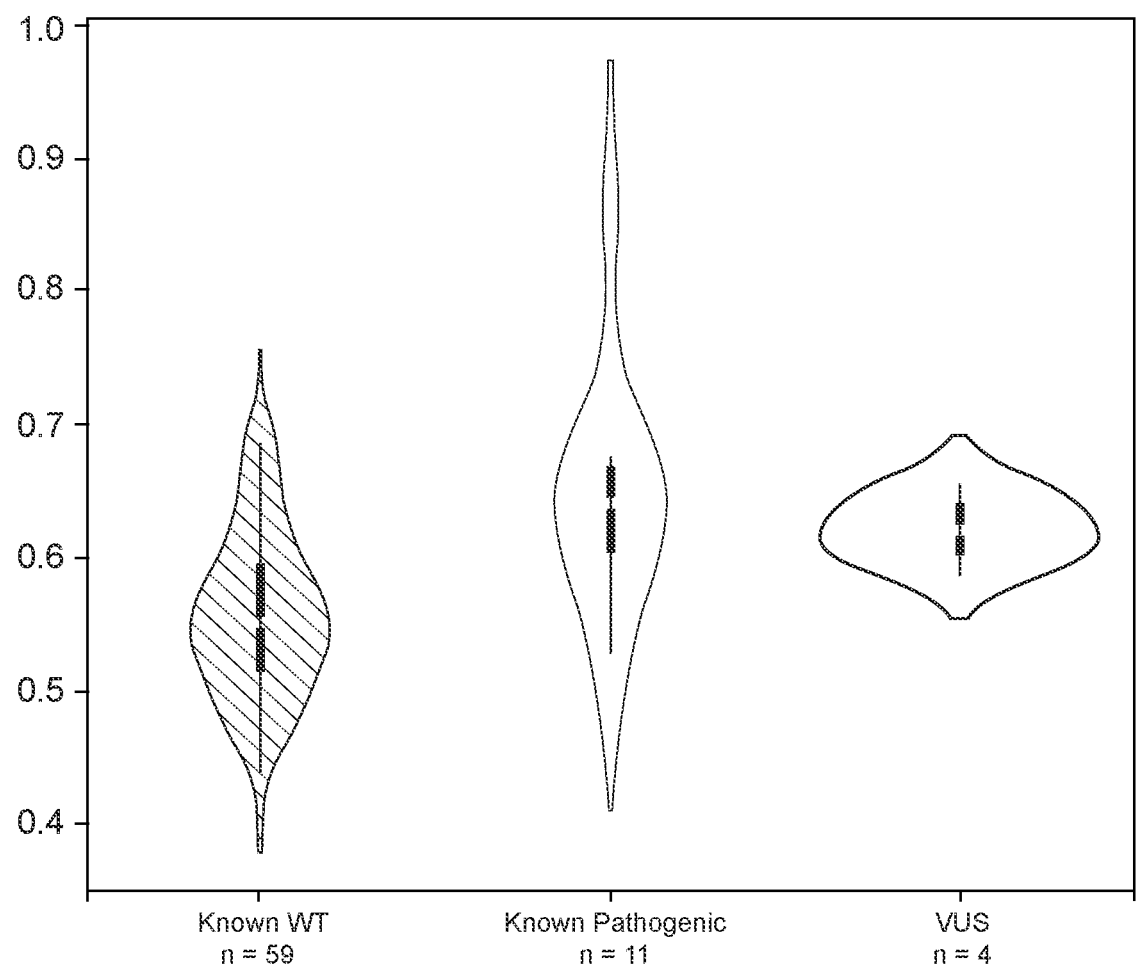
FIG. 6Q shows distributions of cohorts.

However, taking the Kullback Leibler Divergences in this way may not work when one distribution is more widely spread out than the other, for instance, in FIG. 6Q.

Using the KLD method above implies that the VUS distribution is more similar to WT than Pathogenic (p<0.5), even though the VUS distribution is very similar to the middle of the Pathogenic Distribution. To fix this, instead of directly comparing the VUS distribution against WT and Pathogenic, the VUS distribution can be added to the WT and Pathogenic distributions separately, then the Divergence between the new distributions and their respective original distributions can be measured, which can measure the perturbation that the VUS distribution causes when it is added to the other distributions. If the VUS distribution perturbs the Pathogenic Distribution less (i.e. it is more similar) than it does WT, then our final result (ratioed and normalized like before) will give a value greater than 0.5. The value for this example is now p=0.62.

In building the reference distributions for Pathogenic and WT, only data that was not used to train the model should be used. Using the training data to make the reference distributions will skew them to their respective extremes.

A generalized approach to test the effect to a VUS on each pathway model can include all individuals into a linear model and test the effect of each VUS mutation on each pathway module score, similar to expression QTL studies. The single variant effects can then be meta-analyzed across each pathway modules of interest. Covariates can be used to control the effects of other potentially pathogenic mutation effects detected on the pathway. The selection of what modules to meta-analyzed could be pre-defined given known pathway gene lists or identified from the RNA data (e.g. network graphs).

For simplicity, assume that the above graph is completely accurate, i.e. that it represents all and only all true interactions between pathway modules. This implies that a VUS in a pathway module will affect (and only affect) that module and possibly the pathways modules downstream of it. For example, if there is a pathogenic mutation in AKT, this should cause dysregulation in AKT, TSC1, TSC2, RHEB, TOR and STK11. Moreover, the amount of dysregulation should be greater in pathway modules closer to AKT, and so the dysregulation in each of these pathways will most likely rank in that same order.

Based on this assumption, a metric that quantifies the global effect of dysregulation on the pathway can be calculated. For an example, assume that there is a VUS in AKT. Define v as the pathway module the VUS is in and M as v∪ the pathway module downstream of v, i.e. the pathway modules with the VUS and all the pathways modules downstream of it. Then, M={AKT, TSC1, TSC2, RHEB, TOR, STK11}. Note each pathway module model m in M is associated with specific dysregulation score, $DS_m$ that is scaled from 0 to 1 and was defined using the Kullback Leibler Divergence in the section above. One metric that can be used to quantifies the global effect of dysregulation is $\Sigma_{m \in M} DS_m$. This is the sum of the dysregulation scores of all the metapathways in M.

To account for the fact that a pathogenic mutation should affect the pathway modules closest to v more than those further, and will affect v more than any other pathway modules, a distance function is introduced:

$d(m,v)=1+$(the shortest distance between m and the pathway modules which contains the VUS).

In our example (where v=AKT), d(AKT, v)=1, d(TSC1/2, v)=2, d(RHEB, v)=3, etc. To weight the dysregulation scores according to the closeness to v, a weighted score $$T_v = \Sigma_{m \in M} \frac{1}{d(m, v)} * DS_m. \quad T_v$$

can be used to generate a weighted sum of the dysregulation scores of the pathway module in M, where the further away an additional pathway module is from m, the less weight it has in the metric. This weighted sum approach defined here assumes that traveling along each connection in pathway has equal weight. Extensions of this approach could include a method of combining the model scores along the pathway such that weights along the pathway are learned and scaled given their effect size.

$T_v$ may not normalize for the number of pathway models in M. For example, a pathway may have two VUSs, one VUS in RAS and one VUS in RAF. Then $T_{RAS}=1/1*DS_{RAS}+ \frac{1}{2}*DS_{RAF}$ and $T_{RAF}=1/1*DS_{RAF}$. The fact that $T_{RAS}$ has two terms in its sum and $T_{RAF}$ has one unfairly biases $T_{RAS}$ to be greater than $T_{RAF}$. To fix this, $T_v$ can be normalized by dividing $T_v$ by the maximum possible value it could have (i.e. DSm=1 for all m in M), which is the value $$\Sigma_{m \in M} \frac{1}{d(m, v)}.$$

A final metric that can be used to calculate the global dysregulation score is:

$$G_v = \sum_{m \in M} \frac{1}{d(m, v)} * DS_m \bigg/ \sum_{m \in M} \frac{1}{d(m, v)}. \quad (3)$$

Example: VUS in AKT

Figure 6R:
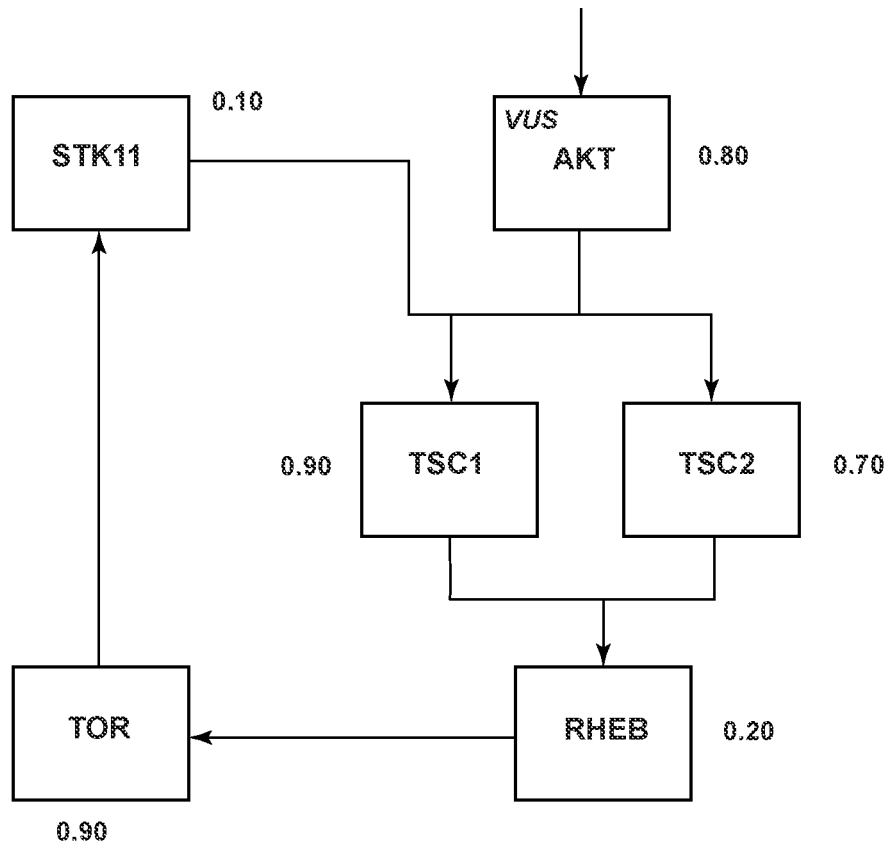
FIG. 6R shows dysregulation scores in a pathway.

Assume that the VUS being considered is in AKT and that AKT and its downstream pathways have the dysregulation scores shown in FIG. 6R. Then $$G_v = \frac{\frac{1}{1}*DS_{AKT} + \frac{1}{2}*DS_{TSC1} + \frac{1}{2}*DS_{TSC2} + \frac{1}{3}*DS_{RHEB} + \frac{1}{4}*DS_{TOR} + \frac{1}{5}*DS_{STK11}}{\frac{1}{1} + \frac{1}{2} + \frac{1}{2} + \frac{1}{3} + \frac{1}{4} + \frac{1}{5}}$$

$$G_v = \frac{\frac{1}{1}*0.80 + \frac{1}{2}*0.90 + \frac{1}{2}*0.70 + \frac{1}{3}*0.20 + \frac{1}{4}*0.90 + \frac{1}{5}*0.10}{\frac{1}{1} + \frac{1}{2} + \frac{1}{2} + \frac{1}{3} + \frac{1}{4} + \frac{1}{5}} = \frac{1.92}{2.78} = 0.69$$

VUS Cohort Selection

For any VUS, the patients selected for a cohort that is used to measure its pathogenicity should satisfy two properties to make VUS signal as clear as possible:

1) they should not have any other Somatic, Pathogenic, or VUS mutation in the gene of the VUS, and 2) they should not have any pathogenic mutations in any of the pathway module that link to the pathway module in question containing the VUS.

For the first property, if a patient has another Somatic, Pathogenic, or VUS mutation in the same gene, then any disruption in the downstream pathways module may be due to that mutation and not the VUS of interest.

Figure 6S:
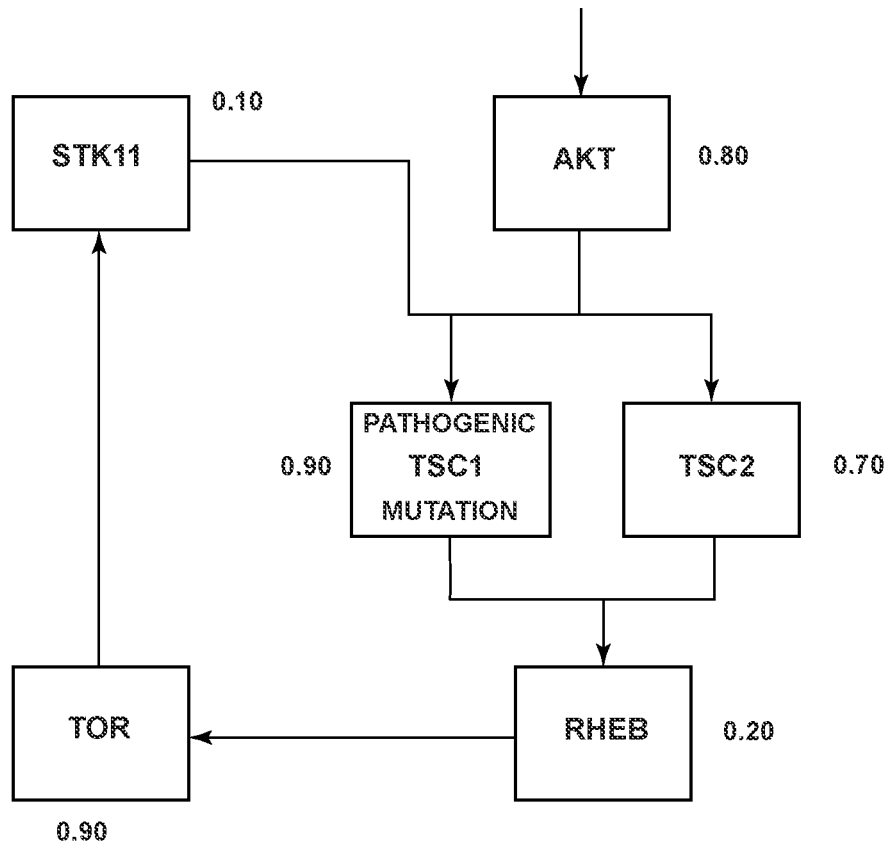
FIG. 6S shows the pathway of FIG. 6R and a pathogenic mutation in a TSC1 module.

For the second property, if a pathway module has the same scores as in the VUS in AKT example above, but TSC1 had a pathogenic mutation as shown in FIG. 6S, the high TSC1 score here is more likely to be due to the presence of the pathogenic mutation than a VUS in AKT because the TSC1 model was trained to have high scores for patients with pathogenic mutations in TSC1, thus confounding the disruption score.

Figure 6T:
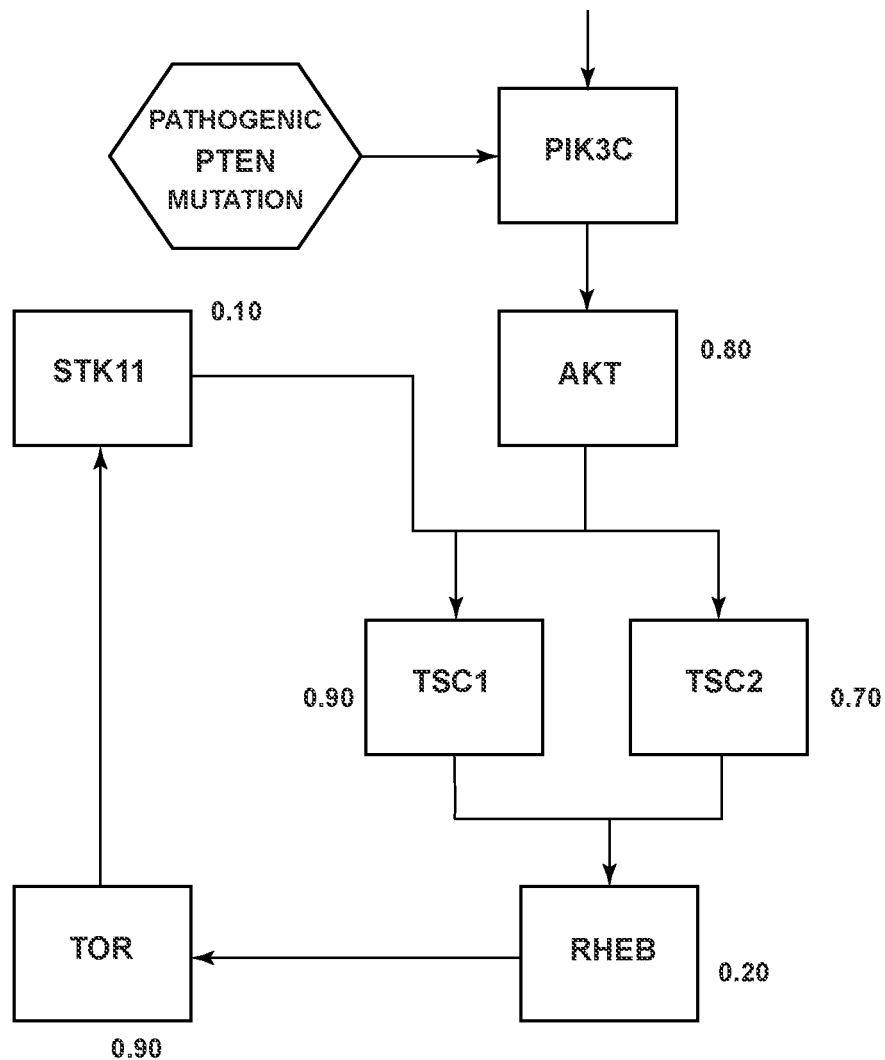
FIG. 6T shows the pathway of FIG. 6R and a pathogenic mutation in a PTEN module.

As another example, assume that there is a pathogenic mutation upstream of AKT, for example in PTEN as shown in FIG. 6T. Then it is possible that the dysregulation in AKT and its downstream pathways module score is due to the pathogenic mutation in PTEN instead of a VUS in AKT. Again, this confounds the results.

Figure 6U:
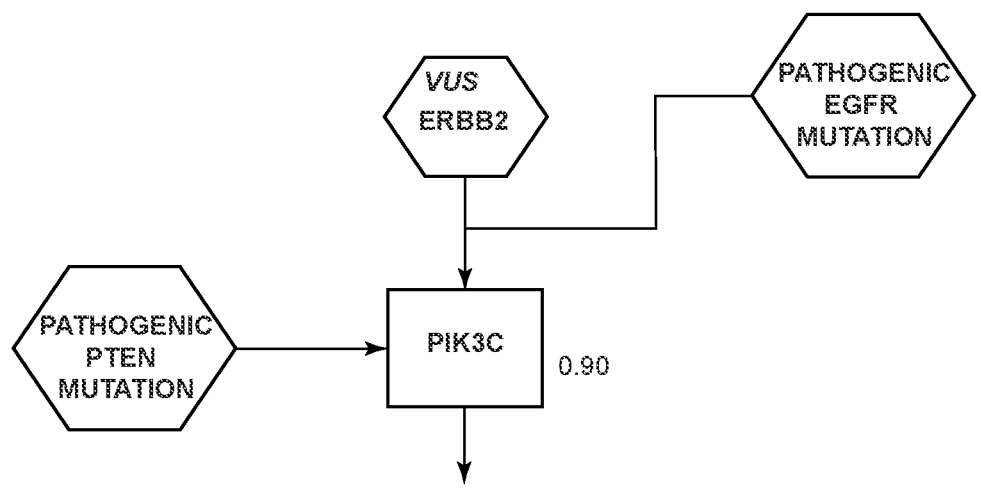
FIG. 6U shows a portion of a pathway with a PIK3C dysregulation score and pathogenic mutations in EGFR and PTEN.

The patients in the cohort for the VUS of interest should have no pathogenic mutations in any pathway module upstream or downstream of the pathway module that contains the VUS of interest. However, this filter is still not stringent enough. For example, assume that you are considering a VUS in ERBB2. Given the current rules, patients with no pathogenic mutations in the metapathways upstream and downstream of ERBB2 would be chosen. Now say that the PIK3C dysregulation score is high, but that there are also pathogenic mutations in EGFR and PTEN, as shown in FIG. 6U. It is likely that the high PIK3C score is being caused by the pathogenic mutations in EGFR and PTEN. Therefore, it is also necessary to filter out patients that have pathogenic mutations in any pathway module that is upstream of any pathway module that is downstream of the pathway module that contains the VUS of interest.

In summary, a method to determine the pathogenicity of a VUS in a gene in a pathway can include finding a set of patients that have no other somatic, pathogenic, or VUS mutation in the same gene as the VUS, and that also have no pathogenic mutation in any pathway module upstream of the pathway module that contains the VUS or any pathway module upstream of any pathway module that is downstream of the pathway that contains the VUS, generating a probability distribution for the VUS cohort for each of the pathway module models including and downstream of the pathway module that contains the VUS, calculating the ratio between the similarity of the VUS cohort distribution and the pathogenic distribution and the VUS and the WT distribution for each model using the Kullback-Leibler Divergence, and calculate the global dysregulation score $G_v$ by doing a weighted average of the module that contains the VUS and the modules downstream of it.

Figure 6V:
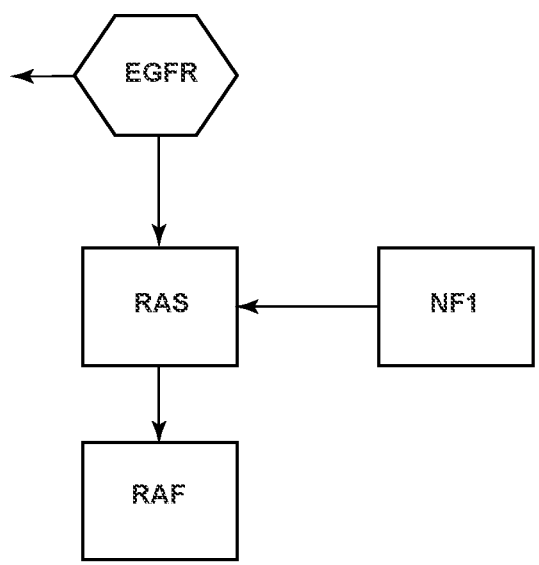
FIG. 6V shows an NF1 gene which connects to the RAS pathway.

A technique is now presented to extend VUS pathogenicity determination to genes outside a pathway. The above methods can be extended to genes that have a known connection to the pathway but do not have a model trained for them, such as for NF1 which connects to the RAS pathway as shown in FIG. 6V.

A method, which may be referred to as an all genes method, to classify a VUS in a gene without a trained model can include finding patients that have no other somatic, pathogenic, or VUS mutation in a gene without a trained model (e.g., NF1), and also have no pathogenic mutations upstream or downstream (e.g., in EGFR, RAS, or RAF), calculating the dysregulation scores of this cohort for downstream modules (e.g., RAS and RAF), and calculating the global dysregulation score $G_v$ by combining the dysregulation scores of this cohort for downstream modules (e.g., RAS and RAF dysregulation scores).

Notably, the way a gene is connected to the pathway is vital to every part of this process. To properly evaluate the VUS, several metrics need to be known, including knowing which metapathways the patients need to have no pathogenic mutations in, knowing which metapathways to calculate a dysregulation score for; and knowing how to weight the dysregulations scores to calculate the global dysregulation score. This is not possible to know for a gene with an unknown connection to the pathway.

To solve the above problem for a VUS in gene GENE whose connection to the pathway is not known, all possible global dysregulation scores for GENE can be calculated by assuming that GENE (e.g., GENE 762 in FIG. 6M) is directly connected to each pathway module in turn.

Figure 6W:
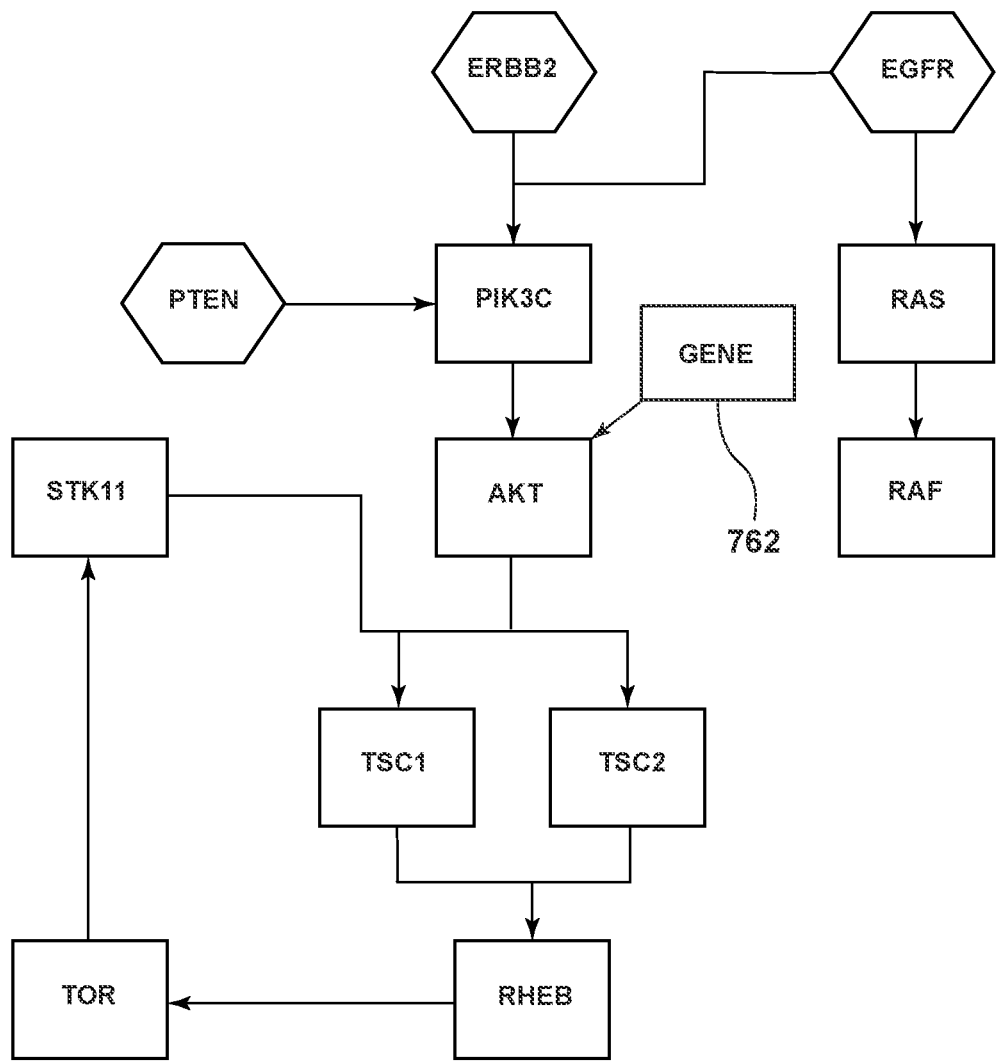
FIG. 6W shows a gene to an AKT module individually.

In one iteration, GENE is assumed to be connected to AKT as shown in FIG. 6W.

The global dysregulation score for the VUS in GENE can be calculated the exact same way that it was calculated for NF1 connected to RAS. First, a cohort that is composed of patients with no other Somatic, Pathogenic, or VUS mutation in GENE, and also no Pathogenic mutation in {EGFR, ERBB2, PTEN, PIK3C, AKT, TSC1/2, RHEB, TOR, STK11} is generated. Next, dysregulation scores can be calculated for {AKT, TSC1/2, RHEB, TOR, STK11}. Lastly, a global dysregulation score can be calculated by weighing the dysregulation scores of {AKT, TSC1/2, RHEB, TOR, STK11} using the distance of each module from GENE.

Figure 6X:
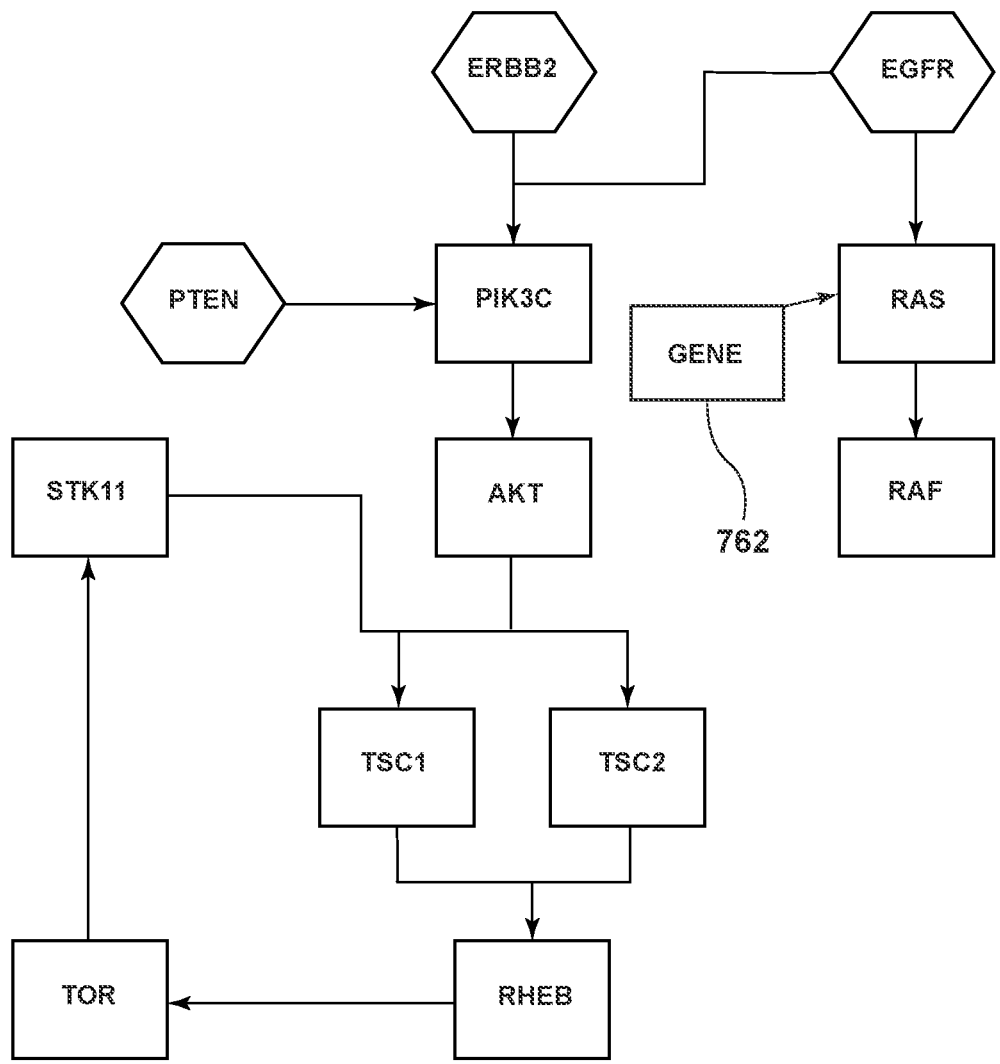
FIG. 6X shows a gene to a RAS module individually.

In another iteration, GENE is assumed to be connected to RAS as shown in FIG. 6X. The steps to find the global dysregulation score in this case can include generating a cohort composed of patients with no other Somatic, Pathogenic, or VUS mutation in GENE, and also no Pathogenic mutation in {EGFR, RAS, RAF}, calculating dysregulation scores for {RAS, RAF}, and calculating a global dysregulation score by weighting the dysregulation scores of {RAS, RAF} using their distance from GENE.

FIG. 6Y shows an exemplary dataframe that can be generated using the above methods.

Analyzing the Results of the all Gene Analysis

Figure 6Z:
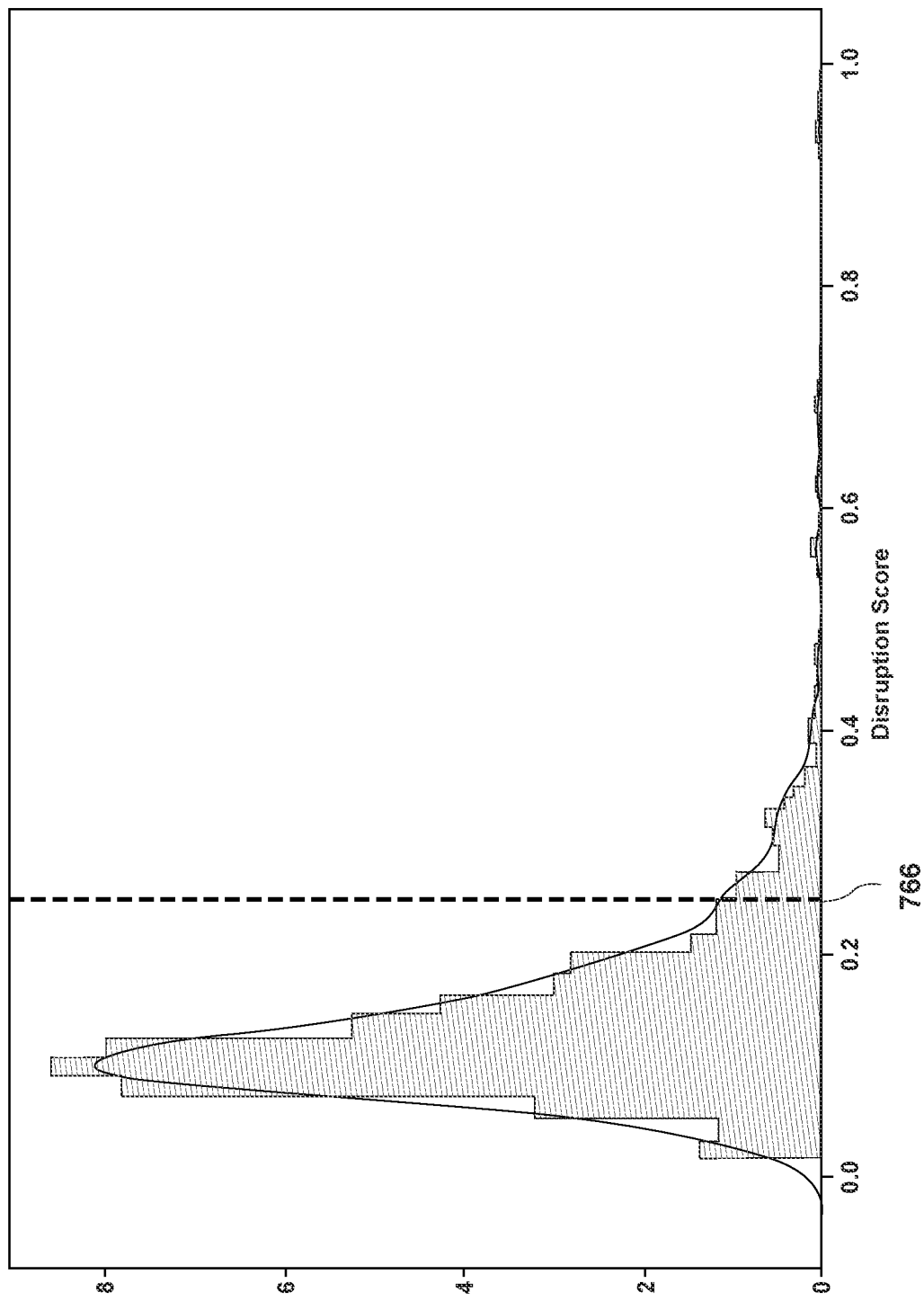
FIG. 6Z shows an exemplary histogram of all the global dysregulation scores.

FIG. 6Z shows an exemplary histogram of all the global dysregulation scores after analyzing every gene (filtering for VUS with a cohort >5). A potential likely pathogenic VUS threshold 766 is shown at a Disruption Score value of 0.25.

To test the efficacy of the method, disruption scores were calculated for known NF1 pathogenic mutations using the above all genes method. Given that the NF1 is connected to the RAS pathway module, it is expected that when these mutations are tested as being connected to the RTK_RAS pathway they will yield higher global dysregulation scores that when they are tested as being connected to the PI3K pathway. Only two mutations in NF1 had cohorts >1 for all possible metapathways and their results shown in FIGS. 7A and 7B respectively.

These NF1 mutations yield higher global dysregulation scores when they are tested as connected to a pathway module in RTK_RAS than PI3K, suggesting that the method works as expected. It is important to be aware that even the tests with the highest disruption scores for NF1 LOF would fall below the proposed p=0.25 cutoff that was derived looking tests for all genes and that many of the disruption scores for NF1 c.3198-2A>G fall above the p=0.25 cutoff even when NF1 is connected to a PI3K pathway. This might suggest that VUS classification should be done on a mutation-by-mutation level as well as a global level.

FIG. 7C shows an exemplary process 702 that can generate a pathway disruption score using a trained pathway engine. The process 702 can be implemented as computer readable instructions on one or more memories or other non-transitory computer readable media, and executed by one or more processors in communication with the one or more memories or media. In some embodiments, the process 702 can be implemented as computer readable instructions on the memory 222 and/or the memory 262 and executed by the processor 214 and/or the processor 254.

At 705, the process 702 can receive transcriptome data. The transcriptome data can include one or more one transcriptome value sets. In one example, each transcriptome value set can be a file having a tabular format in which each column represents a gene and contains a normalized expression value associated with that gene. In another example, the transcriptome value set can be a file having a tabular format in which each column represents a gene and contains a raw expression value associated with that gene (for example, read counts or copies detected by a next-generation sequencer or other genetic analyzer). The transcriptome value set can be associated with a specimen and/or patient.

The transcriptome may have an associated cancer type, which may determine which pathway engines are used for generating a pathway disruption score for the transcriptome. For example, one or more pathway engines associated with the same cancer type as the transcriptome may be selected. If the transcriptome has no associated cancer type or the associated cancer type may be incorrect, then a cancer type may be determined for the transcriptome, for example, by analyzing histopathological slides associated with the transcriptome or by analyzing the transcriptome and any associated data, for example, as described in U.S. Prov. Patent App. No. 62/855,750, titled Systems and Methods for Multi-label Cancer Classification and filed on May 31, 2019 and incorporated herein by reference. One example of a transcriptome without an associated cancer type or with an associated cancer type that may be inaccurate is a transcriptome associated with a tumor of unknown origin, a metastatic tumor, or a cancer sample that was inaccurately labeled.

In addition to the transcriptome data, the process 702 may receive supplemental data including DNA variant data, methylation data, cancer type, and/or proteomics data. All of the data received at 705 may be included in data inputs 100 described above.

At 708, the process 702 can provide the transcriptome data to one or more trained pathway engines. The pathway engines can be included in the computing device 210 and can include the trained pathway engines. Based on the type of data received at 705, the process 702 can determine which pathway engines to provide the transcriptome data to, along with any supplemental data. The transcriptome data may have one or more associated cancer types.

The process 702 may provide the transcriptome data to any pathway engines that are associated with pathways that may be associated with the cancer type(s). Some pathway engines may be configured to only accept transcriptome data, while others may also accept supplemental data, including DNA variant data, methylation data, cancer type, and/or proteomics data. The process 702 may provide only the transcriptome data to certain pathway engines, and provide the transcriptome data and supplemental data (e.g., the DNA variant data) to other pathway engines. The process 702 may provide applicable data to as many relevant pathway engines as possible. The trained pathway engines can include engines that accept the same inputs but were trained on different sets of training data.

At 710, the process 702 can receive one or more pathway disruption scores from the one or more trained pathway engines. Each trained pathway engine can generate a pathway disruption score for each transcriptome value set (and any supplemental data). The pathway disruption score may be a numerical value, graded score output and/or a qualitative readout.

The trained pathway engine may generate the pathway disruption score by simultaneously comparing the expression level for each DEG in the transcriptome value set to the range of expected expression levels for that DEG in the positive controls and the range of expected expression levels for that DEG in the negative controls. The pathway disruption score may reflect the degree to which the transcriptome value set is similar to the dysregulated positive control transcriptome value sets versus the wild type negative control transcriptome value sets.

In various embodiments, the systems and methods produce a graded score output that predicts the degree of pathway disruption (for example, a numeric value in the range of negative two to two, or the range zero to one). In such embodiments, statistical thresholds may be generated to produce a qualitative readout of pathway disruption (for example, disrupted or undisrupted, or additional classes such as greatly disrupted, mildly disrupted, undisrupted, etc.). This qualitative readout may be a clinician-friendly indicator of pathway disruption (e.g., "High," "Medium," "Low"). In one example, the qualitative readout may be determined by comparing the graded score output to a threshold. For example, all graded score outputs equal to or less than 0 may be labeled as undisrupted, and all graded score outputs equal to or above 0 may be labeled as disrupted. In this example, 0 would be the selected cutoff threshold value. In one example, the thresholds may be chosen by selecting the threshold value that maximizes the F1 score, as described above. In one example, the pathway engine may output a normalized pathway disruption score ranging from zero to one, inclusive. "High" pathway disruption scores may include pathway disruption scores of at least 0.8, "medium" pathway disruption scores can include pathway disruption scores of at least 0.6, and all pathway disruption scores below 0.6 may be considered "low."

The trained pathway engine may output a score for each module included in a pathway associated with the trained pathway engine. The trained pathway engine may include a trained model (e.g., a trained linear regression model) for each module in the pathway. The score for each module may indicate dysregulation at the associated module. The process 702 may grade each score generated by the models to a qualitative score (e.g., High," "Medium," "Low") as described above.

The pathway disruption score(s) may be added to a dataset for analysis of pathway disruption scores in a larger population of specimens. The pathway disruption score(s) may be used to determine a degree of confidence in predicting a particular treatment response based on clinical data and/or therapy response data associated with other generated pathway disruption scores. For example, the process 702 can compare, for each specimen in a group of specimens, pathway disruption scores generated by pathway engines and the clinical data and/or therapy response data associated with the specimen. The pathway disruption score(s) may be used in the development of models for the prediction of patient outcome/treatment response.

The pathway disruption score may be used to classify variants of unknown significance (VUS) based on observed correlations between a pathway disruption score generated by the systems and methods disclosed herein that predicts a disruption status for a pathway and a detected VUS in the specimen, especially in cases where no pathogenic variant was detected in the specimen. The process 710 can include determining a global dysregulation score using equation (3) described above. The process 710 can include performing the all genes method described above in order to generate the global dysregulation score.

The correlation observation may utilize a database of variant calls associated with specimens, which may contain every variant detected in a patient, whether it has clinical import or not (i.e., all VUS).

The pathway disruption score may be used to rank therapy matches for a specimen, based on observed correlations between a pathway disruption score as estimated by the systems and methods disclosed herein and clinical response data, especially data associated with a patient's or organoid's response to a therapy. In one example, the systems and methods would first robustly correlate pathway disruption scores with treatment response, accounting for several covariates.

At 715, the process 702 can generate a meta-pathway depiction. Exemplary meta-pathway depictions are shown in FIGS. 12A through 12E and described below. The meta-pathway depiction can include one or more pathways that may be color coded or otherwise shaded based on the pathway disruption scores and/or supplemental data.

At 718, the process 702 can cause the meta-pathway depiction to be output to a display (e.g., the display 290, the display 256, and/or the display 216) and/or a memory (e.g., the memory 222 and/or the memory 262).

At 720, the process 702 can generate an optional ensemble pathway disruption score based on multiple pathway disruption score outputs. An ensemble model may receive pathway disruption score outputs from at least two trained pathway engines associated with a common pathway and accepting the same differentially expressed genes, but that were trained with different sets of training data. The process 702 can provide the pathway disruption score outputs to an optional ensemble model. The ensemble model may convert the pathway disruption scores into an ensemble pathway score by summing the weighted scores, wherein the weights are determined by training the ensemble model with pathway disruption scores and a type of data related to a cancer characteristic, including clinical response data, cancer stage status, consensus molecular subtype (CMS) classification, etc. The ensemble pathway score may reflect an overall cellular state and/or the biological interaction between the at least two gene sets used to train the models. The process 702 can receive the ensemble pathway disruption score from the ensemble model.

The ensemble pathway disruption score may be added to a dataset for analysis of pathway disruption scores in a larger population of specimens. The ensemble pathway disruption score may be used to determine a degree of confidence in predicting a particular treatment response based on clinical data and/or therapy response data associated with ensemble pathway disruption scores generated by the systems and methods, for example, by comparing, for each specimen in a group of specimens, ensemble pathway disruption scores generated by pathway engines 200n and the clinical data and/or therapy response data associated with the specimen. The ensemble pathway disruption score may be used in the development of models for the prediction of patient outcome/treatment response.

The ensemble pathway disruption score may be used to classify variants of unknown significance (VUS) based on observed correlations between an ensemble pathway disruption score generated by the systems and methods disclosed herein that predicts a disruption status for a pathway and detected VUS in the specimen, especially in cases where no pathogenic variant was detected in the specimen.

The correlation observation may utilize a database of variant calls associated with specimens, which may contain every variant detected in a patient, whether it has clinical import or not (i.e., all VUS).

At 725, the process 702 can cause the ensemble pathway disruption score to be output to a display (e.g., the display 290, the display 256, and/or the display 216) and/or to a memory (e.g., the memory 222 and/or the memory 262). The ensemble pathway disruption score may be used to rank therapy matches for a specimen, based on observed correlations between a pathway disruption score as estimated by the systems and methods disclosed herein and clinical response data, especially data associated with a patient's or organoid's response to a therapy. In one example, the systems and methods would first robustly correlate ensemble pathway disruption scores with treatment response, accounting for several covariates.

At 730, the process 702 can generate a pathway disruption report based on any pathway disruption score(s) received at 710. The process 702 can generate the pathway disruption report further based on meta-pathway depiction data generated at 715 and/or any ensemble pathway disruption score(s) generated at 720. The pathway disruption report may communicate results from 710 and/or 720, including pathway disruption scores and/or ensemble pathway disruption scores generated for the patient specimen or organoid associated with the transcription value set. In one example, the report may include one or more pathway disruption scores and/or the relationship of the pathway scores (for example, as shown in FIGS. 10A-10H, FIGS. 11A-11D, FIGS. 12A-12E, FIG. 22, FIG. 23, FIG. 24, and FIG. 25 described below). For example, if the pathway disruption scores are −0.5 and −0.5 (one score for each of two treatable arms or branches of a pathway), reporting the score for each arm of the pathway may be more informative than an ensemble pathway score of −1 for the overall pathway.

The pathway report may also contain the likelihood of drug sensitivity of cancer cells in the original specimen, especially to drugs that target a pathway of interest that is reported to be activated or suppressed, and prognostics, including predicted patient survival and/or progression free survival. The pathway report may contain schematics or depictions of the cellular pathway(s) or gene set(s) of interest, and/or a meta-pathway (see FIGS. 10A-H, FIGS. 11A through 11D, and/or FIGS. 12A through 12E). The pathway report may contain citations, especially of references related to the pathway of interest and/or therapies targeting the pathway of interest. The numeric value of a pathway score and/or ensemble pathway score may determine which therapies and/or clinical trials are matched with a specimen and presented on the pathway disruption report.

The report may be digital (for example, available as a digital file such as a PDF or JPG, or accessible through a user interface such as a portal or website) or it may be a hard copy (for example, printed on paper).

In one example, for each patient specimen in a population that receives RNA sequencing, their normalized RNA data and, if applicable, ssGSEA scores for the relevant pathways, will be subjected to at least one pathway engine, resulting in a score for pathway disruption as described above. Patients may receive on the report an indicator of whether their cancer has any activated or suppressed cellular pathways, and if so, they may be matched with certain therapies or clinical trials, especially trials that have an inclusion criterion related to the activated or suppressed pathway(s).

Figure 11A:
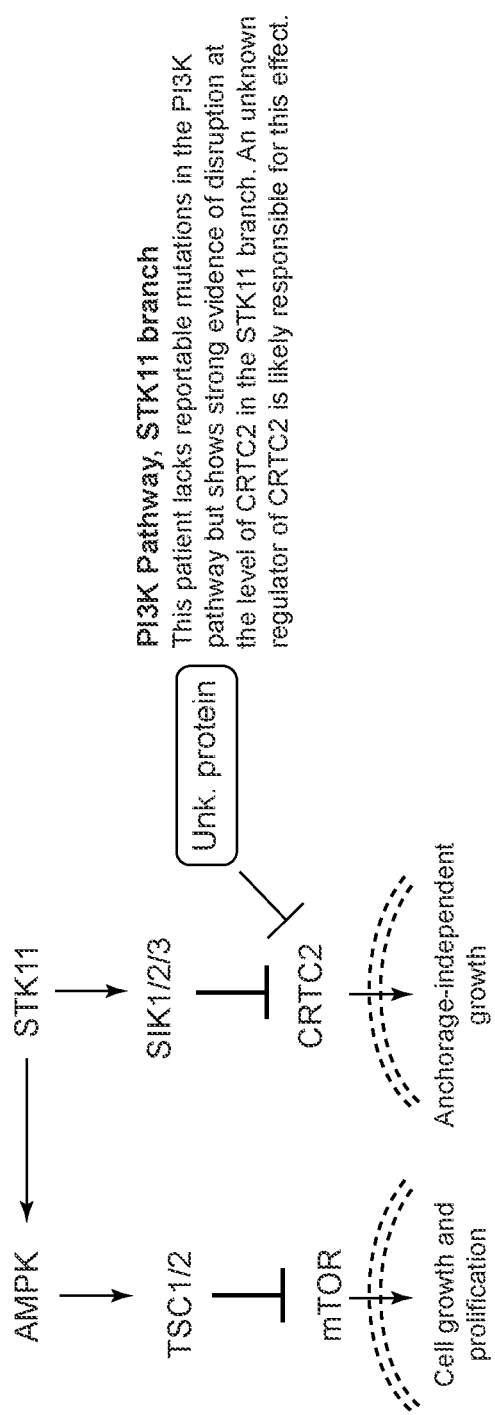

In some embodiments, the pathway disruption report can include information about what genes in a pathway may be causing pathway disruption indicated by a pathway disruption score, even if there are no measurable mutations in the pathway. For example, FIG. 11A shows a pathway graphic that can be included in a pathway disruption report for the PI3K pathway. The PI3K pathway was not detected to have pathogenic mutation, but a high pathway disruption score was generated (e.g., at steps 708 and 710) by a pathway engine, indicating pathway disruption. While the mutation causing the high pathway disruption score (e.g., a pathway disruption score of 0.85 from a pathway engine that outputs normalized pathway disruption scores from zero to one) may be unknown, the level of pathway disruption may be inferred by the pathway disruption score. In this example, a therapy designed to target CRTC2 may be matched. The report may indicate that the CRTC2 gene could be targeted by circling the CRTC2 gene in the pathway, color coding the CRTC2 gene, or otherwise visually indicating that the CRTC2 gene could be targeted. The pathway disruption report may include information or a link to information (e.g., a URL link to an NIG webpage) about one or more therapies that could be used to target the CRTC2 gene. The pathway disruption report can include information about or a link to information about a clinical trial that could be matched based on inclusion and/or exclusion criteria of the trial. Currently, clinical trials may require a pathogenic DNA mutation in the PI3K pathway detected in the patient for enrollment, but it is contemplated that a clinical trial may be matched to a patient based on a pathway disruption score generated by pathway engine.

Figure 22:
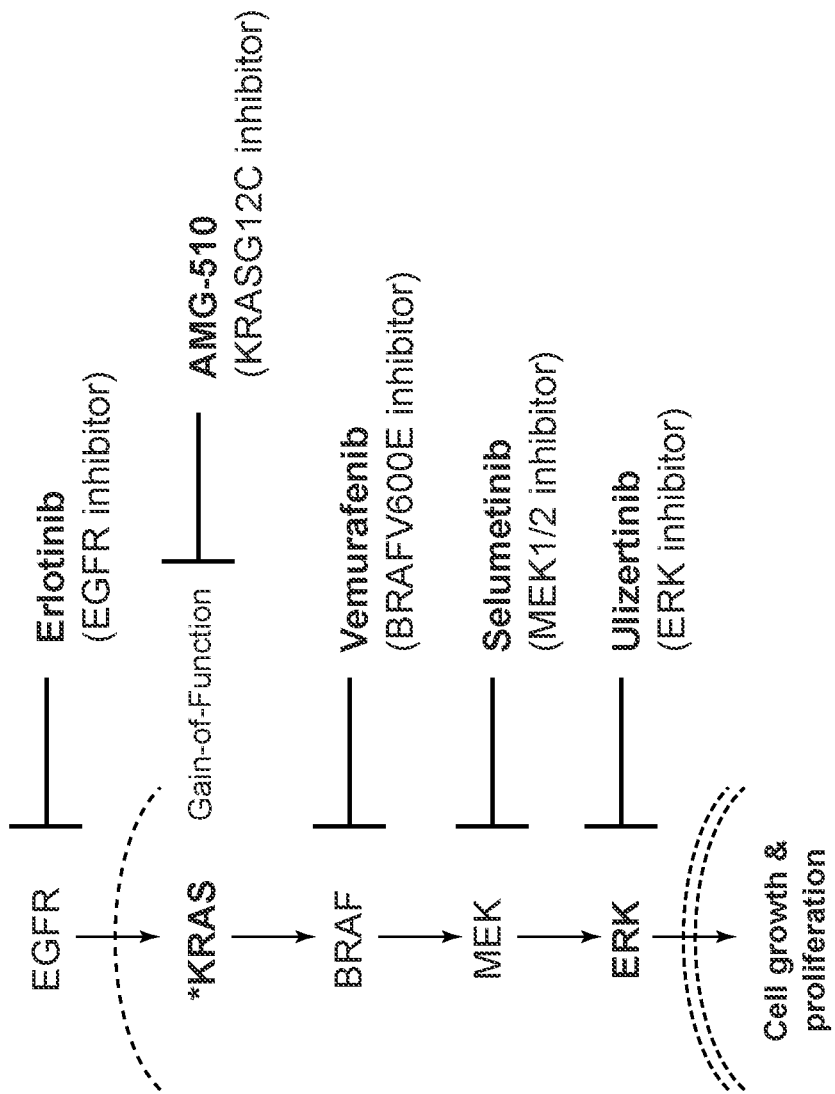
FIG. 22 shows an exemplary pathway disruption report generated by the process of FIG. 7C.

Certain pathways may have multiple targetable genes or modules. For example, FIG. 22 shows an example of pathway disruption report including a subset of the MAPK pathway. The pathway disruption report can include information about where in the MAPK pathway a patient can be treated. The patient may have been determined to have a high pathway disruption score for the MAPK pathway using one or more pathway engines. The process 702 can determine one or more therapies that could be used to treat the patient. The pathway disruption report can include one or more treatments that could be used to target one or more genes and/or modules in the MAPK pathway. Furthermore, the treatments can be marked (e.g., visually) as potentially more or less effective based on any detected mutations in the pathway (e.g., DNA mutations in the pathway), as well as based on information about the patient, such as treatment history including any therapies the patient has received.

The patient may have a detectable mutation in the RAS module, as shown in FIG. 22 (exemplified by a KRAS mutation). While certain therapies could be used to treat the RAS module, the therapies may not be approved (e.g., FDA approved) and therefore cannot be used as treatment unless in a trial. Additionally therapies that are applied to modules above the RAS module may not treat the mutation at the RAS module level. Other treatments that occur below the RAS module may be potentially less effective or less usable because the treatments are experimental and/or the patient has already received the treatment without a positive outcome. Thus, the potential treatments for the EGFR and RAS modules may be marked in different colors or have different shading than other treatments, or otherwise identified as potentially less effective or less usable treatments. The process 702 can determine one or more treatments that may be more effective for the patient, e.g., by determining approved treatments for modules downstream of the module with known mutation, in this example, the RAS module.

Additionally, the process 702 may determine more treatments based on what treatments applicable to modules downstream from the module with the known mutation have been effective for similar patients. More specifically, the process can compare the transcriptome data, any supplemental data including DNA variant data, methylation data, cancer type, and/or proteomics data received at step 705, and/or any pathway disruption scores generated for the patient, to data about similar patients. The process 702 can receive the data about similar patients from one or more databases such as the databases 500, 600, 700 described above. The process 702 can compare the one or more pathway disruption scores received at 710, the transcriptome data, and/or any supplemental data received at step 705 to a database of results from many specimens.

The process 702 may identify specimen groups that are most similar to the patient based on generated pathway score(s) by identifying which of the patient's pathway disruption scores are above/below the thresholds identified as indicating pathway disruption in other specimen sets, or which scores fall into a quantile (e.g., the top quintile) of the scores in other specimen sets. The process 702 may determine which specimens have transcriptomic data that, when subjected to dimensionality reduction algorithms (e.g., Uniform Manifold Approximation and Projection (UMAP) or Principal Component Analysis (PCA)) and plotted on a two-dimensional Cartesian grid, cluster with the patient. The process 702 may also compare the supplemental data associated with the patient to supplemental data associated with the specimens. The process 702 can determine that specimens with supplemental data within a predetermined threshold of the supplemental data of the patient are similar to the patient.

In some embodiments, the process 702 can include a portion of the methods and system in U.S. Prov. Patent Application No. 62/786,739, titled "A Method and Process for Predicting and Analyzing Patient Cohort Response, Progression and Survival", and filed Dec. 31, 2018. At step 730, the process 702 may compare the data received at step 705 to data in a database of results as disclosed in U.S. Prov. Patent Application No. 62/786,739.

After the process 702 determines specimens that are similar to the patient, the process 702 can determine what treatment(s) had the greatest positive effect in the specimens, and include the treatment(s) in the pathway disruption report. In some embodiments, the process 702 can determine what treatments were most effective based on information from the therapy response database 600.

Still referring to FIG. 7C, at 735, the process 702 can cause the pathway disruption report to be output to at least one of a display or a memory. For example, the process 702 can cause the pathway disruption report to be output to a display (e.g., the display 290, the display 256, and/or the display 216) for viewing by a user. Thus, the process 702 can cause the pathway disruption report to be displayed. As another example, the process 702 can cause the pathway disruption report to be output to a memory (e.g., the memory 222 and/or the memory 262) for storage. In some embodiments, at 735, the process 735 can cause the pathway disruption report to be printed out. The process 702 can cause the pathway disruption report to be delivered to a physician, medical professional, patient, pharmaceutical designer or manufacturer, or organoid culturing laboratory, especially to guide treatment decisions and design of clinical trials or experiments.

These systems and methods (e.g., the system 10 and/or the processes 502, 602, 630, 650, 660, 670, 750, and/or 702) described above may detect a greater number of patients with activated or suppressed pathways and match them to possibly beneficial therapies and clinical trials. The patient report generator 800 described above can include and/or cause any number of the processes 502, 602, 630, 650, 660, 670, 750, and/or 702 to be executed.

Clinicians may benefit from these systems and methods by being able to make a more informed choice of treatment based on molecular evidence beyond the DNA mutational profile. Patients may also benefit in that they will be more likely to respond to a therapy chosen based on multiple orthogonal lines of evidence provided by these systems and methods. Pharmaceutical companies may also benefit by being able to use the systems and methods to select patients with particular pathway disruption statuses for inclusion in relevant clinical trials.

The systems and methods may help provide underlying scientific basis for insights, matched therapies, and/or matched clinical trials in a clinical and/or pathway disruption report, as well as clinically actionable molecular evidence substantiated and driven by the context of oncogenic pathways/networks. Pathway information may also act as a 'prior' and/or feature in statistical models for associating integrated-omic and imaging data with therapies and outcomes.

The systems and methods may drive the discovery of novel biomarkers, diagnostic signatures, and/or prognostic signatures for pathways (including therapeutically targeting pathways), enhancing the ability to match therapies in reports.

In various embodiments, the systems and methods include a method of detecting cellular pathway dysregulation in a specimen, including the steps of receiving a set of genetic data derived from and/or otherwise associated with the specimen and analyzing the set of genetic data to estimate a dysregulation likelihood (pathway disruption score) for a cellular pathway of interest.

A pathway of interest may be any set of genes. The set of genes may represent a cellular pathway. The set of genes may have gene products that interact with each other in a cell during cellular activity. The pathway of interest may be a well-defined cellular pathway (for example, a RAS/RTK or PI3K pathway). The pathway of interest may be a TCGA-curated pathway.

Analyzing the set of genetic data may include providing at least a portion of the genetic data to one or more pathway dysregulation engines and receiving a result from each pathway dysregulation engine that reflects a likelihood of dysregulation in the cellular pathway. The pathway dysregulation engine may be trained by a set of training data that includes training RNA data sets, each of which is associated with at least one dysregulation indicator. Each pathway dysregulation engine may be specific to one cellular pathway, and the dysregulation indicators used to train a pathway dysregulation engine may be associated with the cellular pathway.

The genetic data includes RNA data and may further include DNA data and protein data.

The specimen may be a cancer specimen from a human patient or an organoid (for example, an organoid derived from a human cancer specimen).

The dysregulation likelihood may be a numerical value or a qualitative label. This method may further include comparing the dysregulation likelihood to a threshold to determine a qualitative label for the specimen.

This method may further include estimating many dysregulation likelihoods (for example, one for each of many cellular pathways of interest) and combining the dysregulation likelihoods to calculate an overall pathway disruption score or reporting each pathway disruption score and possibly reporting the relationship between the pathway disruption scores (for example, by reporting the biological interaction between the pathways or pathway portions associated with each pathway disruption score).

This method may further include associating a dysregulation likelihood label or value with a protein expression level and predicting a protein expression level for the specimen.

This method may further include detecting a variant having unknown significance in the set of genetic data and determining that the variant is pathogenic, based on the dysregulation likelihood.

These systems and methods may include a method of prescribing a treatment, including the steps of receiving a dysregulation likelihood and prescribing the treatment to a patient from which the specimen originated, based on the dysregulation likelihood.

These systems and methods may include a method of designing an experiment to test treatment response in organoids, including the steps of receiving a dysregulation likelihood for the organoids and suggesting that the organoids be monitored after exposure to a treatment, based on the dysregulation likelihood.

These systems and methods may include a method of matching a patient to a clinical trial, including the steps of receiving a dysregulation likelihood for a specimen from the patient and matching at least one clinical trial, based on the dysregulation likelihood. This method may further include reporting a list of matched clinical trials to the patient or a medical professional caring for the patient.

These systems and methods may include a method of designing a clinical trial, including the steps of analyzing clinical data for an association of a dysregulation likelihood and response to at least one treatment and suggesting a study of the response to at least one treatment in each of a plurality of patients having the dysregulation likelihood.

These systems and methods may include a medical device that receives a set of genetic data and detects cellular pathway dysregulation as described above. In one example, the medical device may include a genetic analyzer system and/or a laboratory developed test.

These systems and methods may include a method of sequencing a cancer specimen, including the steps of generating a set of genetic data and detecting cellular pathway dysregulation as described above.

These systems and methods may include a cloud-based information processing system that receives a set of genetic data and detects cellular pathway dysregulation as described above.

FIGS. 8A through 8D collectively display an example flowchart of certain methods that may be used to analyze pathway disruption status based on RNA data.

Figure 8A:
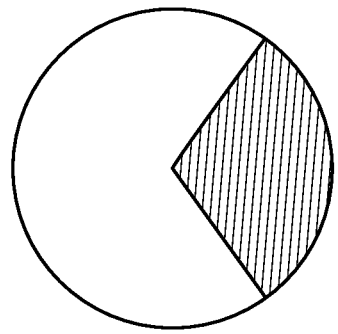
FIG. 8A shows a pie chart of a cancer of interest.
Figure 8B:
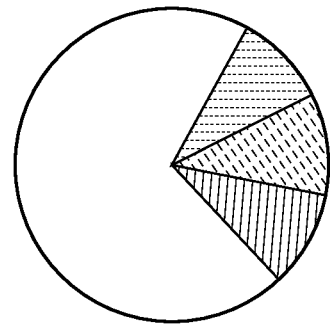
FIG. 8B shows a pie chart that subsets the cancer type in FIG. 8A by mutation status.

FIG. 8A shows a pie chart of a cancer of interest. In one example, patients with a particular cancer type are selected (FIG. 8A, one area of the pie chart), and all relevant mutation data for the pathway of interest is acquired, e.g., using the oncogenic signaling pathways defined by The Cancer Genome Atlas (TCGA) consortium. The mutation data is used to define sets of patients with known pathway disruption (e.g., KRAS G12V mutations for the RAS/RTK pathway, considered "positive controls") and patients who are wild type (WT) for all members of the pathway ("negative controls"). FIG. 8B shows a pie chart that subsets the selected cancer type by mutation status.

Figure 8C:
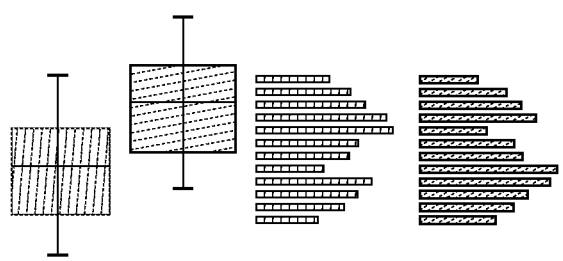
FIG. 8C shows various graphs of differentially expressed genes (DEGs) between the groups.

FIG. 8C shows various graphs of differentially expressed genes (DEGs) between the groups that can be determined with edgeR, a publicly available package in the R software environment. If applicable, single-sample Gene Set Enrichment Analysis (ssGSEA) pathway scores are generated for all samples for all relevant pathways. (FIG. 8C).

Figure 8D:
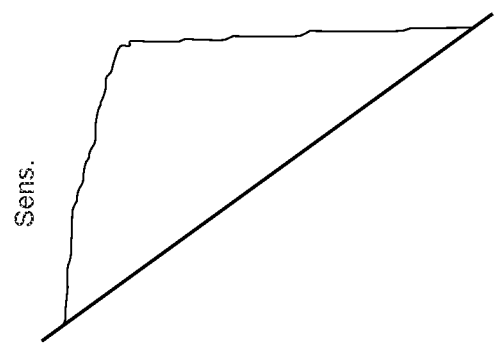
FIG. 8D shows validation results of a logistic regression model

FIG. 8D shows validation results of a logistic regression model trained according to the process 502 described above. Pathway engine 200$n$ cross-validation is performed according to the process 602 described above.

When the final alpha parameter value has been determined, a final pathway engine (e.g., the pathway engine 200$n$) can be trained using all samples, using the final alpha parameter value.

Figure 9B:
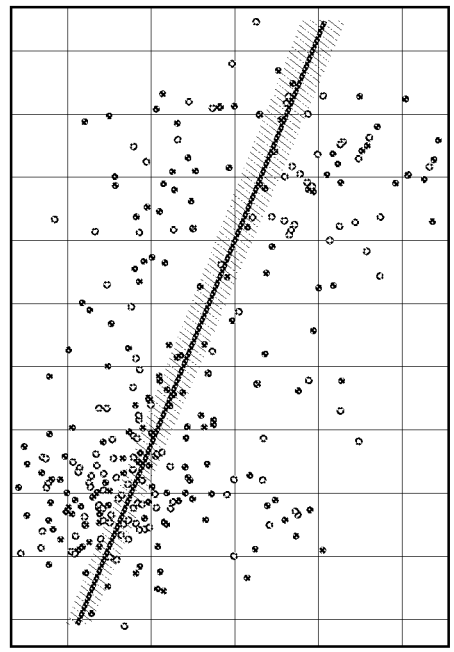
FIG. 9B shows an example of biological validation results using a protein activation data.
Figure 9A:
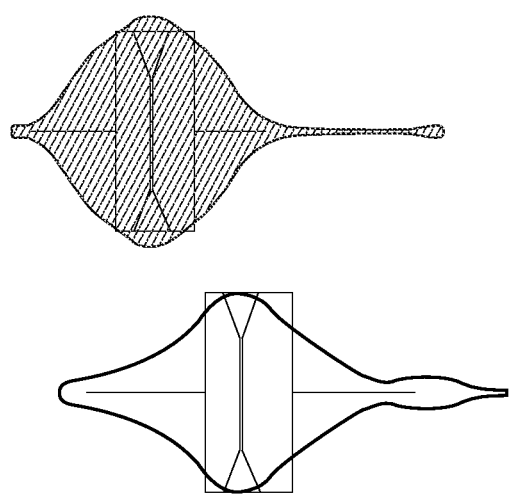
FIG. 9A shows an example of validation results using an external data set.

FIGS. 9A and 9B collectively display an example output of certain methods that may be used to test the systems and methods in an optional pathway engine 200$n$ validation step, as described in FIGS. 6B and 6E, respectively.

In some embodiments, to ensure that the systems and methods have biological validity and that predictive performance is not dependent on specific features of the training dataset, the pathway engine 200$n$ is validated using publicly available external TCGA data.

In the first step of validation, as described in process 602, TCGA RNA mutation data for the cancer type of interest can be collected and subsetted into positive and negative control samples, as was done with the training data.

FIG. 9A shows an example of validation results using an external data set. All samples are subjected to the trained pathway engine 200$n$, and the outputs for the positive and negative controls are compared. A significant difference between the scores associated with these groups in the same direction as for the training data is evidence for the robustness and generalizability of the pathway engine 200$n$ (FIG. 9A).

FIG. 9B shows an example of biological validation results using a protein activation data. Although detectable at the transcriptional level, the ground truth for pathway disruption/disruption may be defined as the protein status of the pathway's effectors, i.e., the levels of these proteins and/or their activation as indicated by their phosphorylation status. For example, RAS/RTK activation can be quantified by the levels of phosphorylated downstream effector kinases MEK, MAPK1, MAP2K2, and others. The degree of correlation between the pathway engine 200*n* output and measures of protein activation is determined for TCGA patients, as described in 654, with strong correlation indicating that the pathway engine 200*n* is biologically meaningful (FIG. 9B).

As described herein, some embodiments are directed to methods and systems for creating and presenting diagnostic and/or treatment data, including matching to clinical trials, to a physician, based on patient information such as genetic, imaging, and clinical information, as described above. In some embodiments, the data provided to the physician may be in the form of a report document, presented digitally or in hard copy. In some embodiment, the report includes but is not limited to an easy-to-understand, stylized, visual depiction of the diagnostic and/or treatment pathway in question, information such as the identity of any relevant clinical trials, eligibility criteria for either the clinical trial or for the administration of a particular therapeutic or combination of therapeutics, and a therapies section providing additional information related to any therapies identified.

FIGS. 10A through 10I collectively illustrate examples of a pathway disruption report generated at 730 in FIG. 7C, especially for the MAPK (RAS) pathway. One aspect of the utility of the described embodiments derives from the potential for communicating to physicians treatment options for a particular patient's cancer state. That is, for a given cancer state, there may be a variety of effective or potentially effective treatments (therapies) targeting one or more elements in the pathway (i.e., exerting a biological effect on the pathway). For instance, various treatment options for a KRAS gain-of-function mutation target the ERK module (e.g., ERK inhibitors), the MEK module (e.g., MEK inhibitors), the RAF module (e.g., RAF inhibitors), etc. Thus, even for a particular mutation or pathogen (which may be depicted in a diagnostic pathway), there may be a variety of treatment options, and reports may include depictions of the different effective or potentially effective treatments.

Figure 10A:
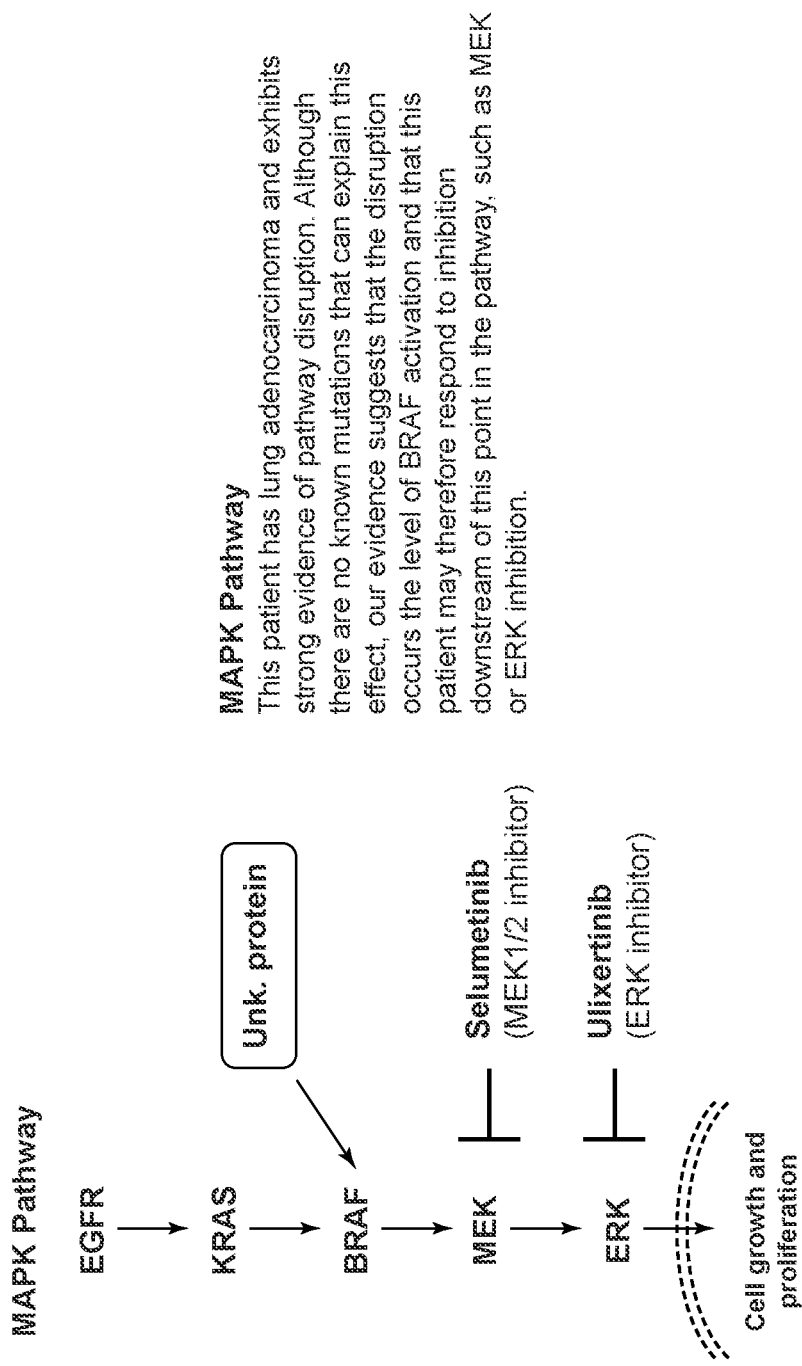
FIGS. 10A through 10I collectively illustrate examples of a pathway disruption report generated using the process in FIG. 7C.

FIG. 10A illustrates an example of a pathway disruption report generated for a hidden responder having no detected pathogenic mutation in the RAS pathway but having a high pathway disruption score generated by the pathway engine 200*n*. The mutation causing the high pathway disruption score may be unknown, but the level of pathway disruption may be inferred by the pathway disruption score. Therapies inhibiting MEK or ERK could be matched for this patient. A clinical trial could be matched based on inclusion and/or exclusion criteria of the trial. Currently, clinical trials may require a pathogenic DNA mutation detected in the patient for enrollment, but in the future, a clinical trial may be matched to a patient based on a pathway disruption score generated by pathway engine 200*n*. In some embodiments, eligibility criteria are added to the report, e.g., as shown in FIG. 10I. Each treatment may have associated eligibility criteria related to the efficacy of the therapy, and/or in the case of a clinical trial, to participation in the trial. The eligibility criteria may include the cancer diagnosis, (e.g., type of cancer, cancer stage, type of mutation, presence and/or absence of other mutations), patient's geographical location, patient age, other health conditions, etc. The eligibility criteria may be stored in the database as metadata associated with each treatment pathway and/or with each mutation or pathogen associated with the diagnostic pathway. By way of example but not by way of limitation, eligibility criteria for the report shown in FIG. 10B could be as follows:

Eligibility Criteria:
 a. Diagnosis: Pancreatic Adenocarcinoma;
 b. KRAS gain of function mutation;
 c. Clinical Trial NCT03051035 is matched on patient report;
 d. No other actionable mutation are present other than TP53 or SMAD4.

Figure 10B:
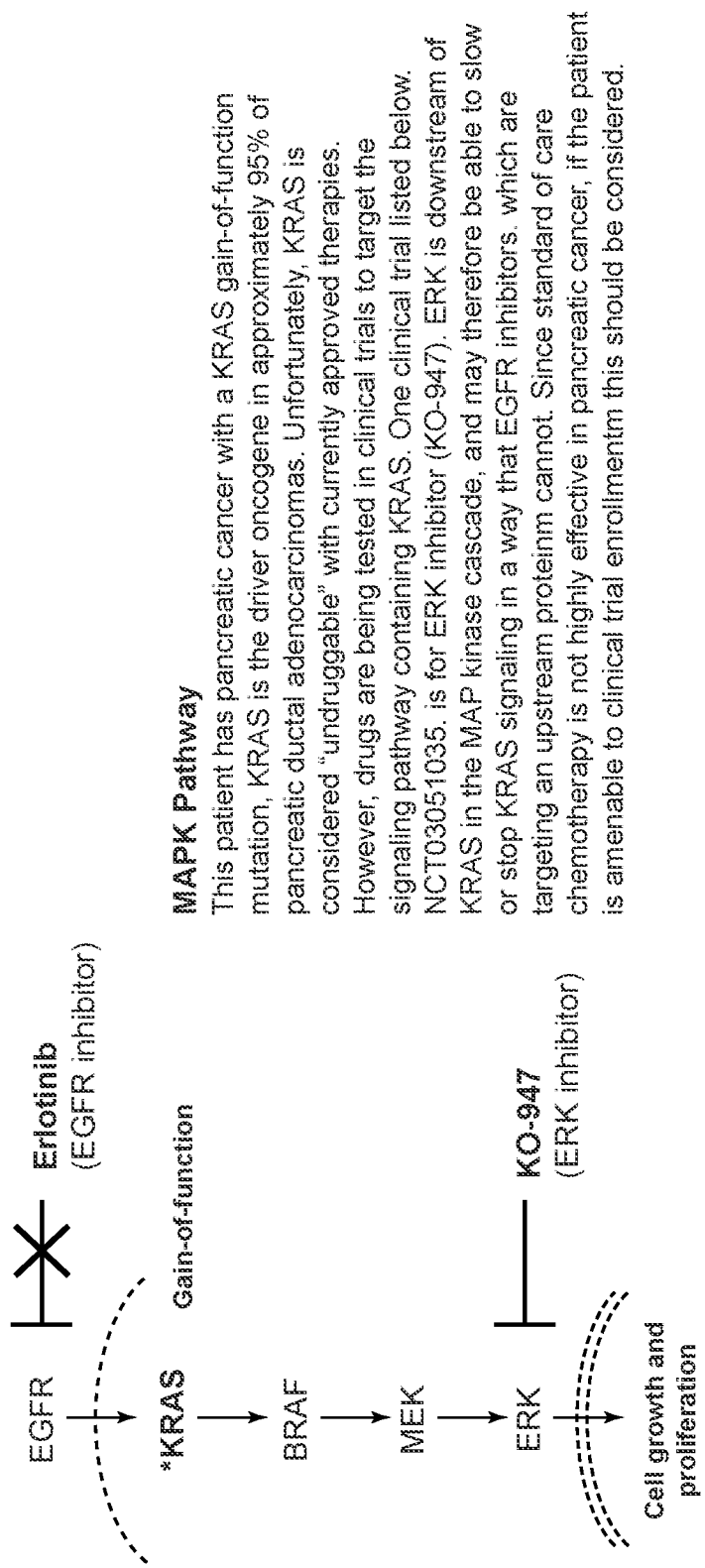
Figure 10C:
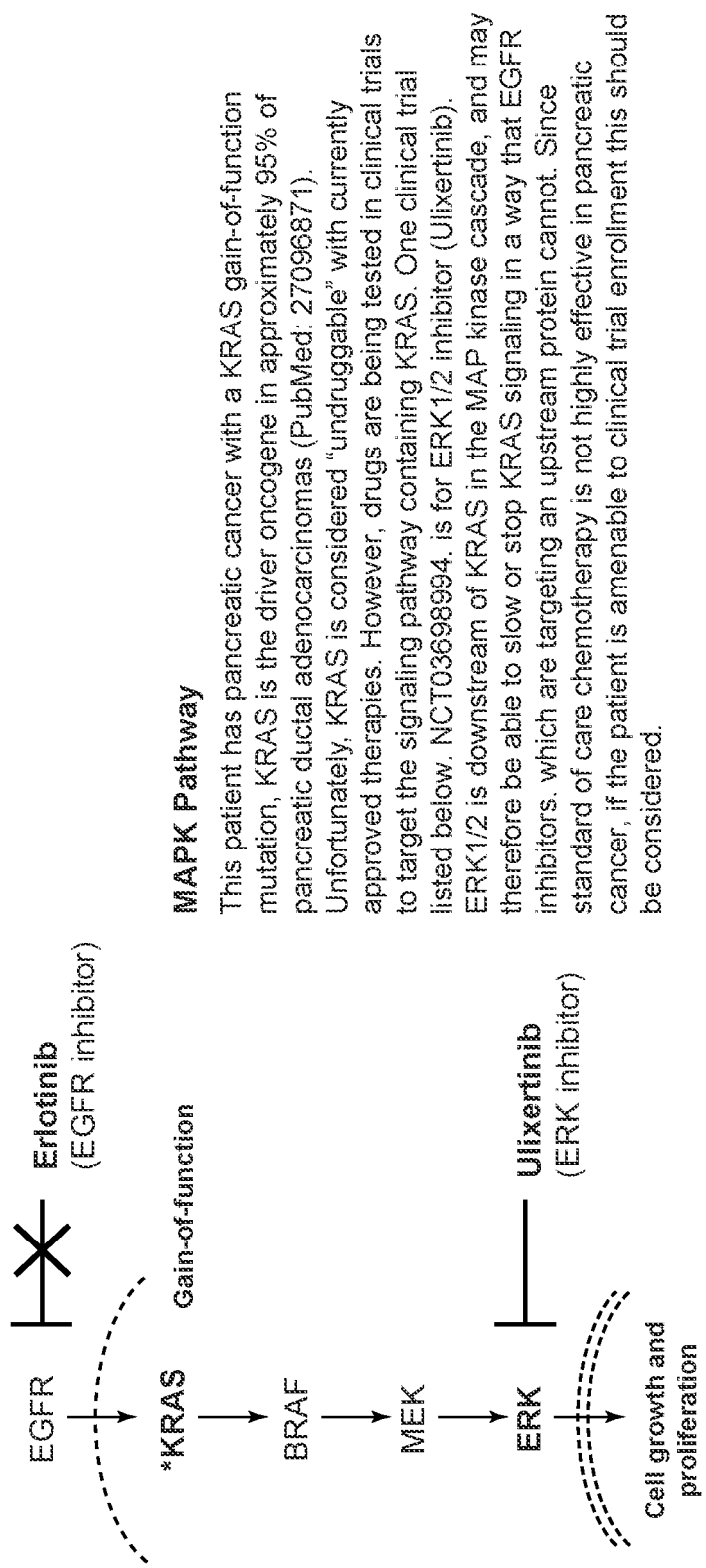
Figure 10D:
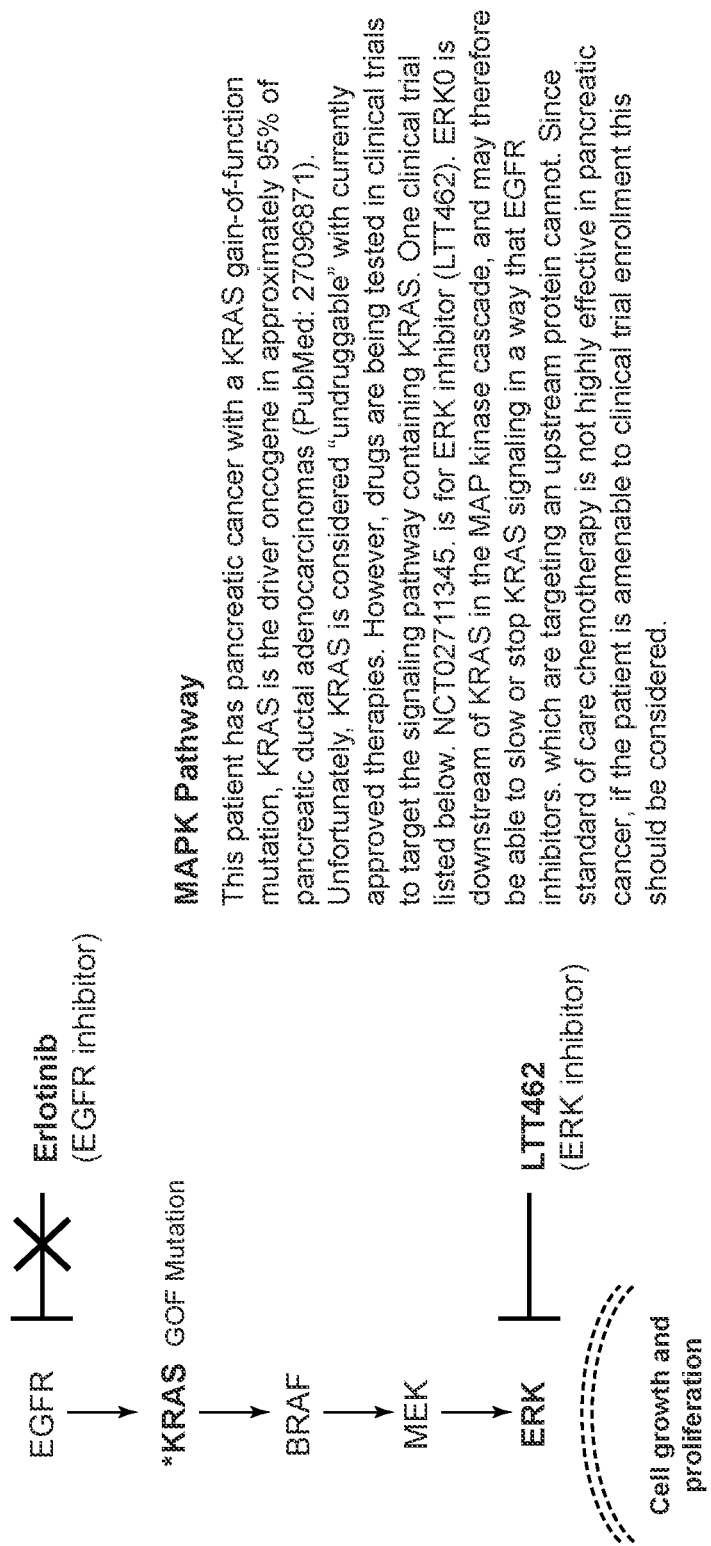
Figure 10E:
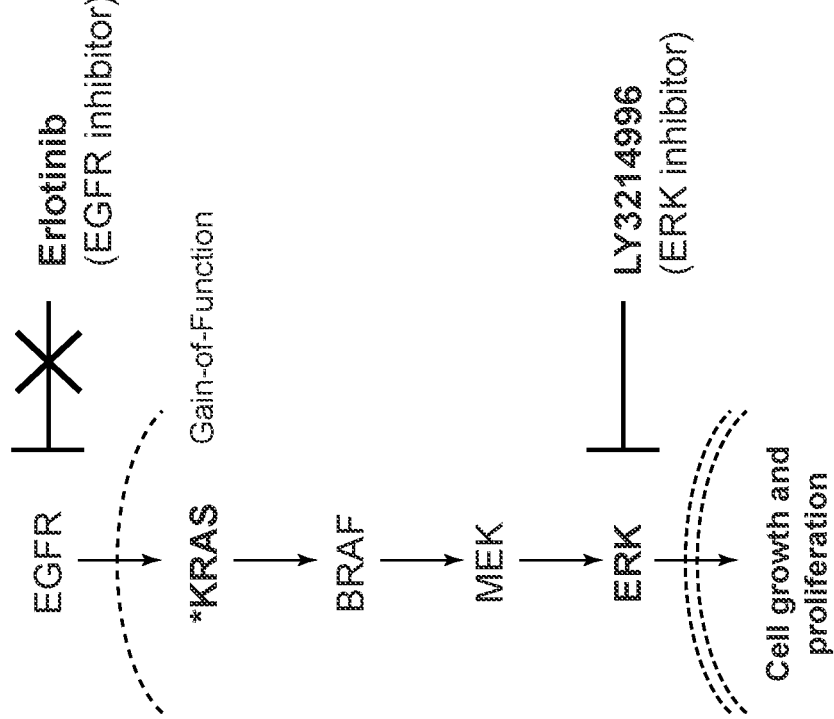
Figure 10F:
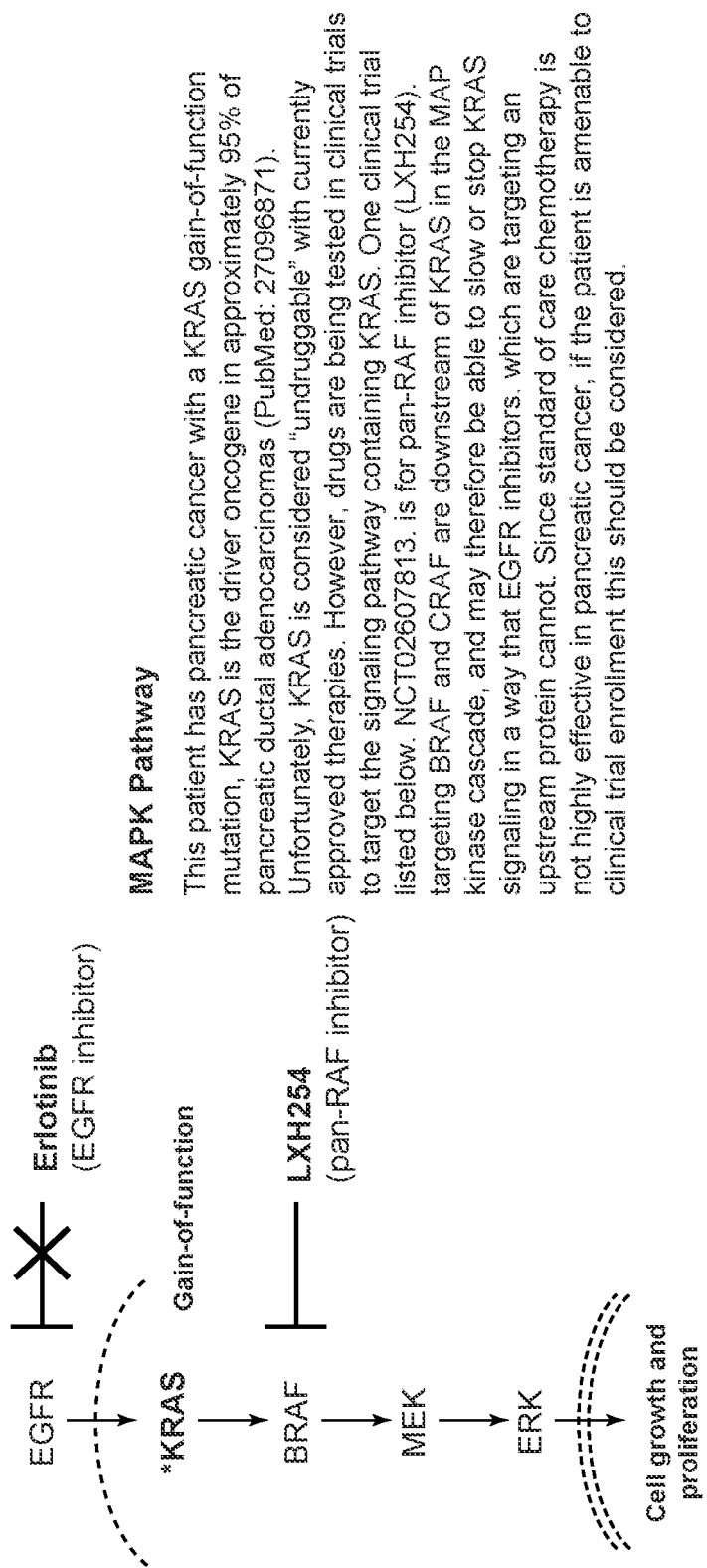
Figure 10G:
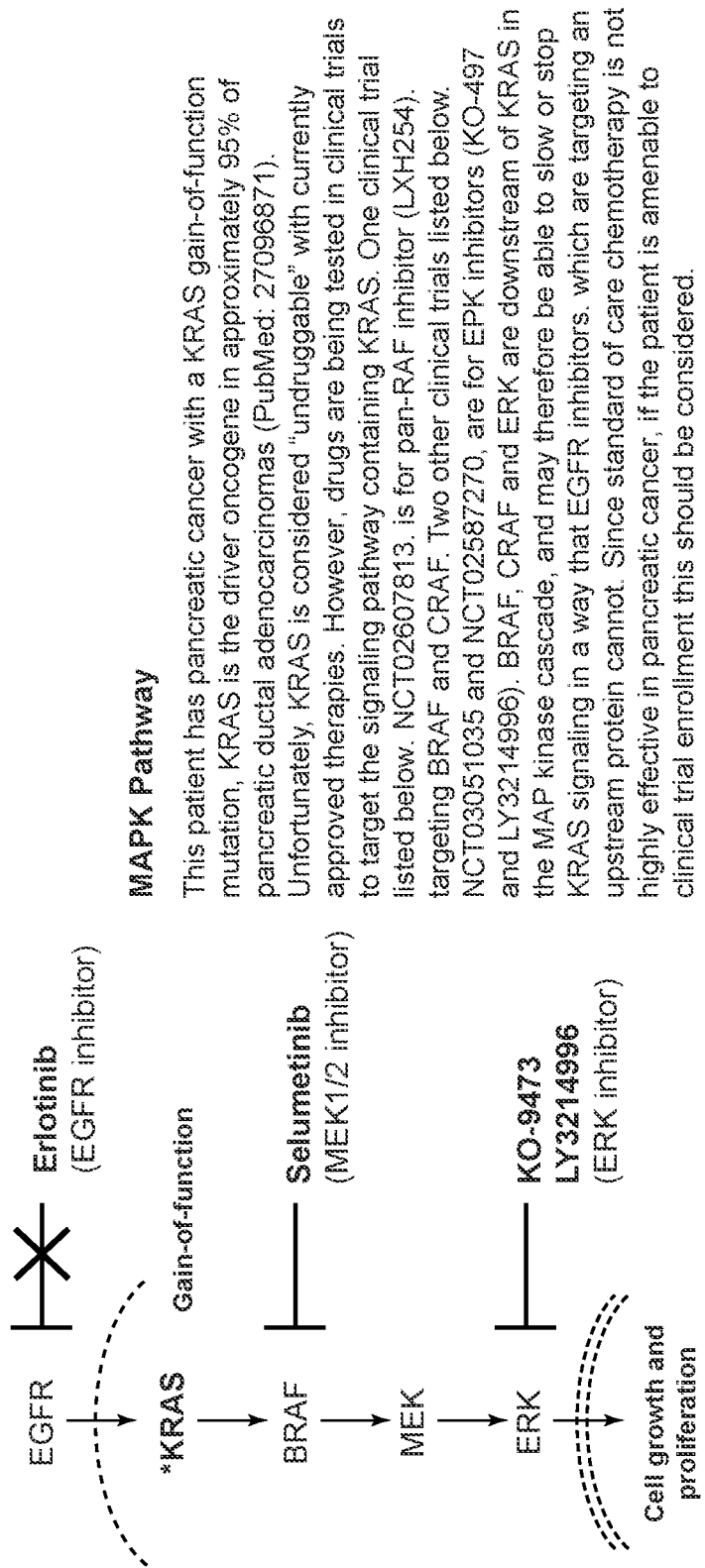
Figure 10H:
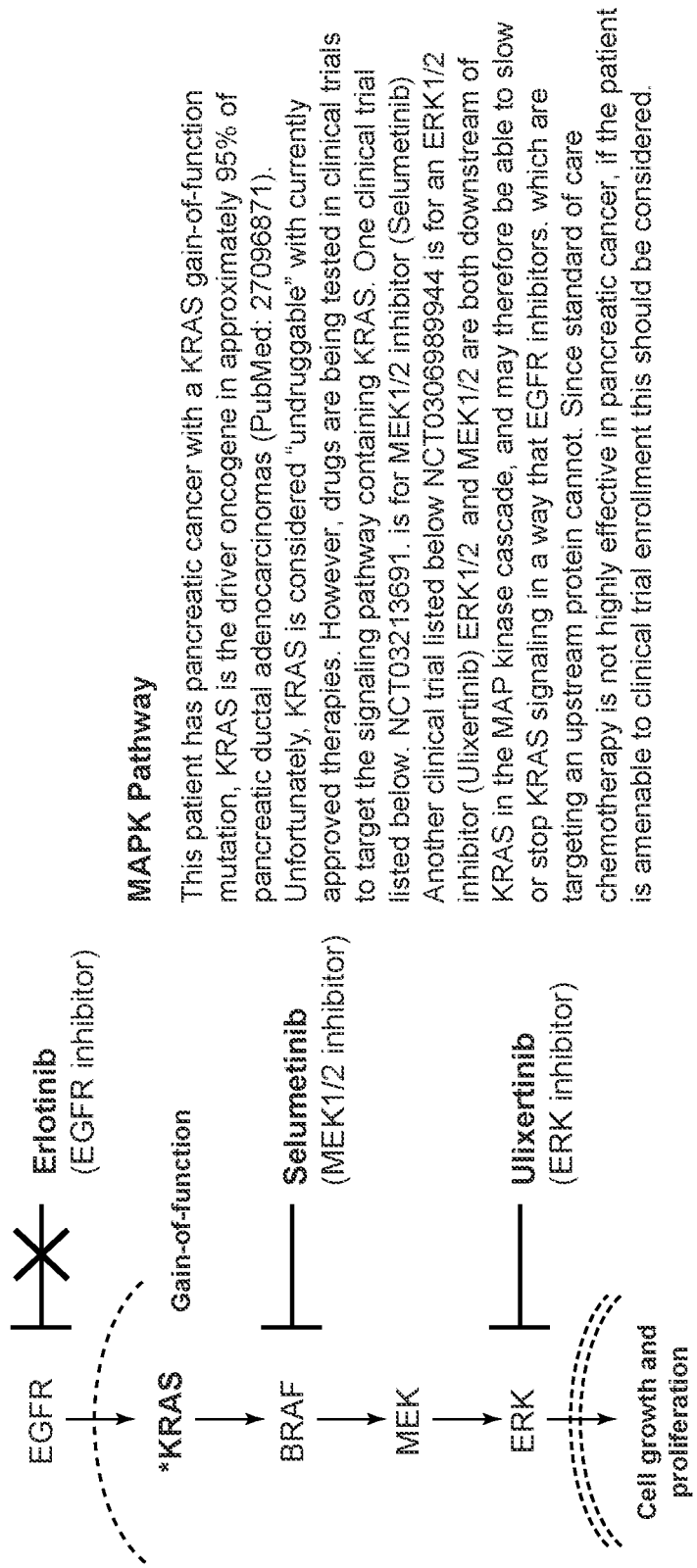
Figure 10I:
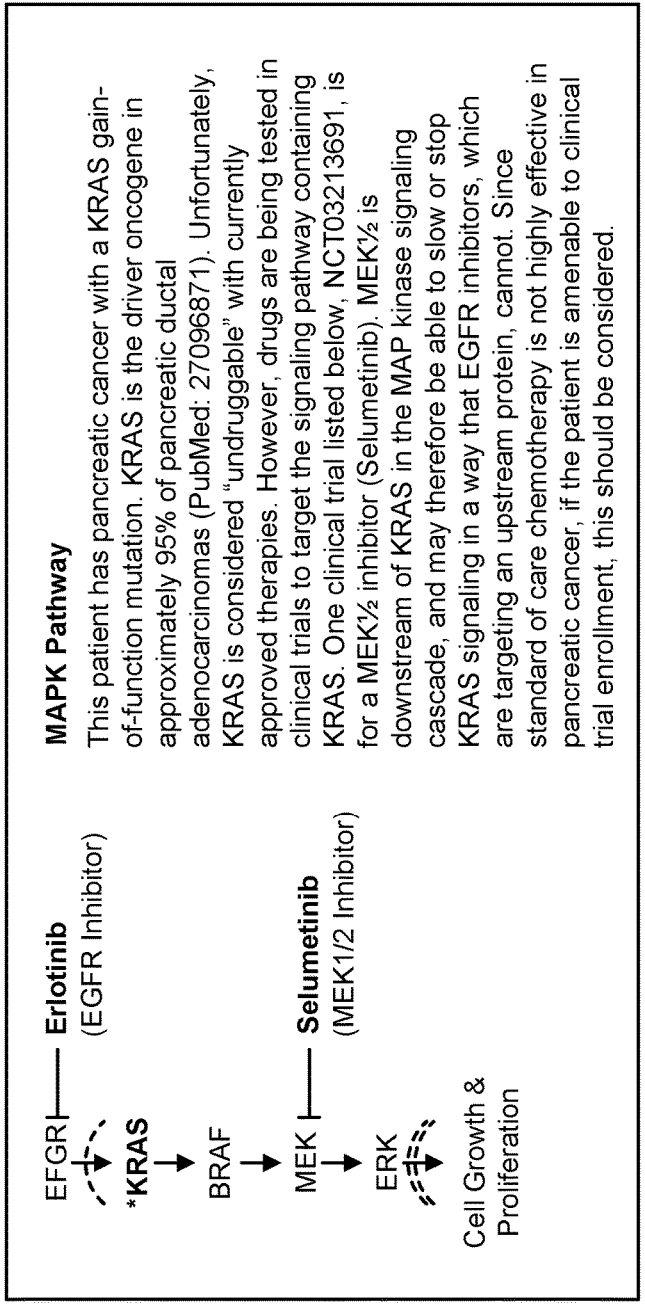

In various embodiments, such as the example provided in FIG. 10B, these pathway reports may be generated for patients with cancer, such as pancreatic adenocarcinoma, a KRAS gain of function mutation, and no other actionable mutations other than TP53 or SMAD4. A clinical trial for a therapy targeting BRAF, MEK and/or ERK may be matched on the patient report.

FIGS. 11A through 11E collectively illustrate examples of a pathway disruption report generated at 730 in FIG. 7C, especially for the PI3K pathway.

FIG. 11A illustrates an example of a pathway disruption report generated for a hidden responder having no detected pathogenic mutation in the PI3K pathway but having a high pathway disruption score generated by the pathway engine 200*n*. The mutation causing the high pathway disruption score may be unknown, but the level of pathway disruption may be inferred by the pathway disruption score. In this example, a therapy designed to target CRTC2 may be matched. PD-L1 inhibitors may be contraindicated in this example due to research indicating that PD-L1 inhibitors may be less effective for patients with STK11 mutations. A clinical trial could be matched based on inclusion and/or exclusion criteria of the trial. Currently, clinical trials may require a pathogenic DNA mutation in the PI3K pathway detected in the patient for enrollment, but it is contemplated that a clinical trial may be matched to a patient based on a pathway disruption score generated by pathway engine 200*n*.

Figure 11B:
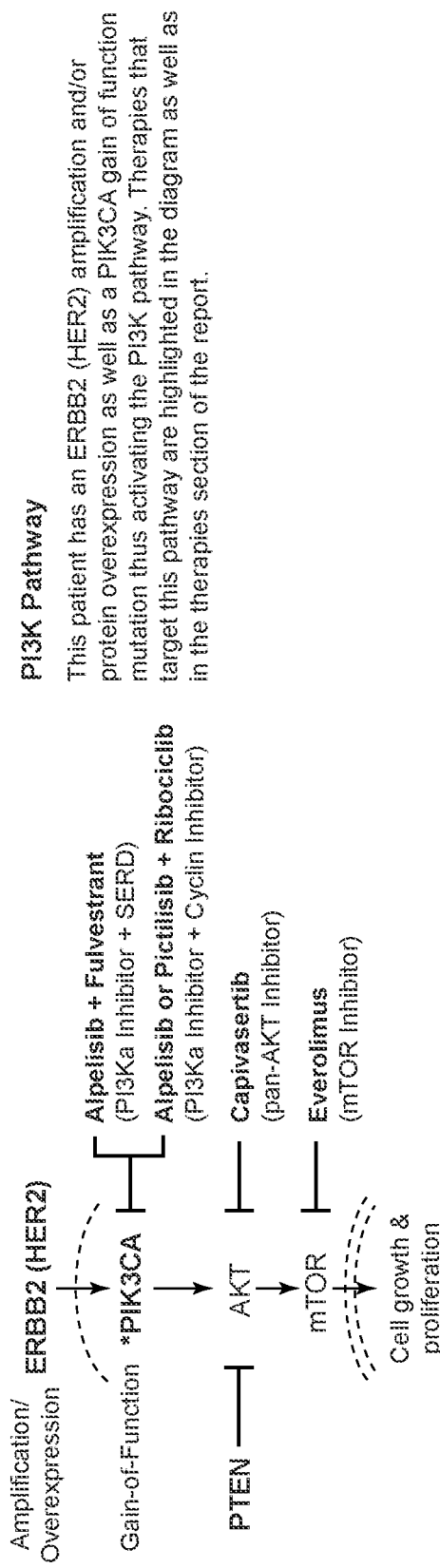
Figure 11C:
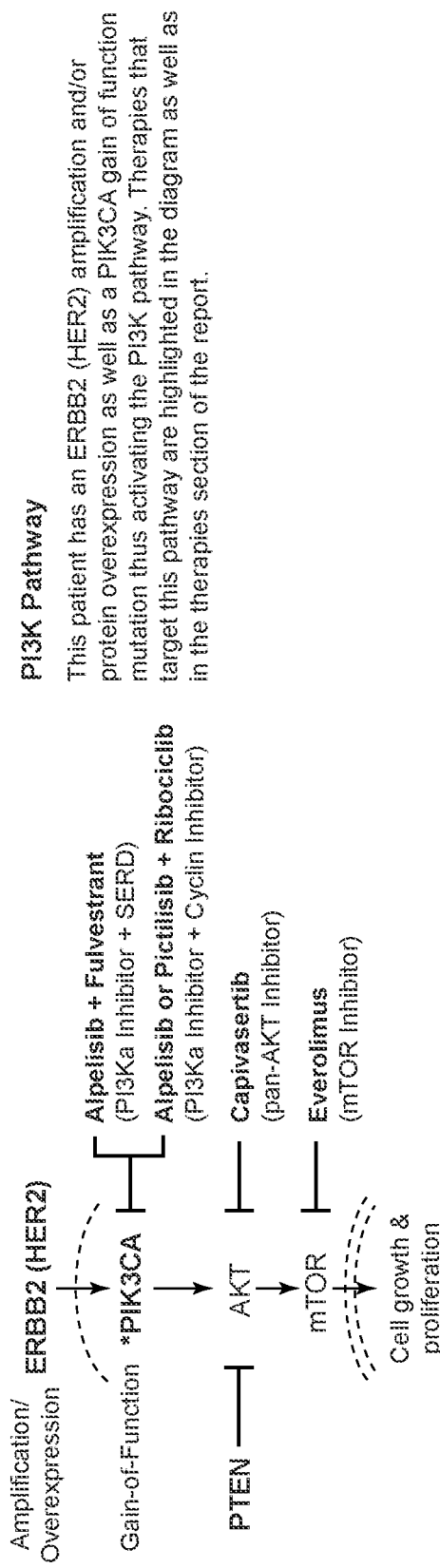

In FIGS. 11B and 11C, the patient receiving the pathway report may be HER2 positive (for example, the HER2 status may be determined by FISH, IHC, or NGS).

Figure 11D:
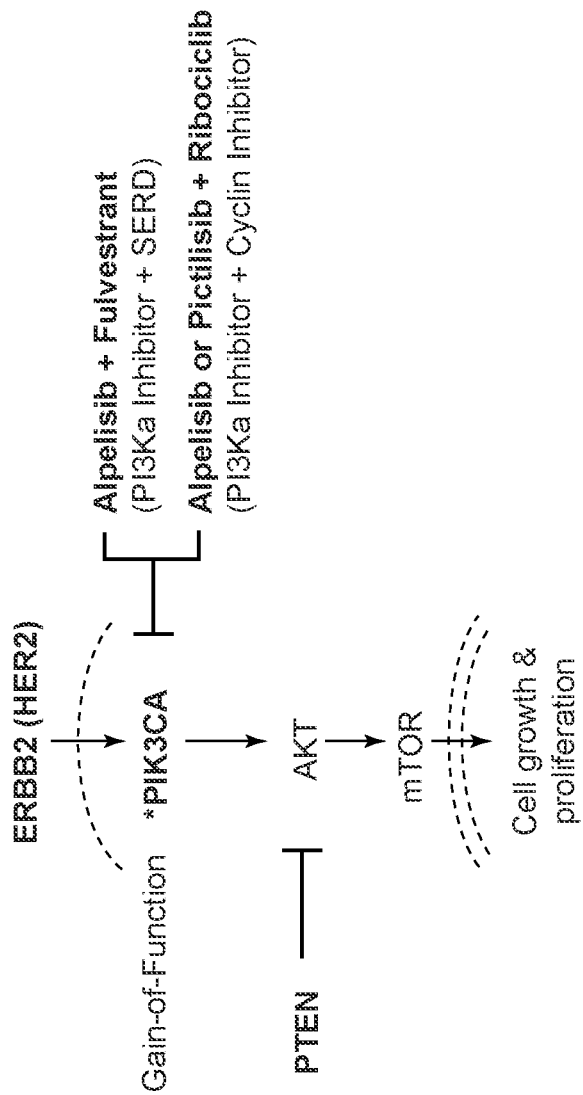

In FIG. 11D, the patient's HER2 status may be unknown.

In various embodiments, these pathway reports may be generated for patients with breast cancer and a PI3K gain of function mutation. A Clinical Trial for a therapy targeting PIK3CA, AKT and/or mTOR may be matched on the patient report.

In some embodiments, a therapies section may added to any report. Such information may be included to enhance any therapeutic information provided in a pathway diagram for example, or to add additional therapeutic information that is generally associated with the disease state (see e.g., FIG. 11E).

FIGS. 12A, 12B, 12C, 12D, 12E and 12F collectively illustrate the results of a meta-pathway analysis of a patient's transcriptome using the systems and methods disclosed herein. (See Example 6)

FIGS. 12A, 12B, 12C, 12D, 12E and 12F each illustrate a cellular pathway, where groups of proteins in the pathway are represented by polygons. Arrows show activation of one protein group by another protein group, and a "T"-shaped line shows inhibition of one protein by another protein.

Each polygon in the pathway represents a class of genes (for example, RAS genes, which include KRAS, NRAS, and HRAS). In this analysis, a pathway engine was trained for each gene group (each represented here by a polygon in each of the FIGS. 14A-F, as described in process 502, where all positive controls had at least one mutation in a gene in the gene class associated with the polygon and all negative controls were wild type for all genes in the pathway. Then, each trained pathway engine 200 was used to analyze a transcriptome associated with one patient to generate a pathway activity score, as described in FIG. 7C.

If a polygon is color coded blue, the pathway engine 200 associated with that polygon generated a pathway activity score that indicated no disruption. If white, the pathway engine 200 associated with that polygon generated an intermediate pathway disruption score indicating that the pathway may be disrupted. If red, the pathway engine 200 associated with that polygon generated a pathway disruption score indicating that the pathway is disrupted.

In another example, instead of or in addition to color-coding the polygons, each numeric pathway disruption score may be added to the image, near or within each polygon.

If a polygon is color coded gray, that means there were too few positive control transcriptome value sets for training and a pathway engine 200 was not trained for that polygon. In one example, at least 30 positive control transcriptome value sets would be desirable for training a pathway engine 200n.

In these examples, the RTK/RAS-PI3K-EGFR pathways are depicted. The RTK/RAS-PI3K-EGFR pathway depictions shown in FIGS. 12A, 12B, 12C, 12D, 12E and 12F may be included in a pathway disruption report and may assist a physician in determining a therapy or therapies to prescribe to a patient. In some embodiments, the report includes a therapy recommendation.

Each of the pathways can include a number of modules. Each module can be associated with a trained model (e.g., a linear model trained using the process 670 in FIG. 6G) that can be included in a pathway engine. The modules can be marked with a color and/or pattern that indicates a level of dysregulation or non-dysregulation at the module. In the examples below, red modules have been determined to show signs of dysregulation using the associated trained models. Blue modules have been determined to show signs of non-dysregulation using the associated trained models. The darkness of the red or blue can correspond to how dysregulated or non-dysregulated the module is, respectively. White can represent a neutral level of dysregulation.

In FIG. 12A, the patient transcriptome being analyzed by the pathway engine 200 has no detected mutations in any of the genes in the pathway (the patient is a wild type, negative control). As expected, none of the pathway disruption scores generated by the pathway engines 200 indicate that there is any pathway disruption.

Figure 12B:
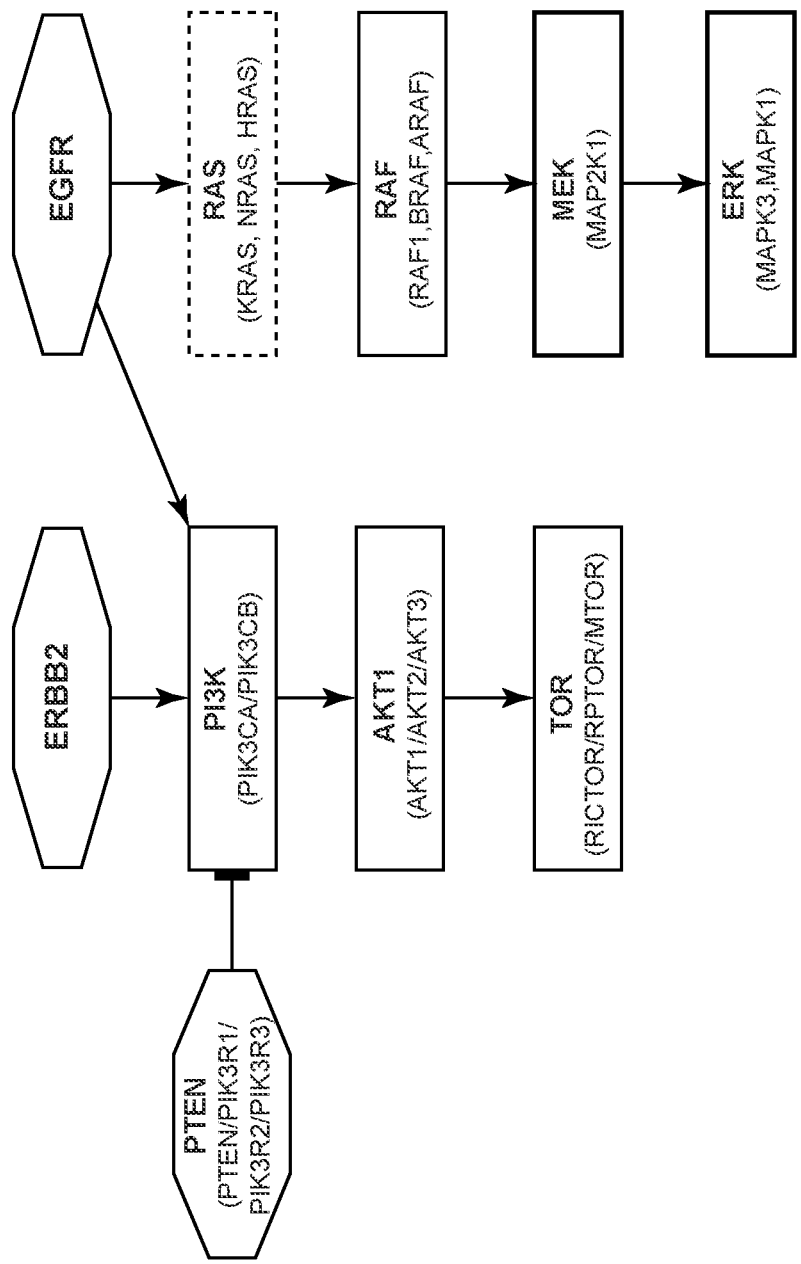
FIG. 12B shows more results of a patient transcriptome being analyzed by a plurality of pathway engines.

In FIG. 12B, the patient had a KRAS mutation and no RAF mutations, but the systems and methods predicted that the KRAS mutation caused elevated activity in the RAF class of proteins. In this example, there are no approved therapies that target RAS, so the patient would be matched with therapies that target MEK or ERK. Approved RAS-targeting therapies or clinical trial(s) for RAS-targeting therapies may be matched if they exist. In one example, therapies are approved by a regulatory agency, for example, the Federal Drug Administration (FDA), (see e.g., FIG. 27, listing binimetinib and cobimetinib as exemplary FDA-approved MEK inhibitors). In some embodiments, the patient is treated with the recommended therapeutic.

Figure 12C:
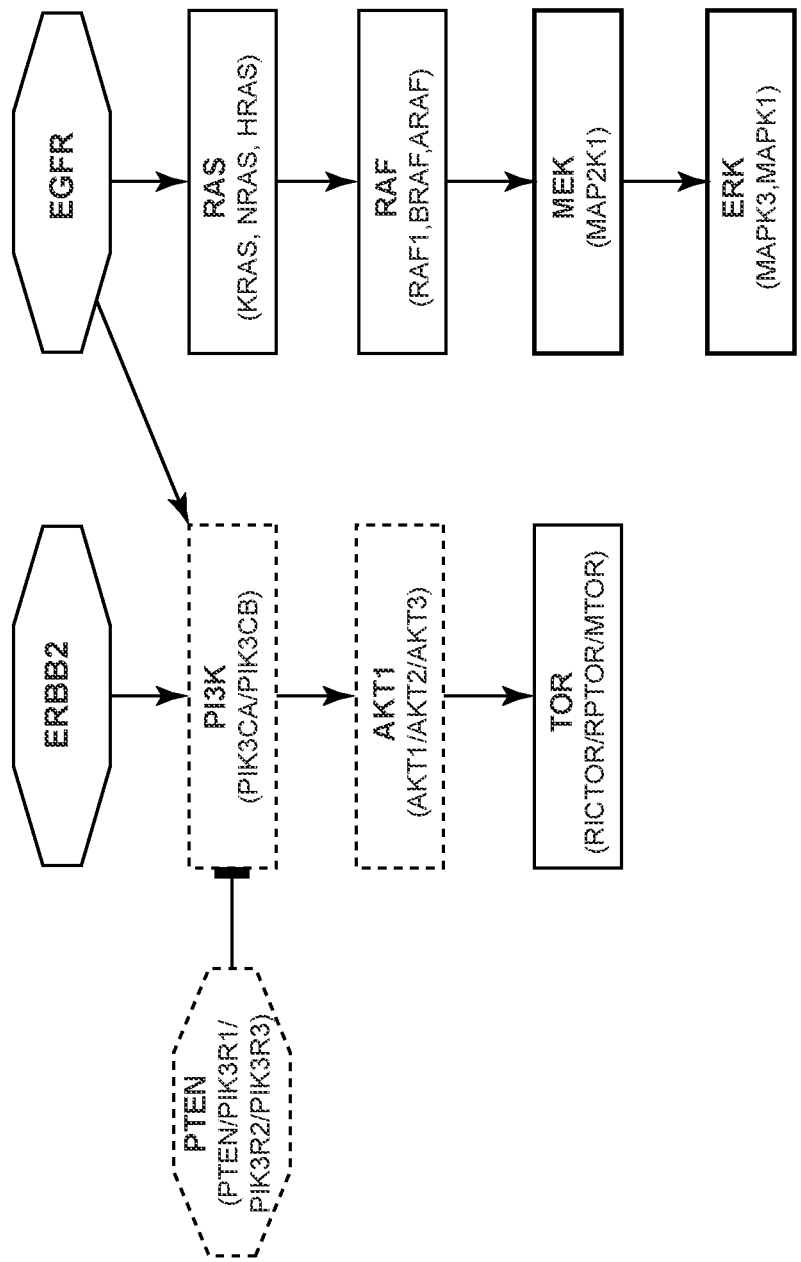
FIG. 12C shows further results of a patient transcriptome being analyzed by a plurality of pathway engines.

In FIG. 12C, the patient has a PIK3CA amplification and an AKT2 amplification in the PI3K pathway but no evident disruption in the RTK/RAS pathway. As AKT2 is further downstream in the PI3K pathway, the patient may be matched with therapies targeting AKT.

Figure 12D:
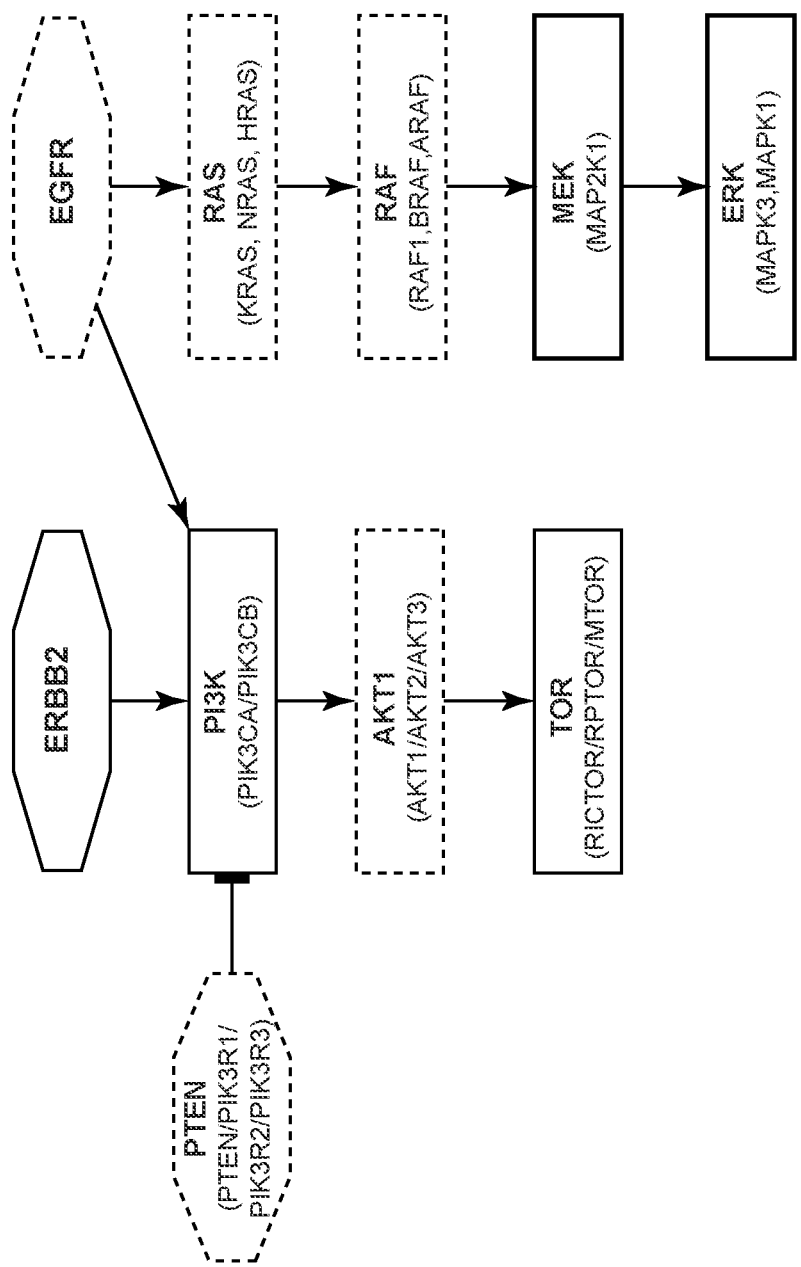
FIG. 12D shows still further results of a patient transcriptome being analyzed by a plurality of pathway engines.

In FIG. 12D, the patient has an EGFR mutation. Even though the patient has no RAS or RAF mutations, the patient is predicted to have elevated RAS and RAF activity. This patient may therefore not respond as expected to EGFR-targeted therapy but may be treated with a MEK or ERK inhibitor.

Figure 12E:
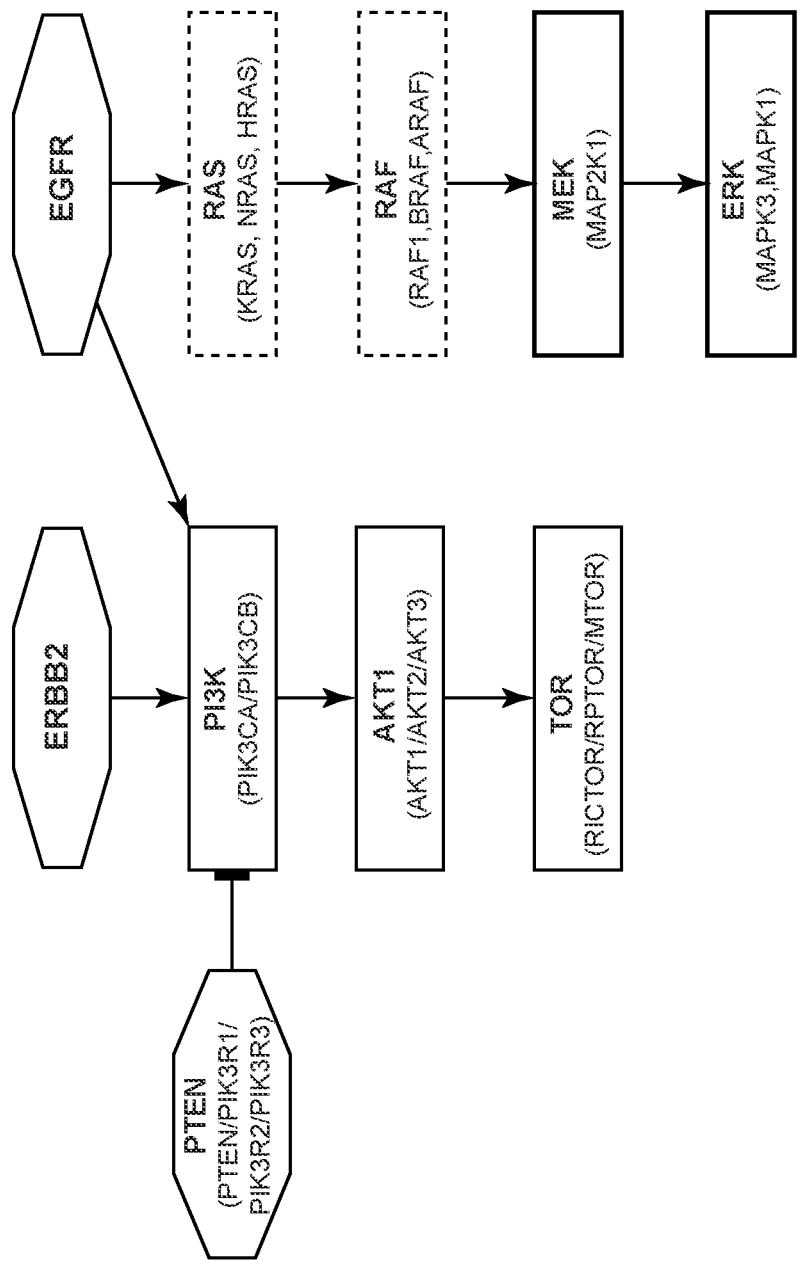
FIG. 12E shows additional results of a patient transcriptome being analyzed by a plurality of pathway engines.

In FIG. 12E, the patient has a pathogenic KRAS mutation and an inactivating BRAF mutation that leads to paradoxical activation of downstream pathway members. Therapies and/or clinical trials with MEK/ERK inhibitors would be matched for this patient.

Figure 12F:
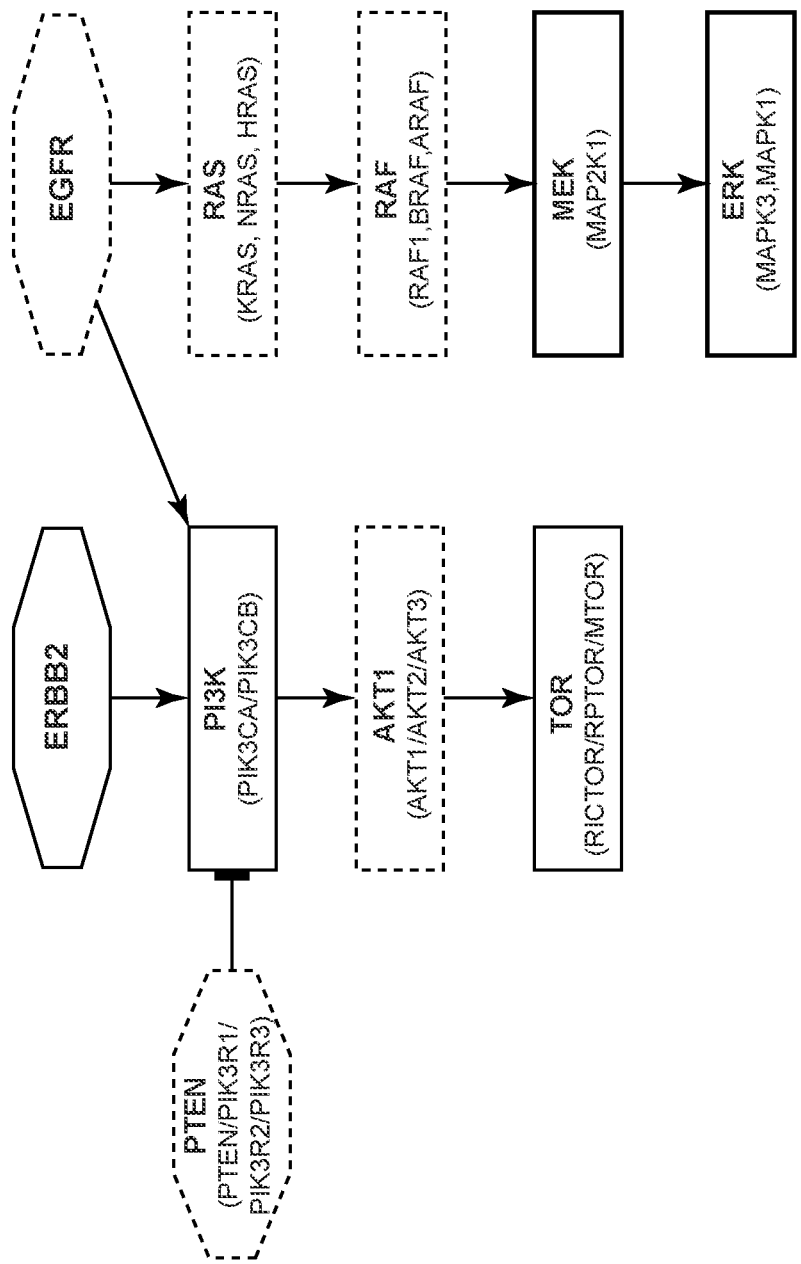
FIG. 12F shows additional results of a patient transcriptome being analyzed by a plurality of pathway engines.

In FIG. 12F, the patient has a pathogenic EGFR mutation and an EGFR amplification, with evidence of disruption in the EGFR, RAS, and RAF submodules. A triple therapy and/or clinical trials combining inhibitors of EGFR, MEK, and BRAF may be matched.

Figure 13:
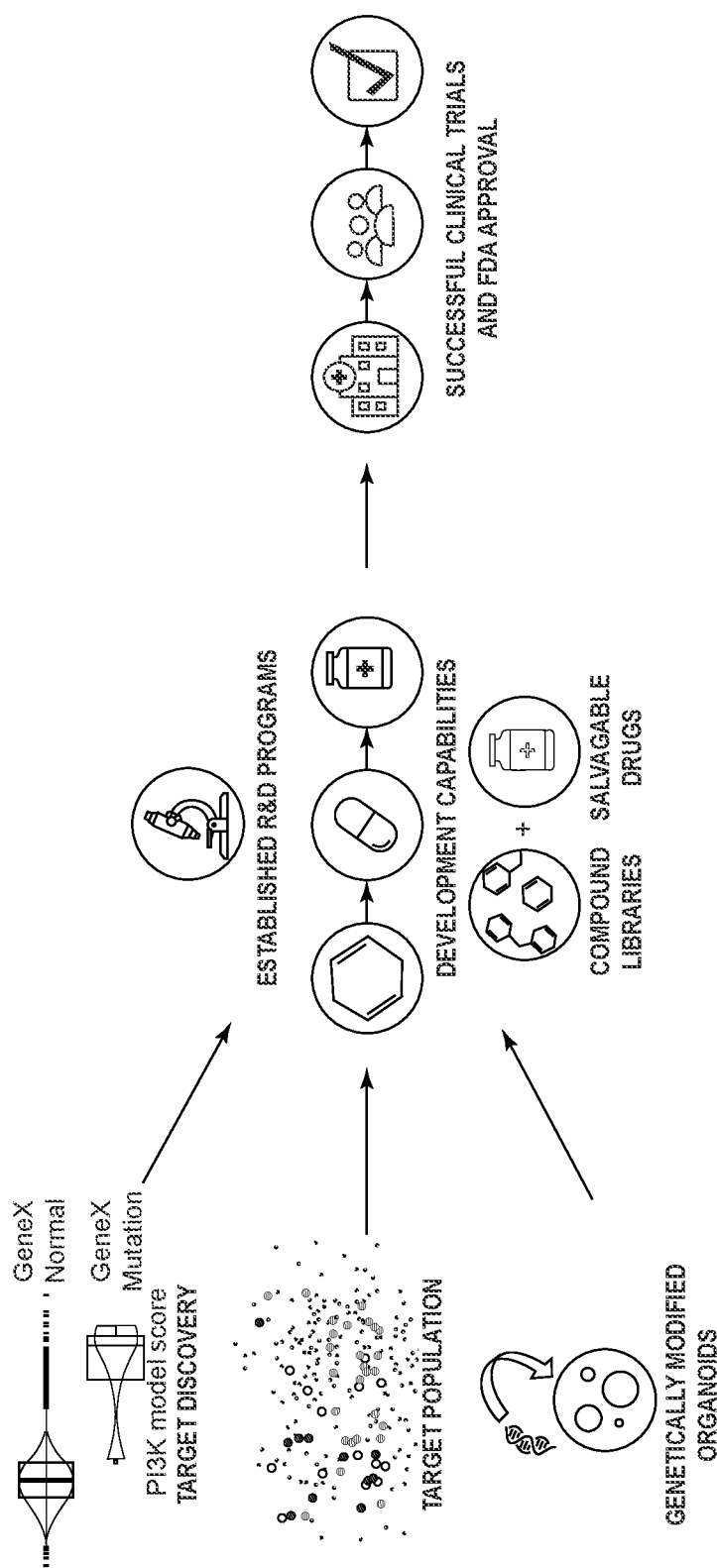
FIG. 13 is a schematic illustrating the integration of clinical and molecular data and data science resources with the expertise of drug development companies in translating knowledge to product.

FIG. 13 is a schematic illustrating the integration of clinical and molecular data and data science resources with the expertise of drug development companies in translating knowledge to product, presenting an opportunity to use the systems and methods to accelerate drug discovery and repurposing. For example, the knowledge in this context may include a target gene or mutation identified and/or tested in vitro (for example, in tumor organoids or cell lines) by the systems and methods disclosed herein, represented by the left column. For example, methods for translating knowledge to product may include screening compounds for efficacy in inhibiting a target gene product, testing drug efficacy and safety in animal experiments, conducting clinical trials with human patients, and/or additional methods used for drug development or repurposing, represented by the middle and right columns.

ILLUSTRATIVE EMBODIMENTS

Described below are several non-limiting, exemplary embodiments of the systems and methods described herein.

Embodiment 1

In a first embodiment, a method of detecting cellular pathway dysregulation in a specimen, comprising receiving a set of data, in some embodiments, a set of genetic data, associated with the specimen, the genetic data comprising RNA data; and analyzing the set of data or the set of genetic data to estimate, for at least one cellular pathway of interest, a pathway disruption score.

Embodiment 2

The method of embodiment 2, wherein the pathway dysregulation engine has been trained using a set of training data comprising a first plurality of training RNA data, wherein each training RNA data in the first plurality of the training data is associated with a dysregulation indicator associated with the cellular pathway.

Embodiment 3

The method of embodiment 1, which further comprises comparing the pathway disruption score to a threshold to determine a qualitative label for the specimen, wherein the pathway disruption score is a numerical value.

Embodiment 4

The method of embodiment 1, which further comprises: estimating a first pathway disruption score for a first cellular pathway; estimating a second pathway disruption score for a second cellular pathway; and reporting the first pathway disruption score and the second pathway disruption score.

Embodiment 5

The method of embodiment 1, which further comprises: estimating a first disruption score for a first module included in a pathway; estimating a second disruption score for a second module included in the pathway; and reporting the first disruption score and the second disruption score.

Embodiment 6

The method of embodiment 1, wherein the at least one cellular pathway is a RAS/RTK pathway.

Embodiment 7

The method of embodiment 1, wherein the at least one cellular pathway is a PI3K pathway Embodiment 8

The method of embodiment 1, wherein the at least one cellular pathway is a TCGA-curated pathway.

Embodiment 9

The method of embodiment 1, wherein the set of genetic data includes RNA data.

Embodiment 10

The method of embodiment 1, wherein the set of genetic data includes DNA data.

Embodiment 11

The method of embodiment 1, wherein the set of data includes protein data.

Embodiment 12

The method of embodiment 1, wherein the specimen is a cancer specimen from a human patient.

Embodiment 13

The method of embodiment 1, wherein the specimen is an organoid.

Embodiment 14

The method of embodiment 1, wherein the specimen is an organoid derived from a human cancer specimen.

Embodiment 15

The method of embodiment 1, which further comprises associating at least one pathway disruption score with a protein level and predicting a protein level for the specimen.

Embodiment 16

The method of embodiment 1, which further comprises detecting a variant having unknown significance in the set of genetic data and determining the likelihood that the variant is pathogenic, based on the pathway disruption score.

Embodiment 17

A method of prescribing a treatment, comprising: receiving the results of a cellular pathway dysregulation detection, in accordance with the method of embodiment 1; and recommending the treatment to a patient from which the specimen originated, based on the pathway disruption score.

Embodiment 18

A method of designing an experiment to test treatment response in an organoid, comprising: receiving the results of a cellular pathway dysregulation detection, in accordance with the method of embodiment 1, wherein the specimen is derived from an organoid; and suggesting that the organoid be monitored after exposure to a treatment, based on the pathway disruption score.

Embodiment 19

A method of matching a patient to a clinical trial, comprising: receiving the results of a cellular pathway dysregulation detection, in accordance with the method of claim 1; and matching at least one clinical trial, based on the pathway disruption score.

Embodiment 20

The method of embodiment 20, which further comprises the step of reporting a list of matched clinical trials to the patient.

Embodiment 21

The method of embodiment 20, which further comprises the step of reporting a list of matched clinical trials to a medical professional caring for the patient.

Embodiment 22

A method of designing a clinical trial, comprising: analyzing clinical data for an association of response to at least one treatment and a range of pathway disruption scores generated in accordance with embodiment 1; and suggesting a study of the response to the at least one treatment in each of a plurality of patients having a pathway disruption score within the range.

Embodiment 23

A medical device that: receives a set of genetic data; and detects cellular pathway dysregulation in accordance with the method of embodiment 1.

Embodiment 24

The medical device of embodiment 24, wherein the medical device is a genetic analyzer system.

Embodiment 25

The medical device of embodiment 24, wherein the medical device is a laboratory developed test.

Embodiment 26

A method of sequencing a cancer specimen, comprising: generating a set of genetic data; and detecting cellular pathway dysregulation in accordance with the method of embodiment 1.

Embodiment 27

A cloud-based information processing system that: receives a set of genetic data; and detects cellular pathway dysregulation in accordance with the method of embodiment 1.

Embodiment 28

A cloud-based information processing system that: receives a set of genetic data; and detects cellular pathway dysregulation in accordance with the method of embodiment 1.

Embodiment 29

The method of embodiment 1, wherein the method is performed in conjunction with a digital and laboratory health care platform.

Embodiment 30

The method of embodiment 1, wherein the method is performed after completion of a processing of a bioinformatics pipeline.

Embodiment 31

The method of embodiment 1, wherein the method is performed in one or more micro-services.

Embodiment 32

The method of embodiment 1, wherein the method is performed in one or more micro-services as a sub-service of a bioinformatics engine.

Embodiment 33

The method of embodiment 1, wherein the method is performed in one or more micro-services as a sub-service of a variant characterization engine.

Embodiment 34

The method of embodiment 1, further comprising sending a result of the method to a variant calling engine.

Embodiment 35

The method of embodiment 1, further comprising sending a result of the method to an insight engine.

Embodiment 36

The method of embodiment 1, further comprising sending a result of the method to a tumor of unknown origin engine.

Embodiment 37

The method of embodiment 1, further comprising sending a result of the method to a PD-L1 status engine.

Embodiment 38

The method of embodiment 1, further comprising sending a result of the method to a homologous recombination deficiency engine.

Embodiment 39

The method of embodiment 1, further comprising sending a result of the method to a cellular pathway disruption report engine.

Embodiment 40

The method of embodiment 1, further comprising sending a result of the method to a human leukocyte antigen (HLA) loss of homozygosity (LOH) engine

Embodiment 41

The method of embodiment 1, further comprising sending a result of the method to a tumor mutational burden engine

Embodiment 42

The method of embodiment 1, further comprising sending a result of the method to a microsatellite instability engine.

Embodiment 43

The method of embodiment 1, further comprising sending a result of the method to an immune infiltration engine.

Embodiment 44

A method for detecting dysregulation in a cellular pathway for a specimen, the method comprising: receiving genetic data associated with the specimen, the genetic data comprising transcriptome data; providing a portion of the transcriptome data to at least one trained pathway disruption engine; receiving at least one pathway disruption score indicative of cellular pathway dysregulation in a cellular pathway from at least one trained pathway disruption engine; generating a pathway disruption report based on the at least one pathway disruption score; and causing the pathway disruption report to be output to at least one of a display or a memory.

Embodiment 45

The method of embodiment 44, wherein the at least one trained disruption engine comprises a model configured to output a model score based on the transcriptome data, and wherein the at least one trained disruption engine is configured to determine the at least one pathway score based on the model score and a predetermined threshold value.

Embodiment 46

The method of embodiment 45, wherein the threshold value is determined based on an area under the curve calculated based on a first probability distribution generated based on dysregulated training data using the model and a second probability distribution generated based on non-dysregulated training data using the model.

Embodiment 47

The method of embodiment 45, wherein model scores below the predetermined threshold indicate non-dysregulation, and wherein model scores above the predetermined threshold indicates dysregulation.

Embodiment 48

The method of embodiment 44, wherein the at least one trained pathway disruption engine comprises a number of trained models, each of the trained models being configured to output a model score associated with a different genetic module included in the cellular pathway.

Embodiment 49

The method of embodiment 48, wherein each of the trained models is a linear regression model.

Embodiment 50

The method of embodiment. 48 further comprising: calculating a global dysregulation score based on the model score output by each of the trained models.

Embodiment 51

The method of embodiment 44, further comprising calculating a global dysregulation score based on a weighted average of a disruption score associated with a module comprising a variant of unknown significance (VUS) and at least one disruption score associated with at least one module downstream of the module comprising the VUS Embodiment 52

The method of embodiment 44 further comprising: calculating a number of differential metrics between the positively labeled samples and negatively labeled samples associated with a module in a pathway, each differential metric being associated with a gene included in the transcriptome data; and determining, for each gene included in the transcriptome data, a set of differentially expressed genes based on the differential metric and a predetermined threshold, wherein the portion of the transcriptome data provided to the at least one trained pathway disruption engine is associated with the differentially expressed genes.

Embodiment 53

The method of embodiment 52, wherein the portion of the transcriptome data provided to the at least one trained pathway disruption engine only includes gene expression levels of the differentially expressed genes.

Embodiment 54

The method of embodiment 52, wherein the differential metric includes a Benjamini-Hochberg false discovery rate.

Embodiment 55

The method of embodiment 44, wherein the at least one trained pathway disruption engine comprises a model associated with a module in a pathway and configured to receive the portion of the transcriptome data and output a model score, and wherein the at least one pathway engine is configured to: determine whether the model score is above a threshold; and output an indication that the module is disrupted in response to determining the model score is above the threshold.

Embodiment 56

The method of embodiment 55, wherein the threshold is predetermined based on an area under the curve calculated based on a probability distribution of dysregulated patients generated using the model and a probability distribution of non-dysregulated patients generated using the model.

Embodiment 57

The method of embodiment 44, wherein the at least one trained pathway disruption engine comprises a model associated with a module in a pathway, the module comprising a group of genes, the module being configured to receive the portion of the transcriptome data and output a model score, and wherein the module is configured to receive transcriptome data associated with at least one gene included in the group of genes.

Embodiment 58

The method of embodiment 44 further comprising providing at least one of DNA data or protein data to the at least one trained pathway disruption engine, and wherein the at least one pathway disruption score is generated based on at least one of the DNA data or the protein data.

Embodiment 59

The method of embodiment 44, the pathway disruption report comprises information associated with the at least one pathway disruption score, the information comprising at least one of potential causative mutations, variants of unknown significance, recommended therapies for a pathway module included in the cellular pathway, or reference medical literature.

Embodiment 60

The method of embodiment 59, wherein the recommended therapies are presented in a ranked fashion.

Embodiment 61

The method of embodiment 44 further comprising comparing the at least one pathway disruption score to at least one threshold to determine a qualitative label for the specimen, wherein the pathway disruption score is a numerical value.

Embodiment 62

The method of embodiment 44 further comprising: estimating a first pathway disruption score for a first cellular pathway; estimating a second pathway disruption score for a second cellular pathway; and reporting the first pathway disruption score and the second pathway disruption score.

Embodiment 63

The method of embodiment 44 further comprising: estimating a first disruption score for a first module included in a pathway; estimating a second disruption score for a second module included in the pathway; and reporting the first disruption score and the second disruption score.

Embodiment 64

The method of embodiment 44, wherein the cellular pathway is a RAS/RTK pathway.

Embodiment 65

The method of embodiment 44, wherein the cellular pathway is a PI3K pathway.

Embodiment 66

The method of embodiment 44, wherein the cellular pathway is a TCGA-curated pathway.

Embodiment 67

The method of embodiment 44, wherein the transcriptome data comprises RNA expression level data.

Embodiment 68

The method of embodiment 44, wherein the genetic data further comprises DNA data.

Embodiment 69

The method of embodiment 44, wherein the genetic data further comprises protein data.

Embodiment 70

The method of embodiment 44, wherein the specimen is a cancer specimen from a human patient.

Embodiment 71

The method of embodiment 44, wherein the specimen is an organoid.

Embodiment 72

The method of embodiment 44, wherein the specimen is an organoid derived from a human cancer specimen.

Embodiment 73

The method of embodiment 44 further comprising: associating at least one pathway disruption score with a protein level; and predicting a protein level for the specimen.

Embodiment 74

The method of embodiment 44 further comprising: detecting a variant having unknown significance in the set of genetic data; and determining the likelihood that the variant is pathogenic based on the pathway disruption score.

Embodiment 75

The method of embodiment 44 further comprising: receiving the pathway disruption report; and determining a treatment for a patient associated with the specimen based on the pathway disruption score.

Embodiment 76

The method of embodiment 44, wherein the specimen is derived from an organoid, and wherein the method further comprises: receiving the pathway disruption report; and outputting a suggestion that the organoid be monitored after exposure to a treatment, based on the pathway disruption score.

Embodiment 77

The method of embodiment 44 further comprising: receiving the pathway disruption report; and matching at least one clinical trial to a patient associated with the specimen based on the pathway disruption score.

Embodiment 78

The method of embodiment 77 further comprising: reporting a list of matched clinical trials to the patient.

Embodiment 79

The method of embodiment 77 further comprising reporting a list of matched clinical trials to a medical professional caring for the patient.

Embodiment 80

The method of embodiment 44 further comprising: analyzing clinical data for an association of response to at least one treatment and the at least one pathway disruption score; and suggesting a study of the response to the at least one treatment in each of a plurality of patients having a pathway disruption score within the range.

Embodiment 81

A medical device configured to: execute the method of claim 44.

Embodiment 82

The medical device of embodiment 81, wherein the medical device is a genetic analyzer system.

Embodiment 83

The medical device of embodiment 81, wherein the medical device is a laboratory developed test.

Embodiment 84

The method of embodiment 44 further comprising generating the genetic data.

Embodiment 85

A cloud-based information processing system configured to: execute the method of embodiment 44.

Embodiment 86

The method of embodiment 44, wherein the method is performed in conjunction with a digital and laboratory health care platform.

Embodiment 87

The method of embodiment 44, wherein the method is performed after completion of a processing of a bioinformatics pipeline.

Embodiment 88

The method of embodiment 44, wherein the method is performed in one or more micro-services.

Embodiment 89

The method of embodiment 44, wherein the method is performed in one or more micro-services as a sub-service of a bioinformatics engine.

Embodiment 90

The method of embodiment 44, wherein the method is performed in one or more micro-services as a sub-service of a variant characterization engine.

Embodiment 91

The method of embodiment 44 further comprising sending a result of the method to a variant calling engine.

Embodiment 92

The method of embodiment 44 further comprising sending a result of the method to an insight engine.

Embodiment 93

The method of embodiment 44 further comprising sending a result of the method to a tumor of unknown origin engine.

Embodiment 94

The method of embodiment 44 further comprising sending a result of the method to a PD-L1 status engine.

Embodiment 95

The method of embodiment 44 further comprising sending a result of the method to a homologous recombination deficiency engine.

Embodiment 96

The method of embodiment 44 further comprising sending a result of the method to a cellular pathway disruption report engine.

Embodiment 97

The method of embodiment 44 further comprising sending a result of the method to a human leukocyte antigen (HLA) loss of homozygosity (LOH) engine.

Embodiment 98

The method of embodiment 44 further comprising sending a result of the method to a tumor mutational burden engine.

Embodiment 99

The method of embodiment 44 further comprising sending a result of the method to a microsatellite instability engine.

Embodiment 100

The method of embodiment 44 further comprising sending a result of the method to an immune infiltration engine.

Embodiment 101

A method for detecting dysregulation in a pathway comprising a plurality of modules, the method comprising: receiving transcriptome data associated with a tissue specimen; providing a first portion of the transcriptome data to a first trained pathway disruption engine comprising a trained model associated with a first module included in the pathway; receiving a first pathway dysregulation score from the first trained pathway disruption engine; providing a second portion of the transcriptome data to a second trained pathway disruption engine comprising a trained model associated with a second module included in the pathway; receiving a second pathway dysregulation score from the second trained pathway disruption engine; generating a meta-pathway depiction based on the pathway, the first pathway dysregulation score, and the second pathway dysregulation score; and causing the meta-pathway depiction to be displayed to a medical practitioner.

Embodiment 102

A cellular pathway dysregulation analysis system comprising at least one processor an at least one memory, the system configured to: receive a set of data, in some embodiments, genetic data, associated with a specimen, the genetic data comprising transcriptome data; provide a portion of the set of data or the transcriptome data to at least one trained pathway disruption engine; receive at least one pathway disruption score indicative of cellular pathway dysregulation in a cellular pathway from at least one trained pathway disruption engine; generate a pathway disruption report based on the at least one pathway disruption score; and cause the pathway disruption report to be output to at least one of a display or a memory.

Embodiment 103

The system of embodiment 102, wherein the at least one trained disruption engine comprises a model configured to output a model score based on the transcriptome data, and wherein the at least one trained disruption engine is configured to determine the at least one pathway score based on the model score and a predetermined threshold value.

Embodiment 104

The system of embodiment 103 wherein the threshold value is determined based on an area under the curve calculated based on a first probability distribution generated based on dysregulated training data using the model and a second probability distribution generated based on non-dysregulated training data using the model.

Embodiment 105

The system of embodiment 103, wherein model scores below the predetermined threshold indicate non-dysregulation, and wherein model scores above the predetermined threshold indicates dysregulation.

Embodiment 106

The system of embodiment 102, wherein the at least one trained pathway disruption engine comprises a number of trained models, each of the trained models being configured to output a model score associated with a different genetic module included in the cellular pathway.

Embodiment 107

The system of embodiment 106, wherein each of the trained models is a linear regression model.

Embodiment 108

The system of embodiment 106, wherein the system is further configured to: calculate a global dysregulation score based on the model score output by each of the trained models.

Embodiment 109

The system of embodiment 102, wherein the system is further configured to: calculate a global dysregulation score based on a weighted average of a disruption score associated with a module comprising a VUS and at least one disruption score associated with at least one module downstream of the module comprising the VUS.

Embodiment 110

The system of embodiment 102, wherein the system is further configured to: calculate a number of differential metrics between the positively labeled samples and negatively labeled samples associated with a module in a pathway, each differential metric being associated with a gene included in the transcriptome data; and determine, for each gene included in the transcriptome data, a set of differentially expressed genes based on the differential metric and a predetermined threshold, wherein the portion of the transcriptome data provided to the at least one trained pathway disruption engine is associated with the differentially expressed genes.

Embodiment 111

The system of embodiment 110, wherein the portion of the transcriptome data provided to the at least one trained pathway disruption engine only includes gene expression levels of the differentially expressed genes.

Embodiment 112

The system of embodiment 110, wherein the differential metric includes a Benjamini-Hochberg false discovery rate.

Embodiment 113

The system of embodiment 102, wherein the at least one trained pathway disruption engine comprises a model associated with a module in a pathway and configured to receive the portion of the transcriptome data and output a model score, and wherein the at least one pathway engine is configured to: determine whether the model score is above a threshold; and output an indication that the module is disrupted in response to determining the model score is above the threshold.

Embodiment 114

The system of embodiment 113, wherein the threshold is predetermined based on an area under the curve calculated based on a probability distribution of dysregulated patients generated using the model and a probability distribution of non-dysregulated patients generated using the model.

Embodiment 115

The system of embodiment 102, wherein the at least one trained pathway disruption engine comprises a model associated with a module in a pathway, the module comprising a group of genes, the module being configured to receive the portion of the transcriptome data and output a model score, and wherein the module is configured to receive transcriptome data associated with at least one gene included in the group of genes.

Embodiment 116

The system of embodiment 102, wherein the system is further configured to: provide at least one of DNA data or protein data to the at least one trained pathway disruption engine, and wherein the at least one pathway disruption score is generated based on at least one of the DNA data or the protein data.

Embodiment 117

The system of embodiment 102, wherein the system is further configured to: compare the at least one pathway disruption score to at least one threshold to determine a qualitative label for the specimen, wherein the pathway disruption score is a numerical value.

Embodiment 118

The system of embodiment 102, wherein the system is further configured to: estimate a first pathway disruption score for a first cellular pathway; estimate a second pathway disruption score for a second cellular pathway; and report the first pathway disruption score and the second pathway disruption score.

Embodiment 119

The system of embodiment 102, wherein the system is further configured to: estimate a first disruption score for a first module included in a pathway; estimate a second disruption score for a second module included in the pathway; and report the first disruption score and the second disruption score.

Embodiment 120

The system of embodiment 102, wherein the cellular pathway is a RAS/RTK pathway.

Embodiment 121

The system of embodiment 102, wherein the cellular pathway is a PI3K pathway.

Embodiment 122

The system of embodiment 102, wherein the cellular pathway is a TCGA-curated pathway.

Embodiment 123

The system of embodiment 102, wherein the transcriptome data comprises RNA data.

Embodiment 124

The system of embodiment 102, wherein the genetic data further comprises DNA data.

Embodiment 125

The system of embodiment 102, wherein the set of data further comprises protein data.

Embodiment 126

The system of embodiment 102, wherein the specimen is a cancer specimen from a human patient.

Embodiment 127

The system of c embodiment 102, wherein the specimen is an organoid.

Embodiment 128

The system of embodiment 102, wherein the specimen is an organoid derived from a human cancer specimen.

Embodiment 129

The system of embodiment 102, wherein the system is further configured to: associate at least one pathway disruption score with a protein level; and predict a protein level for the specimen.

Embodiment 130

The system of embodiment 102, wherein the system is further configured to: detect a variant having unknown significance in the set of genetic data; and determine the likelihood that the variant is pathogenic based on the pathway disruption score.

Embodiment 131

The system of embodiment 102, wherein the system is further configured to: receive the pathway disruption report; and determine a treatment for a patient associated with the specimen based on the pathway disruption score.

Embodiment 132

The system of embodiment 102, wherein the specimen is derived from an organoid, and wherein the system is further configured to: receive the pathway disruption report; and output a suggestion that the organoid be monitored after exposure to a treatment based on the pathway disruption score.

Embodiment 133

The system of embodiment 102, wherein the system is further configured to: receive the pathway disruption report; and match at least one clinical trial to a patient associated with the specimen based on the pathway disruption score.

Embodiment 134

The system of embodiment 102, wherein the system is further configured to: report a list of matched clinical trials to the patient.

Embodiment 135

The system of embodiment 102, wherein the system is further configured to: report a list of matched clinical trials to a medical professional caring for the patient.

Embodiment 136

The system of embodiment 102, wherein the system is further configured to: analyze clinical data for an association of response to at least one treatment and the at least one pathway disruption score; and suggest a study of the response to the at least one treatment in each of a plurality of patients having a pathway disruption score within the range.

Embodiment 137

The system of embodiment 102, wherein the system comprises a genetic analyzer sub-system.

Embodiment 138

The system of embodiment 102, wherein the system is further configured to: generate the genetic data.

Embodiment 139

The system of embodiment 102, wherein the system is implemented by a cloud-based computing system.

Embodiment 140

The system of embodiment 102, wherein the system is further configured to: perform one or more micro-services.

Embodiment 141

The system of embodiment 102, wherein the system is further configured to: send the pathway disruption report to a variant calling engine

Embodiment 142

The system of embodiment 102, wherein the system is further configured to: send the pathway disruption report to an insight engine

Embodiment 143

The system of embodiment 102, wherein the system is further configured to: send the pathway disruption report to a tumor of unknown origin engine.

Embodiment 144

The system of embodiment 102, wherein the system is further configured to: send the pathway disruption report to a PD-L1 status engine.

Embodiment 145

The system of embodiment 102, wherein the system is further configured to: send the pathway disruption report to a homologous recombination deficiency engine.

Embodiment 146

The system of embodiment 102, wherein the system is further configured to: send the pathway disruption report to a cellular pathway disruption report engine.

Embodiment 147

The system of embodiment 102, wherein the system is further configured to: send the pathway disruption report to a human leukocyte antigen loss of homozygosity engine.

Embodiment 148

The system of embodiment 102, wherein the system is further configured to: send the pathway disruption report to a tumor mutational burden engine.

Embodiment 149

The system of embodiment 102, wherein the system is further configured to: send the pathway disruption report to a microsatellite instability engine.

Embodiment 150

The system of embodiment 102, wherein the system is further configured to: send the pathway disruption report to an immune infiltration engine.

Embodiment 151

The system of embodiment 102, wherein the pathway disruption report comprises information associated with the at least one pathway disruption score, the information comprising at least one of potential causative mutations, variants of unknown significance, recommended therapies for a pathway module included in the cellular pathway, or reference medical literature.

Embodiment 152

The system of embodiment 151, wherein the recommended therapies are presented in a ranked fashion.

Embodiment 153

The method of embodiment 18, further comprising treating the patient.

Embodiment 154

The method of embodiment 75, further comprising treating the patient.

Embodiment 155

A method comprising: receiving a biopsy taken from a cancer site; sequencing a nucleic acid sample retrieved from the biopsy to produce sequence information for the nucleic acid sample; identifying from the sequence information a mutation or pathogen; determining one or more pathways associated with the mutation or pathogen; selecting for inclusion on a sequencing report at least one of the one or more pathways; displaying on the sequencing report a stylized visual depiction of the one or more pathways selected for inclusion.

Embodiment 156

A method according to embodiment 155, wherein the stylized visual depiction of each of the pathways selected for inclusion comprises a directional chain of elements in the pathway.

Embodiment 157

A method according embodiment 155 or 156, wherein the stylized visual depiction of each of the pathways selected for inclusion comprises an emphasized element representing the mutation or pathogen.

Embodiment 158

A method according to any one of embodiments 155 to 158, wherein the stylized visual depiction of at least one of the pathways selected for inclusion comprises a therapy that exerts a biological effect on the pathway.

Embodiment 159

A method according to embodiment 4, wherein the therapy that exerts a biological effect on the at least one of the pathways is depicted as associated with the mutation.

Embodiment 160

A method according to any one of embodiments 155 to 159, wherein the stylized visual depiction of at least one of the pathways presents diagnostic information depicting the mechanism by which the mutation or pathogen causes the cancer.

Embodiment 161

A method according to any one of embodiments 155 to 160, further comprising: determining, for each of the one or more pathways associated with the mutation or pathogen, whether a therapy that exerts a biological effect on the pathway is available, and wherein selecting for inclusion on the sequencing report at least one of the one or more pathways comprises, for each of the one or more pathways, selecting the pathway if a therapy that exerts a biological effect on the pathway is available and deselecting the pathway for inclusion on the sequencing report if a therapy that exerts a biological effect on the pathway is not available.

Embodiment 162

A method according to any one of embodiments 155 to 160, further comprising: determining, for each of the one or more pathways associated with the mutation or pathogen, whether a therapy that exerts a biological effect on the pathway is available; and determining for each available therapy a set of eligibility criteria, and wherein selecting for inclusion on the sequencing report at least one of the one or more pathways comprises, for each of the one or more pathways, (i) selecting the pathway if (a) a therapy that exerts a biological effect on the pathway is available and (b) a patient from which the biopsy was taken meets the criteria, and (ii) deselecting the pathway for inclusion on the sequencing report if (a) a therapy that exerts a biological effect on the pathway is not available or (b) the patient from which the biopsy was taken does not meet the eligibility criteria for the therapy.

Embodiment 163

A method according to any one of embodiments 155 to 160, wherein determining one or more pathways associated with the mutation comprises determining a plurality of pathways and further wherein selecting for inclusion on the sequencing report at least one of the one or more pathways comprises selecting the plurality of pathways for inclusion on the sequencing report.

Embodiment 164

A method according to any one of embodiments 155 to 163, wherein determining one or more pathways associated with the mutation or pathogen comprises querying a database storing pathway-mutation or pathway-pathogen associations.

Embodiment 165

A method according to any one of embodiments 155 to 164, wherein sequencing a nucleic acid sample comprises performing short-read NGS.

Embodiment 166

A method according to any one of embodiments 155 to 165, wherein sequencing a nucleic acid sample comprises performing long-read NGS.

Embodiment 167

A method according to any one of embodiments 155 to 164, wherein sequencing a nucleic acid sample comprises performing Sanger sequencing.

Embodiment 168

A method according to any one of embodiments 155 to 167, wherein identifying from the sequence information a mutation present in the nucleic acid sample comprises identifying a copy number variant present in the nucleic acid sample.

Embodiment 169

A method according to any one of embodiments 155 to 168, wherein identifying from the sequence information a mutation present in the nucleic acid sample comprises identifying a single nucleotide variant present in the nucleic acid sample.

Embodiment 170

A method according to any one of embodiments 15 to 169, wherein identifying from the sequence information a mutation present in the nucleic acid sample comprises identifying an indel present in the nucleic acid sample.

Embodiment 171

A method according to any one of embodiments 155 to 170, wherein sequencing a nucleic acid sample comprises sequencing an RNA sample.

Embodiment 172

A method according to any one of embodiments 155 to 170, wherein sequencing a nucleic acid sample comprises sequencing a DNA sample.

Embodiment 173

A method according to any one of embodiments 155 to 172, wherein: the stylized visual depiction comprises an indication of a therapy; and the therapy is associated with a therapeutic target element downstream of the identified mutation.

Embodiment 174

A method according to embodiment 173, wherein the indication of a therapy is graphically depicted as associated with the therapeutic target element.

Embodiment 175

A method according to either embodiment 173 or embodiment 174, wherein the therapy is associated with a clinical trial.

Embodiment 176

A method according to any one of embodiments 173 to 175, wherein the therapy comprises an off-label use of an approved therapeutic agent.

Embodiment 177

A method according to any one of embodiments 173 to 175, wherein the therapy is comprises use of an approved therapeutic agent.

Embodiment 178

A method according to any one of embodiments 173 to 177, wherein the therapy inhibits pathway signaling.

Embodiment 179

A method according to any one of embodiments 173 to 178, wherein the therapy comprises an immunotherapy.

Embodiment 180

A method according to any one of embodiments 155 to 179, wherein: the stylized visual depiction comprises an

Embodiment 181

A method according to embodiment 180, wherein the indication of the non-therapy is graphically depicted as associated with the corresponding therapeutic target element and wherein the graphical depiction indicates that the therapy should not be used.

Embodiment 182

A method according to any one of embodiments 155 to 181, wherein the one or more pathways includes all or part of the Ras/Raf/MAPK pathway.

Embodiment 183

A method according to any one of embodiments 155 to 181, wherein the one or more pathways includes all or part of the PI3K/AKT/mTOR pathway.

Embodiment 184

A method according to any one of embodiments 155 to 181, wherein the one or more pathways includes all or part of the Wnt pathway.

Embodiment 185

A method according to any one of embodiments 155 to 181, wherein the one or more pathways includes all or part of the JAK/STAT pathway.

Embodiment 186

A method according to any one of embodiments 155 to 181, wherein the one or more pathways includes all or part of the Notch pathway.

Embodiment 187

A method according to any one of embodiments 155 to 181, wherein the one or more pathways includes all or part of the Hedgehog pathway.

Embodiment 188

A method according to any one of embodiments 155 to 183, wherein the mutation is a KRAS mutation.

Embodiment 189

A method according to any one of embodiments 155 to 183, wherein the mutation is a PIK3CA mutation.

Embodiment 190

A method according to any one of embodiments 155 to 183, wherein the mutation is a BRAF mutation.

Embodiment 191

A method according to any one of embodiments 155 to 183, wherein the mutation is a MEK mutation.

Embodiment 192

A method according to any one of embodiments 155 to 183, wherein the mutation is an ERK mutation.

Embodiment 193

A method according to any one of embodiments 155 to 192, further comprising displaying eligibility criteria for a therapy associated with at least one of the one or more pathways selected for inclusion.

Embodiment 194

A method according to any one of embodiments 155 to 193, wherein receiving the biopsy taken from a cancer site comprises receiving a biopsy of a pancreatic tumor, and wherein the one or more pathways relate to pancreatic cancer.

Embodiment 195

A method according to any one of embodiments 155 to 193, wherein receiving the biopsy taken from a cancer site comprises receiving a biopsy of a lung tumor, and wherein the one or more pathways relate to lung cancer.

Embodiment 196

A method according to any one of embodiments 155 to 193, wherein receiving the biopsy taken from a cancer site comprises receiving a biopsy of a brain tumor, and wherein the one or more pathways relate to brain cancer.

Embodiment 197

A method according to any one of embodiments 155 to 193, wherein receiving the biopsy taken from a cancer site comprises receiving a biopsy of a bone tumor, and wherein the one or more pathways relate to bone cancer.

Embodiment 198

A method according to any one of embodiments 155 to 193, wherein receiving the biopsy taken from a cancer site comprises receiving a biopsy of a skin tumor, and wherein the one or more pathways relate to skin cancer.

Embodiment 199

A method according to any one of embodiments 155 to 193, wherein receiving the biopsy taken from a cancer site comprises receiving a biopsy of a breast tumor, and wherein the one or more pathways relate to breast cancer.

Embodiment 200

A method according to any one of embodiments 155 to 193, wherein receiving the biopsy taken from a cancer site comprises receiving a biopsy of a prostate tumor, and wherein the one or more pathways relate to prostate cancer.

Embodiment 201

A method according to any one of embodiments 155 to 193, wherein receiving the biopsy taken from a cancer site indication of a non-therapy; and the non-therapy is associated with a corresponding therapeutic target element upstream of the identified mutation.

comprises receiving a biopsy of a kidney tumor, and wherein the one or more pathways relate to kidney cancer.

Embodiment 202

A method according to any one of embodiments 155 to 193, wherein receiving the biopsy taken from a cancer site comprises receiving a biopsy of a bladder tumor, and wherein the one or more pathways relate to bladder cancer.

Embodiment 203

A method according to any one of embodiments 155 to 193, wherein receiving the biopsy taken from a cancer site comprises receiving a blood sample, and wherein the one or more pathways relate to a blood cancer.

Embodiment 204

A method according to any one of embodiments 155 to 203, wherein displaying a stylized visual depiction of the one or more pathways comprises, for each of the stylized visual depictions: displaying a plurality of genes in an order from upstream to downstream; displaying arrows between adjacent genes in the order; and displaying an indication of where a downstream gene interacts with cell growth and proliferation.

Embodiment 205

A method according to any one of embodiments 155 to 204, further comprising displaying on the sequencing report, for each of the one or more pathways selected for inclusion, a pathway description.

Embodiment 206

A method according to embodiment 205, wherein the pathway description comprises a description of the mutation and the effects of the mutation on a type of cancer.

Embodiment 207

A method according to either embodiment 205 or 206, wherein the pathway description comprises a description of a clinical trial, the description of the clinical trial comprising one or more of the group consisting of: a clinical trial number, a therapeutic agent, an action of the therapeutic agent, a target element in the pathway upon which the therapeutic agent acts, eligibility criteria for the clinical trial, an effect of the mutation or pathogen on a type of cancer, a mechanism by which a mutation or pathogen causes cancer.

Embodiment 208

A method according to any one of embodiments 155 to 207, wherein: identifying a mutation or pathogen comprises identifying a mutation, the one or more pathways comprises one or more pathways associated with the mutation, and the one or more pathways indicates whether the mutation is associated with a gain-of function mutation or a loss-of-function mutation.

Embodiment 209

A method according to any one of embodiments 155 to 207, wherein: identifying a mutation or pathogen comprises identifying a pathogen, and displaying the one or more pathways comprises displaying one or more pathways depicting pathogen-mediated oncogenesis.

Embodiment 210

A method according to embodiment 209, further wherein displaying the one or more pathways comprises displaying, as associated with an element of the one or more pathways, a therapy that exerts a biological effect on the one or more pathways.

Embodiment 211

A method according to either embodiment 209 or 210, further wherein displaying the one or more pathways comprises displaying an indication of one or more cancer types associated with the pathogen or pathway.

Example 1: Module Construction for Pathway RAS/RTK and Pathway PI3K

As discussed in previously (see e.g., paragraph 151), it is often useful for pathways to be subdivided into modules rather than their individual proteins, with the modules including proteins with a relevant similarity, e.g., sequence similarity; function in terms of their effects on pathway activity; and/or level/position within the pathway, i.e., the proteins receive signals from the same upstream proteins and transmit their signal to the same downstream proteins. Several of these characteristics are related; for instance, proteins with similar amino acid sequences often have similar functions and similar levels within the pathway. For the purposes of constructing a pathway engine, the total set of proteins defined by the set of modules may not comprise the entire pathway as defined in the literature, which can often consist of dozens of proteins. Rather, only those modules with clinical relevance would be included, such as modules with proteins that a) are directly targetable by existing or experimental therapeutics; b) are commonly mutated or otherwise disrupted in a particular cancer type or subtype of interest; c) when mutated or otherwise disrupted, confer sensitivity or resistance to a particular therapy or class of therapy; d) when mutated or otherwise disrupted, confer prognostic significance, including an effect on progression free survival, overall survival, or metastasis risk; or e) a combination of these factors. This should not be considered an exhaustive list of clinical variables that may inform module generation. In the cases of the modules in both pathways described herein (RTK/RAS and PI3K), the constituent proteins were driven by the factors above, in combination with curated pathway definitions, such as that provided in doi: 10.1016/j.cell.2018.03.035 (depicted in FIG. 1A).

RTK/RAS Pathway, (see e.g., FIG. 1A; FIG. 12A)

In this example for the RTK/RAS pathway, three modules were constructed based on the above criteria, the RAS, RAF, and MEK modules. The RAS protein family consists of three members, KRAS, NRAS, and HRAS. These are highly similar, powerful growth-promoting proteins that are mutated in several cancers, including lung adenocarcinoma. KRAS is the most commonly mutated protein in this cancer type, and mutations in this gene have important significance for treatment choice. For example, patients with the KRAS G12C mutation can be treated with a targeted therapy. The RAF module also consists of three structurally similar proteins, namely, ARAF, BRAF, and CRAF/RAF1, which integrate signaling from the upstream RAS proteins. RAF protein mutations also have significant relevance to treatment given that a) the most common BRAF mutation (V600E) is targetable by a precision therapy, and b) cancers with mutated RAF proteins may be less likely to respond to therapies that target higher in the RTK/RAS pathway (e.g., KRAS- or EGFR-targeted therapies). The third and fourth modules selected from the RTK/RAS pathway are the MEK (MAP2K1) and ERK (MAPK1, MAPK3) modules. These proteins integrate signaling from the upstream RAS and RAF modules and are the most commonly mutated members of this protein family in lung adenocarcinoma. Moreover, there are multiple targeted therapies that inhibit the proteins in this module.

PI3K Pathway, (See e.g., FIGS. 1A and 12A)

In this example the PI3K pathway is herein composed of four modules: PIK3C, PTEN, AKT, and TOR. The first of these consists of PIK3CA and PIK3CB, which are two versions of the protein p110, the catalytic subunit of the PI3K complex, which is the central mediator of PI3K signaling. PIK3CA is more commonly mutated in lung adenocarcinoma and also has an FDA-approved targeted therapy (doi: 10.18632/oncotarget.2834). The PTEN module consists of those proteins that negatively regulate PIK3C activity, namely, PTEN, PIK3R1, PIK3R2, and PIK3R3. Loss of these proteins can therefore promote cancer growth. Although there are no targeted therapies for mutations in these genes, it can be expected that a loss of function of one of these inhibitors will have a distinct (but similar) effect than an activating mutation in PIK3CA/B, which is the rationale for including the inhibitors and activators in separate modules. Difference between the transcriptional effects of activator/inhibitor disruption may be due to a) PTEN module proteins signaling through separate pathways to mediate different functions, and/or b) PIK3CA/B being negatively regulated by other proteins or complexes. The third and fourth PI3K modules are AKT (AKT1, AKT2, AKT3) and TOR (MTOR, RICTOR, RPTOR). The proteins in these modules are responsible for mediating PI3K signaling and therefore promote growth. They are included as separate modules because there are targeted therapies that can inhibit the activity of either module.

Additional Considerations

During the course of model training, there may be an advance in the field that would necessitate a change to the modules or the addition of a new module. For example, it may be discovered that overexpression of the protein RHEB, another positive regulator of PI3K activity, is common in the cancer of interest and has a targeted inhibitor. A new module containing RHEB would then be included in the pathway, and a disruption model would be trained to detect disruption.

EGFR and ERBB2 are treated differently from the other modules in that they are not considered a priori to be part of the RTK/RAS or PI3K pathways. The reason for this is that these proteins signal through both pathways simultaneously. Deciding upon which proteins are part of each pathway is important for several reasons, but the relevance in this context is that module disruption is determined by comparing the transcriptional output of samples with disrupted modules (positive samples) to samples with no pathway member mutations (negative samples). As EGFR and ERBB2 feed into both pathways, when generating disruption scores for these proteins, it would not be appropriate to designate negative samples as those that are free of either RAS/RTK or PI3K pathway mutations. Two options remain, the first being to require that the negative samples have no mutations in either pathway, and the second being to treat EGFR and ERBB2 independently and require that negative samples have no mutations in these genes only. The first option is excluded because the vast majority of samples will have RTK/RAS or PI3K pathway mutations, and the number of samples without mutations in either pathway would be insufficient to serve as a negative control group. The second option is therefore selected. For example, the EGFR disruption model is trained using samples with pathogenic/likely pathogenic EGFR mutations as positive samples and samples without any EGFR mutations as negative samples. EGFR and ERBB2 are themselves considered separately because they each have distinct targeted therapies that inhibit their function. Importantly, when disruption scores for other modules are being generated, although EGFR and ERBB2 are considered distinct modules from the RTK/RAS and PI3K pathways, samples with mutations in EGFR and/or ERBB2 are not permitted in the negative sample groups because their disruption is likely to result in transcriptional effects that are in some ways similar to disruption of both pathways. Accordingly, other pathways that include genes with a diverse signaling activity similar to that of EGFR and ERBB2 can be similarly addressed in model development and training.

Example 2: Survey of KRAS and PI3K Pathway Dysregulation in a Cohort of More than 1,500 Solid Tumors In a cohort of more than 1,500 patients with lung adenocarcinoma, logistic regression analysis was performed on exome-capture RNA-seq expression profiles to identify the transcriptomic characteristics of disrupted KRAS and PI3K signaling using the pathway modules as described in Example 1.

In this example, patient samples were processed through RNA whole exome short-read next generation sequencing (NGS) to generate RNA sequencing data, and the RNA sequencing data were processed by a bioinformatics pipeline to generate a RNA-seq expression profile for each patient sample.

Specifically, solid tumor total nucleic acid (DNA and RNA) was extracted from macrodissected FFPE tissue sections and digested by proteinase K to eliminate proteins. RNA was purified from the total nucleic acid by TURBO DNase-I to eliminate DNA, followed by a reaction cleanup using RNA clean XP beads to remove enzymatic proteins. The isolated RNA was subjected to a quality control protocol using RiboGreen fluorescent dye to determine concentration of the RNA molecules.

Library preparation was performed using the KAPA Hyper Prep Kit in which 100 ng of RNA was heat fragmented in the presence of magnesium to an average size of 200 bp. The libraries were then reverse transcribed into cDNA and Roche SeqCap dual end adapters were ligated onto the cDNA. cDNA libraries were then purified and subjected to size selection using KAPA Hyper Beads. Libraries were then PCR amplified for 10 cycles and purified using Axygen MAG PCR clean up beads. Quality control was performed using a PicoGreen fluorescent kit to determine cDNA library concentration. cDNA libraries were then pooled into 6-plex hybridization reactions. Each pool was treated with Human COT-1 and IDT xGen Universal Blockers before being dried in a vacufuge. RNA pools were then resuspended in IDT xGen Lockdown hybridization mix, and IDT xGen Exome Research Panel v1.0 probes were added to each pool. Pools were incubated to allow probes to hybridize. Pools were then mixed with Streptavidin-coated beads to capture the hybridized molecules of cDNA. Pools were amplified and purified once more using the KAPA HiFi Library Amplification kit and Axygen MAG PCR clean up beads, respectively. A final quality control step involving PicoGreen pool quantification, and LabChip GX Touch was performed to assess pool fragment size. Pools were cluster amplified using Illumina Paired-end Cluster Kits with a PhiX-spike in on Illumina C-Bot2, and the resulting flow cell containing amplified target-captured cDNA libraries were sequenced on an Illumina HiSeq 4000 to an average unique on-target depth of 500× to generate a FASTQ file.

In this example, the cDNA library preparation was performed with an automated system, using a liquid handling robot (SciClone NGSx).

Each FASTQ file contained paired-end reads, each of which was associated with a quality rating. The reads in each FASTQ file were processed by a bioinformatics pipeline. FASTQ files were analyzed using FASTQC for rapid assessment of quality control and reads. For each FASTQ file, each read in the file was aligned to a reference genome (GRch37) using kallisto alignment software. This alignment generated a SAM file, and each SAM file was converted to BAM, BAM files were sorted, and duplicates were marked for deletion.

For each gene, the raw RNA read count for a given gene was calculated by kallisto alignment software as a sum of the probability, for each read, that the read aligns to the gene. Raw counts are therefore not integers in this example. The raw read counts were saved in a tabular file for each patient, where columns represented genes and each entry represented the raw RNA read count for that gene.

Raw RNA read counts were then normalized to correct for GC content and gene length using full quantile normalization and adjusted for sequencing depth via the size factor method. Normalized RNA read counts were saved in a tabular file for each patient, where columns represented genes and each entry represented the raw RNA read count for that gene. For training, positive cases were defined as patients with pathogenic KRAS or STK11 mutations, respectively, and negative cases were defined as patients with no pathogenic or potentially pathogenic mutations in the considered pathway. (See FIG. 14)

In this example, the distinction between pathogenic, potentially pathogenic, and other mutations is made separately for mutations at the nucleotide level (e.g., single nucleotide variations (SNVs), insertions/deletions (indels)) and mutations at the gene level (i.e., gene copy number variations (CNVS)). For SNV/indels, classifications are primarily made using criteria set forth by the American College of Medical Genetics and Genomics (ACMG). In these criteria, multiple levels of evidence for a variant's level of pathogenicity, including the frequency of the variant in the population, direct clinical evidence, and the expected effects of the variant on gene expression and/or the function of the translated protein, are integrated to generate a final determination, ranging from "Pathogenic" to "Benign". Additional, limited, criteria for SNV/indel pathogenicity were generated using a proprietary DNA variant database. For CNVs, the determination of pathogenicity may be based on information in a pathogenic database. For instance, the pathogenic database may contain pathogenicity information based on various factors, such as whether the particular variant can be targeted by an FDA-approved therapy.

The final models (pathway engines) for both RAS (KRAS, HRAS, NRAS) and PI3K (PIK3CA and PIKCB) disruption were statistically powerful, with AUCs greater than or equal to ≈0.84. In one example, the AUC was 0.90. Moreover, both models were validated using external datasets, and the outputs were correlated with relevant protein expression data. Notably, in both models, more than 10% of patients defined as wild type for the pathway scored greater than the selected cutoff threshold value for pathway disruption, suggesting that these patients may be hidden responders having pathway disruption that would not be detected by DNA analysis alone.

The cutoff threshold value for each model was chosen by selecting the value that maximized the F1 score, a statistical measure defined as the harmonic mean of the precision (True positives)/(True positives+False positives) and the recall (True positives)/(True positives+False negatives). For the PI3K disruption model, due to the irregular distribution of scores returned for the negative control group, it was required that outliers first be removed before the maximum F1 score was determined. In other embodiments, due to unbalanced group sizes or the importance of one metric of success over another (e.g., precision over recall), the threshold that maximizes another metric may be desirable, including a) Youden's J statistic (specificity+sensitivity−1), b) accuracy (True positives+True negatives)/(Total number of samples), c) precision, or d) recall.

Preliminary analyses indicate that many of these patients carry variants of unknown significance in genes that tangentially interact with the considered pathway. This provides further evidence that the models' outputs reflect true pathway disruption and indicates that these variants of unknown significance and others to be revealed by additional analyses may be novel target mutations in novel target genes, discovered using the systems and methods disclosed herein. In conclusion, highly sensitive transcriptomic models are developed to detect oncogenic signaling in the absence of canonical pathway mutations and identify additional patients who may respond to targeted therapeutics.

Example 3: Pathway Dysregulation Identification in a Subject Diagnosed with Lung Adenocarcinoma—RAS/RTK Pathway In one example, a cancer specimen was collected from a patient having lung adenocarcinoma cancer. The specimen was processed as described above in Example 2. Briefly, the cancer specimen was processed by whole exome RNA-seq to generate a BAM file with mapped RNA reads, which were analyzed by a bioinformatics pipeline to determine raw and normalized counts for RNA molecules for each gene to generate a transcriptome value set containing a collection of numeric values wherein each numeric value was associated with a gene and represented a normalized number of detected read counts that aligned to that gene, also described as an expression level of that gene. The dataset contained expression levels for approximately 19,000 distinct genes.

The transcriptome value set was analyzed as described in 710 by a pathway engine 200$n$ (trained as described in 520, with positive controls and negative controls determined based on the presence or absence of genetic variants in RAS/RTK pathway genes, which include, for this example, the genes of the following modules: the EGFR module, the RAS module, the RAF module, the MEK module, the ERK module, see e.g., FIG. 12A). The RAS/RTK pathway engine generated a score of 2.0, indicating likely dysregulation of the RAS/RTK pathway.

A pathway disruption report was generated including the score and the predicted dysregulation status of the RAS/RTK pathway. The pathway disruption report further included the matched therapies trametinib and dabrafenib, and the following matched clinical trials: NCT03543306, Dabrafenib and Trametinib in Patients With Non-small Cell Lung Cancer Harboring V600E BRAF Mutation, and histograms comparing the patient's score to a collection of patient scores in a database. Also included were a list of the variant(s) considered to be responsible for driving the dysregulation. Examples of a dysregulation-causing variant could include a KRAS gain of function mutation (see FIGS. 10B through 10H).

Example 4: Identify Pathway Dysregulation in a Tumor Sample of Unknown Origin—RAS/RTK Pathway In one example, a cancer specimen was collected from a patient having a tumor of unknown origin. The specimen was processed as described above in Example 2. Briefly, the cancer specimen was processed by whole exome RNA-seq to generate a BAM file with mapped RNA reads, which were analyzed by a bioinformatics pipeline to determine raw and normalized counts for RNA molecules for each gene to generate a transcriptome value set containing a collection of numeric values wherein each numeric value was associated with a gene and represented a normalized number of detected read counts that aligned to that gene, also described as an expression level of that gene. The dataset contained expression levels for approximately 19,000 distinct genes.

The transcriptome value set was analyzed to assign a cancer type as described in U.S. Prov. Patent App. No. 62/855,750 and the most likely cancer type for the transcriptome was determined to be lung adenocarcinoma.

The transcriptome value set was analyzed as described in 710 by a lung cancer-specific pathway engine 200n (trained as described in 520, where all training data transcriptomes had been associated with lung cancer and positive controls and negative controls were determined based on the presence or absence of genetic variants in RAS/RTK pathway genes, which include, for this example, the genes of the following modules: the EGFR module, the RAS module, the RAF module, the MEK module, the ERK module, see e.g., FIG. 12A). The RAS/RTK pathway engine generated a score of 2.2, strongly indicating dysregulation of the RAS/RTK pathway, although no causative mutations were detected in the patient's DNA.

A pathway disruption report was generated including the score and the predicted dysregulation status of the RAS/RTK pathway, as well as information indicating that the cause of the disruption was unknown. The point on the pathway showing disruption was indicated, and potential targets downstream of this point were indicated, as were suggested therapies. Histograms comparing the patient's score to a collection of patient scores in a database would also be provided (see FIG. 10A).

Example 5: Identify Pathway Dysregulation in a Subject Diagnosed with Lung Adenocarcinoma—PIK3 Pathway In one example, a cancer specimen was collected from a patient having lung adenocarcinoma cancer. The specimen was processed as described above in Example 2. Briefly, the cancer specimen was processed by whole exome RNA-seq to generate a BAM file with mapped RNA reads, which were analyzed by a bioinformatics pipeline to determine raw and normalized counts for RNA molecules for each gene to generate a transcriptome value set containing a collection of numeric values wherein each numeric value was associated with a gene and represented a normalized number of counts of that gene, also described as an expression level of that gene. The dataset contained expression levels for approximately 19,000 distinct genes.

The transcriptome value set was analyzed as described in 710 by a pathway engine 200n (trained as described in 520, with positive controls and negative controls determined based on the presence or absence of genetic variants in PI3K pathway genes, which include, for this example, the genes of the following modules: ERBB2, PI3K, PTEN, AKT, and TOR, see e.g., FIG. 12A). The PI3K pathway engine generated a score of 0.5, indicating likely dysregulation of the PI3K pathway.

The pathway disruption report further recommended against the use of PDL1 inhibitors, which have been shown to have reduced efficacy in STK11 mutant cancers. There are currently no specific matched therapies for patients with STK11 mutations, but the following matched clinical trial was recommended: NCT02664935, National Lung Matrix Trial: Multi-drug Phase II Trial in Non-Small Cell Lung Cancer. Also included were histograms comparing the patient's score to a collection of patient scores in a database and the variant(s) considered to be responsible for driving the dysregulation. Examples of a dysregulation-causing variant could include a PIK3CA gain of function mutation (see FIGS. 11B through 11D).

Example 6: Identify Pathway Dysregulation in a Tumor Sample of Unknown Origin—PI3K Pathway In one example, a cancer specimen was collected from a patient having lung adenocarcinoma cancer. The specimen was processed as described above in Example 2. Briefly, the cancer specimen was processed by whole exome RNA-seq to generate a BAM file with mapped RNA reads, which were analyzed by a bioinformatics pipeline to determine raw and normalized counts for RNA molecules for each gene to generate a transcriptome value set containing a collection of numeric values wherein each numeric value was associated with a gene and represented a normalized number of counts of that gene, also described as an expression level of that gene. The dataset contained expression levels for approximately 19,000 distinct genes.

The transcriptome value set was analyzed as described in 710 by a pathway engine 200n (trained as described in 520, with positive controls and negative controls determined based on the presence or absence of genetic variants in PI3K pathway genes which include, for this example, the genes of the following modules: ERBB2, PI3K, PTEN, AKT, and TOR, see e.g., FIG. 12A). The PI3K pathway engine generated a score of 1.0, strongly indicating dysregulation of the PI3K pathway.

Although no causative mutations were detected in the patient's DNA, the pathway disruption report nonetheless recommended against the use of PDL1 inhibitors due to the pathway disruption score, which have been shown to have reduced efficacy in STK11 mutant cancers. Also included were histograms comparing the patient's score to a collection of patient scores in a database. There were no detected pathogenic variants considered to be responsible for driving the dysregulation (see FIG. 11A).

Example 7: STK11 Disruption Score is Predictive of Response to Immunotherapy at 6 Months In addition to guiding treatment choice, the methods disclosed herein are also useful in predicting treatment response, survival, or other outcome parameters. In this example, biopsy samples from 114 lung cancer patients were analyzed. All patients were receiving PD-L1 inhibitor immunotherapy. It is known that STK11 mutations are contraindicated for this class of drugs.

We hypothesized that the STK11 disruption score would correlate with response, regardless of mutation status. Accordingly, all samples were analyzed in the STK11 disruption model, and scores were plotted by progression for patients having 6-month response data.

Figure 28:
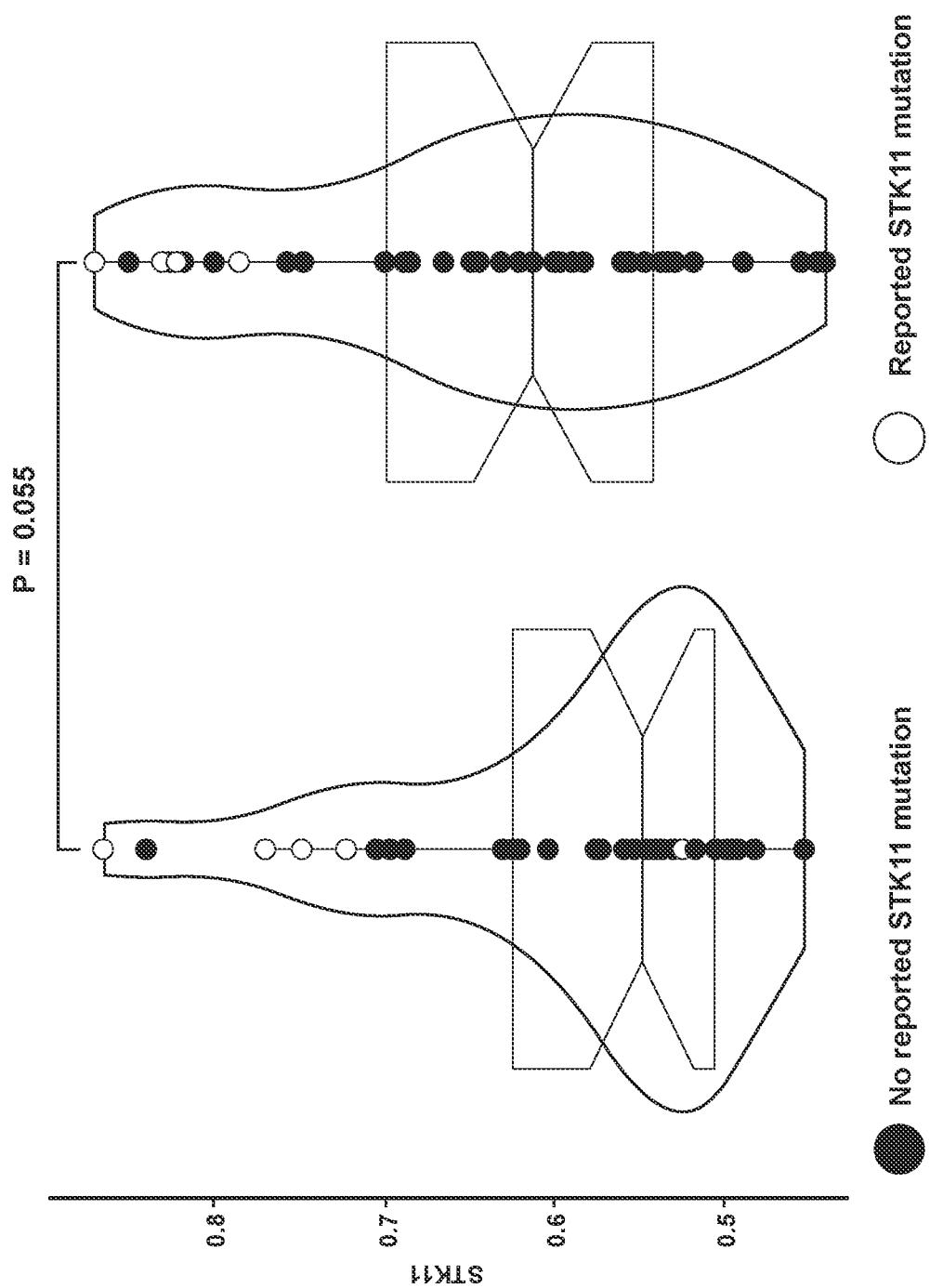
FIG. 28 shows violin plots indicating STK11 disruption score (Y-axis) and progression or no progression (X-axis) of disease 6-months after immunotherapy regimen.

As shown in FIG. 28, patients with progression do have higher scores, with colored dots indicating individual samples, yellow dots representing patients with pathogenic STK11 mutations and red dots representing patients without pathogenic STK11 mutations. The difference is maintained even when considering only patients without mutations (red dots only, p=0.042), showing that the score is capturing relevant treatment, solely from a transcriptome-based score.

Figure 29:
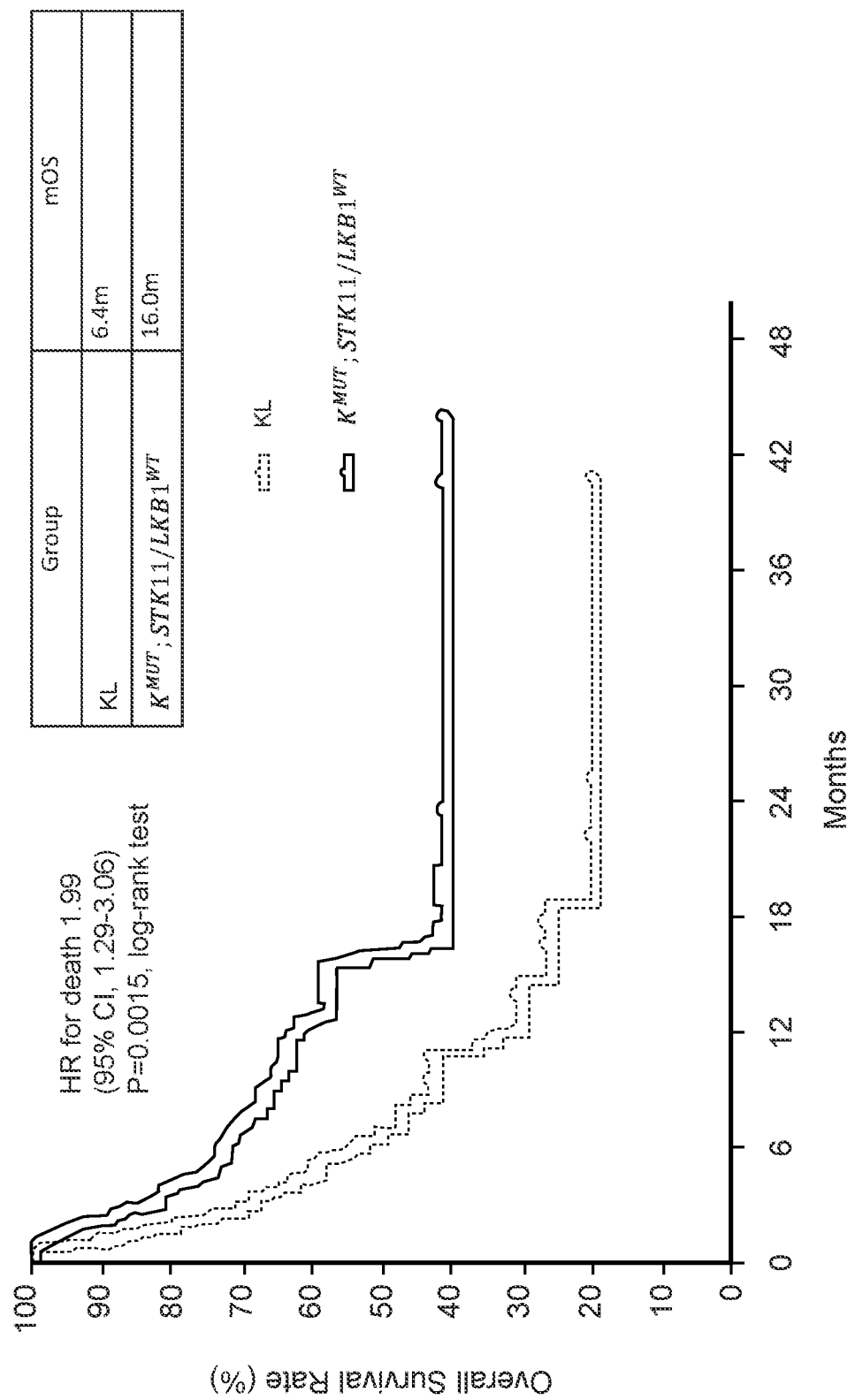
FIG. 29 is a graph that illustrates overall survival % (Y-axis) versus time (X-axis) for KRAS-mutant lung adenocarcinoma patients with or without STK11ILKB1 mutations, treated with PD-1 inhibitor (Skoulidis et al, Cancer Discov. 2018 DOI: 10.1158/2159-8290.CD-18-0099, FIG. 2B, right panel).

FIG. 29 (see Skoulidis et al, Cancer Discov. 2018 DOI: 10.1158/2159-8290.CD-18-0099, FIG. 2B, right panel) shows that this trend is consistent with the literature; patients harboring both KRAS and STK11 mutations respond more poorly to PD-L1 inhibition than patients with a KRAS mutation alone. Group KL includes subjects with both a KRAS and STK11 mutation.

Figure 30:
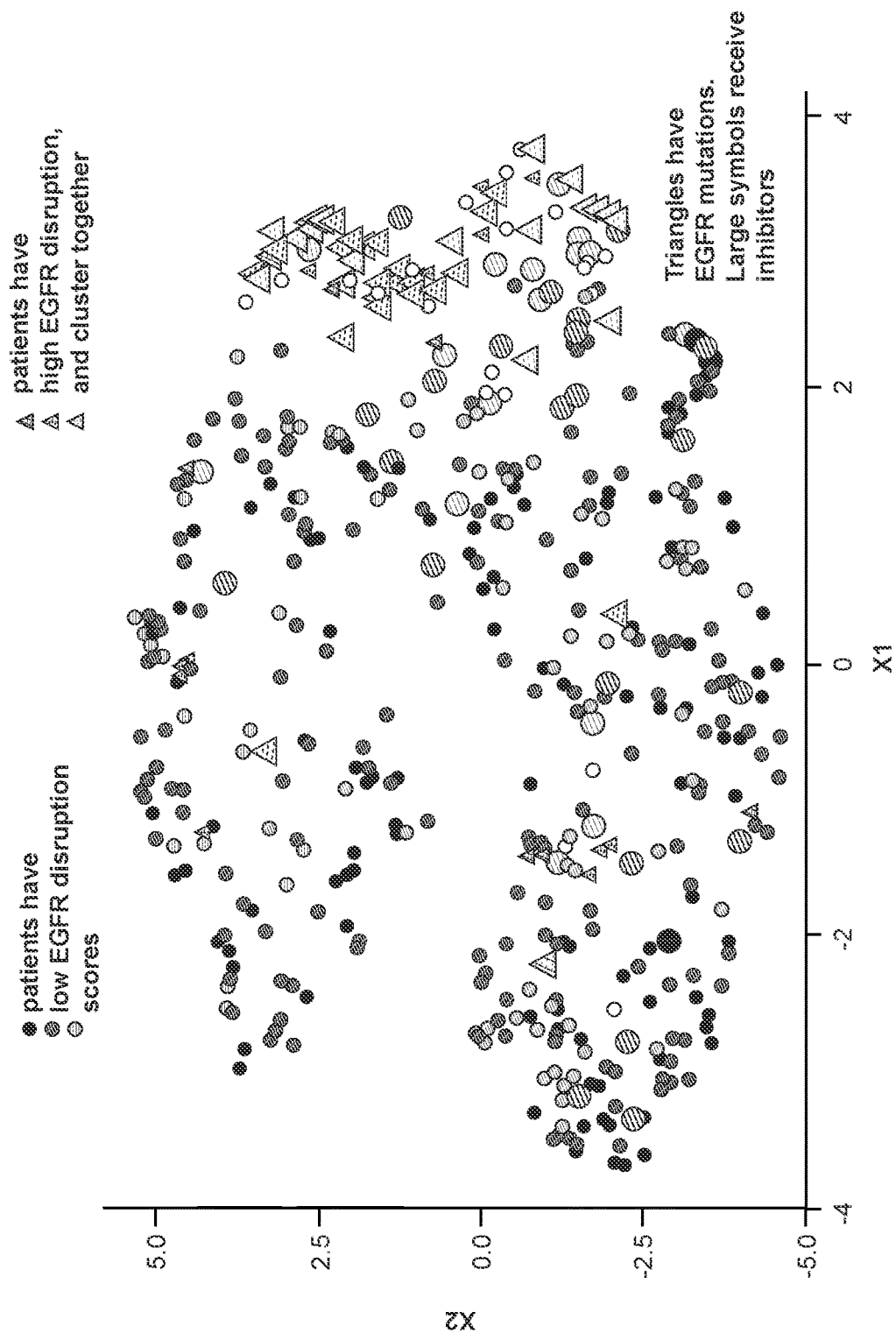
FIG. 30 is a graph that shows a 2-dimensional clustering of 527 patients based on their disruption scores for the constituent modules of the PI3K and RTK/RAS pathways.

Example 8: EGFR Disruption Score Identifies Additional Patients Who May Benefit from Inhibitor Therapy In this example, biopsy samples from 527 lung cancer subjects with treatment data were analyzed using a metapathway approach (see e.g., Example 8, below). FIG. 30 shows a UMAP of the cohort created using the metapathway scores for the RTK/RAS and PI3K pathways. The colors are determined by the degree of EGFR disruption, with green and yellow indicating high disruption, and clustering on the right. These lighter colors correlate well with EGFR mutation status, with the triangles representing those patients with pathogenic EGFR mutations. There is also a strong correlation between high EGFR disruption scores and patients who received an EGFR inhibitor, represented by the larger symbols. Those patients with high scores (defined as the top quintile) and without mutations, and who did not receive inhibitors, are shown as red dots. These patients represent a population that could have potentially benefitted from inhibitor treatment and comprise 4% of the population. That is, 4% of patients are potential hidden responders. These patients have high EGFR pathway disruption but were not treated with EGFR inhibitor therapy because they lack known pathogenic EGFR mutation. Seventeen percent of the cohort received an inhibitor; therefore, an additional 4% of patients who could potentially benefit from this treatment reflects a substantial increase.

Example 9: Exemplary Metapathway Assembly and Sample Analysis

Example 8 discloses a system comprising a plurality of pathways engines 200n for the RTK/RAS-PI3K-EGFR pathway, which may also be referred to as the RTK-RAS pathway 1200. See FIGS. 12A through 12F, 23, 24, and 25 for example reports generated by this system. Each pathway engine is trained (as described in FIG. 5) in association with one gene class in the RTK/RAS-PI3K-EGFR pathway and/ or a module included in the RTK-RAS pathway 1200. For example, each pathway engine can include a model (e.g., a linear regression model) trained using the process 502 in FIG. 5. The EGFR module 1205 can include the genes in the EGFR gene class. The RAS module 1210 can include the genes in the RAS gene class. The RAF module 1215 can include the genes in the RAF gene class. The PTEN module 1220 can include the genes in the PTEN gene class. The ERBB2 module 1225 can include the genes in the ERBB2 gene class. The PI3K module 1230 can include the genes in the PI3K gene class. The AKT module 1235 can include the genes in the AKT gene class. The TOR module 1240 can include the genes in the TOR gene class. The MEK module 1245 can include the genes in the MEK gene class. The ERK module 1250 can include the genes in the ERK gene class.

Each pathway engine can be trained on a number of positive controls and a number of negative controls. In Example 8, each positive control can include a DNA mutation (e.g., a pathogenic variant) associated with dysregulation in the gene class (e.g., the RAS gene class) and/or the module (e.g., the RAS module 1210) associated with the pathway engine. The DNA mutation may be germline or somatic. For example, the positive controls used to train a first pathway engine have mutations in at least one of the genes in the PTEN gene class (including PTEN, PIK3R1, PIK3R2, and PIK3R3); the positive controls used to train a second pathway engine have mutations in at least one of the genes in the ERBB2 gene class (including ERBB2); the positive controls used to train a third pathway engine have mutations in at least one of the genes in the PI3K gene class (including PIK3CA and PIK3CB); the positive controls used to train a fourth pathway engine have mutations in at least one of the genes in the AKT gene class (including AKT, AKT2, and AKT3); the positive controls used to train a fifth pathway engine have mutations in at least one of the genes in the TOR gene class (including RICTOR, RPTOR, and MTOR); the positive controls used to train a sixth pathway engine have mutations in at least one of the genes in the EGFR gene class (including EGFR); the positive controls used to train a seventh pathway engine have mutations in at least one of the genes in the RAS gene class (including KRAS, NRAS, and HRAS); the positive controls used to train an eighth pathway engine have mutations in at least one of the genes in the RAF gene class (including RAF1, BRAF, and ARAF); the positive controls used to train a ninth pathway engine have mutations in at least one of the genes in the MEK gene class (including MAP2K1); the positive controls used to train a tenth pathway engine have mutations in at least one of the genes in the ERK gene class (including MAPK3, MAPK1).

Each negative control used to train the pathway engine can include no DNA mutations of any type in any gene included in the module associated with the pathway engine or any other module included in the entire pathway that includes the module. For example, for a pathway engine trained to detect dysregulation in the RAS class and/or the RAS module 1210, each negative control includes no mutations in the KRAS, NRAS, and/or HRAS genes included in the RAS module 1210, as well as no mutations in any gene included in every other module included in the RTK-RAS pathway 1200 (e.g., only benign and/or likely benign germline variants may be included in the genes included in the pathway). For example, the negative controls used to train each of the first pathway engine, the second pathway engine, the third pathway engine, the fourth pathway engine, the fifth pathway engine, the sixth pathway engine, the seventh pathway engine, the eighth pathway engine, the ninth pathway engine, and the tenth pathway engine include no mutations of any kind (e.g., pathogenic variants, likely pathogenic variants, variant of unknown origin, etc.) in any of the genes included in the PTEN gene class, the ERBB2 gene class, the PI3K gene class, the AKT gene class, the TOR gene class, the EGFR gene class, the RAS gene class, the RAF gene class, the MEK gene class, and the ERK gene class.

Figure 14:
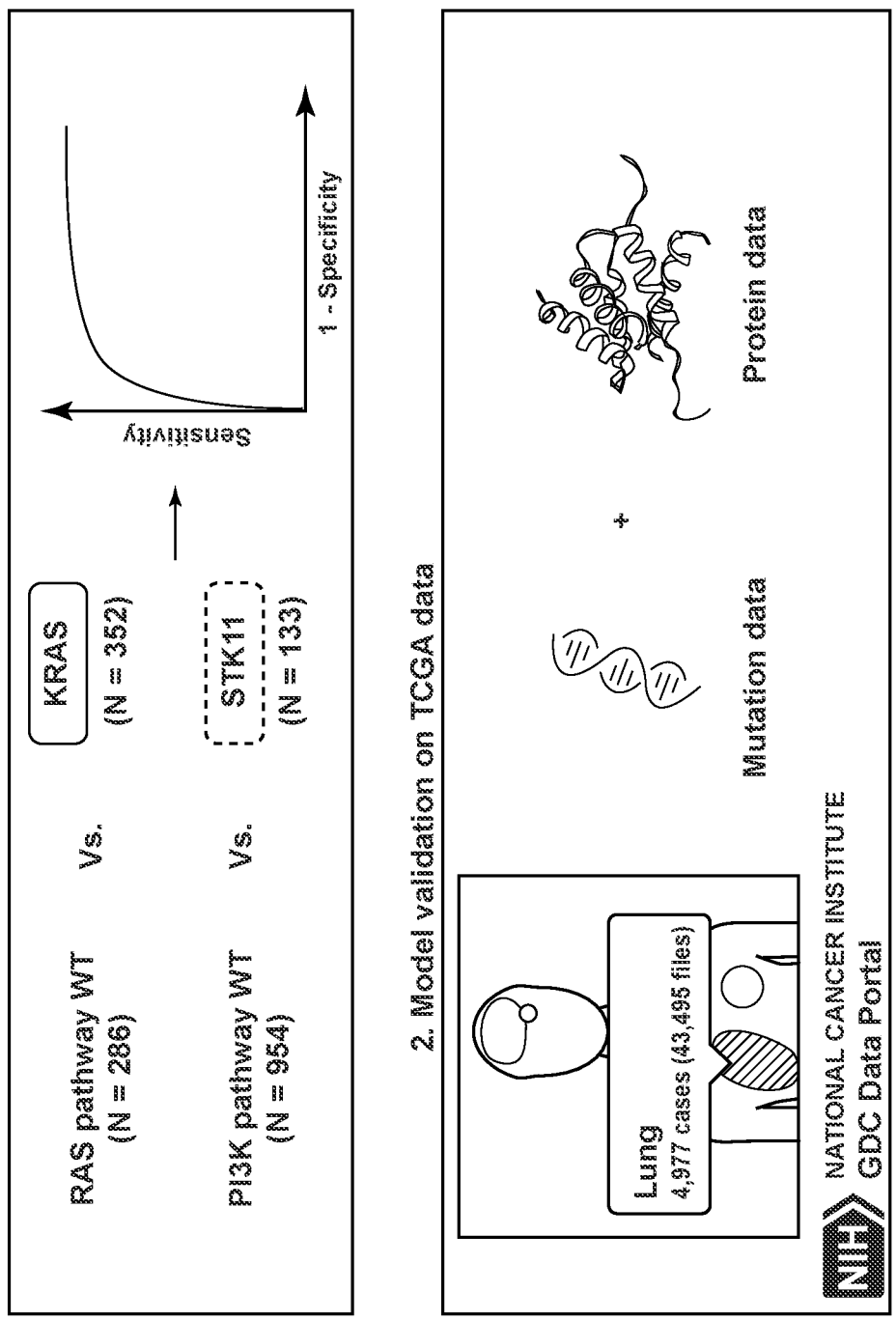
FIG. 14 is an example of analyzing transcriptomes from a cohort of LUAD patients using the systems and methods.

FIG. 14 is an example of analyzing transcriptomes from a cohort of LUAD patients using the systems and methods. In this example, the systems and methods distinguish patients with known activation, such as those having either a KRAS or STK11 mutation, from patients for whom there is some degree of confidence that the pathway is not active, for example, patients having wild type copies of all genes known to be relevant to the pathway of interest.

In this example, a measure of pathway activity was generated for both groups and the pathway activity measure for the groups is significantly separated, as demonstrated by a statistical measurement, for example, a high AUC value.

Figures 15A, 15B:
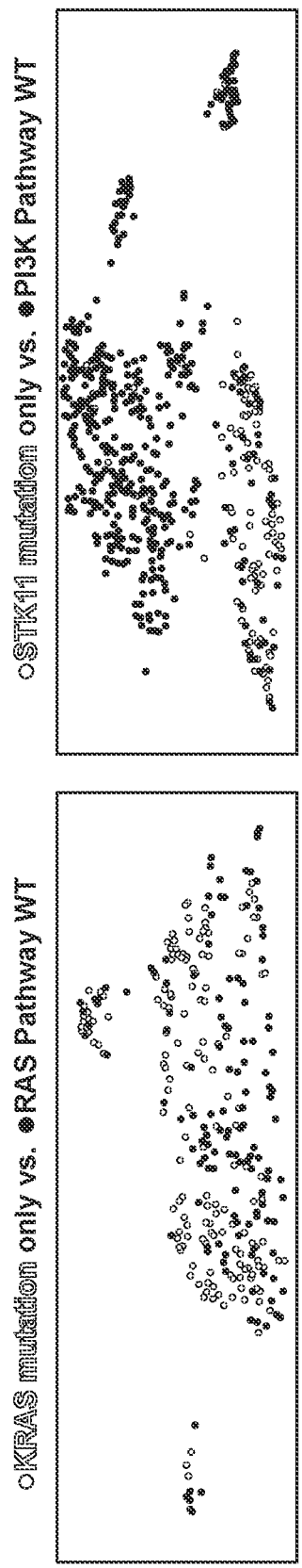
FIGS. 15A and 15B are examples of testing the ability of an alternative method to separate positive controls from negative controls through dimensionality reduction using DEGs and pathway scores.

FIGS. 15A and 15B are examples of testing the ability of an alternative method to separate positive controls from negative controls through dimensionality reduction using DEGs and pathway scores.

In FIG. 15A, dimensionality reduction, including principal component analysis (PCA) and/or Uniform Manifold Approximation and Projection (UMAP), is not universally applicable for distinguishing between positive controls (specimens having KRAS or STK11 mutations, shown as red circles) and negative controls (specimens having wild type RAS or PI3K pathways, shown as blue circles), which do not form sufficiently distinct PCA/UMAP clusters in this example.

In FIG. 15B, an additional, alternative method, including standard ssGSEA methods, could not sufficiently distinguish between positive controls (red) and negative controls (blue). One potential reason is that these methods rely on relatively small gene sets and the transcriptional effect of disruption is going to be more varied and richer, and may require the analysis of a larger gene set in order to distinguish between the two groups.

In conclusion, these older methods may not be sufficient for distinguishing between positive and negative controls and for training a model to calculate pathway disruption scores.

Figures 16A, 16B:
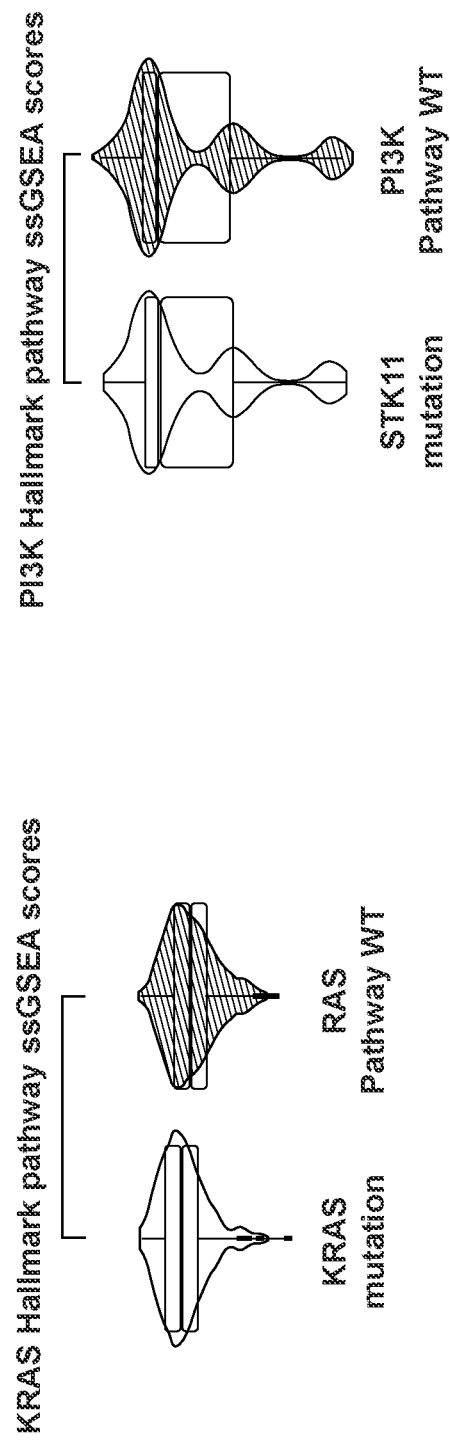
FIGS. 16A and 16B collectively illustrate that the systems and methods disclosed herein can distinguish between negative and positive controls for the pathway of interest.

FIGS. 16A and 16B collectively illustrate that the systems and methods disclosed herein can distinguish between negative and positive controls for the pathway of interest.

A logistic regression model trained according to 520, using DEGs, separates KRAS (FIGS. 17A-B) or STK11 (FIGS. 17C-D) mutation carriers from pathway WT groups. WT groups are groups of specimens with no mutations in the TCGA-defined pathway (RAS or PI3K).

In this example, 10-fold cross-validation was performed using DEGs defined for each in-fold, as described in 610.

In this example, the final model was trained on DEGs determined using all considered samples.

Figures 17A, 17B:
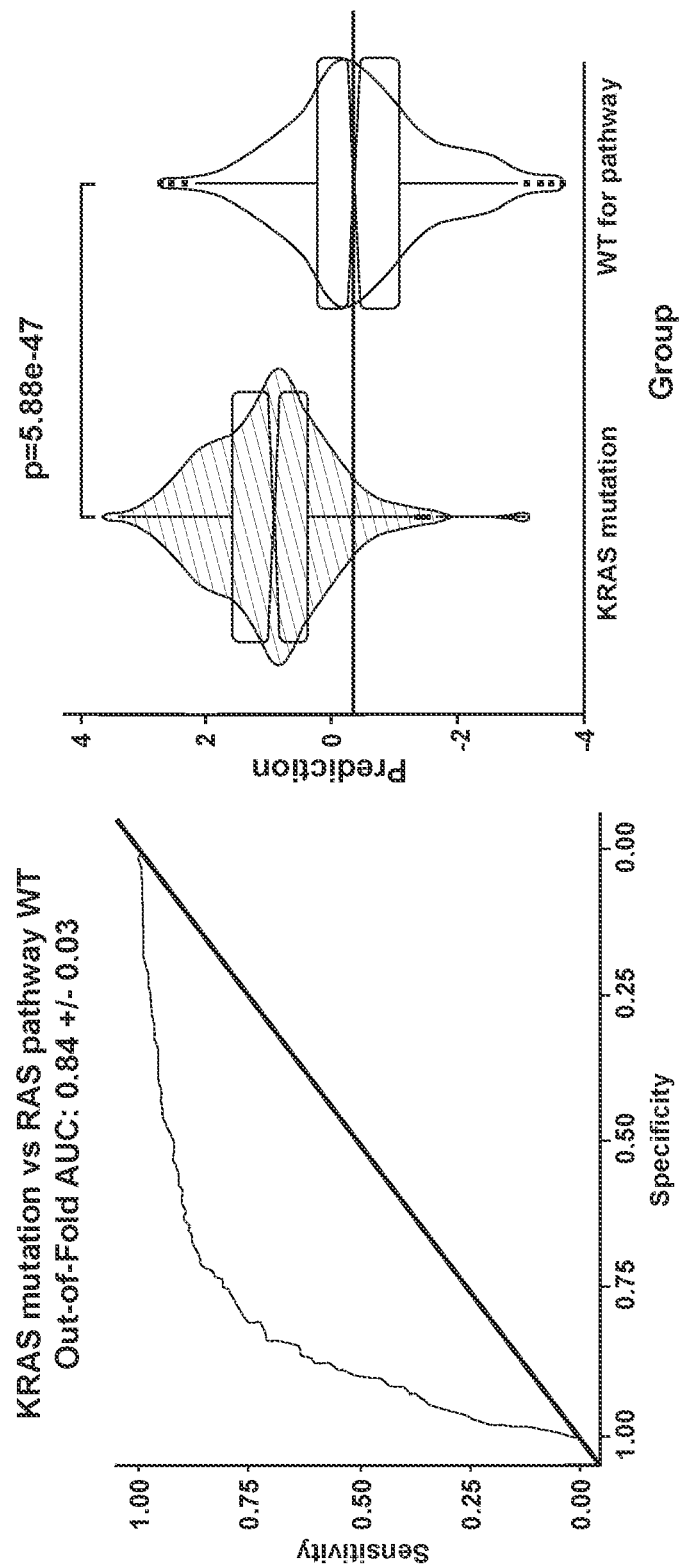
FIG. 17A and FIG. 17B show area under the curve (AUC) and prediction performance graphs that illustrate that the systems and methods disclosed herein can distinguish between negative and positive controls for the RAS pathway.

FIG. 17A and FIG. 17B show AUC and prediction performance graphs that illustrate that the systems and methods disclosed herein can distinguish between negative and positive controls for the RAS pathway.

Figures 17C, 17D:
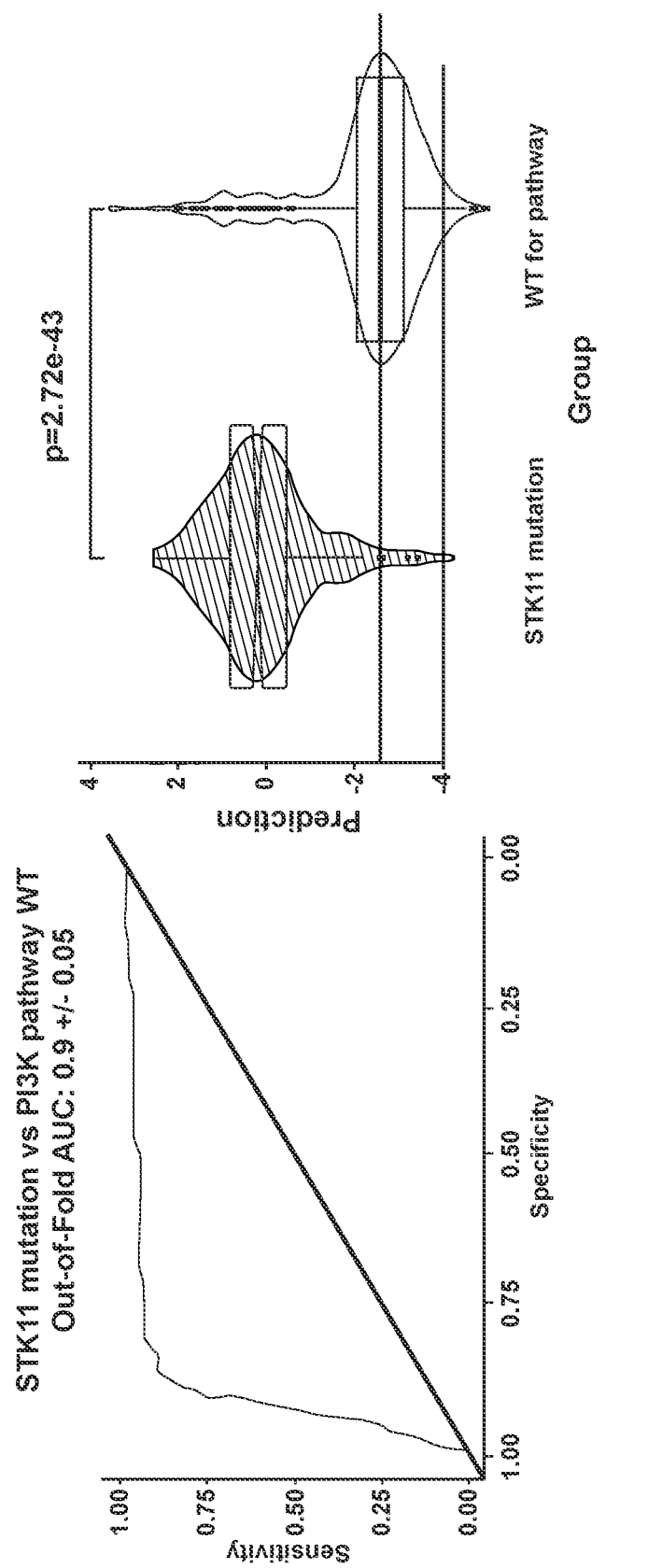
FIG. 17C and FIG. 17D show AUC and prediction performance graphs that illustrate that the systems and methods disclosed herein can distinguish between negative and positive controls for the PI3K pathway.

FIG. 17C and FIG. 17D show AUC and prediction performance graphs that illustrate that the systems and methods disclosed herein can distinguish between negative and positive controls for the PI3K pathway.

Figure 18:
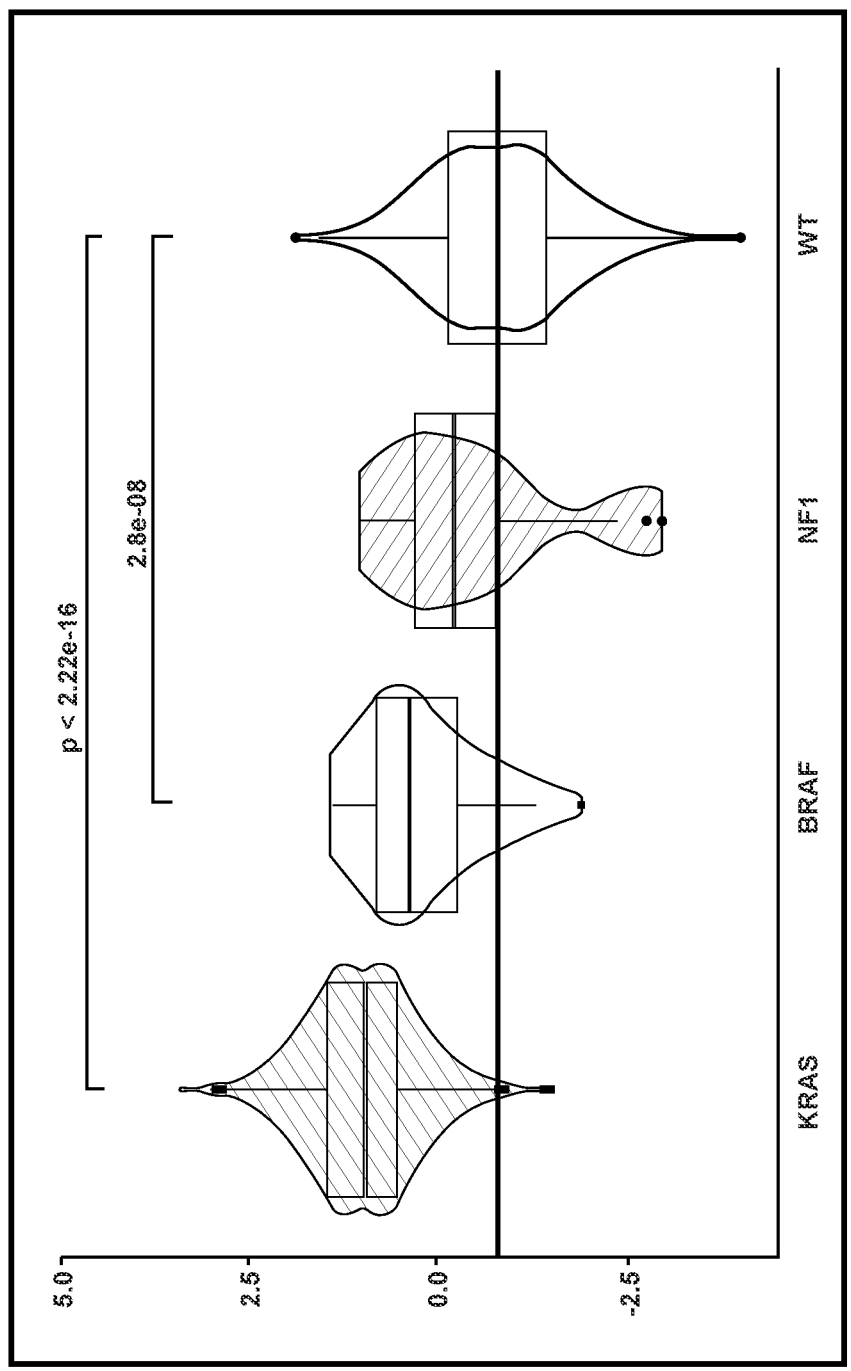
FIG. 18 is a performance graph that illustrates that other mutation groups exhibit expected model output.

FIG. 18 is a performance graph that illustrates that other mutation groups exhibit expected model output. This violin plot shows pathway disruption scores (y-axis) generated by the systems and methods disclosed herein for specimens having a mutation in a gene represented on the x-axis or no mutation (WT). In this example, the systems and methods can distinguish between WT specimens and KRAS mutation specimens or WT and BRAF mutations.

Figure 19A:
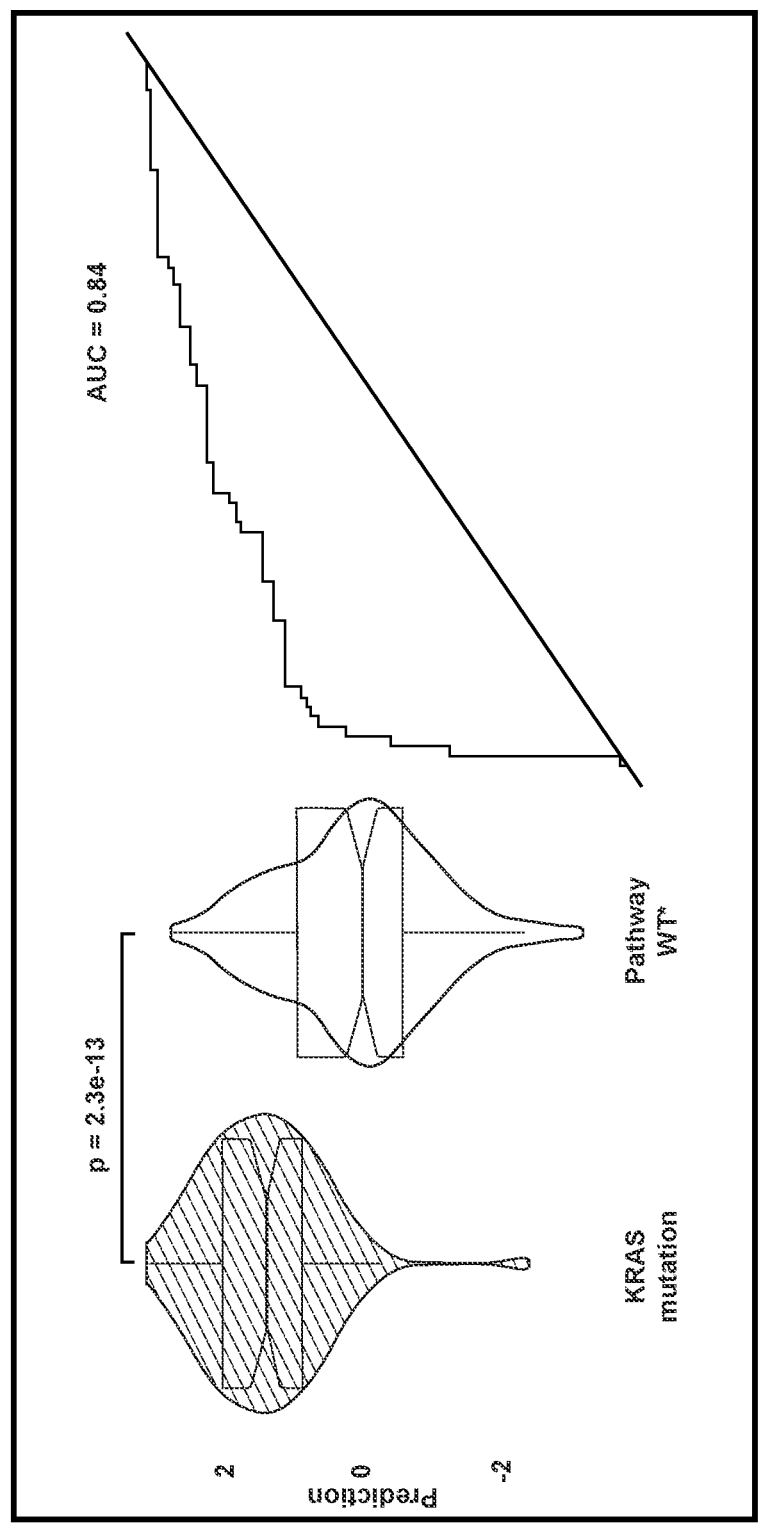
FIG. 19A is a performance graph that shows the results of validating a KRAS mutation vs. RAS Pathway WT model on a TCGA lung adenocarcinoma cohort.
Figure 19B:
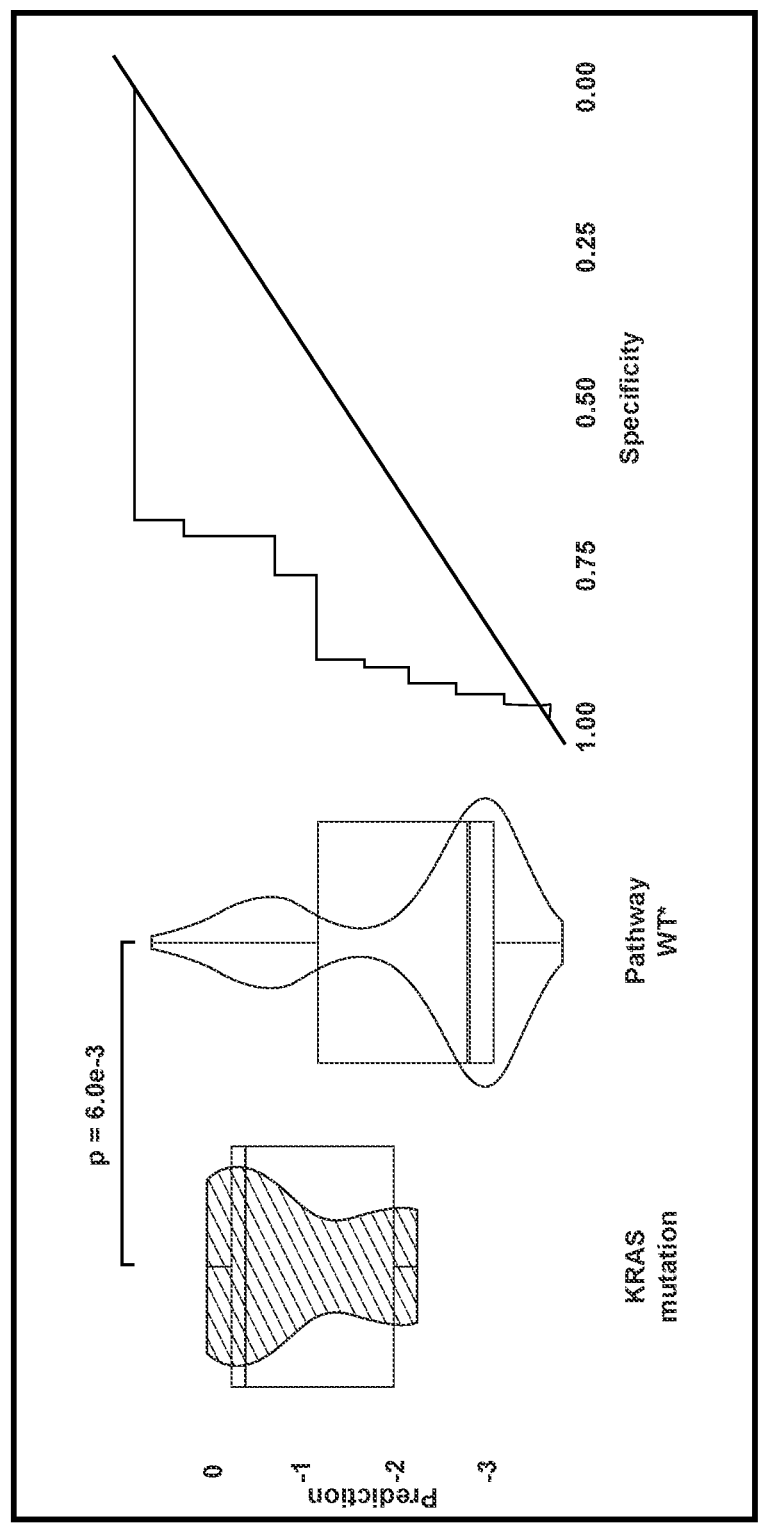
FIG. 19B is a performance graph that shows the results of validating a STK11 mutation vs. PI3K Pathway WT model on a TCGA lung adenocarcinoma cohort.

FIGS. 19A and 19B collectively illustrate the systems and methods validated on the TCGA lung adenocarcinoma cohort for the models trained by either KRAS mutant positive controls or STK11 mutant positive controls and the corresponding pathway WT specimens as negative controls.

FIG. 19A is a performance graph that shows the results of validating the KRAS mutation vs. RAS Pathway WT model on the TCGA lung adenocarcinoma cohort. In this example, the wild type (WT) specimens have no detected mutations in the TCGA-defined RAS pathway genes.

FIG. 19B is a performance graph that shows the results of validating the STK11 mutation vs. PI3K Pathway WT model on the TCGA lung adenocarcinoma cohort. In this example, the wild type (WT) specimens have no detected mutations in TCGA-defined PI3K pathway genes.

Figure 20A:
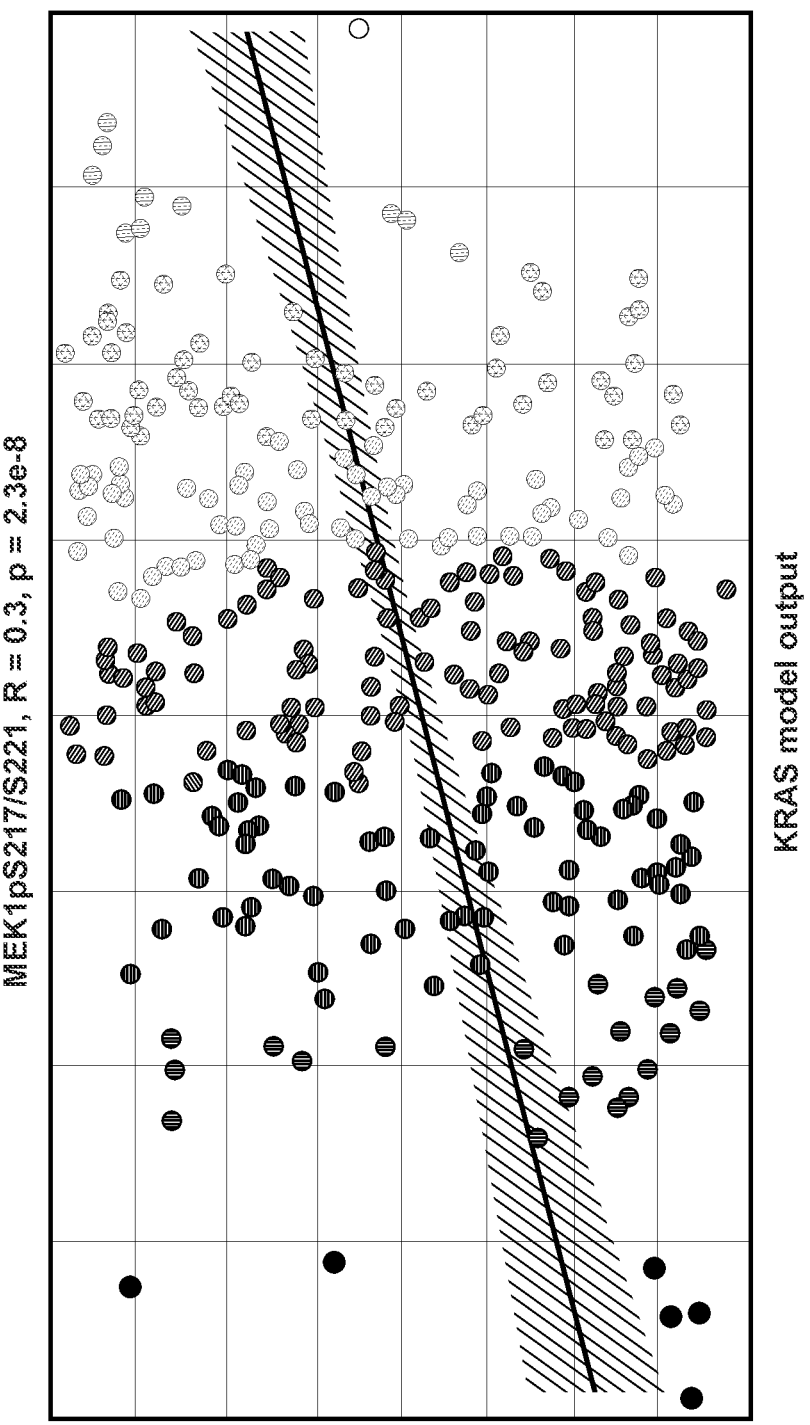
FIG. 20A is a graph that illustrates the relationship between the pathway disruption score generated by the systems and methods and protein expression levels of phosphorylated (i.e., activated) MEK1.
Figure 20B:
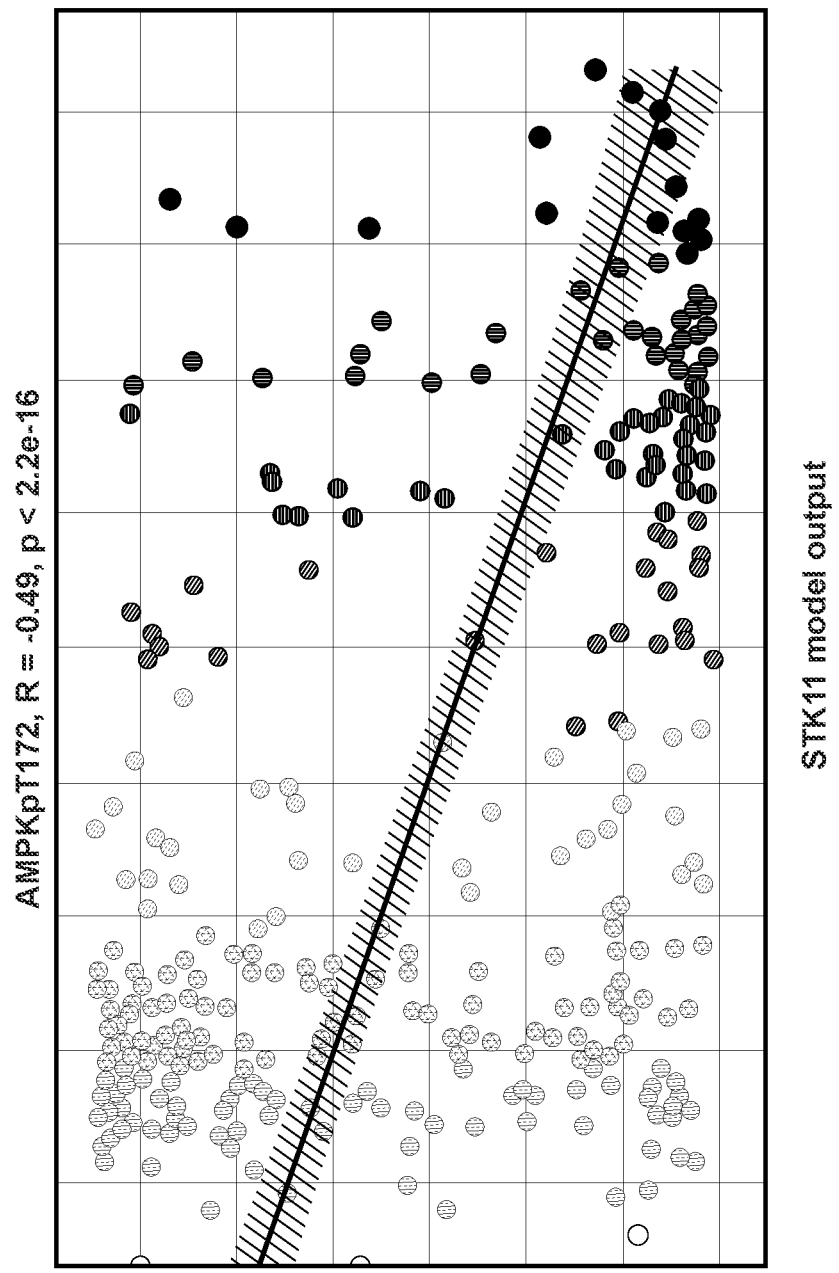
FIG. 20B is a graph that illustrates the relationship between the pathway disruption score generated by the systems and methods and protein expression levels of phosphorylated AMPK.

FIGS. 20A and 20B collectively illustrate that the pathway disruption score generated by the systems and methods correlate with, and thus predict, protein expression levels.

FIG. 20A is a graph that illustrates the relationship between the pathway disruption score generated by the systems and methods and protein expression levels of phosphorylated (i.e., activated) MEK1.

FIG. 20B is a graph that illustrates the relationship between the pathway disruption score generated by the systems and methods and protein expression levels of phosphorylated AMPK.

Figure 21:
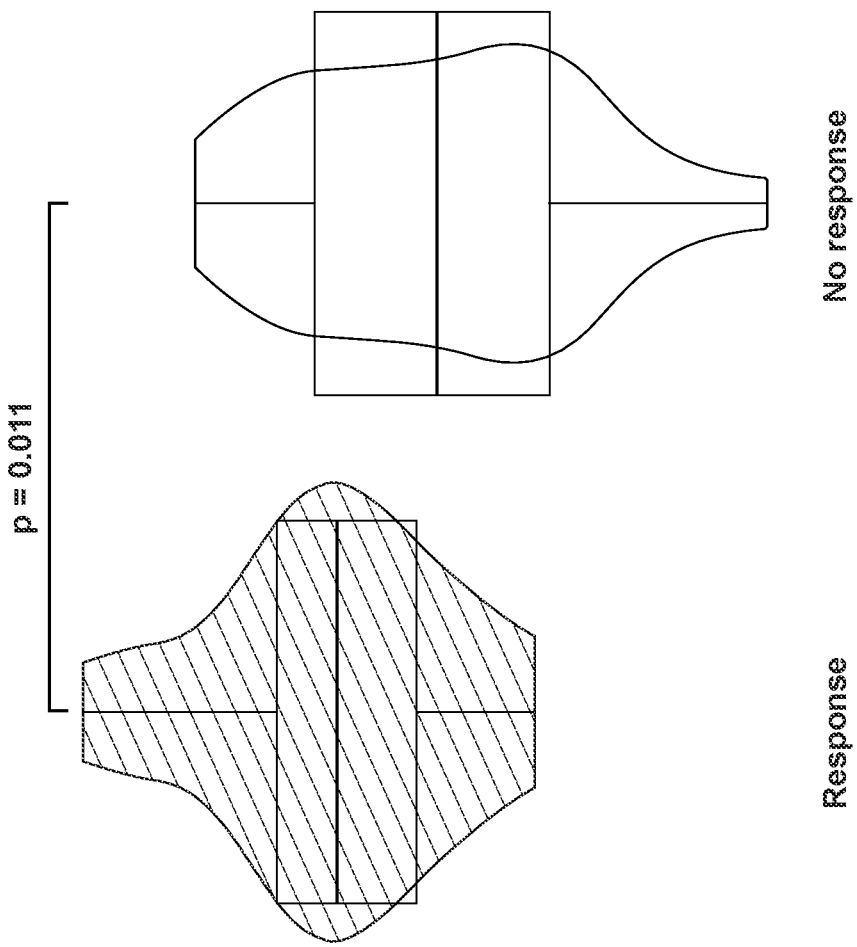
FIG. 21 is a graph that illustrates that the systems and methods are able to distinguish between a group of responders and non-responders to a particular therapy.

FIG. 21 is a graph that illustrates that the systems and methods are able to distinguish between a group of responders and non-responders to a particular therapy. In this example, this violin plot illustrates a KRAS score (y-axis) generated by the systems and methods for a specimen and the treatment response data associated with the specimen, in an example cohort of NSCLC patients with gain of function KRAS mutations. In this example, "no response" is defined by clinical data describing that the patient or organoid showed progressive disease even with treatment and "response" is defined by any other outcome. In one example, the treatment is any treatment that would be prescribed to a patient based on the presence of a KRAS or related variant in the patient's cancer specimen. In one example, the treatment may be prescribed according to FDA and/or NCCN guidelines (see e.g., FIGS. 26A-27P or FIGS. 27Q-V), and in some embodiments, the patient is treated by a physician.

FIG. 22 shows an exemplary pathway disruption report generated at 730. The pathway disruption report can include a subset of the MAPK pathway, as well as information about potential treatment methods. The treatment methods may be approved or unapproved by certain organizations such as the FDA. The unapproved treatments may be available through a clinical trial. For example, selumetinib, vemurafenib and erlotinib are currently FDA-approved therapeutics (see, e.g., FIGS. 26A-27P), while AMG-510, and ulixertinib are unapproved, but are in clinical trials.

Figure 23:
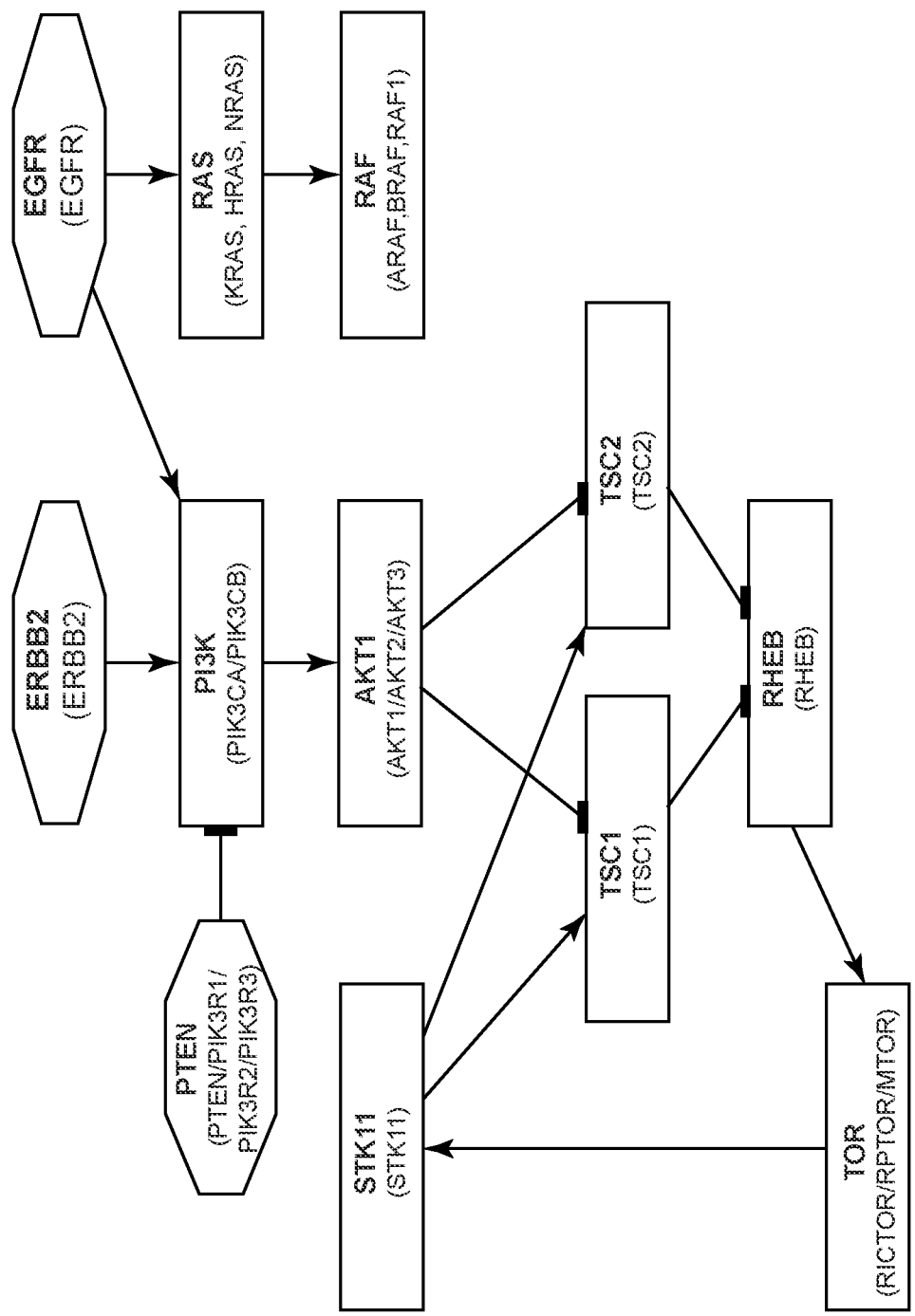
FIG. 23 shows another exemplary pathway disruption report generated by the process of FIG. 7C.

FIG. 23 shows another exemplary pathway disruption report generated at 730. The pathway disruption report can include a meta-pathway that may include subsets or modules of the RAS and PI3K pathways, such as the ERBB2 module and the PTEN module. In FIG. 23, none of the modules and/or submodules may have detectable mutations.

Figure 24:
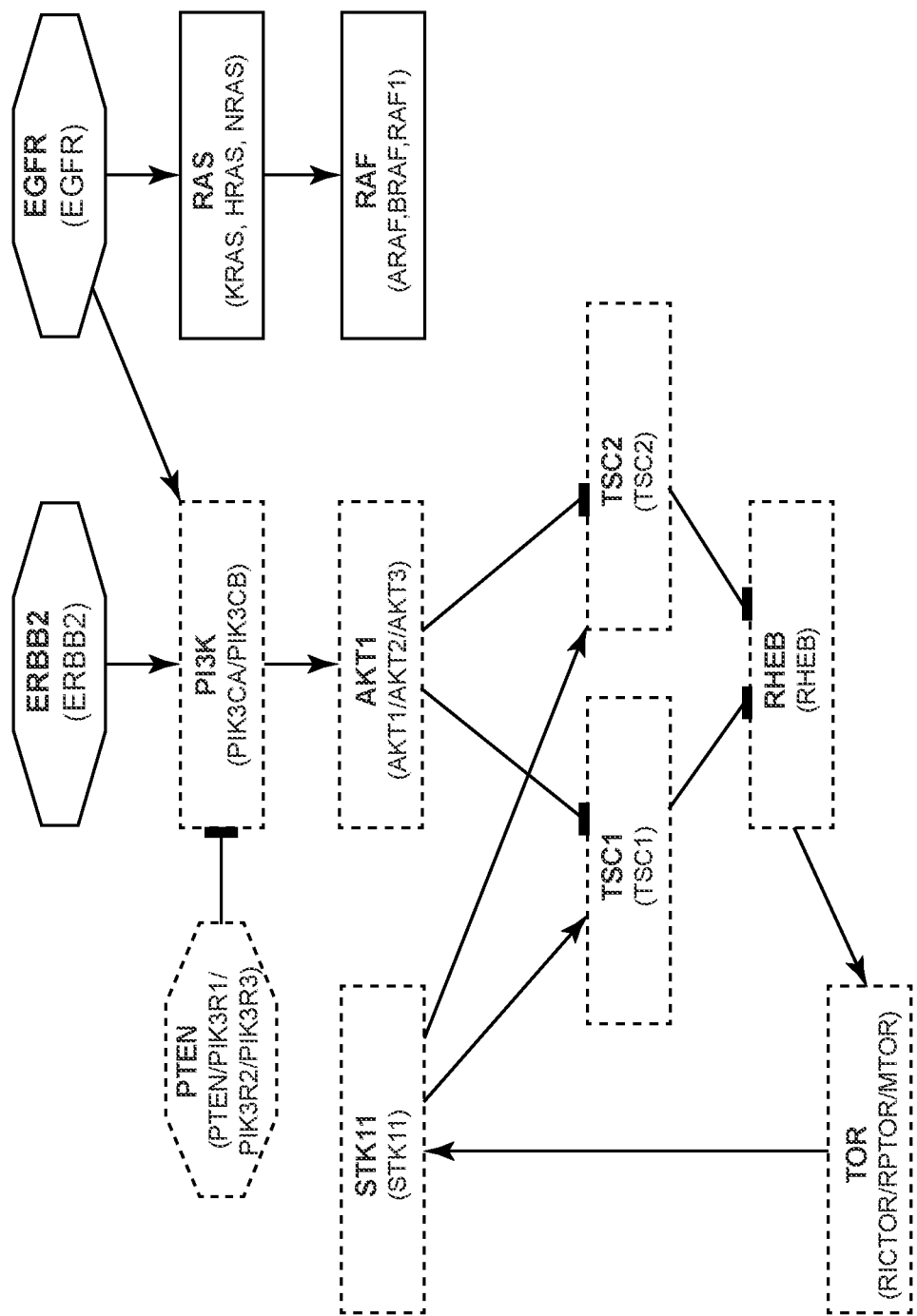
FIG. 24 shows yet another exemplary pathway disruption report generated by the process of FIG. 7C.

FIG. 24 shows yet another exemplary pathway disruption report generated at 730. The pathway disruption report can include the meta-pathway shown in FIG. 23 as well as a table including details of the genes that are mutated in this particular sample. In particular, genes that have detectable mutations may be marked in the table as having "amplification," and submodules that exhibit disruption based on the pathway score may be marked in the meta-pathway with a color (e.g., red) to show the locations in the meta-pathway where the disruption occurs. In FIG. 24, the RICTOR gene, the EMSY gene, and the PAK1 gene have detectable mutations.

Figure 25:
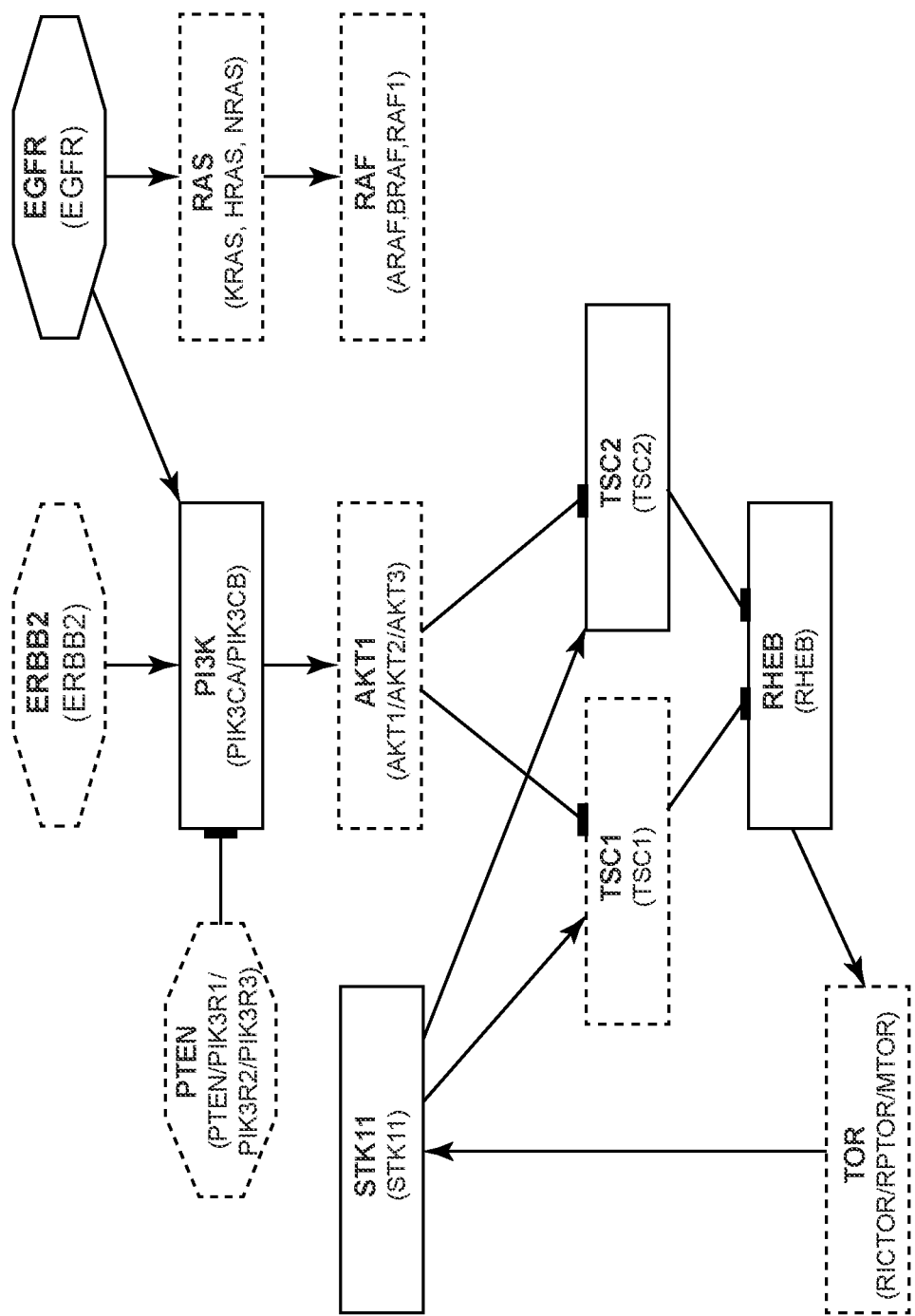
FIG. 25 shows a further exemplary pathway disruption report generated by the process of FIG. 7C.

FIG. 25 shows a further exemplary pathway disruption report generated at 730. The pathway disruption report can include the meta-pathway shown in FIG. 23 as well as a table, similar to FIG. 24. In FIG. 25, only the KRAS gene has a detectable mutation (in this example, a gain of function mutation) that is relevant to the meta-pathway.

The methods and systems described above may be utilized in combination with or as part of a digital and laboratory health care platform that is generally targeted to medical care and research. It should be understood that many uses of the methods and systems described above, in combination with such a platform, are possible. One example of such a platform is described in U.S. patent application Ser. No. 16/657,804, titled "Data Based Cancer Research and Treatment Systems and Methods", and filed Oct. 18, 2019, which is incorporated herein by reference and in its entirety for all purposes.

For example, an implementation of one or more embodiments of the methods and systems as described above may include microservices constituting a digital and laboratory health care platform supporting pathway disruption detection. Embodiments may include a single microservice for executing and delivering pathway disruption detection or may include a plurality of microservices each having a particular role which together implement one or more of the embodiments above. In one example, a first microservice may execute training data generation (which may include selection of differentially expressed genes) in order to deliver training data to a second microservice for training a pathway engine. Similarly, the second microservice may execute pathway engine training to deliver a trained pathway engine according to an embodiment, above. A third microservice may receive a trained pathway engine from a second microservice and may execute pathway disruption detection.

Where embodiments above are executed in one or more microservices with or as part of a digital and laboratory health care platform, one or more of such micro-services may be part of an order management system that orchestrates the sequence of events as needed at the appropriate time and in the appropriate order necessary to instantiate embodiments above. A micro-services based order management system is disclosed, for example, in U.S. Prov. Patent Application No. 62/873,693, titled "Adaptive Order Fulfillment and Tracking Methods and Systems", filed Jul. 12, 2019, which is incorporated herein by reference and in its entirety for all purposes.

For example, continuing with the above first and second microservices, an order management system may notify the first microservice that an order for pathway disruption detection has been received and is ready for processing. The first microservice may execute and notify the order management system once the delivery of pathway disruption detection is ready for the second microservice. Furthermore, the order management system may identify that execution parameters (prerequisites) for the second microservice are satisfied, including that the first microservice has completed, and notify the second microservice that it may continue processing the order to pathway disruption detection according to an embodiment, above.

Where the digital and laboratory health care platform further includes a genetic analyzer system, the genetic analyzer system may include targeted panels and/or sequencing probes. An example of a targeted panel is disclosed, for example, in U.S. Prov. Patent Application No. 62/902,950, titled "System and Method for Expanding Clinical Options for Cancer Patients using Integrated Genomic Profiling", and filed Sep. 19, 2019, which is incorporated herein by reference and in its entirety for all purposes. In one example, targeted panels may enable the delivery of next generation sequencing results for pathway disruption detection according to an embodiment, above. An example of the design of next-generation sequencing probes is disclosed, for example, in U.S. Prov. Patent Application No. 62/924,073, titled "Systems and Methods for Next Generation Sequencing Uniform Probe Design", and filed Oct. 21, 2019, which is incorporated herein by reference and in its entirety for all purposes.

Where the digital and laboratory health care platform further includes a bioinformatics pipeline, the methods and systems described above may be utilized after completion or substantial completion of the systems and methods utilized in the bioinformatics pipeline. As one example, the bioinformatics pipeline may receive next-generation genetic sequencing results and return a set of binary files, such as one or more BAM files, reflecting DNA and/or RNA read counts aligned to a reference genome. The methods and systems described above may be utilized, for example, to ingest the DNA and/or RNA read counts and produce pathway disruption detection as a result.

When the digital and laboratory health care platform further includes an RNA data normalizer, any RNA read counts may be normalized before processing embodiments as described above. An example of an RNA data normalizer is disclosed, for example, in U.S. patent application Ser. No. 16/581,706, titled "Methods of Normalizing and Correcting RNA Expression Data", and filed Sep. 24, 2019.

When the digital and laboratory health care platform further includes a genetic data deconvoluter, any system and method for deconvoluting may be utilized for analyzing genetic data associated with a specimen having two or more biological components to determine the contribution of each component to the genetic data and/or determine what genetic data would be associated with any component of the specimen if it were purified. An example of a genetic data deconvoluter is disclosed, for example, in U.S. patent application Ser. No. 16/732,229 and PCT19/69161, both titled "Transcriptome Deconvolution of Metastatic Tissue Samples", and filed Dec. 31, 2019, U.S. Prov. Patent Application No. 62/924,054, titled "Calculating Cell-type RNA Profiles for Diagnosis and Treatment", and filed Oct. 21, 2019, and U.S. Prov. Patent Application No. 62/944,995, titled "Rapid Deconvolution of Bulk RNA Transcriptomes for Large Data Sets (Including Transcriptomes of Specimens Having Two or More Tissue Types)", and filed Dec. 6, 2019 which are incorporated herein by reference and in their entirety for all purposes.

When the digital and laboratory health care platform further includes an automated RNA expression caller, RNA expression levels may be adjusted to be expressed as a value relative to a reference expression level, which is often done in order to prepare multiple RNA expression data sets for analysis to avoid artifacts caused when the data sets have differences because they have not been generated by using the same methods, equipment, and/or reagents. An example of an automated RNA expression caller is disclosed, for example, in U.S. Prov. Patent Application No. 62/943,712, titled "Systems and Methods for Automating RNA Expression Calls in a Cancer Prediction Pipeline", and filed Dec. 4, 2019, which is incorporated herein by reference and in its entirety for all purposes.

The digital and laboratory health care platform may further include one or more insight engines to deliver information, characteristics, or determinations related to a disease state that may be based on genetic and/or clinical data associated with a patient and/or specimen. Exemplary insight engines may include a tumor of unknown origin engine, a human leukocyte antigen (HLA) loss of homozygosity (LOH) engine, a tumor mutational burden engine, a PD-L1 status engine, a homologous recombination deficiency engine, a cellular pathway disruption report engine, an immune infiltration engine, a microsatellite instability engine, a pathogen infection status engine, and so forth. An example tumor of unknown origin engine is disclosed, for example, in U.S. Prov. Patent Application No. 62/855,750, titled "Systems and Methods for Multi-Label Cancer Classification", and filed May 31, 2019, which is incorporated herein by reference and in its entirety for all purposes. An example of an HLA LOH engine is disclosed, for example, in U.S. Prov. Patent Application No. 62/889,510, titled "Detection of Human Leukocyte Antigen Loss of Heterozygosity", and filed Aug. 20, 2019, which is incorporated herein by reference and in its entirety for all purposes. An example of a tumor mutational burden (TMB) engine is disclosed, for example, in U.S. Prov. Patent Application No. 62/804,458, titled "Assessment of Tumor Burden Methodologies for Targeted Panel Sequencing", and filed Feb. 12, 2019, which is incorporated herein by reference and in its entirety for all purposes. An example of a PD-L1 status engine is disclosed, for example, in U.S. Prov. Patent Application No. 62/854,400, titled "A Pan-Cancer Model to Predict The PD-L1 Status of a Cancer Cell Sample Using RNA Expression Data and Other Patient Data", and filed May 30, 2019, which is incorporated herein by reference and in its entirety for all purposes. An additional example of a PD-L1 status engine is disclosed, for example, in U.S. Prov. Patent Application No. 62/824,039, titled "PD-L1 Prediction Using H&E Slide Images", and filed Mar. 26, 2019, which is incorporated herein by reference and in its entirety for all purposes. An example of a homologous recombination deficiency engine is disclosed, for example, in U.S. Prov. Patent Application No. 62/804,730, titled "An Integrative Machine-Learning Framework to Predict Homologous Recombination Deficiency", and filed Feb. 12, 2019, which is incorporated herein by reference and in its entirety for all purposes. An example of a cellular pathway disruption report engine is disclosed, for example, in U.S. Prov. Patent Application No. 62/888,163, titled "Cellular Pathway Report", and filed Aug. 16, 2019, which is incorporated herein by reference and in its entirety for all purposes. An example of an immune infiltration engine is disclosed, for example, in U.S. patent application Ser. No. 16/533,676, titled "A Multi-Modal Approach to Predicting Immune Infiltration Based on Integrated RNA Expression and Imaging Features", and filed Aug. 6, 2019, which is incorporated herein by reference and in its entirety for all purposes. An additional example of an immune infiltration engine is disclosed, for example, in U.S. Patent Application No. 62/804,509, titled "Comprehensive Evaluation of RNA Immune System for the Identification of Patients with an Immunologically Active Tumor Microenvironment", and filed Feb. 12, 2019, which is incorporated herein by reference and in its entirety for all purposes. An example of an MSI engine is disclosed, for example, in U.S. patent application Ser. No. 16/653,868, titled "Microsatellite Instability Determination System and Related Methods", and filed Oct. 15, 2019, which is incorporated herein by reference and in its entirety for all purposes. An additional example of an MSI engine is disclosed, for example, in U.S. Prov. Patent Application No. 62/931,600, titled "Systems and Methods for Detecting Microsatellite Instability of a Cancer Using a Liquid Biopsy", and filed Nov. 6, 2019, which is incorporated herein by reference and in its entirety for all purposes.

When the digital and laboratory health care platform further includes a report generation engine, the methods and systems described above may be utilized to create a summary report of a patient's genetic profile and the results of one or more insight engines for presentation to a physician. For instance, the report may provide to the physician information about the extent to which the specimen that was sequenced contained tumor or normal tissue from a first organ, a second organ, a third organ, and so forth. For example, the report may provide a genetic profile for each of the tissue types, tumors, or organs in the specimen. The genetic profile may represent genetic sequences present in the tissue type, tumor, or organ and may include variants, expression levels, information about gene products, or other information that could be derived from genetic analysis of a tissue, tumor, or organ. The report may include therapies and/or clinical trials matched based on a portion or all of the genetic profile or insight engine findings and summaries. For example, the therapies may be matched according to the systems and methods disclosed in U.S. Prov. Patent Application No. 62/804,724, titled "Therapeutic Suggestion Improvements Gained Through Genomic Biomarker Matching Plus Clinical History", filed Feb. 12, 2019, which is incorporated herein by reference and in its entirety for all purposes. For example, the clinical trials may be matched according to the systems and methods disclosed in U.S. Prov. Patent Application No. 62/855,913, titled "Systems and Methods of Clinical Trial Evaluation", filed May 31, 2019, which is incorporated herein by reference and in its entirety for all purposes.

The report may include a comparison of the results to a database of results from many specimens. An example of methods and systems for comparing results to a database of results are disclosed in U.S. Prov. Patent Application No. 62/786,739, titled "A Method and Process for Predicting and Analyzing Patient Cohort Response, Progression and Survival", and filed Dec. 31, 2018, which is incorporated herein by reference and in its entirety for all purposes. The information may be used, sometimes in conjunction with similar information from additional specimens and/or clinical response information, to discover biomarkers or design a clinical trial.

When the digital and laboratory health care platform further includes application of one or more of the embodiments herein to organoids developed in connection with the platform, the methods and systems may be used to further evaluate genetic sequencing data derived from an organoid to provide information about the extent to which the organoid that was sequenced contained a first cell type, a second cell type, a third cell type, and so forth. For example, the report may provide a genetic profile for each of the cell types in the specimen. The genetic profile may represent genetic sequences present in a given cell type and may include variants, expression levels, information about gene products, or other information that could be derived from genetic analysis of a cell. The report may include therapies matched based on a portion or all of the deconvoluted information. These therapies may be tested on the organoid, derivatives of that organoid, and/or similar organoids to determine an organoid's sensitivity to those therapies. For example, organoids may be cultured and tested according to the systems and methods disclosed in U.S. patent application Ser. No. 16/693,117, titled "Tumor Organoid Culture Compositions, Systems, and Methods", filed Nov. 22, 2019; U.S. Prov. Patent Application No. 62/924,621, titled "Systems and Methods for Predicting Therapeutic Sensitivity", filed Oct. 22, 2019; and U.S. Prov. Patent Application No. 62/944,292, titled "Large Scale Phenotypic Organoid Analysis", filed Dec. 5, 2019, which are incorporated herein by reference and in their entirety for all purposes.

When the digital and laboratory health care platform further includes application of one or more of the above in combination with or as part of a medical device or a laboratory developed test that is generally targeted to medical care and research, such laboratory developed test or medical device results may be enhanced and personalized through the use of artificial intelligence. An example of laboratory developed tests, especially those that may be enhanced by artificial intelligence, is disclosed, for example, in U.S. Provisional Patent Application No. 62/924,515, titled "Artificial Intelligence Assisted Precision Medicine Enhancements to Standardized Laboratory Diagnostic Testing", and filed Oct. 22, 2019, which is incorporated herein by reference and in its entirety for all purposes.

Example 9: Exemplary RNA Sample Preparation

1. RNA Extraction

Transcriptome analysis, the study of the complete set of RNA transcripts that are produced by a cell (i.e., the transcriptome), offers a promising means to identify genetic variants that are correlated with disease state and disease progression. For example, to identify genetic variants that are associated with cancer, transcriptome analysis may be performed on a sample collected from a patient that contains cancer cells. Suitable patient samples include tissue samples, tumors (e.g., a solid tumor), biopsies, and bodily fluids (e.g., blood, serum, plasma, sputum, lavage fluid, cerebrospinal fluid, urine, semen, sweat, tears, saliva). Alternatively, transcriptome analysis may be performed on an organoid that was generated from a human cancer specimen (i.e., a "tumor organoid").

While RNA sequencing (RNA-seq) can be performed on any patient sample that contains RNA, those of skill in the art will appreciate that the sequencing protocol should tailored to the particular sample in use. For instance, RNA tends to be highly degraded in tissue samples that have been processed for histology (e.g., formalin fixed, paraffin embedded (FFPE) tissue sections). Accordingly, investigators will modify several key steps in the RNA-seq protocol to mitigate sequencing artifacts (see, e.g., BMC Medical Genomics 12, 195 (2019)).

Today, transcriptome analysis is predominantly performed using high-throughput RNA sequencing (RNA-Seq), which detects the RNA transcripts in a sample using a next-generation sequencer. The first step in performing RNA-seq is to extract RNA from the sample.

A. Cell Lysis

The first step in extracting RNA from a sample is often to lyse the cells present in that sample. Several physical disruption methods are commonly used to lyse cells, including, for example, mechanical disruption (e.g., using a blender or tissue homogenizer), liquid homogenization (e.g., using a dounce or French press), high frequency sound waves (e.g., using a sonicator), freeze/thaw cycles, heating, manual grinding (e.g., using a mortar and pestle), and bead-beating (e.g., using a Mini-beadbeater-96 from Bio-Spec). Cells are also commonly lysed using reagents that contain a detergent, many of which are commercially available (e.g., QIAzol Lysis Reagent from QIAGEN, Fast-Break™ Cell Lysis Reagent from Promega). Often, physical disruption methods are performed in a "homogenization buffer" that contains, for example, lysis reagents such as detergents or proteases (e.g., proteinase K) that increase the efficiency of lysis. Homogenization buffers may also include anti-foaming agents and/or RNase inhibitors to protect RNA from degradation. Those of skill in the art will appreciate that different cell lysis techniques may be required to obtain the best possible yield from different tissues. Techniques that minimize the degradation of the released RNA and that avoid the release of nuclear chromatin are preferred.

B. RNA Isolation

After the cells have been lysed, RNA can be separated from other cellular components, to generate a sample enriched in RNA. Total RNA is commonly isolated using guanidinium thiocyanate-phenol-chloroform extraction (e.g., using TRIzol) or by performing trichloroacetic acid/acetone precipitation followed by phenol extraction. However, there are also many commercially available column-based systems for extracting RNA (e.g., PureLink RNA Mini Kit by Invitrogen and Direct-zol Miniprep kit by Zymo Research).

Ideally, the RNA sample will contain very little DNA and enzymatic contamination. To this end, the isolation or RNA enrichment method may utilize agents that eliminate DNA (e.g., TURBO DNase-I), and/or remove enzymatic proteins from the sample (e.g., Agencourt® RNAClean® XP beads from Beckman Coulter).

In some cases, whole transcriptome sequencing is used to analyze all of the transcripts present in a cell, including messenger RNA (mRNA) as well as all non-coding RNAs. By looking at the whole transcriptome, researchers are able to map exons and introns and to identify splicing variants. Notably, most whole transcription library preparation protocols include a step to remove ribosomal RNA (rRNA), which would otherwise take up the majority of the sequencing reads and does not provide highly relevant information to the researcher. Depletion of rRNA is commonly accomplished using a kit, e.g., Ribo-Zero Plus rRNA Depletion Kit from Illumina and Seq RiboFree Total RNA Library Kit from Zymo.

In other cases, a more targeted RNA-Seq protocol is used to look at a specific type of RNA. For example, mRNA-seq is commonly used to selectively study the "coding" part of the genome, which accounts for only 1-2% of the entire transcriptome. Enriching a sample for mRNA increases the sequencing depth achieved for coding genes, enabling identification of rare transcripts and variants. Polyadenylated mRNAs are commonly enriched for using oligo dT beads (e.g., Dynabeads™ from Invitrogen). This enrichment step can be performed either on isolated total RNA or on crude cellular lysate.

Targeted approaches have also been developed for the analysis of microRNAs (miRNAs) and small interfering RNAs (siRNAs). These RNAs are commonly isolated using kits that been designed to efficiently recover small RNAs (e.g., mirVana™ miRNA Isolation Kit from Invitrogen).

2. Library Preparation

After RNA has been extracted from the sample, the next major step is to transform the RNA into a form that is suitable for next-generation sequencing (NGS). Through a series of steps, the RNA is converted into a collection of DNA fragments known as a "sequencing library." After the library has been sequenced, the resulting sequencing "reads" are aligned to a reference genome or transcriptome to determine the expression profile of the analyzed cells.

In some cases, library preparation is automated to enable higher sample throughput, minimize errors, and reduce hands-on time. Fully automated library preparation can be performed, for example, using a liquid handling robot (e.g., SciClone® NGSx from PerkinElmer).

A. Reverse Transcription

For sequencing, RNA is transformed or converted to more stable, double-stranded complementary DNA (cDNA) using reverse transcription (RT). In some cases, reverse transcription is performed directly on a sample lysate, prior to RNA isolation. In other cases, reverse transcription is performed on isolated RNA.

Reverse transcription is catalyzed by reverse transcriptase, an enzyme that uses an RNA template and a short primer complementary to the 3' end of the RNA to synthesize a complementary strand of cDNA. This first strand of cDNA is then made double-stranded, either by subjecting it to PCR or using a combination of DNA Polymerase I and DNA Ligase. In the latter method, an RNase (e.g., RNase H) is commonly used to digest the RNA strand, allowing the first cDNA strand to serve as a template for synthesis of the second cDNA strand.

Many reverse transcriptases are commercially available, including Avian Myeloblastosis Virus (AMV) reverse transcriptases (e.g., AMV Reverse Transcriptase from New England BioLabs) and Moloney Murine Leukemia Virus (M-MuLV, MMLV) reverse transcriptases (e.g., SMARTscribe™ from Clontech, SuperScript II™ from Life Technologies, and Maxima H Minus™ from Thermo Scientific). Notably, many of the available reverse transcriptases have been engineered for improved thermostability or efficiency (e.g., by eliminating 3'→5' exonuclease activity or reducing RNase H activity).

The primers, which serve as a starting point for synthesis of the new strand, may be random primers (i.e., for RT of any RNA), oligo dT primers (i.e., for RT of mRNA), or gene-specific primers (i.e., for RT of specific target RNAs).

Following reverse transcription, an exonuclease (e.g., Exonuclease I) may be added to the samples to degrade any primers that remain from the reaction, preventing them from interfering in a subsequent amplification steps.

B. Fragmentation and Size Selection

Because most sequencing technologies cannot readily analyze long DNA strands, DNA is commonly fragmented into uniformly sized fragments prior to sequencing. The optimal fragment length depends on both the sample type and the sequencing platform to be used. For example, whole genome sequencing typically works best with fragments of DNA that are ~350 bp long, while targeted sequencing using hybridization capture (see Section 2G) works best with fragments of DNA that are ~200 bp long.

In some cases, fragmentation is performed after reverse transcription (i.e., on cDNA). Suitable methods for fragmenting DNA include physical methods (e.g., using sonication, acoustics, nebulization, centrifugal force, needles, or hydrodynamics), enzymatic methods (e.g., using NEBNext dsDNA Fragmentase from New England BioLabs), and tagmentation (e.g., using the Nextera™ system from Illumina).

In other cases, fragmentation is performed prior to reverse transcription (i.e., on RNA). In addition to the fragmentation methods that are suitable to DNA, RNA may also be fragmented using heat and magnesium (e.g., using the KAPA Hyper Prep Kit from Roche).

A size selection step may subsequently be performed to enrich the library for fragments of an optimal length or range of lengths. Traditionally, size selection was accomplished by separating differentially sized fragments using agarose gel electrophoresis, cutting out the fragments of the desired sizes, and performing a gel extraction (e.g., using a MinElute Gel Extraction Kit™ from Qiagen). However, size selection is now commonly accomplished using magnetic bead-based systems (e.g., AMPure XP™ from Beckman Coulter, ProNex® Size-Selective Purification System from Promega).

C. Adapter Ligation

Prior to sequencing, the cDNA fragments are ligated to sequencing adapters. Sequencing adapters are short DNA oligonucleotides that contain (1) sequences needed to amplify the cDNA fragment during the sequencing reaction, and (2) sequences that interact with the NGS platform (e.g., the surface of the Illumina flow-cell or Ion Torrent beads). Accordingly, adapters must be selected based on the sequencing platform that is to be used.

Libraries from multiple samples are commonly pooled and analyzed in a single sequencing run (see Section 2F). To track the source of each cDNA in a pooled sample, a unique molecular barcode (or combination of multiple barcodes) is included in the adapters that are ligated to the cDNA fragments in each library. During the sequencing reaction, the sequencer reads this barcode sequence in addition to the cDNA's biological base sequence. The barcodes are then used to assign each cDNA to its sample of origin during data analysis, a process termed "demultiplexing".

The indexing strategy used for a sequencing reaction should be selected based on the number of pooled samples and the level of accuracy desired. For example, unique dual indexing, in which unique identifiers are added to both ends of the cDNA fragments, is commonly used to ensure that libraries will demultiplex with high accuracy. Adapters may also include unique molecular identifiers (UMIs), short sequences, often with degenerate bases, that incorporate a unique barcode onto each molecule within a given sample library. UMIs reduce the rate of false-positive variant calls and increase sensitivity of variant detection by allowing true variants to be distinguished from errors introduced during library preparation, target enrichment, or sequencing. Many index sequences and adapter sets are commercially available including, for example, SeqCap Dual End Adapters from Roche, xGen Dual Index UMI Adapters from IDT, and TruSeq UD Indexes from Illumina.

D. Amplification

While it may not be required for some sequencing applications, library preparation typically includes at least one amplification step to enrich for sequencing-competent DNA fragments (i.e., fragments with adapter ligated ends) and to generate a sufficient amount of library material for downstream processing. Amplification may be performed using a standard polymerase chain reaction (PCR) technique. However, when possible, care should be taken to minimize amplification bias and limit the introduction of sequencing artifacts. This is accomplished through selection of an appropriate enzyme and protocol parameters. To this end, several companies offer high-fidelity DNA polymerases (e.g., KAPA HiFi DNA Polymerase from Roche), which have been shown to produce more accurate sequencing data. Often these DNA polymerases are purchased as part of a PCR master mix (e.g., NEBNext® High-Fidelity 2×PCR Master Mix from New England BioLabs) or as part of a kit (e.g., KAPA HiFi Library Amplification kit by Roche).

Those of skill in the art will appreciate that PCR conditions must be fine-tuned for each sequencing experiment, even when a highly-optimized PCR protocol is used. For example, depending on the initial concentration of DNA in the library and on the input requirement of the sequencer to be used, it may be desirable to subject the library to anywhere from 4-14 cycles of PCR.

In some cases, library preparation protocols include multiple rounds of library amplification. For example, in some cases, an additional round of amplification followed by PCR clean-up is performed after the libraries have been pooled.

E. Clean-Up

Following PCR, the amplified DNA is typically purified to remove enzymes, nucleotides, primers, and buffer components that remain from the reaction. Purification is commonly accomplished using phenol-chloroform extraction followed by ethanol precipitation or using a spin column that contains a silica matrix to which DNA selectively binds in the presence of chaotropic salts. Many column-based PCR cleanup kits are commercially available including, for example, those from Qiagen (e.g., MinElute PCR Purification Kit), Zymo Research™ (DNA Clean & Concentrator™-5), and Invitrogen (e.g., PureLink™ PCR Purification Kit). Alternatively, purification may be accomplished using paramagnetic beads (e.g., Axygen™ AxyPrep Mag™ PCR Clean-up Kit).

F. Pooling

To keep sequencing cost-effective, researchers often pool together multiple libraries, each with a unique barcode (see section 2C), to be sequenced in a single run. The sequencer to be used and the desired sequencing depth should dictate the number of samples that are pooled. For example, for some applications it is advantageous to pool fewer than 12 libraries to achieve greater sequencing depth, whereas for other applications it may be advisable to pool more than 100 libraries.

Importantly, if multiple libraries are sequenced in a single run, care should be taken to ensure that the sequencing coverage is roughly equal for each library. To this end, an equal amount of each library (based on molarity) should be pooled. Further, the total molarity of the pooled libraries must be compatible with the sequencer. Thus, it is important to accurately quantify the DNA in the libraries (e.g., using the methods discussed in Section 2I) and to perform the necessary calculations before pooling the libraries. In some cases, to achieve a suitable total molarity, it may be necessary to concentrate the pooled libraries, e.g., using a vacufuge.

G. Enrichment

For some applications, it is not necessary to sequence the entire transcriptome of a sample. Instead, "targeted sequencing" may be used to study a select set of genes or specific genomic elements. Libraries that are enriched for target sequences are commonly prepared using hybridization-based methods (i.e., hybridization capture-based target enrichment). Hybridization may be performed either on a solid surface (microarray) or in solution. In the solution-based method, a pool of biotinylated oligonucleotide probes that specifically hybridize with the genes or genomic elements of interest is added to the library. The probes are then captured and purified using streptavidin-coated magnetic beads, and the sequences that hybridized to these probes are subsequently amplified and sequenced. Many probe panels for library enrichment are commercially available, including those from IDT (e.g., xGen Exome Research Panel v1.0 probes) and Roche (e.g., SeqCap® probes). Importantly, many available probe panels can be customized, allowing investigators to design sets of capture probes that are precisely tailored to a particular application. In addition, many kits (e.g., SeqCap EZ MedExome Target Enrichment Kit from Roche) and hybridization mixes (e.g., xGen Lockdown from IDT) that facilitate target enrichment are available for purchase.

In some cases, it may be advantageous to treat the libraries with reagents that reduce off-target capture prior to performing target enrichment. For example, libraries are commonly treated with oligonucleotides that bind to adapter sequences (e.g., xGen Blocking Oligos) or to repetitive sequences (e.g., human Cot DNA) to reduce non-specific binding to the capture probes.

H. Spike-in Control

Because cells from different experimental conditions do not yield identical amounts of RNA, investigators must normalize sequencing data to accurately identify changes across experimental conditions. Normalization is particularly important when there are global changes in transcription between different experimental conditions. Accordingly, investigators commonly add a "spike-in control" to sequencing libraries for normalization. A spike-in control constitutes DNA sequences that are added at a known ratio to the experimental cells. The control DNA can be any DNA that is readily distinguished from the experimental cDNA during data analysis. For example, control libraries commonly comprise synthetic DNA or DNA from an organism other than the organism of interest (e.g., a PhiX spike-in control may be added to a human-derived library).

I. Quality Assessment

Prior to sequencing, libraries should be evaluated to ensure that they comprise DNA of sufficient quantity and quality to generate useful sequencing results. To verify that the concentration of the library is sufficient for loading on the sequencer, the DNA must be quantified. Commonly used methods of DNA quantification include gel electrophoresis, UV spectrophotometry (e.g., NanoDrop®), fluorometry (e.g., Qubit™, Picofluor™), real-time PCR (also known as quantitative PCR), or droplet digital emulsion PCR (ddPCR). DNA quantification is often aided by the use of dyes and stains, of which an extensive assortment is commercially available (e.g., ethidium bromide, SYBR Green, RiboGreen®). Notably, given that the recommended input range is very narrow for NGS, it is preferable that a highly precise method of quantitation is used to verify that the concentration of the final library is suitable.

Additionally, the fragment size distribution of the final library should be assessed to verify that the length of the fragments is suitable for sequencing. Traditionally, fragment size distribution was determined by running out sample on an agarose gel. However, more advanced capillary electrophoretic methods (e.g., Bioanalyzer®, TapeStation®, Fragment Analyzer™, all from Agilent) that require less sample input are now more commonly employed. Conveniently, these methods can be used to analyze both the fragment size and the concentration of the DNA.

J. Clonal Amplification

To sequence a library, it is applied to a device, typically a flow cell (Illumina) or chip (Ion Torrent), in which the sequencing chemistry occurs. These devices are decorated with short oligonucleotides that are complementary to the adapter sequences, allowing the cDNAs in the library to attach to the device. Prior to sequencing, the cDNAs are subjected to clonal amplification (e.g., by cluster generation (Illumina) or by microemulsion PCR (Ion Torrent)), which generates clusters of many copies of each cDNA on the surface of the device, thereby amplifying the signal produced by each cDNA during the sequencing reaction. Often clonal amplification is performed using a commercially available kit (e.g., Paired-end Cluster Kit from Illumina). Following clonal amplification, the library is ready for sequencing.

2. Differential Gene Expression Analysis

One of the primary uses of RNA-seq data is to identify genes that are differentially expressed between two or more experimental groups. For example, RNA sequencing data can be used to identify genes that are expressed at significantly higher or lower levels in cancer patients as compared to healthy individuals. This is accomplished by performing a statistical analysis to compare the normalized read count of each gene across the different experimental groups. The aim of this analysis is to determine whether any observed difference in read count is significant, i.e., whether it is greater than what would be expected just due to natural random variation.

Several data processing steps must be performed to prepare the raw sequencing data for analysis. Sequencing data is typically supplied in FASTQ format, in which each sequencing read is associated with a quality score. First, the data is processed to remove sequencing artifacts, e.g., adaptor sequences and low-complexity reads. Sequencing errors are identified based on the read quality score and are removed or corrected. Publicly available tools, such as TagDust, SeqTrim, and Quake, can be used to perform these "data grooming" steps.

During the next stage of data processing, the reads are aligned to a reference genome using an alignment tool. Several publicly available tools can be used for this step including, for example, kallisto, TopHat, Cufflinks, and Scripture (these and other alignment tools are well known in the art and are readily available). These programs can be used to reconstruct transcripts, identify variants, and quantitate expression levels for each transcript and gene.

After the reads have been aligned and quantitated, a differential expression analysis may be performed. Statistical methods that are commonly used for differential expression analysis include those based on negative binomial distributions (e.g., edgeR and DESeq) and Bayesian approaches based on a negative binomial model (e.g., baySeq and EBSeq).

It should be understood that the examples given above are illustrative and do not limit the uses of the systems and methods described herein in combination with a digital and laboratory health care platform.

APPLICATIONS INCORPORATED BY REFERENCE

Each of the following US patent applications is incorporated herein in its entirety by reference.
(1) U.S. Prov. Patent Application No. 62/786,739, filed Dec. 31, 2018;
(2) U.S. Prov. Patent Application No. 62/804,458, filed Feb. 12, 2019;
(3) U.S. Prov. Patent Application No. 62/804,509, filed Feb. 12, 2019;
(4) U.S. Prov. Patent Application No. 62/804,724, filed Feb. 12, 2019;
(5) U.S. Prov. Patent Application No. 62/804,730, filed Feb. 12, 2019;
(6) U.S. Prov. Patent Application No. 62/824,039, filed Mar. 26, 2019;
(7) U.S. Prov. Patent Application No. 62/854,400, filed May 30, 2019;
(8) U.S. Prov. Patent Application No. 62/855,913, filed May 31, 2019;
(9) U.S. Prov. Patent Application No. 62/855,750, filed May 31, 2019;
(10) U.S. Prov. Patent Application No. 62/873,693, filed Jul. 12, 2019;
(11) U.S. Prov. Patent Application No. 62/888,163, filed Aug. 16, 2019;
(12) U.S. Prov. Patent Application No. 62/889,510, filed Aug. 20, 2019;
(13) U.S. Prov. Patent Application No. 62/902,950, filed Sep. 19, 2019;
(14) U.S. Prov. Patent Application No. 62/924,054, filed Oct. 21, 2019;
(15) U.S. Prov. Patent Application No. 62/924,073, filed Oct. 21, 2019;
(16) U.S. Prov. Patent Application No. 62/924,515, filed Oct. 22, 2019.
(17) U.S. Prov. Patent Application No. 62/924,621, filed Oct. 22, 2019;
(18) U.S. Prov. Patent Application No. 62/931,600, filed Nov. 6, 2019;
(19) U.S. Prov. Patent Application No. 62/943,712, filed Dec. 4, 2019;
(20) U.S. Prov. Patent Application No. 62/944,292, filed Dec. 5, 2019;
(21) U.S. Prov. Patent Application. No. 62/944,995, filed Dec. 6, 2019;
(22) U.S. Prov. Patent Application. No. 62/786,756, filed Dec. 31, 2019;
(23) U.S. patent application Ser. No. 16/533,676, filed Aug. 6, 2019;
(24) U.S. patent application Ser. No. 16/581,706, filed Sep. 24, 2019;
(25) U.S. patent application Ser. No. 16/653,868, filed Oct. 15, 2019;
(26) U.S. patent application Ser. No. 16/657,804, filed Oct. 18, 2019;
(27) U.S. patent application Ser. No. 16/693,117, filed Nov. 22, 2019;
(28) U.S. patent application Ser. No. 16/732,229, filed Dec. 31, 2019;
(29) U.S. PCT Application PCT/US2019/52801, filed Sep. 24, 2019;
(30) U.S. PCT Application PCT/US2019/69161, filed Dec. 31, 2019;

What is claimed:

1. A method for preparing transcriptome data from a patient tumor sample in order to detect dysregulation in a cellular pathway in the sample, the method comprising:
    (a) extracting RNA from the sample;
    (b) generating double-stranded cDNA using the extracted RNA of (a) as template to create a cDNA sample;
    (c) producing a cDNA fraction from the cDNA sample of (b) by:
        1) fragmenting the double-stranded cDNA of the cDNA sample;
        2) size-selecting fragments of about 200 base-pairs to about 400 base-pairs in length to produce the cDNA fraction;
    (d) sequencing the cDNA fragments present in the cDNA fraction to generate transcriptome data;
    (e) providing the transcriptome data, in the form of a transcriptome value set comprising an identifier and an expression level for one or more genes in the transcriptome data, to one or more trained pathway disruption engines, the pathway disruption engines comprising a plurality of trained machine learning models;

wherein the plurality of trained machine learning models comprises;
1) at least one pathway level machine learning model trained to identify dysregulation in the input transcriptome value set associated with the cellular pathway;
2) at least one module level machine learning model trained to identify dysregulation in the input transcriptome value set associated with the module;
3) at least one gene level machine learning model trained to identify dysregulation in the input transcriptome value set associated with the gene; and
4) at least one variant level machine learning model trained to identify dysregulation in the input transcriptome value set associated with the variant, or associated with a variant of unknown significance;

(f) selecting a plurality of trained machine learning models from the at least one pathway disruption engine to apply to the transcriptome value set;

(g) applying the selected plurality of the trained machine learning models to the transcriptome value set, to generate at least one pathway disruption score indicative of dysregulation in the cellular pathway.

2. The method of claim 1, wherein each pathway level trained machine learning model is trained based on training data comprising a plurality of positive control specimens and a plurality of negative control specimens, wherein each positive control specimen comprises genetic data, the positive control genetic data comprising at least one detectable, pathogenic variant in at least one gene included in the cellular pathway, wherein each negative control specimen comprises genetic data, the negative control genetic data comprising no pathogenic variants in any gene included in the cellular pathway;

wherein each module level trained machine learning model is trained based on training data comprising a plurality of positive control specimens and a plurality of negative control specimens, wherein each positive control specimen comprises genetic data, the positive control genetic data comprising at least one detectable, pathogenic variant in at least one gene included in the module, wherein each negative control specimen comprises genetic data, the negative control genetic data comprising no pathogenic variants in any gene included in the module;

wherein each gene level trained machine learning model is trained based on training data comprising a plurality of positive control specimens and a plurality of negative control specimens, wherein each positive control specimen comprises genetic data, the positive control genetic data comprising at least one detectable, pathogenic variant in the gene, wherein each negative control specimen comprises genetic data, the negative control genetic data comprising no pathogenic variants in the gene;

wherein each variant level trained machine learning model is trained based on training data comprising a plurality of positive control specimens and a plurality of negative control specimens, wherein each positive control specimen comprises genetic data, the positive control genetic data comprising the variant, wherein each negative control specimen comprises genetic data, the negative control genetic data comprising no pathogenic variants.

3. The method of claim 2, wherein at least one trained pathway level model, at least one trained module level module, at least one trained gene level model, or at least one trained variant level model is trained based on training data comprising a plurality of positive control specimens and a plurality of negative control specimens, wherein the training comprises:

calculating a plurality of differential metric values between the positive control specimens and the negative control specimens, each differential metric value being associated with at least one gene included in the pathway or the module, or associated with the gene or the variant, and selecting the gene(s) with differential metric score at or below a threshold value for inclusion in the model.

4. The method of claim 2, wherein at least a portion of the positive control genetic data and the negative control genetic data comprises DNA data.

5. The method of claim 2, wherein at least a portion of the positive control genetic data and the negative control genetic data comprises RNA data.

6. The method of claim 5, wherein the RNA data comprises transcriptome data.

7. The method of claim 5, wherein the detectable pathogenic variant comprises an RNA expression level.

8. The method of claim 5, wherein the negative control RNA data comprises no detectable variation in expression level when compared to one or more wild-type samples for the expressed RNA.

9. The method of claim 1, comprising:
generating a pathway disruption report based on the at least one pathway disruption score; and
presenting the pathway disruption report to at least one of a display or a memory.

10. The method of claim 9, wherein the pathway disruption report comprises information associated with the at least one pathway disruption score, the information comprising at least one of: a) potential causative mutations; b) identification of one or more variants of unknown significance; c) one or more recommended therapies; d) a suggestion that an organoid be monitored after exposure to a treatment based on the pathway disruption score; e) matching at least one clinical trial to a patient associated with the specimen based on the pathway disruption score; and d) reference medical literature.

11. The method of claim 1, comprising:
receiving a first pathway disruption score indicative of cellular pathway dysregulation in a cellular pathway from a first trained pathway disruption engine;
receiving a second pathway disruption score indicative of cellular pathway dysregulation in a cellular pathway from a second trained pathway disruption engine;
generating a meta-pathway depiction representing the cellular pathway, the first pathway disruption score, and the second pathway disruption score; and
presenting the meta-pathway depiction on a display.

12. The method of claim 1, wherein the at least one trained pathway disruption engine comprises a trained model configured to output a model score, wherein model scores below a predetermined threshold indicate non-dysregulation, and wherein model scores above the predetermined threshold indicates dysregulation.

13. The method of claim 1, wherein the at least one trained pathway disruption engine comprises a plurality of trained models, the cellular pathway comprises one or more genetic modules, and each trained model included in the plurality of trained models is configured to output a model score associated with a different genetic module included in the cellular pathway.

14. The method of claim 13, further comprising:
calculating a global dysregulation score based on the value of the model score output by each of the trained models.

15. The method of claim 1, wherein the plurality of machine learning models comprises one or more linear regression machine learning algorithms or non-linear models.

16. The method of claim 1, wherein the cellular pathway comprises 1 to 5 genes, 6 to 10 genes, 10 to 20 genes, or 20 to 100 genes.

17. The method of claim 1, comprising:
generating a pathway disruption report including a depiction of the cellular pathway, the depiction comprising a number of modules included in the cellular pathway and an indication of dysregulation in at least one of the modules included in the cellular pathway; and
presenting the pathway disruption report to at least one of a display or a memory.

18. The method of claim 1, wherein the at least one trained pathway disruption engine comprises a rat sarcoma/receptor tyrosine kinase (RAS/RTK) pathway level machine learning model.

19. The method of claim 18, wherein the at least one trained pathway disruption engine comprises module level machine learning models for at least the following modules: a RAS module; a RAF module; a MEK module, and a ERK module.

20. The method of claim 19, wherein the RAS model is trained to identify dysregulation in the input transcriptome value set that is associated with an alteration in at least one of the KRAS, NRAS, and HRAS genes; wherein the RAF model is trained to identify dysregulation in the input transcriptome value set that is associated with an alteration in at least one of the RAF1, BRAF, and ARAF genes; wherein the MEK model is trained to identify dysregulation in the input transcriptome value set that is associated with an alteration in the MAP2K1 gene; and wherein the ERK model is trained to identify dysregulation in the input transcriptome value set that is associated with an alteration in at least one of the MAPK3 and MAPK1 genes.

21. The method of claim 20, wherein each trained model outputs a model score to the trained pathway disruption engine, and wherein the pathway disruption engine generates a pathway disruption score indicative of dysregulation in the cellular pathway.

22. The method of claim 18, wherein the at least one trained pathway disruption engine comprises gene level machine learning models for at least one of the following genes: KRAS, NRAS, HRAS, RAF1, BRAF, ARAF, MAP2K1 MAPK3, and MAPK1.

23. The method of claim 22, wherein each trained model outputs a model score to the trained pathway disruption engine, and wherein the trained pathway disruption engine generates a pathway disruption score indicative of dysregulation in the cellular pathway.

24. The method of claim 1, wherein the at least one trained pathway disruption engines comprises a phosphatidylinositol-3kinase (PI3K) pathway level machine learning model.

25. The method of claim 24, wherein the at least one trained pathway disruption engine comprises module level machine learning models for at least one of the following modules: a PI3K module, an AKT1 module, a TOR module, and a PTEN module.

26. The method of claim 25, wherein the PI3K model is trained to detect dysregulation in the input transcriptome value set that is associated with an alteration in at least one of the PIK3CA and PICKCB genes; wherein the AKT1 model is trained to detect dysregulation in the input transcriptome value set that is associated with an alteration in at least one of the AKT1, AKT2, and AKT3 genes, wherein the TOR model is trained to detect dysregulation in the input transcriptome value set that is associated with an alteration in at least one of the RICTOR, RPTOR, and MTOR genes, and wherein the PTEN model is trained to detect dysregulation in the input transcriptome value set that is associated with an alteration in at least one of the PTEN, PIK3R1, PIK3R2, and PIK3R3 genes.

27. The method of claim 26, wherein each trained model outputs a model score to the trained pathway disruption engine, and wherein the pathway disruption engine generates a pathway disruption score indicative of dysregulation in the cellular pathway.

28. The method of claim 24, wherein the at least one trained pathway disruption engine comprises gene level machine learning models for at least one of the following genes: PIK3CA, PICKCB, AKT1, AKT2, AKT3, RICTOR, RPTOR, MTOR, PTEN, PIK3R1, PIK3R2, and PIK3R3.

29. The method of claim 28, wherein each trained model outputs a model score to the trained pathway disruption engine, and wherein the pathway disruption engine generates a pathway disruption score indicative of dysregulation in the cellular pathway.

30. The method of claim 1, wherein the plurality of models are selected by the user.

31. The method of claim 1, wherein the at least one trained pathway disruption engines comprises a custom pathway level machine learning model.

32. The method of claim 2, comprising selecting one or more of the detectable, pathogenic variant positive controls used for training the pathway level model.

33. The method of claim 32, wherein the selected positive controls each comprise more than one detectable, pathogenic variant.

34. The method of claim 2, wherein the positive control detectable, pathogenic variants comprise one or more insertions, deletions, rearrangements, copy number variants, or substitutions.

35. The method of claim 32, wherein selecting comprises filtering positive and negative controls with respect to clinical characteristics.

* * * * *